United States Patent
van Dijk et al.

(10) Patent No.: US 12,391,741 B2
(45) Date of Patent: Aug. 19, 2025

(54) T CELL RECEPTORS THAT BIND TO MIXED LINEAGE LEUKEMIA (MLL)-SPECIFIC PHOSPHOPEPTIDES AND METHODS OF USE THEREOF

(71) Applicant: MiNK Therapeutics, Inc., New York, NY (US)

(72) Inventors: Marc van Dijk, Bosch en Duin (NL); Ekaterina Vladimirovna Breous-Nystrom, Basel (CH); Alessandra Franchino, Basel (CH); Sébastien Lalevée, Saint Louis (FR); Arthur Andrew Hurwitz, Bedford, MA (US); Mark Adrian Exley, Brookline, MA (US); Benjamin Jacob Wolf, Boston, MA (US)

(73) Assignee: MiNK Therapeutics, Inc., New York, NY (US)

( * ) Notice: Subject to any disclaimer, the term of this patent is extended or adjusted under 35 U.S.C. 154(b) by 0 days.

(21) Appl. No.: 18/340,600

(22) Filed: Jun. 23, 2023

(65) Prior Publication Data

US 2024/0301025 A1 Sep. 12, 2024

Related U.S. Application Data

(60) Division of application No. 16/807,742, filed on Mar. 3, 2020, now Pat. No. 11,718,658, which is a continuation of application No. PCT/US2018/049397, filed on Sep. 4, 2018.

(60) Provisional application No. 62/553,957, filed on Sep. 4, 2017.

(51) Int. Cl.
*C07K 14/725* (2006.01)
*A61K 38/00* (2006.01)
*A61K 45/06* (2006.01)
*C12N 15/63* (2006.01)

(52) U.S. Cl.
CPC .......... *C07K 14/7051* (2013.01); *C12N 15/63* (2013.01); *A61K 38/00* (2013.01); *A61K 45/06* (2013.01); *C07K 2317/565* (2013.01)

(58) Field of Classification Search
CPC .......... C07K 14/7051; C07K 2317/565; A61K 38/00; A61K 45/06; A61K 39/4632; A61K 2121/00; A61P 35/00; C12N 5/0636; C12N 2510/00

See application file for complete search history.

(56) References Cited

U.S. PATENT DOCUMENTS

| | | | | |
|---|---|---|---|---|
| 8,354,509 B2 * | 1/2013 | Carven | .......... | G01N 33/57488 530/388.1 |
| 11,718,658 B2 | 8/2023 | van Dijk et al. | | |
| 2020/0308246 A1 | 10/2020 | van Dijk et al. | | |

FOREIGN PATENT DOCUMENTS

| | | | |
|---|---|---|---|
| CN | 101088089 A | 12/2007 | |
| CN | 105683215 A | 6/2016 | |
| WO | WO 2005/080601 A2 | 9/2005 | |
| WO | WO 2011/149909 A2 | 12/2011 | |
| WO | WO-2015160928 A2 * | 10/2015 | .......... A61K 35/17 |
| WO | WO 2017/044672 A1 | 3/2017 | |

OTHER PUBLICATIONS

Doody et al. Glycoprotein 96 Can Chaperone Both MHC Class I- and Class II-Restricted Epitopes for In Vivo Presentation, but Selectively Primes CD8 T Cell Effector Function1. J Immunol (2004) 172 (10): 6087-6092 (Year: 2004).*
Cobbold et al. MHC Class I-Associated Phosphopeptides Are the Targets of Memory-like Immunity in LeukemiaScience Translational Medicine Sep. 18, 2013 vol. 5 Issue 203 203ra125 (Year: 2013).*
International Search Report and Written Opinion for Application No. PCT/US2018/049397, mailed Jan. 15, 2019.
International Preliminary Report on Patentability for Application No. PCT/US2018/049397, mailed Mar. 19, 2020.
Cobbold et al., MHC class I-associated phosphopeptides are the targets of memory-like immunity in leukemia. Sci Transl Med. Sep. 18, 2013;5(203):203ra125. doi: 10.1126/scitranslmed.3006061.
Parkhurst et al., Isolation of T-Cell Receptors Specifically Reactive with Mutated Tumor-Associated Antigens from Tumor-Infiltrating Lymphocytes Based on CD137 Expression. Clin Cancer Res. May 15, 2017;23(10):2491-2505. doi: 10.1158/1078-0432.CCR-16-2680. Epub Nov. 8, 2016.
Plewa et al., Discovery of phospho-peptide neoantigen tumor targets (PTTs) and identification of novel T cell receptors (TCRs) targeting phospho-MLL for adoptive cell therapy AgenTus Therapeutics: differentiated cell therapy. Aug. 31, 2018. http://www.agentustherapeutics.com/wpcontent/uploads/2018/09/AgenTus-PTT_MLL-Poster-2018_0831-FINAL.pdf [retrieved on Dec. 11, 2018].
Rossjohn et al., T cell antigen receptor recognition of antigen-presenting molecules. Annu Rev Immunol. 2015;33:169-200. doi: 10.1146/annurev-immunol-032414-112334. Epub Dec. 10, 2014.
Song et al., Broad TCR repertoire and diverse structural solutions for recognition of an immunodominant CD8+ T cell epitope. Nat Struct Mol Biol. Apr. 2017;24(4):395-406. doi: 10.1038/nsmb.3383. Epub Feb. 27, 2017.

(Continued)

*Primary Examiner* — Janet L Andres
*Assistant Examiner* — Brian Hartnett
(74) *Attorney, Agent, or Firm* — Wolf, Greenfield & Sacks, P.C.

(57) ABSTRACT

Provided are TCRs (e.g., TCRs that bind to MLL, e.g., TCRs that bind to an MLL phosphopeptide, e.g., TCRs that bind to an MLL phosphopeptide/MHC complex), cells and pharmaceutical compositions comprising these TCRs, nucleic acids encoding these TCRs, expression vectors and host cells for making these TCRs, and methods of treating a subject using these TCRs.

20 Claims, 24 Drawing Sheets

Specification includes a Sequence Listing.

(56) References Cited

OTHER PUBLICATIONS

Xianfeng et al., Study of CML Antigen-related TCR Vα13/β21 and Vα18/Vβ21 gene-modified T Cells. Proceedings of the 8th National Conference on Immunology. Chinese Society for Immunology. Presented Oct. 18, 2012.

* cited by examiner

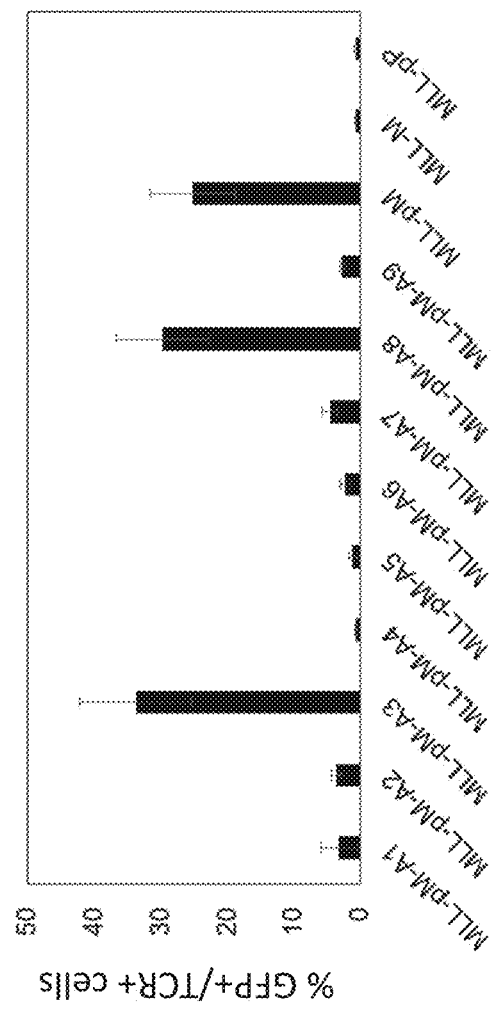
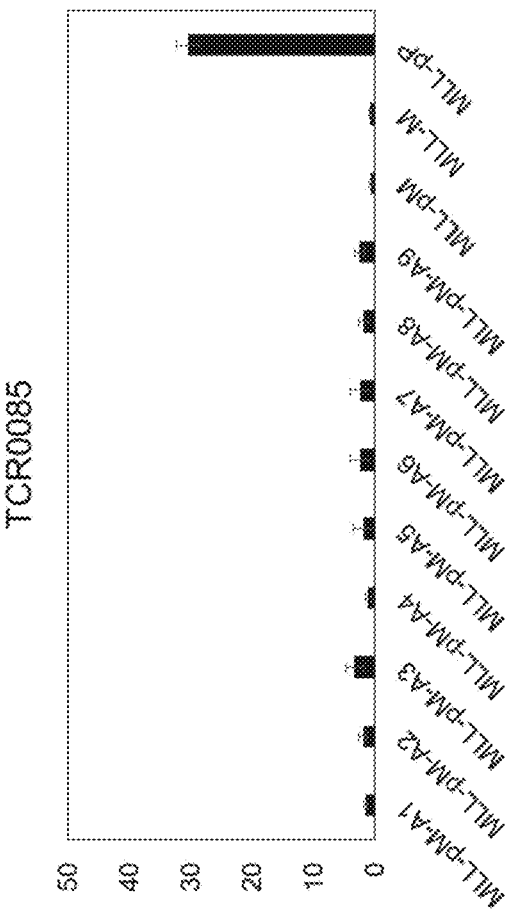
FIG. 6A
FIG. 6B

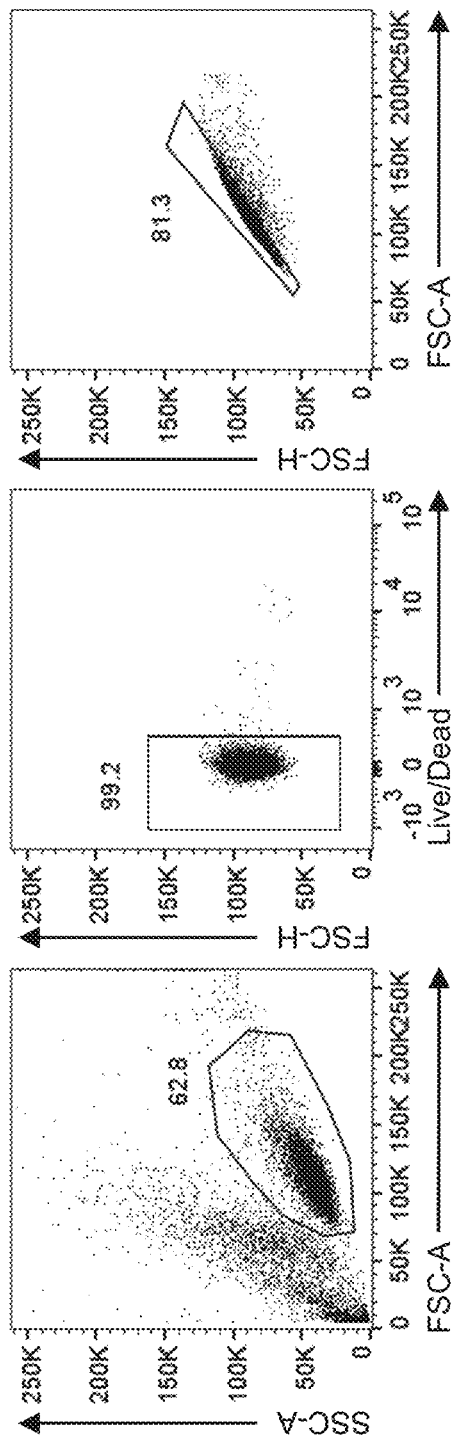
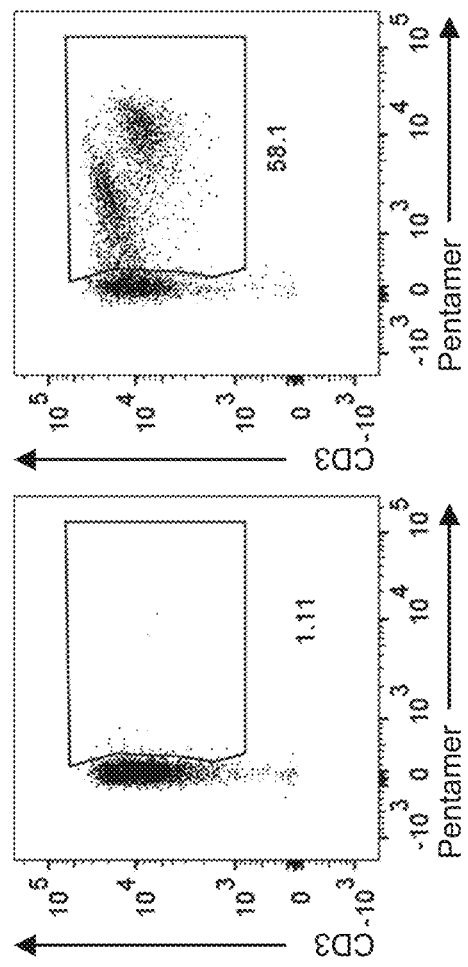
FIG. 9A
FIG. 9B

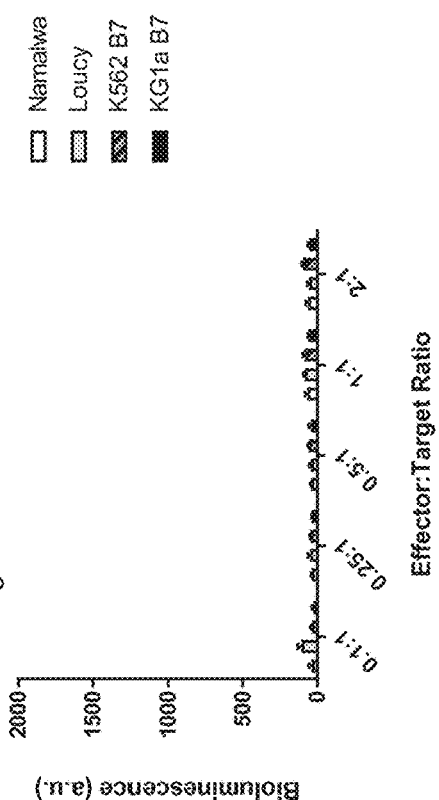
FIG. 12A Effector: Jurkat reporter cells expressing TCR0078
Target: Various tumor cells
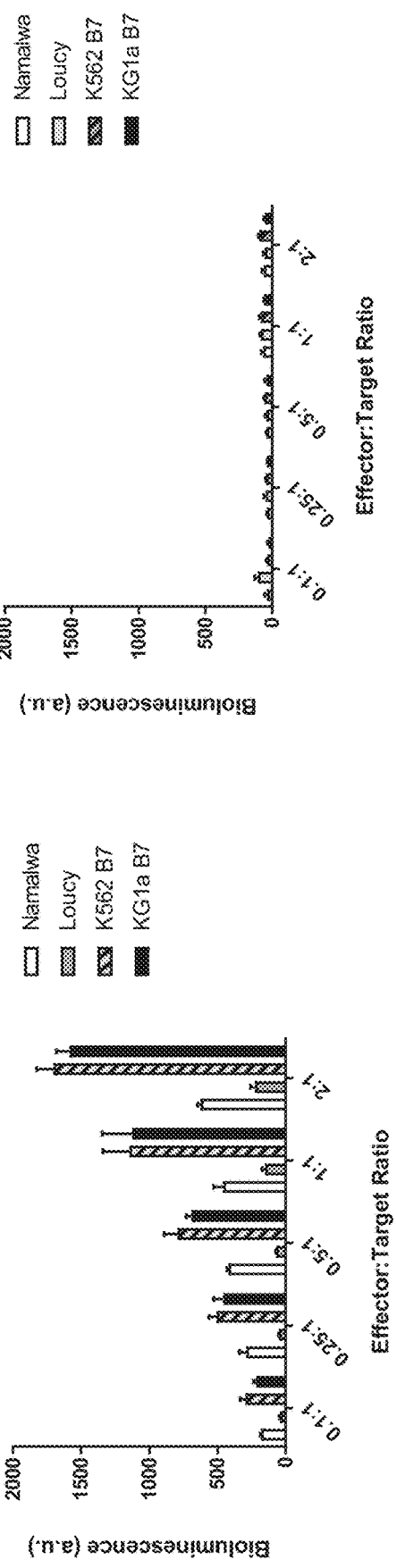
FIG. 12B Effector: non-transduced Jurkat reporter cells
Target: Various tumor cells
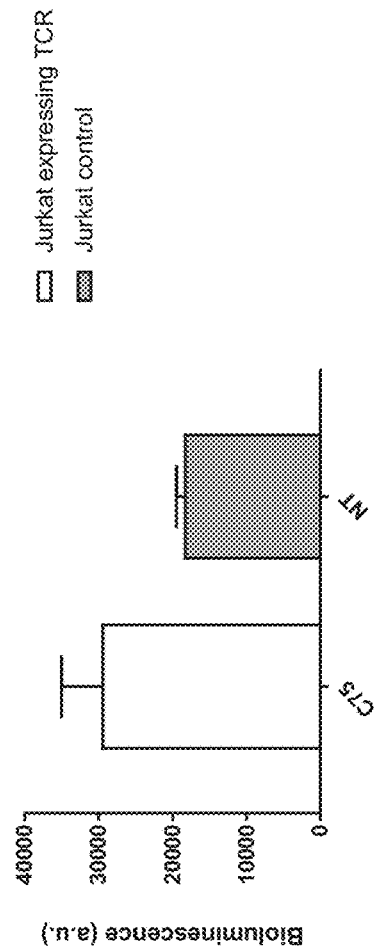
FIG. 12C PMA/Ionomycin Treatment

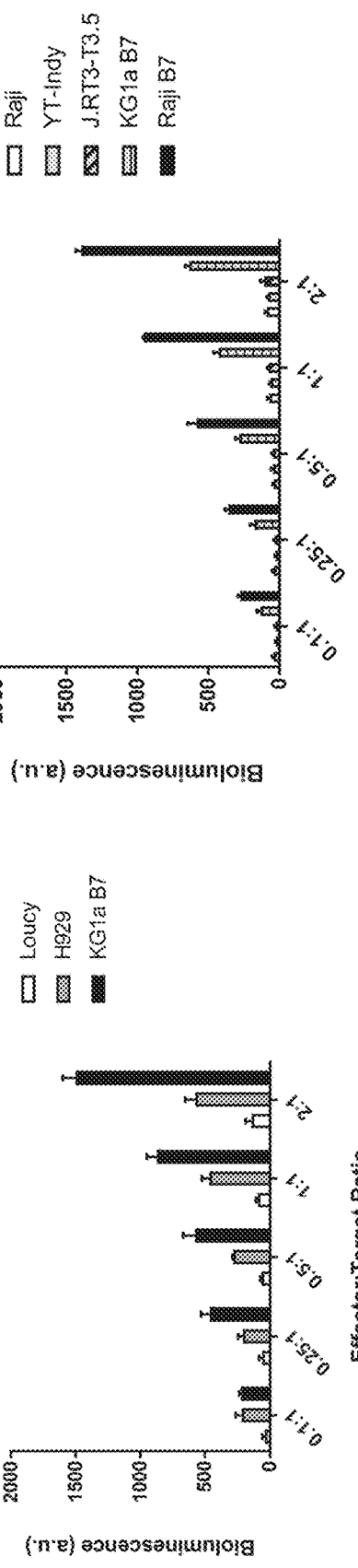
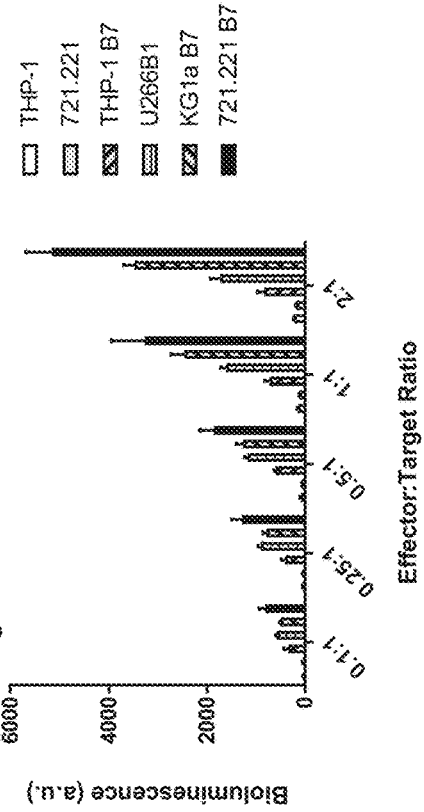
Fig. 13A    Fig. 13B    Fig. 13C

FIG. 14

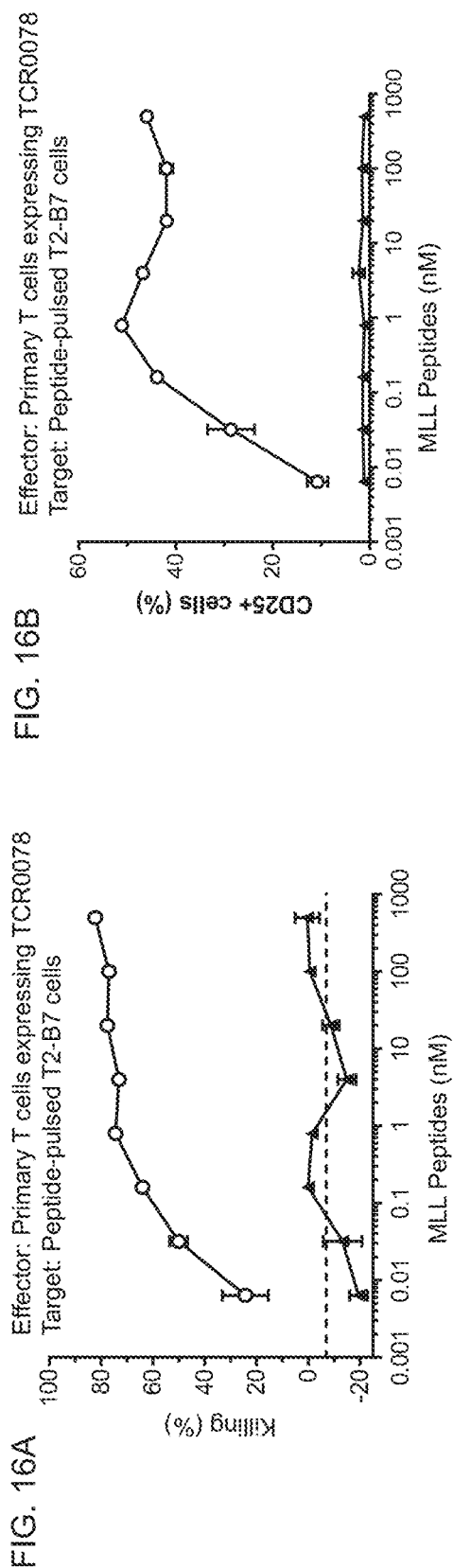
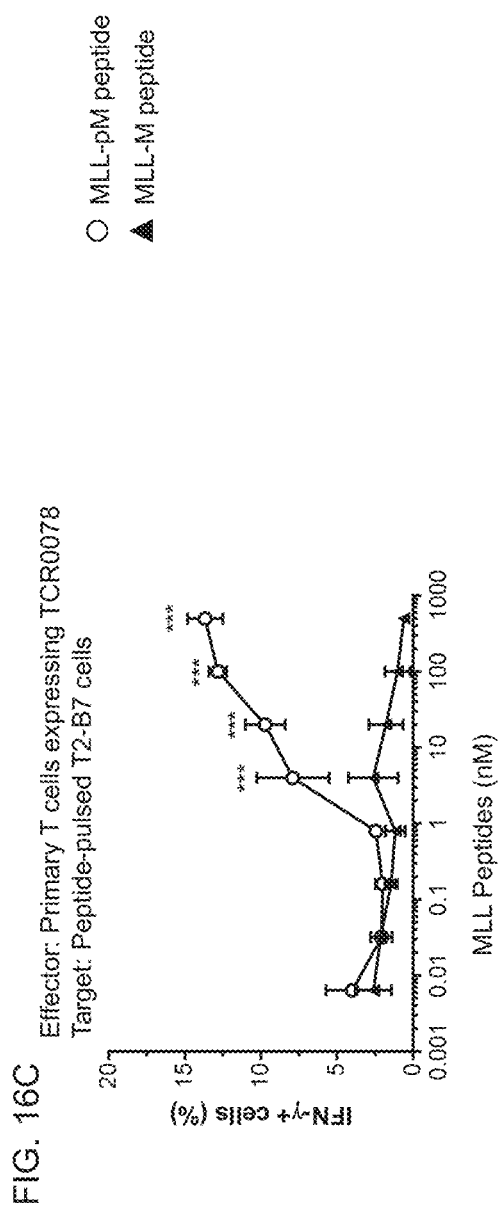
FIG. 16A
FIG. 16B
FIG. 16C

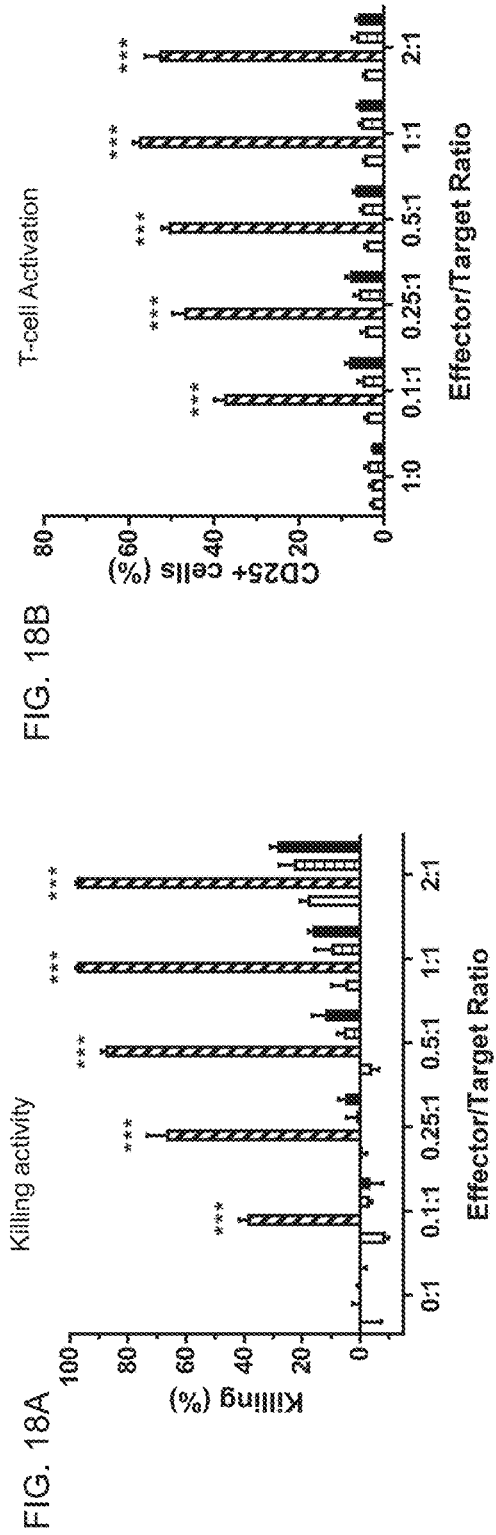
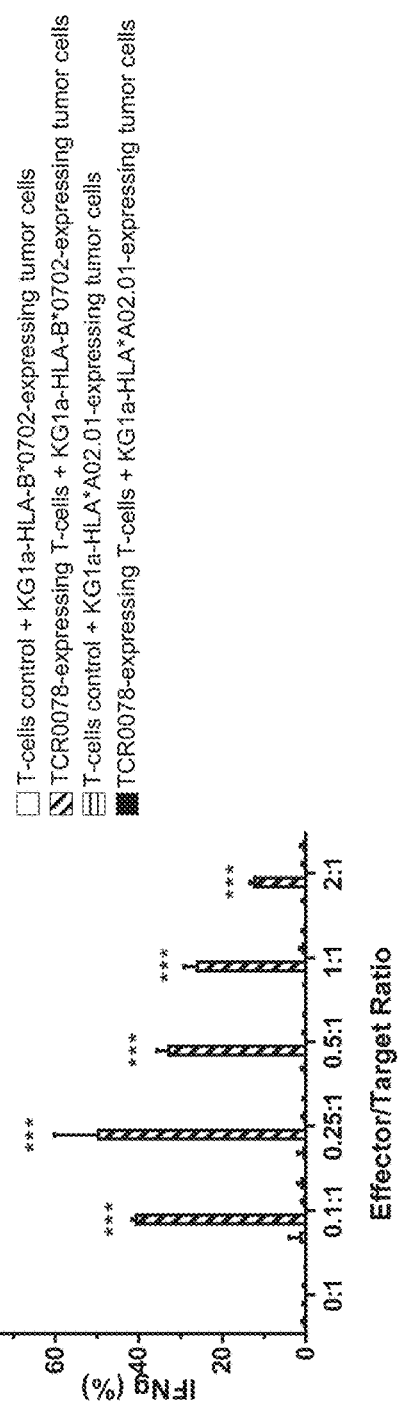
FIG. 18A
FIG. 18B
FIG. 18C

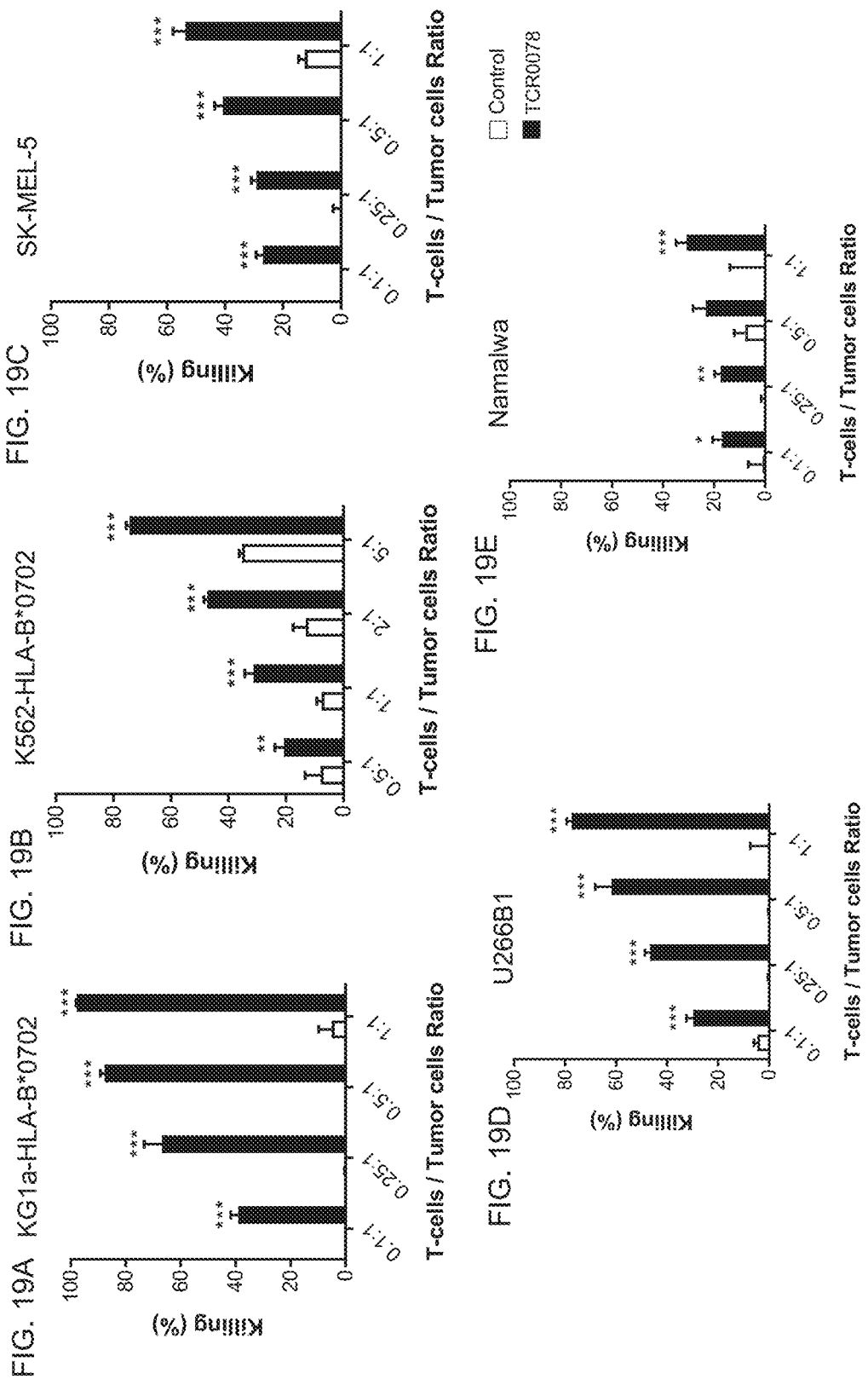

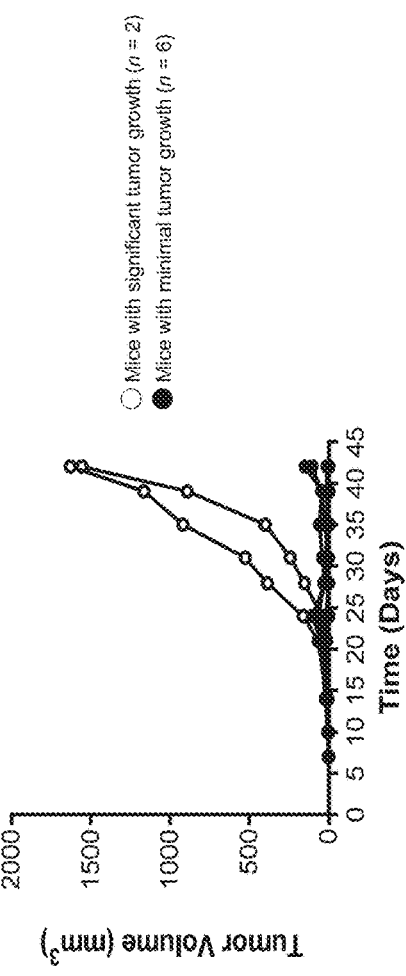
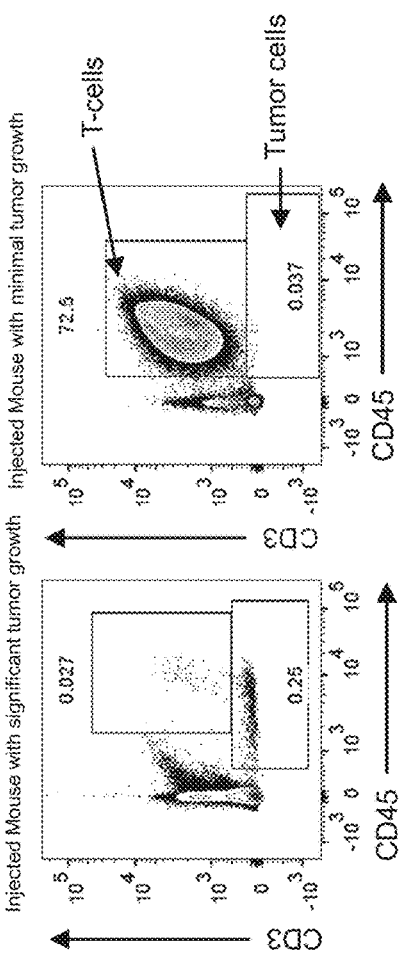
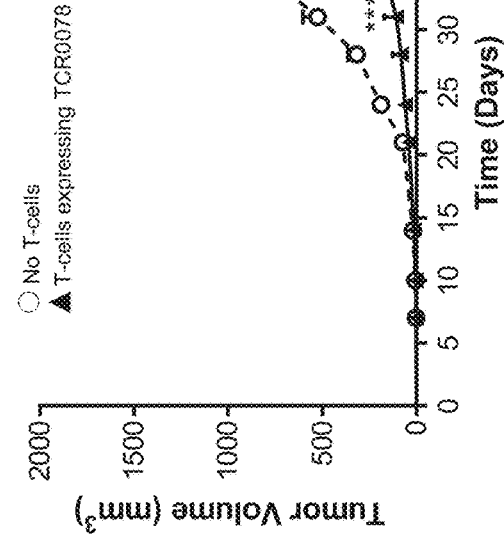
FIG. 21A
FIG. 21B
FIG. 21C

SEQUENCE LISTING

```
Sequence total quantity: 273
SEQ ID NO: 1              moltype = AA  length = 112
FEATURE                   Location/Qualifiers
REGION                    1..112
                          note = Description of Artificial Sequence: Synthetic
                          polypeptide
source                    1..112
                          mol_type = protein
                          organism = synthetic construct
SEQUENCE: 1
TQLLEQSPQF LSIQEGENLT VYCNSSSVFS SLQWYRQEPG EGPVLLVTVV TGGEVKKLKR   60
LTFQFGDARK DSSLHITAAQ PGDTGLYLCA GYGGGSNYKL TFGAGTRLTV KP          112

SEQ ID NO: 2              moltype = AA  length = 113
FEATURE                   Location/Qualifiers
REGION                    1..113
```

-continued

```
                        note = Description of Artificial Sequence: Synthetic
                           polypeptide
source                  1..113
                        mol_type = protein
                        organism = synthetic construct
SEQUENCE: 2
EAQVTQNPRY LITVTGKKLT VTCSQNMNHE YMSWYRQDPG LGLRQIYYSM NVEVTDKGDV    60
PEGYKVSRKE KRNFPLILES PSPNQTSLYF CASRLTGRVH GYTFGPGTRL TVL          113

SEQ ID NO: 3            moltype = AA  length = 113
FEATURE                 Location/Qualifiers
REGION                  1..113
                        note = Description of Artificial Sequence: Synthetic
                           polypeptide
source                  1..113
                        mol_type = protein
                        organism = synthetic construct
SEQUENCE: 3
KNQVEQSPQS LIILEGKNCT LQCNYTVSPF SNLRWYKQDT GRGPVSLTIM TFSENTKSNG    60
RYTATLDADT KQSSLHITAS QLSDSASYIC VVRGGAAGNK LTFGAGTRLT VKP          113

SEQ ID NO: 4            moltype = AA  length = 114
FEATURE                 Location/Qualifiers
REGION                  1..114
                        note = Description of Artificial Sequence: Synthetic
                           polypeptide
source                  1..114
                        mol_type = protein
                        organism = synthetic construct
SEQUENCE: 4
DAGVIQSPRH EVTEMGQEVT LRCKPISGHN SLFWYRQTMM RGLELLIYFN NNVPIDDSGM    60
PEDRFSAKMP NASFSTLKIQ PSEPRDSAVY FCASSSGGAN TEAFFGPGTR LTVL         114

SEQ ID NO: 5            moltype = AA  length = 114
FEATURE                 Location/Qualifiers
REGION                  1..114
                        note = Description of Artificial Sequence: Synthetic
                           polypeptide
source                  1..114
                        mol_type = protein
                        organism = synthetic construct
SEQUENCE: 5
AQSVTQLGSH VSVSEGALIL LRCNYSSSVP PYLFWYVQYP NQGLQLLLKY TTGATLVKGI    60
NGFEAEFKKS ETSFHLTKPS AHMSDAAEYF CAVSARYNFN KFYFGSGTKL SVIP         114

SEQ ID NO: 6            moltype = AA  length = 114
FEATURE                 Location/Qualifiers
REGION                  1..114
                        note = Description of Artificial Sequence: Synthetic
                           polypeptide
source                  1..114
                        mol_type = protein
                        organism = synthetic construct
SEQUENCE: 6
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSASGGRS YEQYFGPGTR LTVV         114

SEQ ID NO: 7            moltype = AA  length = 110
FEATURE                 Location/Qualifiers
REGION                  1..110
                        note = Description of Artificial Sequence: Synthetic
                           polypeptide
source                  1..110
                        mol_type = protein
                        organism = synthetic construct
SEQUENCE: 7
EDQVTQSPEA LRLQEGESSS LNCSYTVSGL RGLFWYRQDP GKGPEFLFTL YSAGEEKEKE    60
RLKATLTKKE SFLHITAPKP EDSATYLCAV RNTGFQKLVF GTGTRLLVSP              110

SEQ ID NO: 8            moltype = AA  length = 115
FEATURE                 Location/Qualifiers
REGION                  1..115
                        note = Description of Artificial Sequence: Synthetic
                           polypeptide
source                  1..115
                        mol_type = protein
                        organism = synthetic construct
SEQUENCE: 8
DTGVSQDPRH KITKRGQNVT FRCDPISEHN RLYWYRQTLG QGPEFLTYFQ NEAQLEKSRL    60
```

```
LSDRFSAERP KGSFSTLEIQ RTEQGDSAMY LCASSWRTGR EETQYFGPGT RLLVL         115

SEQ ID NO: 9             moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 9
KQEVTQIPAA LSVPEGENLV LNCSFTDSAI YNLQWFRQDP GKGLTSLLLI QSSQREQTSG   60
RLNASLDKSS GRSTLYIAAS QPGDSATYLC AVMLWNQGGK LIFGQGTELS VKP          113

SEQ ID NO: 10            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 10
KAGVTQTPRY LIKTRGQQVT LSCSPISGHR SVSWYQQTPG QGLQFLFEYF SETQRNKGNF   60
PGRFSGRQFS NSRSEMNVST LELGDSALYL CASSLGRGYE QYFGPGTRLT VT           112

SEQ ID NO: 11            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 11
SVFSS                                                                5

SEQ ID NO: 12            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 12
VSPFSN                                                               6

SEQ ID NO: 13            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 13
SSVPPY                                                               6

SEQ ID NO: 14            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 14
VSGLRG                                                               6

SEQ ID NO: 15            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 15
DSAIYN                                                               6

SEQ ID NO: 16            moltype = AA  length = 7
FEATURE                  Location/Qualifiers
REGION                   1..7
```

```
source                        note = Description of Artificial Sequence: Synthetic peptide
                              1..7
                              mol_type = protein
                              organism = synthetic construct
SEQUENCE: 16
VVTGGEV                                                                                     7

SEQ ID NO: 17                 moltype = AA  length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 17
MTFSENT                                                                                     7

SEQ ID NO: 18                 moltype = AA  length = 8
FEATURE                       Location/Qualifiers
REGION                        1..8
                              note = Description of Artificial Sequence: Synthetic peptide
source                        1..8
                              mol_type = protein
                              organism = synthetic construct
SEQUENCE: 18
YTTGATLV                                                                                    8

SEQ ID NO: 19                 moltype = AA  length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 19
LYSAGEE                                                                                     7

SEQ ID NO: 20                 moltype = AA  length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 20
IQSSQRE                                                                                     7

SEQ ID NO: 21                 moltype = AA  length = 12
FEATURE                       Location/Qualifiers
REGION                        1..12
                              note = Description of Artificial Sequence: Synthetic peptide
source                        1..12
                              mol_type = protein
                              organism = synthetic construct
SEQUENCE: 21
AGYGGGSNYK LT                                                                              12

SEQ ID NO: 22                 moltype = AA  length = 12
FEATURE                       Location/Qualifiers
REGION                        1..12
                              note = Description of Artificial Sequence: Synthetic peptide
source                        1..12
                              mol_type = protein
                              organism = synthetic construct
SEQUENCE: 22
VVRGGAAGNK LT                                                                              12

SEQ ID NO: 23                 moltype = AA  length = 12
FEATURE                       Location/Qualifiers
REGION                        1..12
                              note = Description of Artificial Sequence: Synthetic peptide
source                        1..12
                              mol_type = protein
                              organism = synthetic construct
SEQUENCE: 23
AVSARYNFNK FY                                                                              12

SEQ ID NO: 24                 moltype = AA  length = 11
FEATURE                       Location/Qualifiers
```

```
REGION                  1..11
                        note = Description of Artificial Sequence: Synthetic peptide
source                  1..11
                        mol_type = protein
                        organism = synthetic construct
SEQUENCE: 24
AVRNTGFQKL V                                                                    11

SEQ ID NO: 25           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 25
AVMLWNQGGK LI                                                                   12

SEQ ID NO: 26           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 26
MNHEY                                                                           5

SEQ ID NO: 27           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 27
SGHNS                                                                           5

SEQ ID NO: 28           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 28
SGDLS                                                                           5

SEQ ID NO: 29           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 29
SEHNR                                                                           5

SEQ ID NO: 30           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 30
SGHRS                                                                           5

SEQ ID NO: 31           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 31
SMNVEV                                                                          6

SEQ ID NO: 32           moltype = AA  length = 6
```

```
FEATURE               Location/Qualifiers
REGION                1..6
                      note = Description of Artificial Sequence: Synthetic peptide
source                1..6
                      mol_type = protein
                      organism = synthetic construct
SEQUENCE: 32
FNNNVP                                                                          6

SEQ ID NO: 33         moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 33
YYNGEE                                                                          6

SEQ ID NO: 34         moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 34
FQNEAQ                                                                          6

SEQ ID NO: 35         moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 35
YFSETQ                                                                          6

SEQ ID NO: 36         moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 36
ASRLTGRVHG YT                                                                  12

SEQ ID NO: 37         moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 37
ASSSGGANTE AF                                                                  12

SEQ ID NO: 38         moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 38
ASSASGGRSY EQY                                                                 13

SEQ ID NO: 39         moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 39
ASSWRTGREE TQY                                                                 13
```

```
SEQ ID NO: 40              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 40
ASSLGRGYEQ Y                                                                    11

SEQ ID NO: 41              moltype = AA   length = 141
FEATURE                    Location/Qualifiers
REGION                     1..141
                           note = Description of Artificial Sequence: Synthetic
                            polypeptide
MOD_RES                    1
                           note = Asn, Tyr, His or Asp
source                     1..141
                           mol_type = protein
                           organism = synthetic construct
SEQUENCE: 41
XIQNPDPAVY QLRDSKSSDK SVCLFTDFDS QTNVSQSKDS DVYITDKTVL DMRSMDFKSN               60
SAVAWSNKSD FACANAFNNS IIPEDTFFPS PESSCDVKLV EKSFETDTNL NFQNLSVIGF              120
RILLLKVAGF NLLMTLRLWS S                                                        141

SEQ ID NO: 42              moltype = AA   length = 141
FEATURE                    Location/Qualifiers
source                     1..141
                           mol_type = protein
                           organism = Homo sapiens
SEQUENCE: 42
YIQNPDPAVY QLRDSKSSDK SVCLFTDFDS QTNVSQSKDS DVYITDKTVL DMRSMDFKSN               60
SAVAWSNKSD FACANAFNNS IIPEDTFFPS PESSCDVKLV EKSFETDTNL NFQNLSVIGF              120
RILLLKVAGF NLLMTLRLWS S                                                        141

SEQ ID NO: 43              moltype = AA   length = 177
FEATURE                    Location/Qualifiers
source                     1..177
                           mol_type = protein
                           organism = Homo sapiens
SEQUENCE: 43
EDLNKVFPPE VAVFEPSEAE ISHTQKATLV CLATGFFPDH VELSWWVNGK EVHSGVSTDP               60
QPLKEQPALN DSRYCLSSRL RVSATFWQNP RNHFRCQVQF YGLSENDEWT QDRAKPVTQI              120
VSAEAWGRAD CGFTSVSYQQ GVLSATILYE ILLGKATLYA VLVSALVLMA MVKRKDF                 177

SEQ ID NO: 44              moltype = AA   length = 179
FEATURE                    Location/Qualifiers
source                     1..179
                           mol_type = protein
                           organism = Homo sapiens
SEQUENCE: 44
EDLKNVFPPE VAVFEPSEAE ISHTQKATLV CLATGFYPDH VELSWWVNGK EVHSGVSTDP               60
QPLKEQPALN DSRYCLSSRL RVSATFWQNP RNHFRCQVQF YGLSENDEWT QDRAKPVTQI              120
VSAEAWGRAD CGFTSESYQQ GVLSATILYE ILLGKATLYA VLVSALVLMA MVKRKDSRG               179

SEQ ID NO: 45              moltype = AA   length = 9
FEATURE                    Location/Qualifiers
MOD_RES                    4
                           note = Phosphoserine
source                     1..9
                           mol_type = protein
                           organism = Homo sapiens
SEQUENCE: 45
EPRSPSHSM                                                                        9

SEQ ID NO: 46              moltype = AA   length = 9
FEATURE                    Location/Qualifiers
source                     1..9
                           mol_type = protein
                           organism = Homo sapiens
SEQUENCE: 46
EPRSPSHSM                                                                        9

SEQ ID NO: 47              moltype = AA   length = 9
FEATURE                    Location/Qualifiers
MOD_RES                    4
                           note = Phosphoserine
source                     1..9
                           mol_type = protein
```

```
                        organism = Homo sapiens
SEQUENCE: 47
RVRSPTRSP                                                                 9

SEQ ID NO: 48           moltype = AA   length = 9
FEATURE                 Location/Qualifiers
source                  1..9
                        mol_type = protein
                        organism = Homo sapiens
SEQUENCE: 48
RVRSPTRSP                                                                 9

SEQ ID NO: 49           moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 49
APRSPSHSM                                                                 9

SEQ ID NO: 50           moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 50
EARSPSHSM                                                                 9

SEQ ID NO: 51           moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 51
EPASPSHSM                                                                 9

SEQ ID NO: 52           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 52
EPRAPSHSM                                                                 9

SEQ ID NO: 53           moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 53
EPRSASHSM                                                                 9

SEQ ID NO: 54           moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
```

-continued

```
SEQUENCE: 54
EPRSPAHSM                                                               9

SEQ ID NO: 55           moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 55
EPRSPSASM                                                               9

SEQ ID NO: 56           moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 56
EPRSPSHAM                                                               9

SEQ ID NO: 57           moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 57
EPRSPSHSA                                                               9

SEQ ID NO: 58           moltype = AA  length = 253
FEATURE                 Location/Qualifiers
REGION                  1..253
                        note = Description of Artificial Sequence: Synthetic
                         polypeptide
source                  1..253
                        mol_type = protein
                        organism = synthetic construct
SEQUENCE: 58
TQLLEQSPQF LSIQEGENLT VYCNSSSVFS SLQWYRQEPG EGPVLLVTVV TGGEVKKLKR   60
LTFQFGDARK DSSLHITAAQ PGDTGLYLCA GYGGGSNYKL TFGKGTLLTV NPYIQNPDPA  120
VYQLRDSKSS DKSVCLFTDF DSQTNVSQSK DSDVYITDKT VLDMRSMDFK SNSAVAWSNK  180
SDFACANAFN NSIIPEDTFF PSPESSCDVK LVEKSFETDT NLNFQNLSVI GFRILLLKVA  240
GFNLLMTLRL WSS                                                    253

SEQ ID NO: 59           moltype = AA  length = 290
FEATURE                 Location/Qualifiers
REGION                  1..290
                        note = Description of Artificial Sequence: Synthetic
                         polypeptide
source                  1..290
                        mol_type = protein
                        organism = synthetic construct
SEQUENCE: 59
EAQVTQNPRY LITVTGKKLT VTCSQNMNHE YMSWYRQDPG LGLRQIYYSM NVEVTDKGDV   60
PEGYKVSRKE KRNFPLILES PSPNQTSLYF CASRLTGRVH GYTFGSGTRL TVVEDLNKVF  120
PPEVAVFEPS EAEISHTQKA TLVCLATGFF PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSVS YQQGVLSATI LYEILLGKAT LYAVLVSALV LMAMVKRKDF            290

SEQ ID NO: 60           moltype = AA  length = 292
FEATURE                 Location/Qualifiers
REGION                  1..292
                        note = Description of Artificial Sequence: Synthetic
                         polypeptide
source                  1..292
                        mol_type = protein
                        organism = synthetic construct
SEQUENCE: 60
EAQVTQNPRY LITVTGKKLT VTCSQNMNHE YMSWYRQDPG LGLRQIYYSM NVEVTDKGDV   60
```

```
PEGYKVSRKE KRNFPLILES PSPNQTSLYF CASRLTGRVH GYTFGSGTRL TVVEDLKNVF   120
PPEVAVFEPS EAEISHTQKA TLVCLATGFY PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSES YQQGVLSATI LYEILLGKAT LYAVLVSALV LMAMVKRKDS RG           292

SEQ ID NO: 61              moltype = AA   length = 254
FEATURE                    Location/Qualifiers
REGION                     1..254
                           note = Description of Artificial Sequence: Synthetic
                             polypeptide
source                     1..254
                           mol_type = protein
                           organism = synthetic construct
SEQUENCE: 61
KNQVEQSPQS LIILEGKNCT LQCNYTVSPF SNLRWYKQDT GRGPVSLTIM TFSENTKSNG    60
RYTATLDADT KQSSLHITAS QLSDSASYIC VVRGGAAGNK LTFGGGTRVL VKPYIQNPDP   120
AVYQLRDSKS SDKSVCLFTD FDSQTNVSQS KDSDVYITDK TVLDMRSMDF KSNSAVAWSN   180
KSDFACANAF NNSIIPEDTF FPSPESSCDV KLVEKSFETD TNLNFQNLSV IGFRILLLKV   240
AGFNLLMTLR LWSS                                                    254

SEQ ID NO: 62              moltype = AA   length = 291
FEATURE                    Location/Qualifiers
REGION                     1..291
                           note = Description of Artificial Sequence: Synthetic
                             polypeptide
source                     1..291
                           mol_type = protein
                           organism = synthetic construct
SEQUENCE: 62
DAGVIQSPRH EVTEMGQEVT LRCKPISGHN SLFWYRQTMM RGLELLIYFN NNVPIDDSGM    60
PEDRFSAKMP NASFSTLKIQ PSEPRDSAVY FCASSSGGAN TEAFFGQGTR LTVVEDLKNV   120
FPPEVAVFEP SEAEISHTQK ATLVCLATGF FPDHVELSWW VNGKEVHSGV STDPQPLKEQ   180
PALNDSRYCL SSRLRVSATF WQNPRNHFRC QVQFYGLSEN DEWTQDRAKP VTQIVSAEAW   240
GRADCGFTSV SYQQGVLSAT ILYEILLGKA TLYAVLVSAL VLMAMVKRKD F            291

SEQ ID NO: 63              moltype = AA   length = 293
FEATURE                    Location/Qualifiers
REGION                     1..293
                           note = Description of Artificial Sequence: Synthetic
                             polypeptide
source                     1..293
                           mol_type = protein
                           organism = synthetic construct
SEQUENCE: 63
DAGVIQSPRH EVTEMGQEVT LRCKPISGHN SLFWYRQTMM RGLELLIYFN NNVPIDDSGM    60
PEDRFSAKMP NASFSTLKIQ PSEPRDSAVY FCASSSGGAN TEAFFGQGTR LTVVEDLKNV   120
FPPEVAVFEP SEAEISHTQK ATLVCLATGF YPDHVELSWW VNGKEVHSGV STDPQPLKEQ   180
PALNDSRYCL SSRLRVSATF WQNPRNHFRC QVQFYGLSEN DEWTQDRAKP VTQIVSAEAW   240
GRADCGFTSE SYQQGVLSAT ILYEILLGKA TLYAVLVSAL VLMAMVKRKD SRG          293

SEQ ID NO: 64              moltype = AA   length = 255
FEATURE                    Location/Qualifiers
REGION                     1..255
                           note = Description of Artificial Sequence: Synthetic
                             polypeptide
source                     1..255
                           mol_type = protein
                           organism = synthetic construct
SEQUENCE: 64
AQSVTQLGSH VSVSEGALVL LRCNYSSSVP PYLFWYVQYP NQGLQLLLKY TSAATLVKGI    60
NGFEAEFKKS ETSFHLTKPS AHMSDAAEYF CAVSARYNFN KFYFGSGTKL NVKPYIQNPD   120
PAVYQLRDSK SSDKSVCLFT DFDSQTNVSQ SKDSDVYITD KTVLDMRSMD FKSNSAVAWS   180
NKSDFACANA FNNSIIPEDT FFPSPESSCD VKLVEKSFET DTNLNFQNLS VIGFRILLLK   240
VAGFNLLMTL RLWSS                                                   255

SEQ ID NO: 65              moltype = AA   length = 291
FEATURE                    Location/Qualifiers
REGION                     1..291
                           note = Description of Artificial Sequence: Synthetic
                             polypeptide
source                     1..291
                           mol_type = protein
                           organism = synthetic construct
SEQUENCE: 65
DSGVTQTPKH LITATGQRVT LRCSPRSGDL SVYWYQQSLD QGLQFLIHYY NGEERAKGNI    60
LERFSAQQFP DLHSELNLSS LELGDSALYF CASSASGGRS YEQYFGPGTR LTVTEDLKNV   120
FPPEVAVFEP SEAEISHTQK ATLVCLATGF FPDHVELSWW VNGKEVHSGV STDPQPLKEQ   180
PALNDSRYCL SSRLRVSATF WQNPRNHFRC QVQFYGLSEN DEWTQDRAKP VTQIVSAEAW   240
GRADCGFTSV SYQQGVLSAT ILYEILLGKA TLYAVLVSAL VLMAMVKRKD F            291
```

```
SEQ ID NO: 66              moltype = AA   length = 293
FEATURE                    Location/Qualifiers
REGION                     1..293
                           note = Description of Artificial Sequence: Synthetic
                            polypeptide
source                     1..293
                           mol_type = protein
                           organism = synthetic construct
SEQUENCE: 66
DSGVTQTPKH LITATGQRVT LRCSPRSGDL SVYWYQQSLD QGLQFLIHYY NGEERAKGNI   60
LERFSAQQFP DLHSELNLSS LELGDSALYF CASSASGGRS YEQYFGPGTR LTVTEDLKNV  120
FPPEVAVFEP SEAEISHTQK ATLVCLATGF YPDHVELSWW VNGKEVHSGV STDPQPLKEQ  180
PALNDSRYCL SSRLRVSATF WQNPRNHFRC QVQFYGLSEN DEWTQDRAKP VTQIVSAEAW  240
GRADCGFTSE SYQQGVLSAT ILYEILLGKA TLYAVLVSAL VLMAMVKRKD SRG         293

SEQ ID NO: 67              moltype = AA   length = 251
FEATURE                    Location/Qualifiers
REGION                     1..251
                           note = Description of Artificial Sequence: Synthetic
                            polypeptide
source                     1..251
                           mol_type = protein
                           organism = synthetic construct
SEQUENCE: 67
EDQVTQSPEA LRLQEGESSS LNCSYTVSGL RGLFWYRQDP GKGPEFLFTL YSAGEEKEKE   60
RLKATLTKKE SFLHITAPKP EDSATYLCAV RNTGFQKLVF GTGTRLLVSP YIQNPDPAVY  120
QLRDSKSSDK SVCLFTDFDS QTNVSQSKDS DVYITDKTVL DMRSMDFKSN SAVAWSNKSD  180
FACANAFNNS IIPEDTFFPS PESSCDVKLV EKSFETDTNL NFQNLSVIGF RILLLKVAGF  240
NLLMTLRLWS S                                                      251

SEQ ID NO: 68              moltype = AA   length = 292
FEATURE                    Location/Qualifiers
REGION                     1..292
                           note = Description of Artificial Sequence: Synthetic
                            polypeptide
source                     1..292
                           mol_type = protein
                           organism = synthetic construct
SEQUENCE: 68
DTGVSQNPRH KITKRGQNVT FRCDPISEHN RLYWYRQTLG QGPEFLTYFQ NEAQLEKSRL   60
LSDRFSAERP KGSFSTLEIQ RTEQGDSAMY LCASSWRTGR EETQYFGPGT RLLVLEDLNK  120
VFPPEVAVFE PSEAEISHTQ KATLVCLATG FFPDHVELSW WVNGKEVHSG VSTDPQPLKE  180
QPALNDSRYC LSSRLRVSAT FWQNPRNHFR CQVQFYGLSE NDEWTQDRAK PVTQIVSAEA  240
WGRADCGFTS VSYQQGVLSA TILYEILLGK ATLYAVLVSA LVLMAMVKRK DF          292

SEQ ID NO: 69              moltype = AA   length = 294
FEATURE                    Location/Qualifiers
REGION                     1..294
                           note = Description of Artificial Sequence: Synthetic
                            polypeptide
source                     1..294
                           mol_type = protein
                           organism = synthetic construct
SEQUENCE: 69
DTGVSQNPRH KITKRGQNVT FRCDPISEHN RLYWYRQTLG QGPEFLTYFQ NEAQLEKSRL   60
LSDRFSAERP KGSFSTLEIQ RTEQGDSAMY LCASSWRTGR EETQYFGPGT RLLVLEDLKN  120
VFPPEVAVFE PSEAEISHTQ KATLVCLATG FYPDHVELSW WVNGKEVHSG VSTDPQPLKE  180
QPALNDSRYC LSSRLRVSAT FWQNPRNHFR CQVQFYGLSE NDEWTQDRAK PVTQIVSAEA  240
WGRADCGFTS ESYQQGVLSA TILYEILLGK ATLYAVLVSA LVLMAMVKRK DSRG        294

SEQ ID NO: 70              moltype = AA   length = 254
FEATURE                    Location/Qualifiers
REGION                     1..254
                           note = Description of Artificial Sequence: Synthetic
                            polypeptide
source                     1..254
                           mol_type = protein
                           organism = synthetic construct
SEQUENCE: 70
KQEVTQIPAA LSVPEGENLV LNCSFTDSAI YNLQWFRQDP GKGLTSLLLI QSSQREQTSG   60
RLNASLDKSS GRSTLYIAAS QPGDSATYLC AVMLWNQGGK LIFGQGTELS VKPYIQNPDP  120
AVYQLRDSKS SDKSVCLFTD FDSQTNVSQS KDSDVYITDK TVLDMRSMDF KSNSAVAWSN  180
KSDFACANAF NNSIIPEDTF FPSPESSCDV KLVEKSFETD TNLNFQNLSV IGFRILLLKV  240
AGFNLLMTLR LWSS                                                   254

SEQ ID NO: 71              moltype = AA   length = 289
FEATURE                    Location/Qualifiers
REGION                     1..289
```

```
                            note = Description of Artificial Sequence: Synthetic
                                polypeptide
source                      1..289
                            mol_type = protein
                            organism = synthetic construct
SEQUENCE: 71
KAGVTQTPRY LIKTRGQQVT LSCSPISGHR SVSWYQQTPG QGLQFLFEYF SETQRNKGNF    60
PGRFSGRQFS NSRSEMNVST LELGDSALYL CASSLGRGYE QYFGPGTRLT VTEDLNKVFP   120
PEVAVFEPSE AEISHTQKAT LVCLATGFFP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSVSY QQGVLSATIL YEILLGKATL YAVLVSALVL MAMVKRKDF               289

SEQ ID NO: 72               moltype = AA  length = 291
FEATURE                     Location/Qualifiers
REGION                      1..291
                            note = Description of Artificial Sequence: Synthetic
                                polypeptide
source                      1..291
                            mol_type = protein
                            organism = synthetic construct
SEQUENCE: 72
KAGVTQTPRY LIKTRGQQVT LSCSPISGHR SVSWYQQTPG QGLQFLFEYF SETQRNKGNF    60
PGRFSGRQFS NSRSEMNVST LELGDSALYL CASSLGRGYE QYFGPGTRLT VTEDLKNVFP   120
PEVAVFEPSE AEISHTQKAT LVCLATGFYP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSESY QQGVLSATIL YEILLGKATL YAVLVSALVL MAMVKRKDSR G            291

SEQ ID NO: 73               moltype = AA  length = 91
FEATURE                     Location/Qualifiers
source                      1..91
                            mol_type = protein
                            organism = Homo sapiens
SEQUENCE: 73
TQLLEQSPQF LSIQEGENLT VYCNSSSVFS SLQWYRQEPG EGPVLLVTVV TGGEVKKLKR    60
LTFQFGDARK DSSLHITAAQ PGDTGLYLCA G                                   91

SEQ ID NO: 74               moltype = AA  length = 93
FEATURE                     Location/Qualifiers
source                      1..93
                            mol_type = protein
                            organism = Homo sapiens
SEQUENCE: 74
EAQVTQNPRY LITVTGKKLT VTCSQNMNHE YMSWYRQDPG LGLRQIYYSM NVEVTDKGDV    60
PEGYKVSRKE KRNFPLILES PSPNQTSLYF CAS                                 93

SEQ ID NO: 75               moltype = AA  length = 92
FEATURE                     Location/Qualifiers
source                      1..92
                            mol_type = protein
                            organism = Homo sapiens
SEQUENCE: 75
KNQVEQSPQS LIILEGKNCT LQCNYTVSPF SNLRWYKQDT GRGPVSLTIM TFSENTKSNG    60
RYTATLDADT KQSSLHITAS QLSDSASYIC VV                                  92

SEQ ID NO: 76               moltype = AA  length = 95
FEATURE                     Location/Qualifiers
source                      1..95
                            mol_type = protein
                            organism = Homo sapiens
SEQUENCE: 76
DAGVIQSPRH EVTEMGQEVT LRCKPISGHN SLFWYRQTMM RGLELLIYFN NNVPIDDSGM    60
PEDRFSAKMP NASFSTLKIQ PSEPRDSAVY FCASS                               95

SEQ ID NO: 77               moltype = AA  length = 94
FEATURE                     Location/Qualifiers
source                      1..94
                            mol_type = protein
                            organism = Homo sapiens
SEQUENCE: 77
AQSVTQLGSH VSVSEGALVL LRCNYSSSVP PYLFWYVQYP NQGLQLLLKY TSAATLVKGI    60
NGFEAEFKKS ETSFHLTKPS AHMSDAAEYF CAVS                                94

SEQ ID NO: 78               moltype = AA  length = 94
FEATURE                     Location/Qualifiers
source                      1..94
                            mol_type = protein
                            organism = Homo sapiens
SEQUENCE: 78
DSGVTQTPKH LITATGQRVT LRCSPRSGDL SVYWYQQSLD QGLQFLIHYY NGEERAKGNI    60
```

```
LERFSAQQFP DLHSELNLSS LELGDSALYF CASS                             94

SEQ ID NO: 79            moltype = AA   length = 90
FEATURE                  Location/Qualifiers
source                   1..90
                         mol_type = protein
                         organism = Homo sapiens
SEQUENCE: 79
EDQVTQSPEA LRLQEGESSS LNCSYTVSGL RGLFWYRQDP GKGPEFLFTL YSAGEEKEKE    60
RLKATLTKKE SFLHITAPKP EDSATYLCAV                                    90

SEQ ID NO: 80            moltype = AA   length = 95
FEATURE                  Location/Qualifiers
source                   1..95
                         mol_type = protein
                         organism = Homo sapiens
SEQUENCE: 80
DTGVSQNPRH KITKRGQNVT FRCDPISEHN RLYWYRQTLG QGPEFLTYFQ NEAQLEKSRL    60
LSDRFSAERP KGSFSTLEIQ RTEQGDSAMY LCASS                              95

SEQ ID NO: 81            moltype = AA   length = 92
FEATURE                  Location/Qualifiers
source                   1..92
                         mol_type = protein
                         organism = Homo sapiens
SEQUENCE: 81
KQEVTQIPAA LSVPEGENLV LNCSFTDSAI YNLQWFRQDP GKGLTSLLLI QSSQREQTSG    60
RLNASLDKSS GRSTLYIAAS QPGDSATYLC AV                                 92

SEQ ID NO: 82            moltype = AA   length = 95
FEATURE                  Location/Qualifiers
source                   1..95
                         mol_type = protein
                         organism = Homo sapiens
SEQUENCE: 82
KAGVTQTPRY LIKTRGQQVT LSCSPISGHR SVSWYQQTPG QGLQFLFEYF SETQRNKGNF    60
PGRFSGRQFS NSRSEMNVST LELGDSALYL CASSL                              95

SEQ ID NO: 83            moltype = AA   length = 604
FEATURE                  Location/Qualifiers
REGION                   1..604
                         note = Description of Artificial Sequence: Synthetic
                          polypeptide
source                   1..604
                         mol_type = protein
                         organism = synthetic construct
SEQUENCE: 83
MGPQLLGYVV LCLLGAGPLE AQVTQNPRYL ITVTGKKLTV TCSQNMNHEY MSWYRQDPGL    60
GLRQIYYSMN VEVTDKGDVP EGYKVSRKEK RNFPLILESP SPNQTSLYFC ASRLTGRVHG   120
YTFGSGTRLT VVEDLNKVFP PEVAVFEPSE AEISHTQKAT LVCLATGFFP DHVELSWWVN   180
GKEVHSGVST DPQPLKEQPA LNDSRYCLSS RLRVSATFWQ NPRNHFRCQV QFYGLSENDE   240
WTQDRAKPVT QIVSAEAWGR ADCGFTSVSY QQGVLSATIL YEILLGKATL YAVLVSALVL   300
MAMVKRKDFG SGATNFSLLK QAGDVEENPG PMVLKFSVSI LWIQLAWVST QLLEQSPQFL   360
SIQEGENLTV YCNSSSVFSS LQWYRQEPGE GPVLLVTVVT GGEVKKLKRL TFQFGDARKD   420
SSLHITAAQP GDTGLYLCAG YGGGSNYKLT FGKGTLLTVN PYIQNPDPAV YQLRDSKSSD   480
KSVCLFTDFD SQTNVSQSKD SDVYITDKTV LDMRSMDFKS NSAVAWSNKS DFACANAFNN   540
SIIPEDTFFP SPESSCDVKL VEKSFETDTN LNFQNLSVIG FRILLLKVAG FNLLMTLRLW   600
SSGS                                                               604

SEQ ID NO: 84            moltype = AA   length = 9
FEATURE                  Location/Qualifiers
source                   1..9
                         mol_type = protein
                         note = Influenza A virus
                         organism = unidentified
SEQUENCE: 84
QPEWFRNVL                                                            9

SEQ ID NO: 85            moltype = AA   length = 10
FEATURE                  Location/Qualifiers
source                   1..10
                         mol_type = protein
                         note = Human cytomegalovirus
                         organism = unidentified
SEQUENCE: 85
TPRVTGGGAM                                                          10

SEQ ID NO: 86            moltype = AA   length = 112
FEATURE                  Location/Qualifiers
```

```
REGION                          1..112
                                note = Description of Artificial Sequence: Synthetic
                                 polypeptide
source                          1..112
                                mol_type = protein
                                organism = synthetic construct
SEQUENCE: 86
TQLLEQSPQF LSIQEGENLT VYCNSSSVFS SLQWYRQEPG EGPVLLVTVV TGGEVKKLKR   60
LTFQFGDARK DSSLHITAAQ PGDTGLYLCA GYGGGSNYKL TFGKGTLLTV NP          112

SEQ ID NO: 87                   moltype = AA  length = 113
FEATURE                         Location/Qualifiers
REGION                          1..113
                                note = Description of Artificial Sequence: Synthetic
                                 polypeptide
source                          1..113
                                mol_type = protein
                                organism = synthetic construct
SEQUENCE: 87
EAQVTQNPRY LITVTGKKLT VTCSQNMNHE YMSWYRQDPG LGLRQIYYSM NVEVTDKGDV   60
PEGYKVSRKE KRNFPLILES PSPNQTSLYF CASRLTGRVH GYTFGSGTRL TVV         113

SEQ ID NO: 88                   moltype = AA  length = 113
FEATURE                         Location/Qualifiers
REGION                          1..113
                                note = Description of Artificial Sequence: Synthetic
                                 polypeptide
source                          1..113
                                mol_type = protein
                                organism = synthetic construct
SEQUENCE: 88
KNQVEQSPQS LIILEGKNCT LQCNYTVSPF SNLRWYKQDT GRGPVSLTIM TFSENTKSNG   60
RYTATLDADT KQSSLHITAS QLSDSASYIC VVRGGAAGNK LTFGGGTRVL VKP         113

SEQ ID NO: 89                   moltype = AA  length = 114
FEATURE                         Location/Qualifiers
REGION                          1..114
                                note = Description of Artificial Sequence: Synthetic
                                 polypeptide
source                          1..114
                                mol_type = protein
                                organism = synthetic construct
SEQUENCE: 89
DAGVIQSPRH EVTEMGQEVT LRCKPISGHN SLFWYRQTMM RGLELLIYFN NNVPIDDSGM   60
PEDRFSAKMP NASFSTLKIQ PSEPRDSAVY FCASSSGGAN TEAFFGQGTR LTVV        114

SEQ ID NO: 90                   moltype = DNA  length = 1821
FEATURE                         Location/Qualifiers
misc_feature                    1..1821
                                note = Description of Artificial Sequence: Synthetic
                                 polynucleotide
source                          1..1821
                                mol_type = other DNA
                                organism = synthetic construct
SEQUENCE: 90
gccaccatgg gacctcagct gctgggatac gttgtgctgt gtctgcttgg agccggacct     60
ctggaagccc aagtgacaca gaaccccaga tacctgatca ccgtgaccgg caagaaactg    120
accgtgacct gcagccagaa catgaaccac gagtacatga ctggtacag acaggaccct    180
ggcctgggcc tgagacagat ctactacagc atgaacgtgg aagtgaccga caagggcgac    240
gtgcccgagg gctacaaggt gtccagaaaa gagaagcgga acttccact gatcctggaa    300
agcccatctc ctaaccagac cagcctgtac ttctgcgcca gcagactgac aggcagagtg    360
cacggctaca catttggcag cggcaccaga ctgactgtgg tggaagatct gaacaaggtg    420
ttccctccag aggtggccgt gttcgagcct tctgaggccg agatcagcca cacacagaaa    480
gccacactcg tgtgcctggc caccggcttt tttcccgatc acgtggaact gtcttggtgg    540
gtcaacggca aagaggtgca cagcggcgtc agcacagatc ccagcctct gaaagaacag    600
cccgctctga cgacagccg gtactgcctg tcctccagac tgagtgtc cgccaccttc      660
tggcagaacc ctcggaacca cttcagatgc caggtgcagt tctacggcct gagcgagaac    720
gatgagtgga cccaggatag agccaagcct gtgactcaga tcgtgtctgc cgaagctgg    780
ggcagagccg attgtggctt taccagcgtg tcctatcga agggcgtgct gtctgccaca    840
atcctgtatg agatcctgct gggcaaagcc actctgtacg ccgtgctggt ttctgccctg    900
gtgctgatgg ccatggtcaa gagaaaggac tttggctccg cgccaccaa cttcagcctg    960
ctgaaacagg ctggcgacgt ggaagagaac cccggaccta tggtgctgaa gttctccgtg   1020
tccatcctgt ggattcagct ggcttgggtg tccacacagc tgctcgaaca gagccctcag   1080
ttcctgagca tccaagaggg cgagaacctg acagtgtact gcaacagcag cagcgtgttc   1140
agcagcctgc agtggtacag gcaagagcct ggcgaaggac ctgtgctgct ggtcacagtt   1200
gtgacaggcg gcgaagtgaa gaagctgaag cggctgacct tccagttcgg cgacgccaga   1260
aaggatagca ccctgcacat taccgctgct cagccaggcg ataccggcct gtatctgtgt   1320
gctggatatg gcggcggaag caactacaag ctgacctttg gcaagggcac cctgctgaca   1380
gtgaaccccc acattcagaa ccccgatcca gccgtgtatc agctgagaga cagcaagagc   1440
```

```
agcgacaaga gcgtgtgtct gttcaccgac ttcgacagcc agaccaacgt gtcccagagc    1500
aaggacagcg acgtgtacat caccgacaag accgtgctgg acatgcggag catggacttc    1560
aagagcaaca gcgccgtggc ctggtccaac aagagcgatt tcgcctgcgc caacgccttc    1620
aacaacagca ttatccccga ggacacattc ttcccaagtc ctgagagcag ctgcgacgtg    1680
aagctggtgg aaaagagctt cgagacagac accaacctga acttccagaa cctgagcgtg    1740
atcggcttca gaatcctgct gctgaaggtg gccggcttca tctgctgat gaccctgaga    1800
ctgtggtcca gcggatcctg a                                              1821

SEQ ID NO: 91           moltype = AA  length = 609
FEATURE                 Location/Qualifiers
REGION                  1..609
                        note = Description of Artificial Sequence: Synthetic
                         polypeptide
source                  1..609
                        mol_type = protein
                        organism = synthetic construct
SEQUENCE: 91
MDSWTFCCVS LCILVAKHTD AGVIQSPRHE VTEMGQEVTL RCKPISGHNS LFWYRQTMMR     60
GLELLIYFNN NVPIDDSGMP EDRFSAKMPN ASFSTLKIQP SEPRDSAVYF CASSSGGANT    120
EAFFGQGTRL TVVEDLNKVF PPEVAVFEPS EAEISHTQKA TLVCLATGFF PDHVELSWWV    180
NGKEVHSGVS TDPQPLKEQP ALNDSRYCLS SRLRVSATFW QNPRNHFRCQ VQFYGLSEND    240
EWTQDRAKPV TQIVSAEAWG RADCGFTSVS YQQGVLSATI LYEILLGKAT LYAVLVSALV    300
LMAMVKRKDF GSGATNFSLL KQAGDVEENP GPMKKHLTTF LVILWLYFYR GNGKNQVEQS    360
PQSLIILEGK NCTLQCNYTV SPFSNLRWYK QDTGRGPVSL TIMTFSENTK SNGRYTATLD    420
ADTKQSSLHI TASQLSDSAS YICVVRGGAA GNKLTFGGGT RVLVKPYIQN PDPAVYQLRD    480
SKSSDKSVCL FTDFDSQTNV SQSKDSDVYI TDKTVLDMRS MDFKSNSAVA WSNKSDFACA    540
NAFNNSIIPE DTFFPSPESS CDVKLVEKSF ETDTNLNFQN LSVIGFRILL LKVAGFNLLM    600
TLRLWSSGS                                                            609

SEQ ID NO: 92           moltype = AA  length = 605
FEATURE                 Location/Qualifiers
REGION                  1..605
                        note = Description of Artificial Sequence: Synthetic
                         polypeptide
source                  1..605
                        mol_type = protein
                        organism = synthetic construct
SEQUENCE: 92
MGSRLLCWVL LCLLGAGPVK AGVTQTPRYL IKTRGQQVTL SCSPISGHRS VSWYQQTPGQ     60
GLQFLFEYFS ETQRNKGNFP GRFSGRQFSN SRSEMNVSTL ELGDSALYLC ASSLGRGYEQ    120
YFGPGTRLTV TEDLNKVFPP EVAVFEPSEA EISHTQKATL VCLATGFFPD HVELSWWVNG    180
KEVHSGVSTD PQPLKEQPAL NDSRYCLSSR LRVSATFWQN PRNHFRCQVQ FYGLSENDEW    240
TQDRAKPVTQ IVSAEAWGRA DCGFTSVSYQ QGVLSATILY EILLGKATLY AVLVSALVLM    300
AMVKRKDFGS GATNFSLLKQ AGDVEENPGP METLLGLLIL WLQLQWVSSK QEVTQIPAAL    360
SVPEGENLVL NCSFTDSAIY NLQWFRQDPG KGLTSLLLIQ SSQREQTSGR LNASLDKSSG    420
RSTLYIAASQ PGDSATYLCA VMLWNQGGKL IFGQGTELSV KPYIQNPDPA VYQLRDSKSS    480
DKSVCLFTDF DSQTNVSQSK DSDVYITDKT VLDMRSMDFK SNSAVAWSNK SDFACANAFN    540
NSIIPEDTFF PSPESSCDVK LVEKSFETDT NLNFQNLSVI GFRILLLKVA GFNLLMTLRL    600
WSSGS                                                                605

SEQ ID NO: 93           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 93
GSGATNFSLL KQAGDVEENP G                                              21

SEQ ID NO: 94           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 94
GVQVETISPG DGRTFPKRGQ TCVVHYTGML EDGKKVDSSR DRNKPFKFML GKQEVIRGWE     60
EGVAQMSVGQ RAKLTISPDY AYGATGHPGI IPPHATLVFD VELLKLE                  107

SEQ ID NO: 95           moltype = AA  length = 282
FEATURE                 Location/Qualifiers
source                  1..282
                        mol_type = protein
                        organism = Homo sapiens
SEQUENCE: 95
GFGDVGALES LRGNADLAYI LSMEPCGHCL IINNVNFCRE SGLRTRTGSN IDCEKLRRRF     60
```

```
SSLHFMVEVK GDLTAKKMVL ALLELAQQDH GALDCCVVVI LSHGCQASHL QFPGAVYGTD    120
GCPVSVEKIV NIFNGTSCPS LGGKPKLFFI QACGGEQKDH GFEVASTSPE DESPGSNPEP    180
DATPFQEGLR TFDQLDAISS LPTPSDIFVS YSTFPGFVSW RDPKSGSWYV ETLDDIFEQW    240
AHSEDLQSLL LRVANAVSVK GIYKQMPGCF NFLRKKLFFK TS                       282

SEQ ID NO: 96             moltype =    length =
SEQUENCE: 96
000

SEQ ID NO: 97             moltype = AA   length = 4
FEATURE                   Location/Qualifiers
REGION                    1..4
                          note = Description of Artificial Sequence: Synthetic peptide
source                    1..4
                          mol_type = protein
                          organism = synthetic construct
SEQUENCE: 97
RAKR                                                                  4

SEQ ID NO: 98             moltype =    length =
SEQUENCE: 98
000

SEQ ID NO: 99             moltype = AA   length = 8
FEATURE                   Location/Qualifiers
REGION                    1..8
                          note = Description of Artificial Sequence: Synthetic peptide
MOD_RES                   1
                          note = Asp or Gly
MOD_RES                   2
                          note = Val or Ile
MOD_RES                   4
                          note = Any amino acid
source                    1..8
                          mol_type = protein
                          organism = synthetic construct
SEQUENCE: 99
XXEXNPGP                                                              8

SEQ ID NO: 100            moltype = AA   length = 19
FEATURE                   Location/Qualifiers
source                    1..19
                          mol_type = protein
                          note = Porcine teschovirus 1
                          organism = unidentified
SEQUENCE: 100
ATNFSLLKQA GDVEENPGP                                                 19

SEQ ID NO: 101            moltype = AA   length = 18
FEATURE                   Location/Qualifiers
source                    1..18
                          mol_type = protein
                          organism = Thosea asigna virus
SEQUENCE: 101
EGRGSLLTCG DVEENPGP                                                  18

SEQ ID NO: 102            moltype = AA   length = 20
FEATURE                   Location/Qualifiers
source                    1..20
                          mol_type = protein
                          organism = Equine rhinitis A virus
SEQUENCE: 102
QCTNYALLKL AGDVESNPGP                                                20

SEQ ID NO: 103            moltype = AA   length = 22
FEATURE                   Location/Qualifiers
source                    1..22
                          mol_type = protein
                          organism = Foot-and-mouth disease virus
SEQUENCE: 103
VKQTLNFDLL KLAGDVESNP GP                                             22

SEQ ID NO: 104            moltype = AA   length = 22
FEATURE                   Location/Qualifiers
source                    1..22
                          mol_type = protein
                          note = Cytoplasmic polyhedrosis virus
                          organism = unidentified
SEQUENCE: 104
```

```
DVFRSNYDLL KLCGDIESNP GP                                               22

SEQ ID NO: 105          moltype = AA  length = 22
FEATURE                 Location/Qualifiers
source                  1..22
                        mol_type = protein
                        organism = Infectious flacherie virus
SEQUENCE: 105
TLTRAKIEDE LIRAGIESNP GP                                               22

SEQ ID NO: 106          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 106
AQSVTQLGSH VSVSEGALVL LRCNYSSSVP PYLFWYVQYP NQGLQLLLKY TSAATLVKGI       60
NGFEAEFKKS ETSFHLTKPS AHMSDAAEYF CAVSARYNFN KFYFGSGTKL NVKP            114

SEQ ID NO: 107          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 107
DSGVTQTPKH LITATGQRVT LRCSPRSGDL SVYWYQQSLD QGLQFLIHYY NGEERAKGNI       60
LERFSAQQFP DLHSELNLSS LELGDSALYF CASSASGGRS YEQYFGPGTR LTVT            114

SEQ ID NO: 108          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 108
DTGVSQNPRH KITKRGQNVT FRCDPISEHN RLYWYRQTLG QGPEFLTYFQ NEAQLEKSRL       60
LSDRFSAERP KGSFSTLEIQ RTEQGDSAMY LCASSWRTGR EETQYFGPGT RLLVL           115

SEQ ID NO: 109          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 109
YTSAATLV                                                                8

SEQ ID NO: 110          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 110
CPRSPSHSM                                                               9

SEQ ID NO: 111          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 111
DPRSPSHSM                                                               9
```

```
SEQ ID NO: 112            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 112
FPRSPSHSM                                                                          9

SEQ ID NO: 113            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 113
GPRSPSHSM                                                                          9

SEQ ID NO: 114            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 114
HPRSPSHSM                                                                          9

SEQ ID NO: 115            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 115
IPRSPSHSM                                                                          9

SEQ ID NO: 116            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 116
KPRSPSHSM                                                                          9

SEQ ID NO: 117            moltype = AA  length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 117
LPRSPSHSM                                                                          9

SEQ ID NO: 118            moltype = AA  length = 9
FEATURE                   Location/Qualifiers
REGION                    1..9
                          note = Description of Artificial Sequence: Synthetic peptide
MOD_RES                   4
                          note = Phosphoserine
```

```
source                  1..9
                        mol_type = protein
                        organism = synthetic construct
SEQUENCE: 118
MPRSPSHSM                                                                       9

SEQ ID NO: 119          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 119
NPRSPSHSM                                                                       9

SEQ ID NO: 120          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 120
PPRSPSHSM                                                                       9

SEQ ID NO: 121          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 121
QPRSPSHSM                                                                       9

SEQ ID NO: 122          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 122
RPRSPSHSM                                                                       9

SEQ ID NO: 123          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 123
SPRSPSHSM                                                                       9

SEQ ID NO: 124          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 124
TPRSPSHSM                                                                       9

SEQ ID NO: 125          moltype = AA  length = 9
```

```
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 125
VPRSPSHSM                                                                        9

SEQ ID NO: 126       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 126
WPRSPSHSM                                                                        9

SEQ ID NO: 127       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 127
YPRSPSHSM                                                                        9

SEQ ID NO: 128       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 128
EPCSPSHSM                                                                        9

SEQ ID NO: 129       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 129
EPDSPSHSM                                                                        9

SEQ ID NO: 130       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 130
EPESPSHSM                                                                        9

SEQ ID NO: 131       moltype = AA  length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
```

```
                        organism = synthetic construct
SEQUENCE: 131
EPFSPSHSM                                                                               9

SEQ ID NO: 132          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 132
EPGSPSHSM                                                                               9

SEQ ID NO: 133          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 133
EPHSPSHSM                                                                               9

SEQ ID NO: 134          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 134
EPISPSHSM                                                                               9

SEQ ID NO: 135          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 135
EPKSPSHSM                                                                               9

SEQ ID NO: 136          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 136
EPLSPSHSM                                                                               9

SEQ ID NO: 137          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 137
EPMSPSHSM                                                                               9

SEQ ID NO: 138          moltype = AA   length = 9
FEATURE                 Location/Qualifiers
REGION                  1..9
```

```
                        note = Description of Artificial Sequence: Synthetic peptide
MOD_RES                 4
                        note = Phosphoserine
source                  1..9
                        mol_type = protein
                        organism = synthetic construct
SEQUENCE: 138
EPNSPSHSM                                                                          9

SEQ ID NO: 139          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 139
EPPSPSHSM                                                                          9

SEQ ID NO: 140          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 140
EPQSPSHSM                                                                          9

SEQ ID NO: 141          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 141
EPSSPSHSM                                                                          9

SEQ ID NO: 142          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 142
EPTSPSHSM                                                                          9

SEQ ID NO: 143          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 143
EPVSPSHSM                                                                          9

SEQ ID NO: 144          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 144
```

```
EPWSPSHSM                                                                              9

SEQ ID NO: 145          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 145
EPYSPSHSM                                                                              9

SEQ ID NO: 146          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 146
EPRCPSHSM                                                                              9

SEQ ID NO: 147          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 147
EPRDPSHSM                                                                              9

SEQ ID NO: 148          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 148
EPREPSHSM                                                                              9

SEQ ID NO: 149          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 149
EPRFPSHSM                                                                              9

SEQ ID NO: 150          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 150
EPRGPSHSM                                                                              9

SEQ ID NO: 151          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 151
EPRHPSHSM                                                                              9

SEQ ID NO: 152          moltype = AA  length = 9
FEATURE                 Location/Qualifiers
REGION                  1..9
                        note = Description of Artificial Sequence: Synthetic peptide
source                  1..9
```

```
                        mol_type = protein
                        organism = synthetic construct
SEQUENCE: 152
EPRIPSHSM                                                                       9

SEQ ID NO: 153          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 153
EPRKPSHSM                                                                       9

SEQ ID NO: 154          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 154
EPRLPSHSM                                                                       9

SEQ ID NO: 155          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 155
EPRMPSHSM                                                                       9

SEQ ID NO: 156          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 156
EPRNPSHSM                                                                       9

SEQ ID NO: 157          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 157
EPRPPSHSM                                                                       9

SEQ ID NO: 158          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 158
EPRQPSHSM                                                                       9

SEQ ID NO: 159          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 159
EPRRPSHSM                                                                       9

SEQ ID NO: 160          moltype = AA  length = 9
FEATURE                 Location/Qualifiers
REGION                  1..9
                        note = Description of Artificial Sequence: Synthetic peptide
```

```
source              1..9
                    mol_type = protein
                    organism = synthetic construct
SEQUENCE: 160
EPRTPSHSM                                                                         9

SEQ ID NO: 161      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 161
EPRVPSHSM                                                                         9

SEQ ID NO: 162      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 162
EPRWPSHSM                                                                         9

SEQ ID NO: 163      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 163
EPRYPSHSM                                                                         9

SEQ ID NO: 164      moltype = AA  length = 9
FEATURE             Location/Qualifiers
REGION              1..9
                    note = Description of Artificial Sequence: Synthetic peptide
MOD_RES             4
                    note = Phosphoserine
source              1..9
                    mol_type = protein
                    organism = synthetic construct
SEQUENCE: 164
EPRSCSHSM                                                                         9

SEQ ID NO: 165      moltype = AA  length = 9
FEATURE             Location/Qualifiers
REGION              1..9
                    note = Description of Artificial Sequence: Synthetic peptide
MOD_RES             4
                    note = Phosphoserine
source              1..9
                    mol_type = protein
                    organism = synthetic construct
SEQUENCE: 165
EPRSDSHSM                                                                         9

SEQ ID NO: 166      moltype = AA  length = 9
FEATURE             Location/Qualifiers
REGION              1..9
                    note = Description of Artificial Sequence: Synthetic peptide
MOD_RES             4
                    note = Phosphoserine
source              1..9
                    mol_type = protein
                    organism = synthetic construct
SEQUENCE: 166
EPRSESHSM                                                                         9

SEQ ID NO: 167      moltype = AA  length = 9
FEATURE             Location/Qualifiers
REGION              1..9
                    note = Description of Artificial Sequence: Synthetic peptide
MOD_RES             4
                    note = Phosphoserine
source              1..9
```

```
SEQUENCE: 167
EPRSFSHSM                                                                    9

SEQ ID NO: 168          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 168
EPRSGSHSM                                                                    9

SEQ ID NO: 169          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 169
EPRSHSHSM                                                                    9

SEQ ID NO: 170          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 170
EPRSISHSM                                                                    9

SEQ ID NO: 171          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 171
EPRSKSHSM                                                                    9

SEQ ID NO: 172          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 172
EPRSLSHSM                                                                    9

SEQ ID NO: 173          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 173
EPRSMSHSM                                                                    9

SEQ ID NO: 174          moltype = AA   length = 9
FEATURE                 Location/Qualifiers
```

|   |   |   |
|---|---|---|
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 174 | | |
| EPRSNSHSM | | 9 |
| | | |
| SEQ ID NO: 175 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 175 | | |
| EPRSQSHSM | | 9 |
| | | |
| SEQ ID NO: 176 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 176 | | |
| EPRSRSHSM | | 9 |
| | | |
| SEQ ID NO: 177 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 177 | | |
| EPRSSSHSM | | 9 |
| | | |
| SEQ ID NO: 178 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 178 | | |
| EPRSTSHSM | | 9 |
| | | |
| SEQ ID NO: 179 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |
| SEQUENCE: 179 | | |
| EPRSVSHSM | | 9 |
| | | |
| SEQ ID NO: 180 | moltype = AA   length = 9 | |
| FEATURE | Location/Qualifiers | |
| REGION | 1..9 | |
|  | note = Description of Artificial Sequence: Synthetic peptide | |
| MOD_RES | 4 | |
|  | note = Phosphoserine | |
| source | 1..9 | |
|  | mol_type = protein | |
|  | organism = synthetic construct | |

```
SEQUENCE: 180
EPRSWSHSM                                                                                 9

SEQ ID NO: 181          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 181
EPRSYSHSM                                                                                 9

SEQ ID NO: 182          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 182
EPRSPCHSM                                                                                 9

SEQ ID NO: 183          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 183
EPRSPDHSM                                                                                 9

SEQ ID NO: 184          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 184
EPRSPEHSM                                                                                 9

SEQ ID NO: 185          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 185
EPRSPFHSM                                                                                 9

SEQ ID NO: 186          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 186
EPRSPGHSM                                                                                 9

SEQ ID NO: 187          moltype = AA  length = 9
FEATURE                 Location/Qualifiers
REGION                  1..9
                        note = Description of Artificial Sequence: Synthetic peptide
```

```
MOD_RES              4
                     note = Phosphoserine
source               1..9
                     mol_type = protein
                     organism = synthetic construct
SEQUENCE: 187
EPRSPHHSM                                                                        9

SEQ ID NO: 188       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 188
EPRSPIHSM                                                                        9

SEQ ID NO: 189       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 189
EPRSPKHSM                                                                        9

SEQ ID NO: 190       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 190
EPRSPLHSM                                                                        9

SEQ ID NO: 191       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 191
EPRSPMHSM                                                                        9

SEQ ID NO: 192       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 192
EPRSPNHSM                                                                        9

SEQ ID NO: 193       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 193
EPRSPPHSM                                                                        9
```

```
SEQ ID NO: 194          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 194
EPRSPQHSM                                                                    9

SEQ ID NO: 195          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 195
EPRSPRHSM                                                                    9

SEQ ID NO: 196          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 196
EPRSPTHSM                                                                    9

SEQ ID NO: 197          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 197
EPRSPVHSM                                                                    9

SEQ ID NO: 198          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 198
EPRSPWHSM                                                                    9

SEQ ID NO: 199          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 199
EPRSPYHSM                                                                    9

SEQ ID NO: 200          moltype = AA   length = 9
FEATURE                 Location/Qualifiers
REGION                  1..9
                        note = Description of Artificial Sequence: Synthetic peptide
MOD_RES                 4
                        note = Phosphoserine
```

```
source                  1..9
                        mol_type = protein
                        organism = synthetic construct
SEQUENCE: 200
EPRSPSCSM                                                                          9

SEQ ID NO: 201          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 201
EPRSPSDSM                                                                          9

SEQ ID NO: 202          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 202
EPRSPSESM                                                                          9

SEQ ID NO: 203          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 203
EPRSPSFSM                                                                          9

SEQ ID NO: 204          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 204
EPRSPSGSM                                                                          9

SEQ ID NO: 205          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 205
EPRSPSISM                                                                          9

SEQ ID NO: 206          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 206
EPRSPSKSM                                                                          9

SEQ ID NO: 207          moltype = AA  length = 9
```

```
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 207
EPRSPSLSM                                                                        9

SEQ ID NO: 208       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 208
EPRSPSMSM                                                                        9

SEQ ID NO: 209       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 209
EPRSPSNSM                                                                        9

SEQ ID NO: 210       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 210
EPRSPSPSM                                                                        9

SEQ ID NO: 211       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 211
EPRSPSQSM                                                                        9

SEQ ID NO: 212       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
                     organism = synthetic construct
SEQUENCE: 212
EPRSPSRSM                                                                        9

SEQ ID NO: 213       moltype = AA   length = 9
FEATURE              Location/Qualifiers
REGION               1..9
                     note = Description of Artificial Sequence: Synthetic peptide
MOD_RES              4
                     note = Phosphoserine
source               1..9
                     mol_type = protein
```

```
                        organism = synthetic construct
SEQUENCE: 213
EPRSPSSSM                                                                       9

SEQ ID NO: 214          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 214
EPRSPSTSM                                                                       9

SEQ ID NO: 215          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 215
EPRSPSVSM                                                                       9

SEQ ID NO: 216          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 216
EPRSPSWSM                                                                       9

SEQ ID NO: 217          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 217
EPRSPSYSM                                                                       9

SEQ ID NO: 218          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 218
EPRSPSHCM                                                                       9

SEQ ID NO: 219          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 219
EPRSPSHDM                                                                       9

SEQ ID NO: 220          moltype = AA   length = 9
FEATURE                 Location/Qualifiers
REGION                  1..9
```

```
                        note = Description of Artificial Sequence: Synthetic peptide
MOD_RES                 4
                        note = Phosphoserine
source                  1..9
                        mol_type = protein
                        organism = synthetic construct
SEQUENCE: 220
EPRSPSHEM                                                                           9

SEQ ID NO: 221          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 221
EPRSPSHFM                                                                           9

SEQ ID NO: 222          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 222
EPRSPSHGM                                                                           9

SEQ ID NO: 223          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 223
EPRSPSHHM                                                                           9

SEQ ID NO: 224          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 224
EPRSPSHIM                                                                           9

SEQ ID NO: 225          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 225
EPRSPSHKM                                                                           9

SEQ ID NO: 226          moltype = AA  length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 226
```

```
EPRSPSHLM                                                                                 9

SEQ ID NO: 227            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 227
EPRSPSHMM                                                                                 9

SEQ ID NO: 228            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 228
EPRSPSHNM                                                                                 9

SEQ ID NO: 229            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 229
EPRSPSHPM                                                                                 9

SEQ ID NO: 230            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 230
EPRSPSHQM                                                                                 9

SEQ ID NO: 231            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 231
EPRSPSHRM                                                                                 9

SEQ ID NO: 232            moltype = AA   length = 9
FEATURE                   Location/Qualifiers
REGION                    1..9
                          note = Description of Artificial Sequence: Synthetic peptide
MOD_RES                   4
                          note = Phosphoserine
source                    1..9
                          mol_type = protein
                          organism = synthetic construct
SEQUENCE: 232
EPRSPSHTM                                                                                 9

SEQ ID NO: 233            moltype = AA   length = 9
FEATURE                   Location/Qualifiers
REGION                    1..9
                          note = Description of Artificial Sequence: Synthetic peptide
MOD_RES                   4
```

```
                        note = Phosphoserine
source                  1..9
                        mol_type = protein
                        organism = synthetic construct
SEQUENCE: 233
EPRSPSHVM                                                                9

SEQ ID NO: 234          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 234
EPRSPSHWM                                                                9

SEQ ID NO: 235          moltype = AA   length = 9
FEATURE                 Location/Qualifiers
REGION                  1..9
                        note = Description of Artificial Sequence: Synthetic peptide
MOD_RES                 4
                        note = Phosphoserine
source                  1..9
                        mol_type = protein
                        organism = synthetic construct
SEQUENCE: 235
EPRSPSHYM                                                                9

SEQ ID NO: 236          moltype = AA   length = 255
FEATURE                 Location/Qualifiers
REGION                  1..255
                        note = Description of Artificial Sequence: Synthetic
                         polypeptide
source                  1..255
                        mol_type = protein
                        organism = synthetic construct
SEQUENCE: 236
TQLLEQSPQF LSIQEGENLT VYCNSSSVFS SLQWYRQEPG EGPVLLVTVV TGGEVKKLKR          60
LTFQFGDARK DSSLHITAAQ PGDTGLYLCA GYGGGSNYKL TFGKGTLLTV NPYIQNPDPA         120
VYQLRDSKSS DKSVCLFTDF DSQTNVSQSK DSDVYITDKT VLDMRSMDFK SNSAVAWSNK         180
SDFACANAFN NSIIPEDTFF PSPESSCDVK LVEKSFETDT NLNFQNLSVI GFRILLLKVA         240
GFNLLMTLRL WSSGS                                                         255

SEQ ID NO: 237          moltype = AA   length = 311
FEATURE                 Location/Qualifiers
REGION                  1..311
                        note = Description of Artificial Sequence: Synthetic
                         polypeptide
source                  1..311
                        mol_type = protein
                        organism = synthetic construct
SEQUENCE: 237
EAQVTQNPRY LITVTGKKLT VTCSQNMNHE YMSWYRQDPG LGLRQIYYSM NVEVTDKGDV          60
PEGYKVSRKE KRNFPLILES PSPNQTSLYF CASRLTGRVH GYTFGSGTRL TVVEDLNKVF         120
PPEVAVFEPS EAEISHTQKA TLVCLATGFF PDHVELSWWV NGKEVHSGVS TDPQPLKEQP         180
ALNDSRYCLS SRLRVSATFW QNPRNHFRCQ VQFYGLSEND EWTQDRAKPV TQIVSAEAWG         240
RADCGFTSVS YQQGVLSATI LYEILLGKAT LYAVLVSALV LMAMVKRKDF GSGATNFSLL         300
KQAGDVEENP G                                                             311

SEQ ID NO: 238          moltype = DNA   length = 1821
FEATURE                 Location/Qualifiers
misc_feature            1..1821
                        note = Description of Artificial Sequence: Synthetic
                         polynucleotide
source                  1..1821
                        mol_type = other DNA
                        organism = synthetic construct
SEQUENCE: 238
gccaccatgg gacctcagct gctgggatac gttgtgctgt gtctgcttgg agccggacct          60
ctggaagccc aagtgacaca gaaccccaga tacctgatca ccgtgaccgg caagaaactg        120
accgtgacct gcagccagaa catgaaccac gagtacatga gctggtacag acaggaccct        180
ggcctgggcc tgagacagat ctactacagc atgaacgtgg aagtgaccga caagggcgac        240
gtgcccgagg gctacaaggt gtccagaaaa gagaagcgga acttcccact gatcctggaa        300
agcccatctc ctaaccagac cagcctgtac ttctgcgcca gcagactgac aggcagagtg        360
cacggctaca catttggcag cggcaccaga ctgactgtgg tggaagatct gaacaaggtg        420
ttcccgccgg aagtggccgt gttcgagcct tctgaggcca gatcagcca cacacagaaa        480
```

```
gccacactcg tgtgcctggc caccggcttt tttcccgatc acgtggaact gtcttggtgg    540
gtcaacggca aagaggtgca cagcggcgtc agcacagatc cccagcctct gaaagaacag    600
cccgctctga acgacagccg gtactgcctg tcctcccgac tgagagtgtc cgccaccttc    660
tggcagaacc ctcggaacca cttcagatgc caggtgcagt tctacggcct gagcgagaac    720
gatgagtgga cccaggatag agccaagcct gtgactgaga tcgtgtctgc cgaagcctgc    780
ggcagagccg attgtggctt taccagcgtg tcctatcagc agggcgtgct gtctgccacc    840
atcctgtatg agatcctgct gggcaaagcc actctgtacg ccgtgctggt ttctgccctg    900
gtgctgatgg ccatggtcaa gagaaaggac tttggctccg cgccaccaa cttcagcctg    960
ctgaaacagg ctggcgacgt ggaagagaac cccggaccta tggtgctgaa gttctccgtg   1020
tccatcctgt ggattcagct ggcttgggtg tccacacagc tgctcgaaca gagccctcag   1080
ttcctgagca tccaagaggg cgagaacctg acagtgtact gcaacagcag cagcgtgttc   1140
agcagcctgc agtggtacag gcaagagcct ggcgaaggac ctgtgctgct ggtcacagtt   1200
gtgacaggcg gcgaagtgaa gaagctgaag cggctgacct ccagttcgg cgacgccaga   1260
aaggatagct ccctgcacat taccgctgct cagccaggcg ataccggcct gtatctgtgt   1320
gctggatatg gcggcggaag caactacaag ctgacctttg gcaagggcac cctgctgaca   1380
gtgaacccct acattcagaa ccccgatcca gccgtgtatc agctgagaga cagcaagagc   1440
agcgacaaga gcgtgtgtct gttcaccgac ttcgacagcc agaccaacgt gtcccagagc   1500
aaggacagca acgtgtacat caccgacaag accgtgctgg acatgcggag catggacttc   1560
aagagcaaca gcgccgtggc ctggtccaac aagagcgatt tcgcctgcgc caacgccttc   1620
aacaacagca ttatcccccga ggacacattc ttcccaagtc tgagagcag ctgcgacgtg   1680
aagctggtgg aaaagagctt cgagacagac accaacctga acttcagaa cctgagcgtg   1740
atcggcttca gaatcctgct gctgaaggtg gccggcttca atctgctgat gaccctgaga   1800
ctgtggtcca gcggatcctg a                                             1821

SEQ ID NO: 239         moltype = AA   length = 22
FEATURE                Location/Qualifiers
source                 1..22
                       mol_type = protein
                       note = Porcine teschovirus 1
                       organism = unidentified
SEQUENCE: 239
GSGATNFSLL KQAGDVEENP GP                                               22

SEQ ID NO: 240         moltype = AA   length = 21
FEATURE                Location/Qualifiers
source                 1..21
                       mol_type = protein
                       organism = Thosea asigna virus
SEQUENCE: 240
GSGEGRGSLL TCGDVEENPG P                                                21

SEQ ID NO: 241         moltype = AA   length = 23
FEATURE                Location/Qualifiers
source                 1..23
                       mol_type = protein
                       organism = Equine rhinitis A virus
SEQUENCE: 241
GSGQCTNYAL LKLAGDVESN PGP                                              23

SEQ ID NO: 242         moltype = AA   length = 25
FEATURE                Location/Qualifiers
source                 1..25
                       mol_type = protein
                       organism = Foot-and-mouth disease virus
SEQUENCE: 242
GSGVKQTLNF DLLKLAGDVE SNPGP                                            25

SEQ ID NO: 243         moltype = AA   length = 25
FEATURE                Location/Qualifiers
source                 1..25
                       mol_type = protein
                       note = Cytoplasmic polyhedrosis virus
                       organism = unidentified
SEQUENCE: 243
GSGDVFRSNY DLLKLCGDIE SNPGP                                            25

SEQ ID NO: 244         moltype = AA   length = 25
FEATURE                Location/Qualifiers
source                 1..25
                       mol_type = protein
                       organism = Infectious flacherie virus
SEQUENCE: 244
GSGTLTRAKI EDELIRAGIE SNPGP                                            25

SEQ ID NO: 245         moltype = AA   length = 37
FEATURE                Location/Qualifiers
REGION                 1..37
                       note = Description of Artificial Sequence: Synthetic
                       polypeptide
```

```
source                   1..37
                         mol_type = protein
                         organism = synthetic construct
SEQUENCE: 245
ATNFSLLKQA GDVEENPGPE GRGSLLTCGD VEENPGP                          37

SEQ ID NO: 246           moltype = AA  length = 40
FEATURE                  Location/Qualifiers
REGION                   1..40
                         note = Description of Artificial Sequence: Synthetic
                          polypeptide
source                   1..40
                         mol_type = protein
                         organism = synthetic construct
SEQUENCE: 246
GSGATNFSLL KQAGDVEENP GPEGRGSLLT CGDVEENPGP                       40

SEQ ID NO: 247           moltype = AA  length = 137
FEATURE                  Location/Qualifiers
source                   1..137
                         mol_type = protein
                         organism = Mus musculus
SEQUENCE: 247
YIQNPEPAVY QLKDPRSQDS TLCLFTDFDS QINVPKTMES GTFITDKTVL DMKAMDSKSN  60
GAIAWSNQTS FTCQDIFKET NATYPSSDVP CDATLTEKSF ETDMNLNFQN LSVMGLRILL  120
LKVAGFNLLM TLRLWSS                                                137

SEQ ID NO: 248           moltype = AA  length = 173
FEATURE                  Location/Qualifiers
source                   1..173
                         mol_type = protein
                         organism = Mus musculus
SEQUENCE: 248
EDLRNVTPPK VSLFEPSKAE IANKQKATLV CLARGFFPDH VELSWWVNGK EVHSGVSTDP  60
QAYKESNYSY CLSSRLRVSA TFWHNPRNHF RCQVQFHGLS EEDKWPEGSP KPVTQNISAE  120
AWGRADCGIT SASYHQGVLS ATILYEILLG KATLYAVLVS GLVLMAMVKK KNS         173

SEQ ID NO: 249           moltype = AA  length = 249
FEATURE                  Location/Qualifiers
REGION                   1..249
                         note = Description of Artificial Sequence: Synthetic
                          polypeptide
source                   1..249
                         mol_type = protein
                         organism = synthetic construct
SEQUENCE: 249
TQLLEQSPQF LSIQEGENLT VYCNSSSVFS SLQWYRQEPG EGPVLLVTVV TGGEVKKLKR  60
LTFQFGDARK DSSLHITAAQ PGDTGLYLCA GYGGGSNYKL TFGAGTRLTV KPYIQNPEPA  120
VYQLKDPRSQ DSTLCLFTDF DSQINVPKTM ESGTFITDKT VLDMKAMDSK SNGAIAWSNQ  180
TSFTCQDIFK ETNATYPSSD VPCDATLTEK SFETDMNLNF QNLSVMGLRI LLLKVAGFNL  240
LMTLRLWSS                                                         249

SEQ ID NO: 250           moltype = AA  length = 286
FEATURE                  Location/Qualifiers
REGION                   1..286
                         note = Description of Artificial Sequence: Synthetic
                          polypeptide
source                   1..286
                         mol_type = protein
                         organism = synthetic construct
SEQUENCE: 250
EAQVTQNPRY LITVTGKKLT VTCSQNMNHE YMSWYRQDPG LGLRQIYYSM NVEVTDKGDV  60
PEGYKVSRKE KRNFPLILES PSPNQTSLYF CASRLTGRVH GYTFGPGTRL TVLEDLRNVT  120
PPKVSLFEPS KAEIANKQKA TLVCLARGFF PDHVELSWWV NGKEVHSGVS TDPQAYKESN  180
YSYCLSSRLR VSATFWHNPR NHFRCQVQFH GLSEEDKWPE GSPKPVTQNI SAEAWGRADC  240
GITSASYHQG VLSATILYEI LLGKATLYAV LVSGLVLMAM VKKKNS                 286

SEQ ID NO: 251           moltype = AA  length = 250
FEATURE                  Location/Qualifiers
REGION                   1..250
                         note = Description of Artificial Sequence: Synthetic
                          polypeptide
source                   1..250
                         mol_type = protein
                         organism = synthetic construct
SEQUENCE: 251
KNQVEQSPQS LIILEGKNCT LQCNYTVSPF SNLRWYKQDT GRGPVSLTIM TFSENTKSNG  60
RYTATLDADT KQSSLHITAS QLSDSASYIC VVRGGAAGNK LTFGAGTRLT VKPYIQNPEP  120
AVYQLKDPRS QDSTLCLFTD FDSQINVPKT MESGTFITDK TVLDMKAMDS KSNGAIAWSN  180
```

```
QTSFTCQDIF KETNATYPSS DVPCDATLTE KSFETDMNLN FQNLSVMGLR ILLLKVAGFN    240
LLMTLRLWSS                                                           250

SEQ ID NO: 252          moltype = AA  length = 287
FEATURE                 Location/Qualifiers
REGION                  1..287
                        note = Description of Artificial Sequence: Synthetic
                         polypeptide
source                  1..287
                        mol_type = protein
                        organism = synthetic construct
SEQUENCE: 252
DAGVIQSPRH EVTEMGQEVT LRCKPISGHN SLFWYRQTMM RGLELLIYFN NNVPIDDSGM    60
PEDRFSAKMP NASFSTLKIQ PSEPRDSAVY FCASSSGGAN TEAFFGPGTR LTVEDLRNV    120
TPPKVSLFEP SKAEIANKQK ATLVCLARGF FPDHVELSWW VNGKEVHSGV STDPQAYKES   180
NYSYCLSSRL RVSATFWHNP RNHFRCQVQF HGLSEEDKWP EGSPKPVTQN ISAEAWGRAD   240
CGITSASYHQ GVLSATILYE ILLGKATLYA VLVSGLVLMA MVKKKNS                287

SEQ ID NO: 253          moltype = AA  length = 251
FEATURE                 Location/Qualifiers
REGION                  1..251
                        note = Description of Artificial Sequence: Synthetic
                         polypeptide
source                  1..251
                        mol_type = protein
                        organism = synthetic construct
SEQUENCE: 253
AQSVTQLGSH VSVSEGALIL LRCNYSSSVP PYLFWYVQYP NQGLQLLLKY TTGATLVKGI    60
NGFEAEFKKS ETSFHLTKPS AHMSDAAEYF CAVSARYNFN KFYFGSGTKL SVIPYIQNPE   120
PAVYQLKDPR SQDSTLCLFT DFDSQINVPK TMESGTFITD KTVLDMKAMD SKSNGAIAWS   180
NQTSFTCQDI FKETNATYPS SDVPCDATLT EKSFETDMNL NFQNLSVMGL RILLLKVAGF   240
NLLMTLRLWS S                                                       251

SEQ ID NO: 254          moltype = AA  length = 287
FEATURE                 Location/Qualifiers
REGION                  1..287
                        note = Description of Artificial Sequence: Synthetic
                         polypeptide
source                  1..287
                        mol_type = protein
                        organism = synthetic construct
SEQUENCE: 254
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSASGGRS YEQYFGPGTR LTVVEDLRNV   120
TPPKVSLFEP SKAEIANKQK ATLVCLARGF FPDHVELSWW VNGKEVHSGV STDPQAYKES   180
NYSYCLSSRL RVSATFWHNP RNHFRCQVQF HGLSEEDKWP EGSPKPVTQN ISAEAWGRAD   240
CGITSASYHQ GVLSATILYE ILLGKATLYA VLVSGLVLMA MVKKKNS                287

SEQ ID NO: 255          moltype = AA  length = 247
FEATURE                 Location/Qualifiers
REGION                  1..247
                        note = Description of Artificial Sequence: Synthetic
                         polypeptide
source                  1..247
                        mol_type = protein
                        organism = synthetic construct
SEQUENCE: 255
EDQVTQSPEA LRLQEGESSS LNCSYTVSGL RGLFWYRQDP GKGPEFLFTL YSAGEEKEKE    60
RLKATLTKKE SFLHITAPKP EDSATYLCAV RNTGFQKLVF GTGTRLLVSP YIQNPEPAVY   120
QLKDPRSQDS TLCLFTDFDS QINVPKTMES GTFITDKTVL DMKAMDSKSN GAIAWSNQTS   180
FTCQDIFKET NATYPSSDVP CDATLTEKSF ETDMNLNFQN LSVMGLRILL LKVAGFNLLM   240
TLRLWSS                                                            247

SEQ ID NO: 256          moltype = AA  length = 288
FEATURE                 Location/Qualifiers
REGION                  1..288
                        note = Description of Artificial Sequence: Synthetic
                         polypeptide
source                  1..288
                        mol_type = protein
                        organism = synthetic construct
SEQUENCE: 256
DTGVSQDPRH KITKRGQNVT FRCDPISEHN RLYWYRQTLG QGPEFLTYFQ NEAQLEKSRL    60
LSDRFSAERP KGSFSTLEIQ RTEQGDSAMY LCASSWRTGR EETQYFGPGT RLLVLEDLRN   120
VTPPKVSLFE PSKAEIANKQ KATLVCLARG FFPDHVELSW WVNGKEVHSG VSTDPQAYKE   180
SNYSYCLSSR LRVSATFWHN PRNHFRCQVQ FHGLSEEDKW PEGSPKPVTQ NISAEAWGRA   240
DCGITSASYH QGVLSATILY EILLGKATLY AVLVSGLVLM AMVKKKNS                288

SEQ ID NO: 257          moltype = AA  length = 250
```

```
FEATURE                 Location/Qualifiers
REGION                  1..250
                        note = Description of Artificial Sequence: Synthetic
                         polypeptide
source                  1..250
                        mol_type = protein
                        organism = synthetic construct
SEQUENCE: 257
KQEVTQIPAA LSVPEGENLV LNCSFTDSAI YNLQWFRQDP GKGLTSLLLI QSSQREQTSG    60
RLNASLDKSS GRSTLYIAAS QPGDSATYLC AVMLWNQGGK LIFGQGTELS VKPYIQNPEP   120
AVYQLKDPRS QDSTLCLFTD FDSQINVPKT MESGTFITDK TVLDMKAMDS KSNGAIAWSN   180
QTSFTCQDIF KETNATYPSS DVPCDATLTE KSFETDMNLN FQNLSVMGLR ILLLKVAGFN   240
LLMTLRLWSS                                                         250

SEQ ID NO: 258          moltype = AA  length = 285
FEATURE                 Location/Qualifiers
REGION                  1..285
                        note = Description of Artificial Sequence: Synthetic
                         polypeptide
source                  1..285
                        mol_type = protein
                        organism = synthetic construct
SEQUENCE: 258
KAGVTQTPRY LIKTRGQQVT LSCSPISGHR SVSWYQQTPG QGLQFLFEYF SETQRNKGNF    60
PGRFSGRQFS NSRSEMNVST LELGDSALYL CASSLGRGYE QYFGPGTRLT VTEDLRNVTP   120
PKVSLFEPSK AEIANKQKAT LVCLARGFFP DHVELSWWVN GKEVHSGVST DPQAYKESNY   180
SYCLSSRLRV SATFWHNPRN HFRCQVQFHG LSEEDKWPEG SPKPVTQNIS AEAWGRADCG   240
ITSASYHQGV LSATILYEIL LGKATLYAVL VSGLVLMAMV KKKNS                   285

SEQ ID NO: 259          moltype = AA  length = 257
FEATURE                 Location/Qualifiers
REGION                  1..257
                        note = Description of Artificial Sequence: Synthetic
                         polypeptide
source                  1..257
                        mol_type = protein
                        organism = synthetic construct
SEQUENCE: 259
TQLLEQSPQF LSIQEGENLT VYCNSSSVFS SLQWYRQEPG EGPVLLVTVV TGGEVKKLKR    60
LTFQFGDARK DSSLHITAAQ PGDTGLYLCA GYGGGSNYKL TFGKGTLLTV NPYIQNPDPA   120
VYQLRDSKSS DKSVCLFTDF DSQTNVSQSK DSDVYITDKT VLDMRSMDFK SNSAVAWSNK   180
SDFACANAFN NSIIPEDTFF PSPESSCDVK LVEKSFETDT NLNFQNLSVI GFRILLLKVA   240
GFNLLMTLRL WSSRAKR                                                 257

SEQ ID NO: 260          moltype = AA  length = 255
FEATURE                 Location/Qualifiers
REGION                  1..255
                        note = Description of Artificial Sequence: Synthetic
                         polypeptide
source                  1..255
                        mol_type = protein
                        organism = synthetic construct
SEQUENCE: 260
TQLLEQSPQF LSIQEGENLT VYCNSSSVFS SLQWYRQEPG EGPVLLVTVV TGGEVKKLKR    60
LTFQFGDARK DSSLHITAAQ PGDTGLYLCA GYGGGSNYKL TFGKGTLLTV NPYIQNPDPA   120
VYQLRDSKSS DKSVCLFTDF DSQTNVSQSK DSDVYITDKT VLDMRSMDFK SNSAVAWSNK   180
SDFACANAFN NSIIPEDTFF PSPESSCDVK LVEKSFETDT NLNFQNLSVI GFRILLLKVA   240
GFNLLMTLRL WSSRA                                                   255

SEQ ID NO: 261          moltype = AA  length = 274
FEATURE                 Location/Qualifiers
REGION                  1..274
                        note = Description of Artificial Sequence: Synthetic
                         polypeptide
source                  1..274
                        mol_type = protein
                        organism = synthetic construct
SEQUENCE: 261
TQLLEQSPQF LSIQEGENLT VYCNSSSVFS SLQWYRQEPG EGPVLLVTVV TGGEVKKLKR    60
LTFQFGDARK DSSLHITAAQ PGDTGLYLCA GYGGGSNYKL TFGKGTLLTV NPYIQNPDPA   120
VYQLRDSKSS DKSVCLFTDF DSQTNVSQSK DSDVYITDKT VLDMRSMDFK SNSAVAWSNK   180
SDFACANAFN NSIIPEDTFF PSPESSCDVK LVEKSFETDT NLNFQNLSVI GFRILLLKVA   240
GFNLLMTLRL WSSGSGATNF SLLKQAGDVE ENPG                              274

SEQ ID NO: 262          moltype = AA  length = 292
FEATURE                 Location/Qualifiers
REGION                  1..292
                        note = Description of Artificial Sequence: Synthetic
                         polypeptide
```

```
source                    1..292
                          mol_type = protein
                          organism = synthetic construct
SEQUENCE: 262
EAQVTQNPRY LITVTGKKLT VTCSQNMNHE YMSWYRQDPG LGLRQIYYSM NVEVTDKGDV    60
PEGYKVSRKE KRNFPLILES PSPNQTSLYF CASRLTGRVH GYTFGSGTRL TVVEDLNKVF   120
PPEVAVFEPS EAEISHTQKA TLVCLATGFF PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSVS YQQGVLSATI LYEILLGKAT LYAVLVSALV LMAMVKRKDF GS           292

SEQ ID NO: 263            moltype = AA  length = 294
FEATURE                   Location/Qualifiers
REGION                    1..294
                          note = Description of Artificial Sequence: Synthetic
                           polypeptide
source                    1..294
                          mol_type = protein
                          organism = synthetic construct
SEQUENCE: 263
EAQVTQNPRY LITVTGKKLT VTCSQNMNHE YMSWYRQDPG LGLRQIYYSM NVEVTDKGDV    60
PEGYKVSRKE KRNFPLILES PSPNQTSLYF CASRLTGRVH GYTFGSGTRL TVVEDLNKVF   120
PPEVAVFEPS EAEISHTQKA TLVCLATGFF PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSVS YQQGVLSATI LYEILLGKAT LYAVLVSALV LMAMVKRKDF RAKR         294

SEQ ID NO: 264            moltype = AA  length = 292
FEATURE                   Location/Qualifiers
REGION                    1..292
                          note = Description of Artificial Sequence: Synthetic
                           polypeptide
source                    1..292
                          mol_type = protein
                          organism = synthetic construct
SEQUENCE: 264
EAQVTQNPRY LITVTGKKLT VTCSQNMNHE YMSWYRQDPG LGLRQIYYSM NVEVTDKGDV    60
PEGYKVSRKE KRNFPLILES PSPNQTSLYF CASRLTGRVH GYTFGSGTRL TVVEDLNKVF   120
PPEVAVFEPS EAEISHTQKA TLVCLATGFF PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSVS YQQGVLSATI LYEILLGKAT LYAVLVSALV LMAMVKRKDF RA           292

SEQ ID NO: 265            moltype = AA  length = 612
FEATURE                   Location/Qualifiers
REGION                    1..612
                          note = Description of Artificial Sequence: Synthetic
                           polypeptide
source                    1..612
                          mol_type = protein
                          organism = synthetic construct
SEQUENCE: 265
MDSWTFCCVS LCILVAKHTD AGVIQSPRHE VTEMGQEVTL RCKPISGHNS LFWYRQTMMR    60
GLELLIYFNN NVPIDDSGMP EDRFSAKMPN ASFSTLKIQP SEPRDSAVYF CASSSGGANT   120
EAFFGQGTRL TVVEDLNKVF PPEVAVFEPS EAEISHTQKA TLVCLATGFF PDHVELSWWV   180
NGKEVHSGVS TDPQPLKEQP ALNDSRYCLS SRLRVSATFW QNPRNHFRCQ VQFYGLSEND   240
EWTQDRAKPV TQIVSAEAWG RADCGFTSVS YQQGVLSATI LYEILLGKAT LYAVLVSALV   300
LMAMVKRKDF RAKRSGSGAT NFSLLKQAGD VEENPGPMKK HLTTFLVILW LYFYRGNGKN   360
QVEQSPQSLI ILEGKNCTLQ CNYTVSPFSN LRWYKQDTGR GPVSLTIMTF SENTKSNGRY   420
TATLDADTKQ SSLHITASQL SDSASYICVV RGGAAGNKLT FGGGTRVLVK PNIQNPDPAV   480
YQLRDSKSSD KSVCLFTDFD SQTNVSQSKD SDVYITDKTV LDMRSMDFKS NSAVAWSNKS   540
DPACANAFNN SIIPEDTFFP SPESSCDVKL VEKSFETDTN LNFQNLSVIG FRILLLKVAG   600
FNLLMTLRLW SS                                                       612

SEQ ID NO: 266            moltype = AA  length = 607
FEATURE                   Location/Qualifiers
REGION                    1..607
                          note = Description of Artificial Sequence: Synthetic
                           polypeptide
source                    1..607
                          mol_type = protein
                          organism = synthetic construct
SEQUENCE: 266
MGPQLLGYVV LCLLGAGPLE AQVTQNPRYL ITVTGKKLTV TCSQNMNHEY MSWYRQDPGL    60
GLRQIYYSMN VEVTDKGDVP EGYKVSRKEK RNFPLILESP SPNQTSLYFC ASRLTGRVHG   120
YTFGSGTRLT VVEDLNKVFP PEVAVFEPSE AEISHTQKAT LVCLATGFFP DHVELSWWVN   180
GKEVHSGVST DPQPLKEQPA LNDSRYCLSS RLRVSATFWQ NPRNHFRCQV QFYGLSENDE   240
WTQDRAKPVT QIVSAEAWGR ADCGFTSVSY QQGVLSATIL YEILLGKATL YAVLVSALVL   300
MAMVKRKDFR AKRSGSGATN FSLLKQAGDV EENPGPMVLK FSVSILWIQL AWVSTQLLEQ   360
SPQFLSIQEG ENLTVYCNSS SVFSSLQWYR QEPGEGPVLL VTVVTGGEVK KLKRLTFQFG   420
DARKDSSLHI TAAQPGDTGL YLCAGYGGGS NYKLTFGKGT LLTVNPYIQN PDPAVYQLRD   480
SKSSDKSVCL FTDFDSQTNV SQSKDSDVYI TDKTVLDMRS MDFKSNSAVA WSNKSDFACA   540
```

```
NAFNNSIIPE DTFFPSPESS CDVKLVEKSF ETDTNLNFQN LSVIGFRILL LKVAGFNLLM   600
TLRLWSS                                                            607

SEQ ID NO: 267          moltype = AA  length = 609
FEATURE                 Location/Qualifiers
REGION                  1..609
                        note = Description of Artificial Sequence: Synthetic
                        polypeptide
source                  1..609
                        mol_type = protein
                        organism = synthetic construct
SEQUENCE: 267
MGPQLLGYVV LCLLGAGPLE AQVTQNPRYL ITVTGKKLTV TCSQNMNHEY MSWYRQDPGL   60
GLRQIYYSMN VEVTDKGDVP EGYKVSRKEK RNFPLILESP SPNQTSLYFC ASRLTGRVHG   120
YTFGSGTRLT VVEDLNKVFP PEVAVFEPSE AEISHTQKAT LVCLATGFFP DHVELSWWVN   180
GKEVHSGVST DPQPLKEQPA LNDSRYCLSS RLRVSATFWQ NPRNHFRCQV QFYGLSENDE   240
WTQDRAKPVT QIVSAEAWGR ADCGFTSVSY QQGVLSATIL YEILLGKATL YAVLVSALVL   300
MAMVKRKDFR AKRSGSGATN FSLLKQAGDV EENPGPMVLK FSVSILWIQL AWVSTQLLEQ   360
SPQFLSIQEG ENLTVYCNSS SVFSSLQWYR QEPGEGPVLL VTVVTGGEVK KLKRLTQFG    420
DARKDSSLHI TAAQPGDTGL YLCAGYGGGS NYKLTFGKGT LLTVNPYIQN PDPAVYQLRD   480
SKSSDKSVCL FTDFDSQTNV SQSKDSDVYI TDKTVLDMRS MDFKSNSAVA WSNKSDFACA   540
NAFNNSIIPE DTFFPSPESS CDVKLVEKSF ETDTNLNFQN LSVIGFRILL LKVAGFNLLM   600
TLRLWSSGS                                                          609

SEQ ID NO: 268          moltype = AA  length = 607
FEATURE                 Location/Qualifiers
REGION                  1..607
                        note = Description of Artificial Sequence: Synthetic
                        polypeptide
source                  1..607
                        mol_type = protein
                        organism = synthetic construct
SEQUENCE: 268
MVLKFSVSIL WIQLAWVSTQ LLEQSPQFLS IQEGENLTVY CNSSSVFSSL QWYRQEPGEG   60
PVLLVTVVTG GEVKKLKRLT FQFGDARKDS SLHITAAQPG DTGLYLCAGY GGGSNYKLTF   120
GKGTLLTVNP YIQNPDPAVY QLRDSKSSDK SVCLFTDFDS QTNVSQSKDS DVYITDKTVL   180
DMRSMDFKSN SAVAWSNKSD FACANAFNNS IIPEDTFFPS PESSCDVKLV EKSFETDTNL   240
NFQNLSVIGF RILLLKVAGF NLLMTLRLWS SRAKRSGSGA TNFSLLKQAG DVEENPGPMG   300
PQLLGYVVLC LLGAGPLEAQ VTQNPRYLIT VTGKKLTVTC SQNMNHEYMS WYRQDPGLGL   360
RQIYYSMNVE VTDKGDVPEG YKVSRKEKRN FPLILESPSP NQTSLYFCAS RLTGRVHGYT   420
FGSGTRLTVV EDLNKVFPPE VAVFEPSEAE ISHTQKATLV CLATGFFPDH VELSWWVNGK   480
EVHSGVSTDP QPLKEQPALN DSRYCLSSRL RVSATFWQNP RNHFRCQVQF YGLSENDEWT   540
QDRAKPVTQI VSAEAWGRAD CGFTSVSYQQ GVLSATILYE ILLGKATLYA VLVSALVLMA   600
MVKRKDF                                                            607

SEQ ID NO: 269          moltype = AA  length = 609
FEATURE                 Location/Qualifiers
REGION                  1..609
                        note = Description of Artificial Sequence: Synthetic
                        polypeptide
source                  1..609
                        mol_type = protein
                        organism = synthetic construct
SEQUENCE: 269
MVLKFSVSIL WIQLAWVSTQ LLEQSPQFLS IQEGENLTVY CNSSSVFSSL QWYRQEPGEG   60
PVLLVTVVTG GEVKKLKRLT FQFGDARKDS SLHITAAQPG DTGLYLCAGY GGGSNYKLTF   120
GKGTLLTVNP YIQNPDPAVY QLRDSKSSDK SVCLFTDFDS QTNVSQSKDS DVYITDKTVL   180
DMRSMDFKSN SAVAWSNKSD FACANAFNNS IIPEDTFFPS PESSCDVKLV EKSFETDTNL   240
NFQNLSVIGF RILLLKVAGF NLLMTLRLWS SRAKRSGSGA TNFSLLKQAG DVEENPGPMG   300
PQLLGYVVLC LLGAGPLEAQ VTQNPRYLIT VTGKKLTVTC SQNMNHEYMS WYRQDPGLGL   360
RQIYYSMNVE VTDKGDVPEG YKVSRKEKRN FPLILESPSP NQTSLYFCAS RLTGRVHGYT   420
FGSGTRLTVV EDLNKVFPPE VAVFEPSEAE ISHTQKATLV CLATGFFPDH VELSWWVNGK   480
EVHSGVSTDP QPLKEQPALN DSRYCLSSRL RVSATFWQNP RNHFRCQVQF YGLSENDEWT   540
QDRAKPVTQI VSAEAWGRAD CGFTSVSYQQ GVLSATILYE ILLGKATLYA VLVSALVLMA   600
MVKRKDFGS                                                          609

SEQ ID NO: 270          moltype = AA  length = 602
FEATURE                 Location/Qualifiers
REGION                  1..602
                        note = Description of Artificial Sequence: Synthetic
                        polypeptide
source                  1..602
                        mol_type = protein
                        organism = synthetic construct
SEQUENCE: 270
MVLKFSVSIL WIQLAWVSTQ LLEQSPQFLS IQEGENLTVY CNSSSVFSSL QWYRQEPGEG   60
PVLLVTVVTG GEVKKLKRLT FQFGDARKDS SLHITAAQPG DTGLYLCAGY GGGSNYKLTF   120
GKGTLLTVNP YIQNPDPAVY QLRDSKSSDK SVCLFTDFDS QTNVSQSKDS DVYITDKTVL   180
DMRSMDFKSN SAVAWSNKSD FACANAFNNS IIPEDTFFPS PESSCDVKLV EKSFETDTNL   240
```

```
NFQNLSVIGF RILLLKVAGF NLLMTLRLWS SGSGATNFSL LKQAGDVEEN PGPMGPQLLG  300
YVVLCLLGAG PLEAQVTQNP RYLITVTGKK LTVTCSQNMN HEYMSWYRQD PGLGLRQIYY  360
SMNVEVTDKG DVPEGYKVSR KEKRNFPLIL ESPSPNQTSL YFCASRLTGR VHGYTFGSGT  420
RLTVVEDLNK VFPPEVAVFE PSEAEISHTQ KATLVCLATG FFPDHVELSW WVNGKEVHSG  480
VSTDPQPLKE QPALNDSRYC LSSRLRVSAT FWQNPRNHFR CQVQFYGLSE NDEWTQDRAK  540
PVTQIVSAEA WGRADCGFTS VSYQQGVLSA TILYEILLGK ATLYAVLVSA LVLMAMVKRK  600
DF                                                                 602

SEQ ID NO: 271          moltype = AA  length = 604
FEATURE                 Location/Qualifiers
REGION                  1..604
                        note = Description of Artificial Sequence: Synthetic
                         polypeptide
source                  1..604
                        mol_type = protein
                        organism = synthetic construct
SEQUENCE: 271
MVLKFSVSIL WIQLAWVSTQ LLEQSPQFLS IQEGENLTVY CNSSSVFSSL QWYRQEPGEG  60
PVLLVTVVTG GEVKKLKRLT FQFGDARKDS SLHITAAQPG DTGLYLCAGY GGGSNYKLTF  120
GKGTLLTVNP YIQNPDPAVY QLRDSKSSDK SVCLFTDFDS QTNVSQSKDS DVYITDKTVL  180
DMRSMDFKSN SAVAWSNKSD FACANAFNNS IIPEDTFFPS PESSCDVKLV EKSFETDTNL  240
NFQNLSVIGF RILLLKVAGF NLLMTLRLWS SGSGATNFSL LKQAGDVEEN PGPMGPQLLG  300
YVVLCLLGAG PLEAQVTQNP RYLITVTGKK LTVTCSQNMN HEYMSWYRQD PGLGLRQIYY  360
SMNVEVTDKG DVPEGYKVSR KEKRNFPLIL ESPSPNQTSL YFCASRLTGR VHGYTFGSGT  420
RLTVVEDLNK VFPPEVAVFE PSEAEISHTQ KATLVCLATG FFPDHVELSW WVNGKEVHSG  480
VSTDPQPLKE QPALNDSRYC LSSRLRVSAT FWQNPRNHFR CQVQFYGLSE NDEWTQDRAK  540
PVTQIVSAEA WGRADCGFTS VSYQQGVLSA TILYEILLGK ATLYAVLVSA LVLMAMVKRK  600
DFGS                                                               604

SEQ ID NO: 272          moltype = AA  length = 256
FEATURE                 Location/Qualifiers
REGION                  1..256
                        note = Description of Artificial Sequence: Synthetic
                         polypeptide
source                  1..256
                        mol_type = protein
                        organism = synthetic construct
SEQUENCE: 272
TQLLEQSPQF LSIQEGENLT VYCNSSSVFS SLQWYRQEPG EGPVLLVTVV TGGEVKKLKR  60
LTFQFGDARK DSSLHITAAQ PGDTGLYLCA GYGGGSNYKL TFGKGTLLTV NPYIQNPDPA  120
VYQLRDSKSS DKSVCLFTDF DSQTNVSQSK DSDVYITDKT VLDMRSMDFK SNSAVAWSNK  180
SDFACANAFN NSIIPEDTFF PSPESSCDVK LVEKSFETDT NLNFQNLSVI GFRILLLKVA  240
GFNLLMTLRL WSSRAK                                                  256

SEQ ID NO: 273          moltype = AA  length = 293
FEATURE                 Location/Qualifiers
REGION                  1..293
                        note = Description of Artificial Sequence: Synthetic
                         polypeptide
source                  1..293
                        mol_type = protein
                        organism = synthetic construct
SEQUENCE: 273
EAQVTQNPRY LITVTGKKLT VTCSQNMNHE YMSWYRQDPG LGLRQIYYSM NVEVTDKGDV  60
PEGYKVSRKE KRNFPLILES PSPNQTSLYF CASRLTGRVH GYTFGSGTRL TVVEDLNKVF  120
PPEVAVFEPS EAEISHTQKA TLVCLATGFF PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSVS YQQGVLSATI LYEILLGKAT LYAVLVSALV LMAMVKRKDF RAK          293
```

T CELL RECEPTORS THAT BIND TO MIXED LINEAGE LEUKEMIA (MLL)-SPECIFIC PHOSPHOPEPTIDES AND METHODS OF USE THEREOF

RELATED APPLICATIONS

This application is a division of U.S. application Ser. No. 16/807,742, filed Mar. 3, 2020, which is a continuation of International Patent Application No. PCT/US2018/049397, filed Sep. 4, 2018, which claims the benefit of U.S. Provisional Application No. 62/553,957, filed Sep. 4, 2017, each of which are incorporated by reference herein in their entireties.

REFERENCE TO AN ELECTRONIC SEQUENCE LISTING

The contents of the electronic sequence listing (A132770001US02-SEQ-LJG.xml; Size: 403,296 bytes; and Date of Creation: Jun. 23, 2023) is herein incorporated by reference in its entirety.

1. FIELD

The instant disclosure relates to T cell receptors (TCRs) that bind to mixed lineage leukemia (MLL) phosphopeptides and methods of using the same.

2. BACKGROUND

Phosphoproteins arising from deregulated post-translational modifications are critical determinants for cancerous cell transformation. Degradation of these phosphoproteins can generate phosphopeptides that are presented by MHC molecules and mediate cancer-specific T cell responses. Mixed lineage leukemia (MLL, also known as Histone-lysine N-methyltransferase 2A (KMT2A)) is a histone-modifying enzyme regulating genome accessibility and transcription. A number of phosphopeptides that are derived from MLL have been reported, see, e.g., Cobbold et al., Sci Transl Med. 2013 Sep. 18; 5(203): 203ra125, incorporated herein by reference in its entirety. In view of their tumor expression profiles, MLL phosphopeptides hold great promise as targets for cancer therapies.

Accordingly, there is a need in the art for novel compositions that can recognize cancer cells presenting MLL phosphopeptides on their surface and direct an immune response against these cells.

3. SUMMARY

The instant disclosure provides TCRs (e.g., TCRs that bind to a MLL phosphopeptide, e.g., the phosphopeptide MLL-pM EPR[pS]PSHSM (SEQ ID NO: 45) or MLL-pP RVR[pS]PTRSP (SEQ ID NO: 47)), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells expressing MLL (e.g., cancer cells displaying a MLL phosphopeptide, e.g., the phosphopeptide MLL-pM EPR[pS]PSHSM (SEQ ID NO: 45) or MLL-pP RVR[pS]PTRSP (SEQ ID NO: 47)), and hence for treating a MLL-expressing cancer in a subject.

Accordingly, in one aspect, the instant disclosure provides an isolated T cell receptor (TCR) that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 21. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising an amino acid sequence selected from the group consisting of SEQ ID NOs: 58, 236, 259, 260, 272, 261, and 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 59, 237, 262, 263, 264, 273, 60, and 250.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 59, 237, 262, 263, 264, 273, 60, and 250.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 73. In certain embodiments, the Vα comprises the amino acid sequence set forth in SEQ ID NO: 73. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 74. In certain embodiments, the Vβ comprises the amino acid sequence set forth in SEQ ID NO: 74.

In another aspect, provided herein is an isolated TCR that binds to a peptide consisting of the amino acid sequence set forth in SEQ ID NO: 45, the TCR comprising a D chain variable region (Vβ) comprising an amino acid sequence at least 75%, 80%, 85%, 90%, 95%, 99%, or 100% identical to the amino acid sequence set forth in SEQ ID NO: 74. In certain embodiments, the Vβ comprises the amino acid sequence set forth in SEQ ID NO: 74.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively.

In another aspect, disclosed herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively. In certain embodiments, the Vα and Vs comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, disclosed herein is an isolated TCR comprising an α chain and a β chain, wherein the α chain comprises the amino acid sequence set forth in SEQ ID NO: 58 and/or the β chain comprises the amino acid sequence set forth in SEQ ID NO: 59. In certain embodiments, the α chain further comprises the amino acid sequence of GS at the C-terminus, and/or the β chain further comprises the amino acid sequence of GSGATNFSLLKQAGDVEENPG (SEQ ID NO: 93) at the C-terminus. In certain embodiments, the α chain comprises the amino acid sequence set forth in SEQ ID NO: 236 and/or the β chain comprises the amino acid sequence set forth in SEQ ID NO: 237. In certain embodiments, the isolated TCR disclosed herein comprises an α chain comprising an amino acid sequence selected from the group consisting of SEQ ID NOs: 58, 236, 259, 260, 272, 261, and 249 and a β chain comprising an amino acid sequence selected from the group consisting of SEQ ID NOs: 59, 237, 262, 263, 264, 273, 60, and 250. In certain embodiments, the TCR comprises an α chain comprising the amino acid sequence set forth in SEQ ID NO: 249 and a β chain comprising the amino acid sequence set forth in SEQ ID NO: 250.

In another aspect, disclosed herein is an isolated TCR comprising an α chain and a β chain, wherein the α chain comprises the amino acid sequence set forth in SEQ ID NO: 58 or 236 and/or the β chain comprises the amino acid sequence set forth in SEQ ID NO: 60. In certain embodiments, the α chain further comprises the amino acid sequence of GS at the C-terminus, and the 1 chain further comprises the amino acid sequence of GSGATNFSLLKQAGDVEENPG (SEQ ID NO: 93) at the C-terminus.

In another aspect, disclosed herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 22. In certain embodiments, the Vα comprises CDR1α and CDR2α comprising the amino acid sequences set forth in SEQ ID NOs: 12 and 17, respectively. In certain embodiments, the Vα comprises the amino acid sequence set forth in SEQ ID NO: 88. In certain embodiments, the Vα comprises the amino acid sequence set forth in SEQ ID NO: 3. In certain embodiments, the TCR comprises an α chain comprising the amino acid sequence set forth in SEQ ID NO: 61. In certain embodiments, the TCR comprises an α chain comprising the amino acid sequence set forth in SEQ ID NO: 251. In certain embodiments, the α chain further comprises the amino acid sequence of GS at the C-terminus. In certain embodiments, the TCR comprises a P chain variable region (Vβ) comprising CDR3β, wherein the CDR3β comprises the amino acid sequence set forth in SEQ ID NO: 37. In certain embodiments, the Vβ comprises CDR1β and CDR2β comprising the amino acid sequences set forth in SEQ ID NOs: 27 and 32, respectively. In certain embodiments, the Vβ comprises the amino acid sequence set forth in SEQ ID NO: 89. In certain embodiments, the Vβ comprises the amino acid sequence set forth in SEQ ID NO: 4. In certain embodiments, the TCR comprises a β chain comprising the amino acid sequence set forth in SEQ ID NO: 62. In certain embodiments, the TCR comprises a β chain comprising the amino acid sequence set forth in SEQ ID NO: 63. In certain embodiments, the TCR comprises a D chain comprising the amino acid sequence set forth in SEQ ID NO: 252. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a 0 chain variable region (Vβ) comprising complementarity determining region CDR3β, wherein the CDR3β comprises the amino acid sequence set forth in SEQ ID NO: 37. In certain embodiments, the Vβ comprises CDR1β and CDR2β comprising the amino acid sequences set forth in SEQ ID NOs: 27 and 32, respectively. In certain embodiments, the Vβ comprises the amino acid sequence set forth in SEQ ID NO: 89. In certain embodiments, the VP comprises the amino acid sequence set forth in SEQ ID NO: 4. In certain embodiments, the TCR comprises a β chain comprising the amino acid sequence set forth in SEQ ID NO: 62. In certain embodiments, the TCR comprises a β chain comprising the amino acid sequence set forth in SEQ ID NO: 63. In certain embodiments, the TCR comprises a β chain comprising the amino acid sequence set forth in SEQ ID NO: 252. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 75. In certain embodiments, the Vα comprises the amino acid sequence set forth in SEQ ID NO: 75. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 76. In certain embodiments, the Vβ comprises the amino acid sequence set forth in SEQ ID NO: 76.

In another aspect, provided herein is an isolated TCR that binds to a peptide consisting of the amino acid sequence set forth in SEQ ID NO: 45, the TCR comprising a β chain variable region (V) comprising an amino acid sequence at least 75%, 80%, 85%, 90%, 95%, 99%, or 100% identical to the amino acid sequence set forth in SEQ ID NO: 76. In certain embodiments, the Vβ comprises the amino acid sequence set forth in SEQ ID NO: 76.

In certain embodiments of the foregoing aspects, the TCR comprises an α chain variable region (Vα) comprising CDR1α, CDR2α, and CDR3α and a β chain variable region (V) comprising CDR1β, CDR2β, and CDR3β, wherein the CDR1α, CDR2α, CDR3α, CDR1β, CDR2β, and CDR3β comprise the amino acid sequences set forth in SEQ ID NOs: 12, 17, 22, 27, 32, and 37, respectively.

In another aspect, provided herein is an isolated TCR comprising an α chain variable region (Vα) comprising complementarity determining regions CDR1α, CDR2α, and CDR3α and a β chain variable region (VP) comprising CDR1β, CDR2β, and CDR3β, wherein the CDR1α, CDR2α, CDR3α, CDR1β, CDR2β, and CDR3β comprise the amino acid sequences set forth in SEQ ID NOs: 12, 17, 22, 27, 32, and 37, respectively. In certain embodiments, the Vα and Vβ comprise the amino acid sequences set forth in SEQ ID NOs: 88 and 89, respectively. In certain embodiments, the Vα and Vβ comprise the amino acid sequences set forth in SEQ ID NOs: 3 and 4, respectively.

In another aspect, provided herein is an isolated TCR comprising an α chain and a β chain, wherein the α chain comprises the amino acid sequence set forth in SEQ ID NO: 61 and the β chain comprises the amino acid sequence set forth in SEQ ID NO: 62. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 61 and the β chain comprises the amino acid sequence set forth in SEQ ID NO: 63. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 251 and/or the β chain comprises the amino acid sequence set forth in SEQ ID NO: 252. In certain embodiment, the α chain further comprises the amino acid sequence of GS at the C-terminus, and/or the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 23. In certain embodiments, the Vα comprises CDR1α and CDR2α comprising the amino acid sequences set forth in SEQ ID NOs: 13 and 109, respectively. In certain embodiments, the Vα comprises the amino acid sequence set forth in SEQ ID NO: 106. In certain embodiments, the TCR comprises an α chain comprising the amino acid sequence set forth in SEQ ID NO: 64. In certain embodiments, the α chain further comprises the amino acid sequence of GS at the C-terminus. In certain embodiments, the TCR comprises a β chain variable region (Vβ) comprising CDR313, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 107. In certain embodiments, the TCR comprises a β chain comprising the amino acid sequence set forth in SEQ ID NO: 65. In certain embodiments, the TCR comprises a β chain comprising the amino acid sequence set forth in SEQ ID NO: 66. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 23. In certain embodiments, the Vα comprises CDR1α and CDR2α comprising the amino acid sequences set forth in SEQ ID NOs: 13 and 18, respectively. In certain embodiments, the Vα comprises the amino acid sequence set forth in SEQ ID NO: 5. In certain embodiments, the TCR comprises an α chain comprising the amino acid sequence set forth in SEQ ID NO; 253. In certain embodiments, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 6. In certain embodiments, the TCR comprises a D chain comprising the amino acid sequence set forth in SEQ ID NO: 254. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a 0 chain variable region (Vβ) comprising complementarity determining region CDR3β, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 107. In certain embodiments, the Vβ comprises the amino acid sequence set forth in SEQ ID NO: 6. In certain embodiments, the TCR comprises a β chain comprising the amino acid sequence set forth in SEQ ID NO; 65. In certain embodiments, the TCR comprises a β chain comprising the amino acid sequence set forth in SEQ ID NO: 66. In certain embodiments, the TCR comprises a β chain comprising the amino acid sequence set forth in SEQ ID NO: 254. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 77. In certain embodiments, the Vα comprises the amino acid sequence set forth in SEQ ID NO: 77. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 78. In certain embodiments, the Vβ comprises the amino acid sequence set forth in SEQ ID NO: 78.

In another aspect, provided herein is an isolated TCR that binds to a peptide consisting of the amino acid sequence set forth in SEQ ID NO: 45, the TCR comprising a β chain variable region (V) comprising an amino acid sequence at least 75%, 80%, 85%, 90%, 95%, 99%, or 100% identical to the amino acid sequence set forth in SEQ ID NO: 78. In certain embodiments, the Vβ comprises the amino acid sequence set forth in SEQ ID NO: 78.

In certain embodiments of the foregoing aspects, the TCR comprises an α chain variable region (Vα) comprising CDR1α, CDR2α, and CDR3α and a β chain variable region (V) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 109, 23, 28, 33, and 38, respectively.

In certain embodiments of the foregoing aspects, the TCR comprises an α chain variable region (Vα) comprising CDR1α, CDR2α, and CDR3α and a β chain variable region (VP) comprising CDR1β, CDR2β, and CDR3β, wherein the CDR1α, CDR2α. CDR3α, CDR1β, CDR2β, and CDR3β comprise the amino acid sequences set forth in SEQ ID NOs: 13, 18, 23, 28, 33, and 38, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 109, 23, 28, 33, and 38, respectively. In certain embodiments, the Vα and Vβ comprise the amino acid sequences set forth in SEQ ID NOs: 106 and 107, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 18, 23, 28, 33, and 38, respectively. In certain embodiments, the Vα and V3 comprise the amino acid sequences set forth in SEQ ID NOs: 5 and 6, respectively.

In another aspect, provided herein is an isolated TCR comprising an α chain and a β chain, wherein the α chain comprises the amino acid sequence set forth in SEQ ID NO: 64 and the β chain comprises the amino acid sequence set forth in SEQ ID NO: 65. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 64 and the β chain comprises the amino acid sequence set forth in SEQ ID NO: 66. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 253 and the β chain comprises the amino acid sequence set forth in SEQ ID NO: 254. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 24. In certain embodiment, the Vα comprises CDR1α and CDR2α comprising the amino acid sequences set forth in SEQ ID NOs: 14 and 19, respectively. In certain embodiments, the Vα comprises the amino acid sequence set forth in SEQ ID NO: 7. In certain embodiments, the TCR comprises an α chain comprising the amino acid sequence set forth in SEQ ID NO: 67. In certain embodiments, the TCR comprises an α chain comprising the amino acid sequence set forth in SEQ ID NO: 255. In certain embodiment, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 39. In certain embodiments, the Vβ comprises CDR1β and CDR2β comprising the amino acid sequences set forth in SEQ ID NOs: 29 and 34, respectively. In certain embodiments, the Vβ comprises the amino acid sequence set forth in SEQ ID NO: 108. In certain embodiments, the Vβ comprises the amino acid sequence set forth in SEQ ID NO: 8. In certain embodiments, the TCR comprises a β chain comprising the amino acid sequence set forth in SEQ ID NO: 68. In certain embodiments, the TCR comprises a β chain comprising the amino acid sequence set forth in SEQ ID NO: 69. In certain embodiments, the TCR comprises a β chain comprising the amino acid sequence set forth in SEQ ID NO: 256. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 39. In certain embodiments, the Vβ comprises CDR1β and CDR2β comprising the amino acid sequences set forth in SEQ ID NOs: 29 and 34, respectively. In certain embodiments, the Vβ comprises the amino acid sequence set forth in SEQ ID NO: 108. In certain embodiments, the Vβ comprises the amino acid sequence set forth in SEQ ID NO: 8. In certain embodiments, the TCR comprises a β chain comprising the amino acid sequence set forth in SEQ ID NO: 68. In certain embodiments, the TCR comprises a β chain comprising the amino acid sequence set forth in SEQ ID NO: 69. In certain embodiments, the TCR comprises a β chain comprising the amino acid sequence set forth in SEQ ID NO: 256. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 79. In certain embodiments, the Vα comprises the amino acid sequence set forth in SEQ ID NO: 79. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 80. In certain embodiments, the Vβ comprises the amino acid sequence set forth in SEQ ID NO: 80.

In another aspect, provided herein is an isolated TCR that binds to a peptide consisting of the amino acid sequence set forth in SEQ ID NO: 45, the TCR comprising a β chain variable region (Vβ) comprising an amino acid sequence at least 75%, 80%, 85%, 90%, 95%, 99%, or 100% identical to the amino acid sequence set forth in SEQ ID NO: 80. In certain embodiments, the Vβ comprises the amino acid sequence set forth in SEQ ID NO: 80.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 14, 19, 24, 29, 34, and 39, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 14, 19, 24, 29, 34, and 39, respectively. In certain embodiments, the Vα and Vβ comprise the amino acid sequences set forth in SEQ ID NOs: 7 and 108, respectively. In certain embodiments, the Vα and Vβ comprise the amino acid sequences set forth in SEQ ID NOs: 7 and 8, respectively.

In another aspect, provided herein is an isolated TCR comprising an α chain and a β chain, wherein the α chain comprises the amino acid sequence set forth in SEQ ID NO: 67 and the β chain comprises the amino acid sequence set forth in SEQ ID NO: 68. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a p chain, wherein the α chain comprises the amino acid sequence set forth in SEQ ID NO: 67 and the β chain comprises the amino acid sequence set forth in SEQ ID NO: 69. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 255 and the β chain comprises the amino acid sequence set forth in SEQ ID NO: 256. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising an α chain variable region (Vα) comprising complementarity determining region CDR3α, wherein the CDR3α comprises the amino acid sequence set forth in SEQ ID NO: 25. In certain embodiments, the Vα comprises CDR1α and CDR2α comprising the amino acid sequences set forth in SEQ ID NOs: 15 and 20, respectively. In certain embodiments, the Vα comprises the amino acid sequence set forth in SEQ ID NO: 9. In certain embodiments, the TCR comprises an α chain comprising the amino acid sequence set forth in SEQ ID NO: 70. In certain embodiments, the TCR comprises an α chain comprising the amino acid sequence set forth in SEQ ID NO: 257. In certain embodiments, the α chain further comprises the amino acid sequence of GS at the C-terminus. In certain embodiments, the TCR comprises a 0 chain variable region (Vβ) comprising CDR3β, wherein the CDR3β comprises the amino acid sequence set forth in SEQ ID NO: 40. In certain embodiments, the Vβ comprises CDR1β and CDR2β comprising the amino acid sequences set forth in SEQ ID NOs: 30 and 35, respectively. In certain embodiments, the Vβ comprises the amino acid sequence set forth in SEQ ID NO: 10. In certain embodiments, the TCR comprises a β chain comprising the amino acid sequence set forth in SEQ ID NO: 71. In certain embodiments, the TCR comprises a D chain comprising the amino acid sequence set forth in SEQ ID NO: 72. In certain embodiments, the TCR comprises a β chain comprising the amino acid sequence set forth in SEQ ID NO: 258. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising a 0 chain variable region (Vβ) comprising complementarity determining region CDR3β, wherein the CDR3β comprises the amino acid sequence set forth in SEQ ID NO: 40. In certain embodiments, the Vβ comprises CDR1β and CDR2β comprising the amino acid sequences set forth in SEQ ID NOs: 30 and 35, respectively. In certain embodiments, the Vβ comprises the amino acid sequence set forth in SEQ ID NO: 10. In certain embodiments, the TCR comprises a β chain comprising the amino acid sequence set forth in SEQ ID NO: 71. In certain embodiments, the TCR comprises a β chain comprising the amino acid sequence set forth in SEQ ID NO: 72. In certain embodiments, the TCR comprises a β chain comprising the amino acid sequence set forth in SEQ ID NO: 258. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising an α chain variable region (Vα) comprising an amino acid sequence at least 75%, 80%, 85%, 90%, 95%, 99%, or 100% identical to the amino acid sequence set forth in SEQ ID NO: 81. In certain embodiments, the Vα comprises the amino acid sequence set forth in SEQ ID NO: 81. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 82. In certain embodiments, the Vβ comprises the amino acid sequence set forth in SEQ ID NO: 82.

In another aspect, provided herein is an isolated TCR that binds to a peptide consisting of the amino acid sequence set forth in SEQ ID NO: 47, the TCR comprising a β chain variable region (Vβ) comprising an amino acid sequence at least 75%, 80%, 85%, 90%, 95%, 99%, or 100% identical to the amino acid sequence set forth in SEQ ID NO: 82. In certain embodiments, the Vs comprises the amino acid sequence set forth in SEQ ID NO: 82.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR p0, CDR2β, and CDR3β comprise the amino acid sequences set forth in SEQ ID NOs: 15, 20, 25, 30, 35, and 40, respectively.

In another aspect, provided herein is an isolated TCR comprising an α chain variable region (Vα) comprising complementarity determining regions CDR1α, CDR2α, and CDR3α and a β chain variable region (V) comprising CDR1β, CDR2β, and CDR3β, wherein the CDR1α, CDR2α, CDR3α, CDR1β, CDR2β, and CDR3β comprise the amino acid sequences set forth in SEQ ID NOs: 15, 20, 25, 30, 35, and 40, respectively. In certain embodiments, the Vα and Vβ comprise the amino acid sequences set forth in SEQ ID NOs: 9 and 10, respectively.

In another aspect, provided herein is an isolated TCR comprising an α chain and a β chain, wherein the α chain comprises the amino acid sequence set forth in SEQ ID NO: 70 and the β chain comprises the amino acid sequence set forth in SEQ ID NO: 71. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 70 and the β chain comprises the amino acid sequence set forth in SEQ ID NO: 72. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 257 and the β chain comprises the amino acid sequence set forth in SEQ ID NO: 258. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to the same epitope as a TCR disclosed herein.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233.

In some embodiments, the isolated TCR described herein does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof. In some embodiments, the isolated TCR described herein does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, and iii) a peptide consisting of the amino acid sequence set forth in SEQ ID NO: 47.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO; 49, 50, 52, 53, 54, 55, or 57, or c) a peptide consisting of the amino acid sequence set forth in SEQ ID NO: 47, or d) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, and c) a peptide consisting of the amino acid sequence set forth in SEQ ID NO: 47.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, or xi) a peptide consisting of the amino acid sequence set forth in SEQ ID NO: 233, or xii) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, and xi) a peptide consisting of the amino acid sequence set forth in SEQ ID NO: 233.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, or xi) a peptide consisting of the amino acid sequence set forth in SEQ ID NO; 233, or xii) any combination thereof, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, or c) a peptide consisting of the amino acid sequence set forth in SEQ ID NO: 47, or d) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO; 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, and xi) a peptide consisting of the amino acid sequence set forth in SEQ ID NO: 233, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, and c) a peptide consisting of the amino acid sequence set forth in SEQ ID NO: 47.

In another aspect, provided herein is an isolated TCR that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO; 135, vii) a peptide consisting of the amino acid sequence set forth in SEQ ID NO: 192, or viii) a peptide consisting of the amino acid sequence set forth in SEQ ID NO: 233, or ix) any combination thereof. In certain embodiments, the TCR binds to i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO; 135, vii) a peptide consisting of the amino acid sequence set forth in SEQ ID NO: 192, and viii) a peptide consisting of the amino acid sequence set forth in SEQ ID NO: 233. In certain embodiments, the TCR does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof. In certain embodiments, the TCR does not bind to, or does not substantially bind to, any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47. In certain embodiments, the binding between the TCR and a peptide consisting of the amino acid sequence set forth in SEQ ID NO: 46, 49, 50, 52, 53, 54, 55, 57, or 47 is substantially weakened relative to the binding between the TCR and a peptide consisting of the amino acid sequence set forth in SEQ ID NO: 45, 51, 56, 117, 128, 135, 192, or 233. In certain embodiments, the binding between the TCR and any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47 is substantially weakened relative to the binding between the TCR and any of: a) a peptide consisting of the amino acid sequence set forth in SEQ ID NO: 45, b) a peptide consisting of the amino acid sequence set forth in SEQ ID NO: 51, c) a peptide consisting of the amino acid sequence set forth in SEQ ID NO: 56, d) a peptide consisting of the amino acid sequence set forth in SEQ ID NO: 117, e) a peptide consisting of the amino acid sequence set forth in SEQ ID NO: 128, f) a peptide consisting of the amino acid sequence set forth in SEQ ID NO: 135, g) a peptide consisting of the amino acid sequence set forth in SEQ ID NO: 192, and h) a peptide consisting of the amino acid sequence set forth in SEQ ID NO: 233.

In another aspect, provided herein is an isolated TCR that binds to at least one of peptide selected from the group consisting of;
i) a peptide consisting of the amino acid sequence set forth in SEQ ID NO: 45,
ii) a peptide consisting of the amino acid sequence set forth in SEQ ID NO: 51,
iii) a peptide consisting of the amino acid sequence set forth in SEQ ID NO: 56,
iv) a peptide consisting of the amino acid sequence set forth in SEQ ID NO: 117,
v) a peptide consisting of the amino acid sequence set forth in SEQ ID NO: 128,
vi) a peptide consisting of the amino acid sequence set forth in SEQ ID NO: 135,
vii) a peptide consisting of the amino acid sequence set forth in SEQ ID NO: 192, and
viii) a peptide consisting of the amino acid sequence set forth in SEQ ID NO: 233,
wherein the isolated TCR does not bind to, or does not substantially bind to at least one of peptide selected from the group consisting of:
a) a peptide consisting of the amino acid sequence set forth in SEQ ID NO: 46,
b) a peptide consisting of the amino acid sequence set forth in SEQ ID NO: 49, 50, 52, 53, 54, 55, or 57, and
c) a peptide consisting of the amino acid sequence set forth in SEQ ID NO: 47.

In another aspect, provided herein is an isolated TCR that:
a) binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof; and
b) comprises an α chain variable region (Vα) comprising CDR3α, wherein the CDR3α comprises the amino acid sequence set forth in SEQ ID NO: 21. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising the amino acid sequence set forth in SEQ ID NO: 259, 260, 272, 261, or 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a P chain comprising the amino acid sequence set forth in SEQ ID NO: 262, 263, 264, 273, or 250.

In another aspect, provided herein is an isolated TCR that:
a) binds to; i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof; and
b) comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO; 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising the amino acid sequence selected from the group consisting of SEQ ID NOs: 262, 263, 264, 273, and 250.

In another aspect, provided herein is an isolated TCR that:
a) binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO; 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof; and
b) comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively. In certain embodiments, the Vα and Vβ comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, provided herein is an isolated TCR, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702), iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), and iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702). In certain embodiments, when the TCR is expressed on the surface of a T cell, the T cell is not activated, or is not substantially activated: i) when co-cultured with a second cell displaying a peptide consisting of the amino acid sequence set forth in SEQ ID NO: 46 (e.g., a second cell displaying a peptide consisting of the amino acid sequence set forth in SEQ ID NO: 46 in the context of HLA-B*0702), ii) when co-cultured with a second cell displaying a peptide consisting of the amino acid sequence set forth in SEQ ID NO: 49, 50, 52, 53, 54, 55, or 57 (e.g., a second cell displaying a peptide consisting of the amino acid sequence set forth in SEQ ID NO: 49, 50, 52, 53, 54, 55, or 57 in the context of HLA-B*0702), or iii) when co-cultured with a second cell displaying a peptide consisting of the amino acid sequence set forth in SEQ ID NO: 47 (e.g., a second cell displaying a peptide consisting of the amino acid sequence set forth in SEQ ID NO: 47 in the context of HLA-B*0702), or iv) any combination thereof. In certain embodiments, when the TCR is expressed on the surface of a T cell, the T cell is not activated, or is not substantially activated, when co-cultured with a second cell displaying any of the following peptides: i) a peptide consisting of the amino acid sequence set forth in SEQ ID NO: 46 (e.g., in the context of HLA-B*0702), ii) a peptide consisting of the amino acid sequence set forth in SEQ ID NO: 49 (e.g., in the context of HLA-B*0702), iii) a peptide consisting of the amino acid sequence set forth in SEQ ID NO: 50 (e.g., in the context of HLA-B*0702), iv) a peptide consisting of the amino acid sequence set forth in SEQ ID NO: 52 (e.g., in the context of HLA-B*0702), v) a peptide consisting of the amino acid sequence set forth in SEQ ID NO: 53 (e.g., in the context of HLA-B*0702), vi) a peptide consisting of the amino acid sequence set forth in SEQ ID NO: 54 (e.g., in the context of HLA-B*0702), vii) a peptide consisting of the amino acid sequence set forth in SEQ ID NO: 55 (e.g., in the context of HLA-B*0702), viii) a peptide consisting of the amino acid sequence set forth in SEQ ID NO: 57 (e.g., in the context of HLA-B*0702), and ix) a peptide consisting of the amino acid sequence set forth in SEQ ID NO: 47 (e.g., in the context of HLA-B*0702). In certain embodiments, when the TCR is expressed on the surface of a T cell, the activation of the T cell is substantially weakened when the T cell is co-cultured with a second cell displaying a peptide consisting of the amino acid sequence set forth in SEQ ID NO: 46, 49, 50, 52, 53, 54, 55, 57, or 47 (e.g., a second cell displaying a peptide consisting of the amino acid sequence set forth in SEQ ID NO: 46, 49, 50, 52, 53, 54, 55, 57, or 47 in the context of HLA-B*0702) relative to the activation of the T cell when the T cell is co-cultured with a third cell displaying a peptide consisting of the amino acid sequence set forth in SEQ ID NO: 45, 51, 56, 117, 128, 135, 192, or 233 (e.g., a third cell displaying a peptide consisting of the amino acid sequence set forth in SEQ ID NO: 45, 51, 56, 117, 128, 135, 192, or 233 in the context of HLA-B*0702). In certain embodiments, when the TCR is expressed on the surface of a T cell, the activation of the T cell is substantially weakened when the T cell is co-cultured with a second cell displaying any of the following peptides: i) a peptide consisting of the amino acid sequence set forth in SEQ ID NO: 46 (e.g., in the context of HLA-B*0702), ii) a peptide consisting of the amino acid sequence set forth in SEQ ID NO: 49 (e.g., in the context of HLA-B*0702), iii) a peptide consisting of the amino acid sequence set forth in SEQ ID NO: 50 (e.g., in the context of HLA-B*0702), iv) a peptide consisting of the amino acid sequence set forth in SEQ ID NO: 52 (e.g., in the context of HLA-B*0702), v) a peptide consisting of the amino acid sequence set forth in SEQ ID NO: 53 (e.g., in the context of HLA-B*0702), vi) a peptide consisting of the amino acid sequence set forth in SEQ ID NO: 54 (e.g., in the context of HLA-B*0702), vii) a peptide consisting of the amino acid sequence set forth in SEQ ID NO: 55 (e.g., in the context of HLA-B*0702), viii) a peptide consisting of the amino acid sequence set forth in SEQ ID NO: 57 (e.g., in the context of HLA-B*0702), and ix) a peptide consisting of the amino acid sequence set forth in SEQ ID NO: 47 (e.g., in the context of HLA-B*0702), relative to the activation of the T cell when the T cell is co-cultured with a third cell displaying any of the following peptides: a) a peptide consisting of the amino acid sequence set forth in SEQ ID NO: 45 (e.g., in the context of HLA-B*0702), b) a peptide consisting of the amino acid sequence set forth in SEQ ID NO: 51 (e.g., in the context of HLA-B*0702), c) a peptide consisting of the amino acid sequence set forth in SEQ ID NO: 56 (e.g., in the context of HLA-B*0702), and d) a peptide consisting of an amino acid sequence selected from the group consisting of SEQ ID NOs: 117, 128, 135, 192, and 233 (e.g., in the context of HLA-B*0702).

In another aspect, provided herein is an isolated TCR, wherein when the TCR is expressed on the surface of a T cell, the activation of the T cell is substantially weakened when the T cell is separately co-cultured with each of: i) a second cell displaying a peptide consisting of the amino acid sequence set forth in SEQ ID NO: 46, ii) a second cell displaying a peptide consisting of the amino acid sequence set forth in SEQ ID NO: 49, iii) a second cell displaying a peptide consisting of the amino acid sequence set forth in SEQ ID NO: 50, iv) a second cell displaying a peptide consisting of the amino acid sequence set forth in SEQ ID NO: 52, v) a second cell displaying a peptide consisting of the amino acid sequence set forth in SEQ ID NO: 53, vi) a second cell displaying a peptide consisting of the amino acid sequence set forth in SEQ ID NO: 54, vii) a second cell displaying a peptide consisting of the amino acid sequence set forth in SEQ ID NO: 55, viii) a second cell displaying a peptide consisting of the amino acid sequence set forth in SEQ ID NO: 57, and ix) a second cell displaying a peptide consisting of the amino acid sequence set forth in SEQ ID NO: 47, relative to the activation of the T cell when the T cell is separately co-cultured with each of: a) a third cell displaying a peptide consisting of the amino acid sequence set forth in SEQ ID NO: 45, b) a third cell displaying a peptide consisting of the amino acid sequence set forth in SEQ ID NO: 51, c) a third cell displaying a peptide consisting of the amino acid sequence set forth in SEQ ID NO: 56, d) a third cell displaying a peptide consisting of the amino acid sequence set forth in SEQ ID NO: 117, e) a third cell displaying a peptide consisting of the amino acid sequence set forth in SEQ ID NO: 128, f) a third cell displaying a peptide consisting of the amino acid sequence set forth in SEQ ID NO: 135, g) a third cell displaying a peptide consisting of the amino acid sequence set forth in SEQ ID NO: 192, and h) a third cell displaying a peptide consisting of the amino acid sequence set forth in SEQ ID NO: 233. In another aspect, provided herein is an isolated TCR comprising an α chain variable region (Vα) comprising CDR3α, wherein the CDR3α comprises the amino acid sequence set forth in SEQ ID NO: 21, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising an amino acid sequence selected from the group consisting of SEQ ID NOs: 259, 260, 272, 261, and 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a § chain comprising the amino acid sequence set forth in SEQ ID NO: 60. In certain embodiments, the D chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 262, 263, 264, 273, and 250.

In another aspect, provided herein is an isolated TCR that comprises a β chain variable region (V) comprising CDR3β, wherein the CDR3β comprises the amino acid sequence set forth in SEQ ID NO: 36, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702); or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702); or v) any combination thereof. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a R chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 262, 263, 264, 273, and 250.

In another aspect, provided herein is an isolated TCR that comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, the Vα and Vβ comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, provided herein is an isolated TCR that binds to a peptide consisting of the amino acid sequence set forth in SEQ ID NO: 47. In certain embodiments, the TCR does not bind to, or does not substantially bind to a peptide consisting of an amino acid sequence selected from the group consisting of SEQ ID NOs: 45, 46, and 49-57. In certain embodiments, the binding between the TCR and a peptide consisting of an amino acid sequence selected from the group consisting of SEQ ID NOs: 45, 46, and 49-57 is substantially weakened relative to the binding between the TCR and a peptide consisting of the amino acid sequence set forth in SEQ ID NO: 47.

In another aspect, provided herein is an isolated TCR, wherein when the TCR is expressed on the surface of a T cell, the T cell is activated when co-cultured with a second cell displaying a peptide consisting of the amino acid sequence set forth in SEQ ID NO: 47 (e.g., a second cell displaying a peptide consisting of the amino acid sequence set forth in SEQ ID NO: 47 in the context of HLA-B*0702). In certain embodiments, when the TCR is expressed on the surface of a T cell, the T cell is not activated, or is not substantially activated when co-cultured with a second cell displaying a peptide consisting of an amino acid sequence selected from the group consisting of SEQ ID NOs: 45, 46, and 49-57 (e.g., a second cell displaying a peptide consisting of an amino acid sequence selected from the group consisting of SEQ ID NOs: 45, 46, and 49-57 in the context of HLA-B*0702). In certain embodiments, when the TCR is expressed on the surface of a T cell, the activation of the T cell is substantially weakened when the T cell is co-cultured with a second cell displaying a peptide consisting of an amino acid sequence selected from the group consisting of SEQ ID NOs: 45, 46, and 49-57 (e.g., a second cell displaying a peptide consisting of an amino acid sequence selected from the group consisting of SEQ ID NOs: 45, 46, and 49-57 in the context of HLA-B*0702) relative to the activation of the T cell when the T cell is co-cultured with a third cell displaying a peptide consisting of the amino acid sequence set forth in SEQ ID NO: 47 (e.g., a third cell displaying a peptide consisting of the amino acid sequence set forth in SEQ ID NO: 47 in the context of HLA-B*0702).

In certain embodiments of the foregoing aspects, the TCR comprises an α chain comprising an α chain constant region comprising the amino acid sequence set forth in SEQ ID NO: 41. In certain embodiments, the α chain constant region comprises the amino acid sequence set forth in SEQ ID NO: 42. In certain embodiments of the foregoing aspects, the TCR comprises an α chain comprising an α chain constant region comprising the amino acid sequence set forth in SEQ ID NO: 247.

In certain embodiments of the foregoing aspects, the TCR comprises a D chain comprising a β chain constant region comprising the amino acid sequence set forth in SEQ ID NO: 43, 44, or 248.

The following embodiments apply to each of the foregoing aspects.

In certain embodiment, the TCR is a human TCR (e.g., a full-length human TCR). In certain embodiment, the TCR is a full-length TCR, a soluble TCR, or a single-chain TCR.

In certain embodiment, the peptide is presented in the context of HLA-B*0702. In certain embodiment, when the TCR is expressed on the surface of a T cell, the T cell is activated when co-cultured with a second cell displaying the peptide (e.g., a second cell displaying the peptide in the context of HLA-B*0702). In certain embodiment, the T cell exhibits (a) increased CD69 surface expression, (b) increased CD25 surface expression, (c) increased CD107a expression, (d) increased T cell proliferation, (e) increased IFNγ secretion, or (f) increased nuclear factor of activated T cells (NFAT) promoter activation when co-cultured with the second cell displaying the peptide (e.g., a second cell displaying the peptide in the context of HLA-B*0702). In certain embodiment, the T cell induces apoptosis or death of the second cell displaying the peptide (e.g., a second cell displaying the peptide in the context of HLA-B*0702).

In certain embodiment, the TCR is conjugated to an effector moiety. In certain embodiments, the effector moiety is a cytotoxic agent, cytostatic agent, toxin, radionuclide, detectable label, or binding moiety. In certain embodiments, the binding moiety is an antibody. In certain embodiments, the binding moiety is an antibody Fc region.

In another aspect, the instant disclosure provides an isolated polynucleotide encoding a polypeptide comprising an α chain variable region and/or a β chain variable region, or an α chain and/or a D chain of a TCR disclosed herein. In certain embodiments, the polynucleotide comprises the nucleic acid sequence of SEQ ID NO: 90. In certain embodiments, the polynucleotide comprises the nucleic acid sequence of SEQ ID NO: 238. In certain embodiments, the polynucleotide encodes a polypeptide comprising an amino acid sequence selected from the group consisting of SEQ ID NOs: 83, 266, 267, 268, 269, 270, and 271. In certain embodiments, the polynucleotide encodes a polypeptide comprising the amino acid sequence of SEQ ID NO: 91. In certain embodiments, the polynucleotide encodes a polypeptide comprising the amino acid sequence of SEQ ID NO: 265. In certain embodiments, the polynucleotide encodes a polypeptide comprising the amino acid sequence of SEQ ID NO: 92.

In another aspect, the instant disclosure provides an isolated vector comprising a polynucleotide disclosed herein. In certain embodiments, the vector is a viral vector selected from the group consisting of a lentiviral vector, a retroviral vector, an adenoviral vector, an adeno-associated viral vector, and a baculoviral vector. In certain embodiments, the vector comprises an amino acid sequence selected from the group consisting of SEQ ID NOs: 83, 266, 267, 268, 269, 270, and 271.

In another aspect, the instant disclosure provides an engineered cell comprising a polynucleotide or vector disclosed herein. In certain embodiments, the polynucleotide or vector encodes an amino acid sequence selected from the group consisting of SEQ ID NOs: 83, 266, 267, 268, 269, 270, and 271. In another aspect, the instant disclosure provides a method of producing a TCR that binds to a peptide consisting of the amino acid sequence set forth in SEQ ID NO: 45 or 47, the method comprising culturing the engineered cell so that the polynucleotide is expressed and the TCR is produced. In another aspect, the instant disclosure provides an isolated TCR produced by such methods.

In another aspect, the instant disclosure provides a TCR encoded by a polynucleotide sequence disclosed herein. In another aspect, the instant disclosure provides a TCR that results from expression of a polynucleotide sequence disclosed herein.

In another aspect, the instant disclosure provides a method of producing an engineered cell expressing a TCR that binds to a peptide consisting of the amino acid sequence set forth in SEQ ID NO: 45 or 47, the method comprising contacting a cell with a polynucleotide (or a vector comprising such polynucleotide) encoding an α chain variable region and/or a β chain variable region, or an α chain and/or a D chain of a TCR disclosed herein (e.g., a polynucleotide comprising the nucleic acid sequence of SEQ ID NO: 90 or 238) under conditions that allow introduction of the vector into the cell. In certain embodiments, the polynucleotide is introduced into the cell using a vector (e.g., a viral vector). In certain embodiments, the polynucleotide is introduced into the cell by electroporation. In certain embodiments, the polynucleotide is mRNA and is introduced into the cell by electroporation.

In another aspect, the instant disclosure provides an engineered cell presenting a TCR disclosed herein on the cell surface. In certain embodiments, the cell expresses the TCR. In certain embodiments, the cell is a human lymphocyte. In certain embodiments, the cell is selected from the group consisting of an alpha beta or gamma delta T cell (e.g., a CD8+ T cell, or a CD4+ T cell), a natural killer T (NKT) cell, an invariant natural killer T (iNKT) cell, a mucosal-associated invariant T (MAiT) cell, and a natural killer (NK) cell. In one embodiment, the cell is an iNKT cell.

In another aspect, the instant disclosure provides a pharmaceutical composition comprising a TCR, polynucleotide, vector, or engineered cell disclosed herein, and a pharmaceutically acceptable carrier.

In another aspect, the instant disclosure provides a method of inducing an immune response to a cell displaying a peptide consisting of the amino acid sequence set forth in SEQ ID NO: 45 or 47 in a subject, the method comprising administering to the subject an effective amount of a TCR, polynucleotide, vector, engineered cell, or pharmaceutical composition disclosed herein. In another aspect, the instant disclosure provides a method of treating cancer in a subject, the method comprising administering to the subject an effective amount of a TCR, polynucleotide, vector, engineered cell, or pharmaceutical composition disclosed herein. In certain embodiments, the TCR, polynucleotide, vector, engineered cell, or pharmaceutical composition is administered intravenously. In certain embodiments, the methods further comprise administering an additional therapeutic agent to the subject. In certain embodiments, the additional therapeutic agent is a chemotherapeutic, a radiotherapeutic, or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist VISTA antibody, an antagonist CD96 antibody, an antagonist anti-CEACAM1 antibody, an antagonist anti-TIGIT antibody, an agonist anti-CD137 antibody, an agonist anti-GITR antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat. F001287, indoximod, and NLG919. In certain embodiments, the inhibitor is epacadostat. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 and is complexed with a tumor-associated antigenic peptide, wherein the HSPPC is derived from a tumor obtained from a subject. In certain embodiments, the cancer is leukemia (e.g., mixed lineage leukemia, acute lymphocytic leukemia, acute myeloid leukemia, chronic lymphocytic leukemia, or chronic myeloid leukemia), alveolar rhabdomyosarcoma, bone cancer, brain cancer (e.g., glioblastoma), breast cancer, cancer of the anus, anal canal, or anorectum, cancer of the eye, cancer of the intrahepatic bile duct (e.g., intrahepatic cholangiocellular cancer), cancer of the joints, cancer of the neck, gallbladder, or pleura, cancer of the nose, nasal cavity, or middle ear, cancer of the oral cavity, cancer of the vulva, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer (e.g., hepatocellular carcinoma), lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma (e.g., myxoid/round cell liposarcoma).

4. BRIEF DESCRIPTION OF THE DRAWINGS

Figure 3:
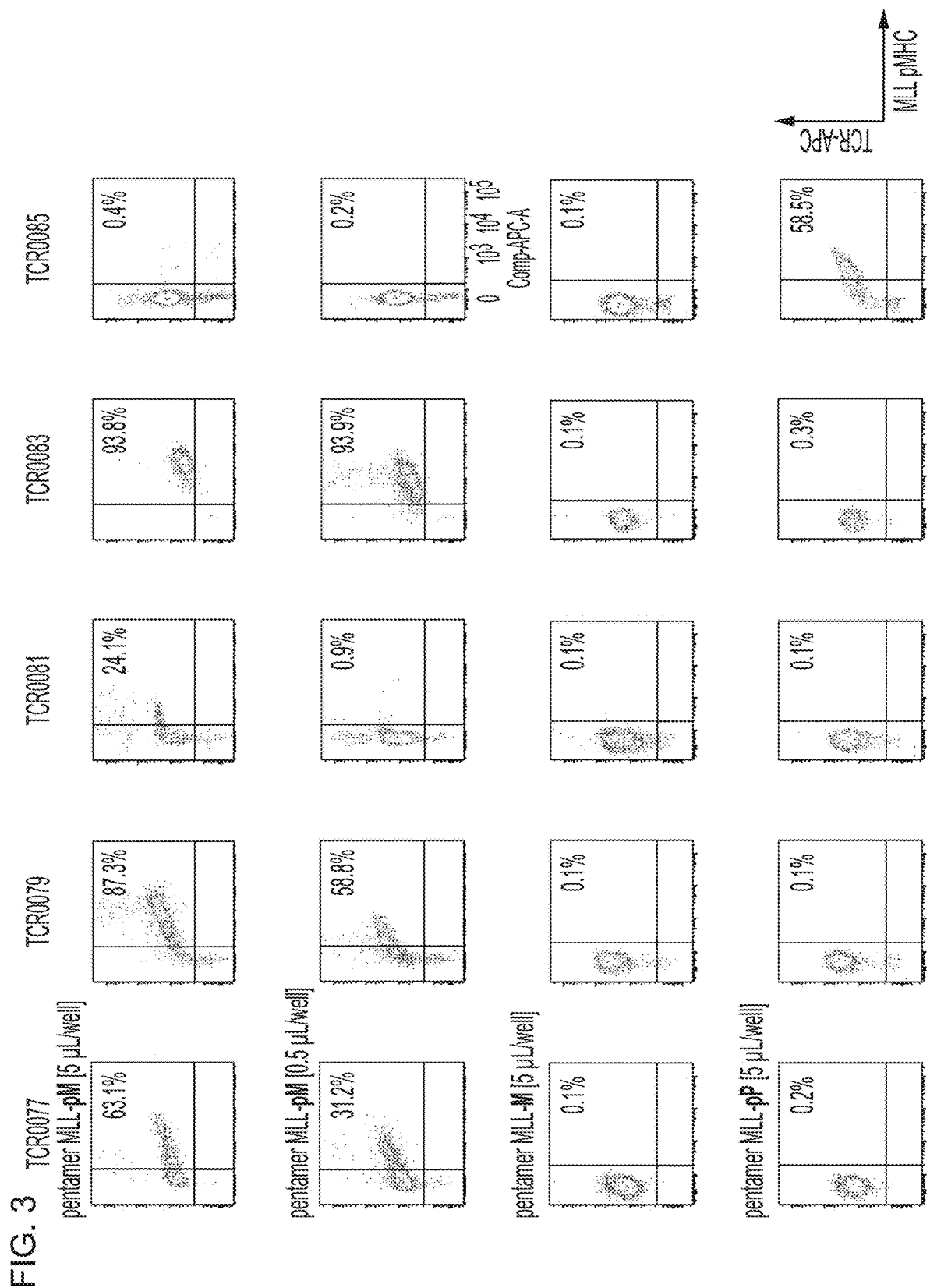

FIG. 3 is a set of flow cytometry plots showing staining of AK-D10R3 cells expressing the chimeric TCRs TCR0077, TCR0079, TCR0081. TCR0083, or TCR0085 with PE-labeled HLA-B*0702 pentamers loaded with the MLL-pM peptide (EPR[pS]PSHSM; SEQ ID NO: 45) (5 μL/well or 0.5 μL/well), the non-phosphorylated MLL-M control peptide (EPRSPSHSM: SEQ ID NO: 46) (5 μL/well) or the MLL-pP peptide (RVR[pS]PTRSP; SEQ ID NO: 47) (5 μL/well). The percentages of pentamer+ TCR+ cells are indicated in the upper right panel of each plot.

Figure 4A:
Figure 4B:
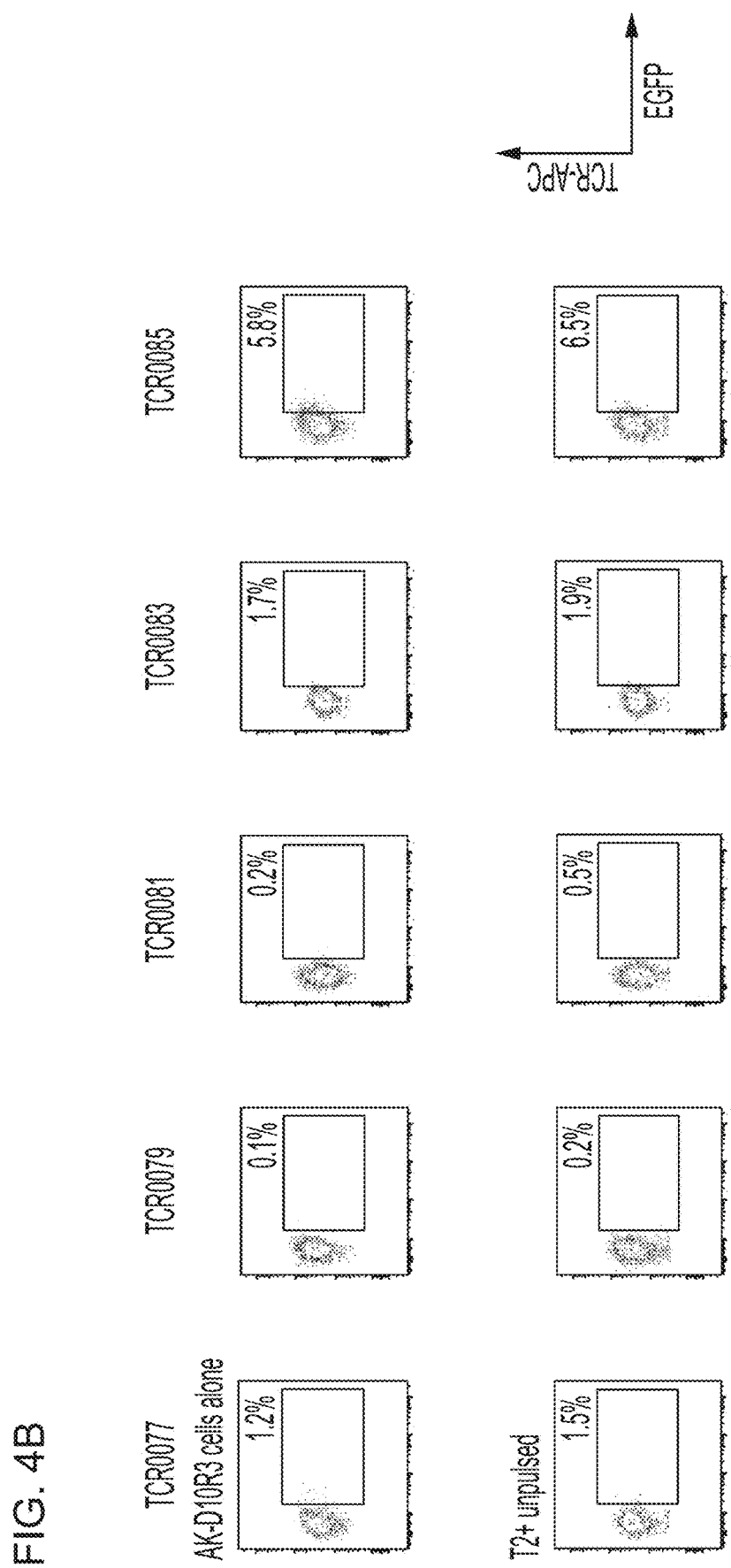

FIGS. 4A and 4B are flow cytometry plots showing the results of an assay testing activation of AK-D10R3 single cell clones expressing the chimeric TCRs TCR0077, TCR0079, TCR0081, TCR0083, or TCR0085 after co-culture with T2-B7 cells (i.e., T2 cells overexpressing HLA-B*0702) pulsed with 50 μg/ml or 5 μg/mL of the MLL-pM peptide (EPR[pS]PSHSM: SEQ ID NO: 45), 50 μg/mL of the MLL-M control peptide (EPRSPSHSM; SEQ ID NO: 46), or 50 μg/mL of the MLL-pP peptide (RVR[pS]PTRSP; SEQ ID NO: 47) at an effector to target cell ratio of 2:1. TCR-expressing AK-D10R3 cells alone or co-cultures containing TCR-expressing AK-D10R3 cells and non-pulsed T2-B7 cells were included as controls. The percentages of TCR+EGFP+ cells are indicated in the upper right panel of each plot.

Figure 5:
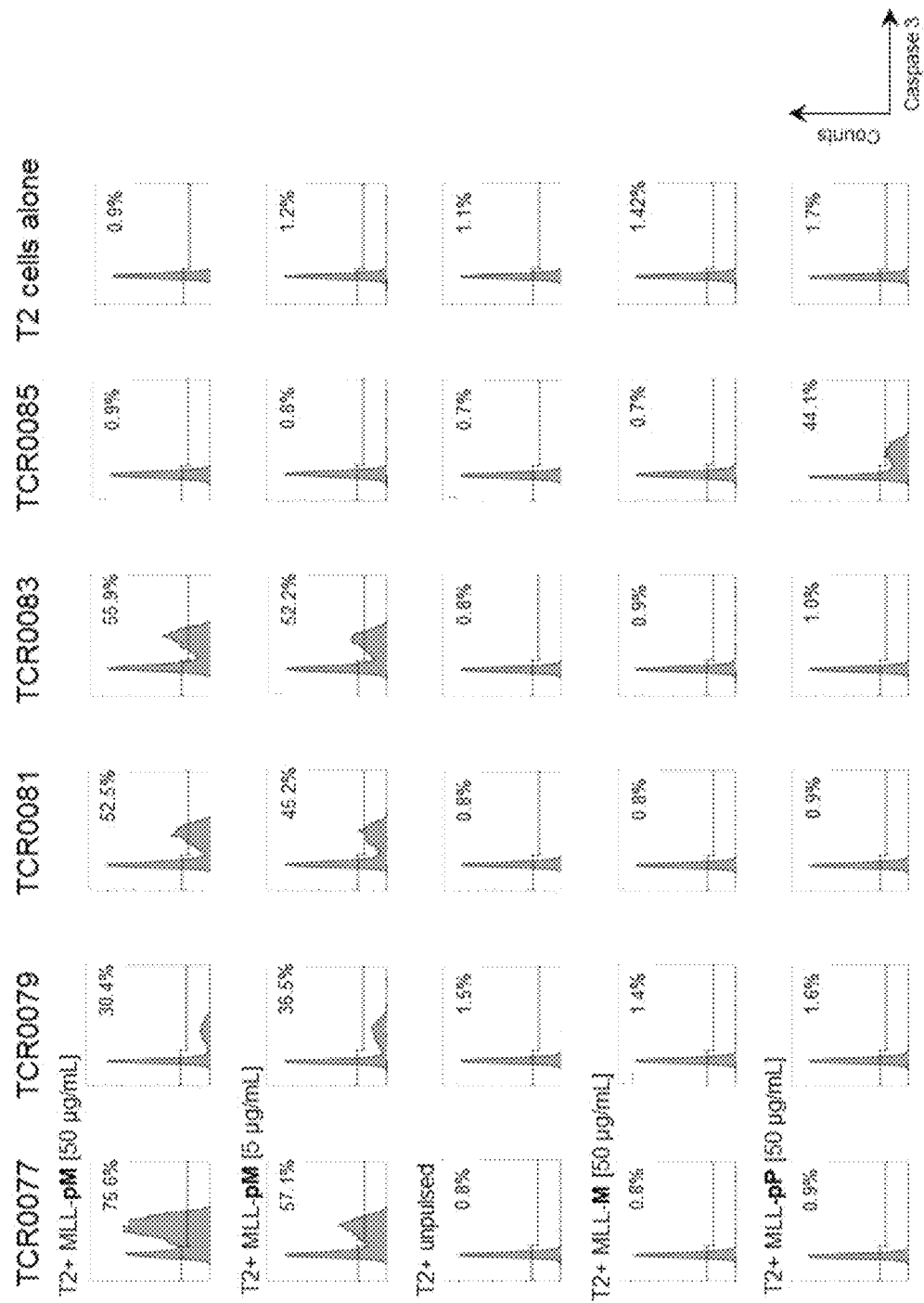

FIG. 5 is a set of histograms showing the results of an assay testing the potential of TCR-expressing AK-D10R3 single cell clones to induce apoptosis in T2-B7 target cells pulsed with 50 μg/ml or 5 μg/mL of the MLL-pM peptide (EPR[pS]PSHSM: SEQ ID NO: 45), 50 μg/mL of the MLL-M control peptide (EPRSPSHSM; SEQ ID NO: 46), or 50 μg/mL of the MLL-pP peptide (RVR[pS]PTRSP: SEQ ID NO: 47). Co-cultures containing non-pulsed T2-B7 cells or T2-B7 cells incubated without TCR-expressing AK-D10R3 cells served as controls. The percentages of caspase+ T2-B7 cells are indicated in the upper right panel of each histogram.

FIGS. 6A and 6B are bar graphs showing activation of TCR0077-expressing or TCR0085-expressing AK-D10R3 cells after co-culturing with T2-B7 target cells pulsed with the MLL-pM peptide (EPR[pS]PSHSM; SEQ ID NO: 45), its alanine-modified variants, the MLL-M peptide, or the MLL-pP peptide. Activation of the AK-D10R3 cells was assessed by measuring EGFP expression resulting from the activation of an IL-2-(NFAT)$_3$-EGFP reporter construct. Assays were performed in triplicate and the y axis shows the percentage of EGFP-positive TCR-positive AK-D10R3 cells.

Figures 7A, 7B:
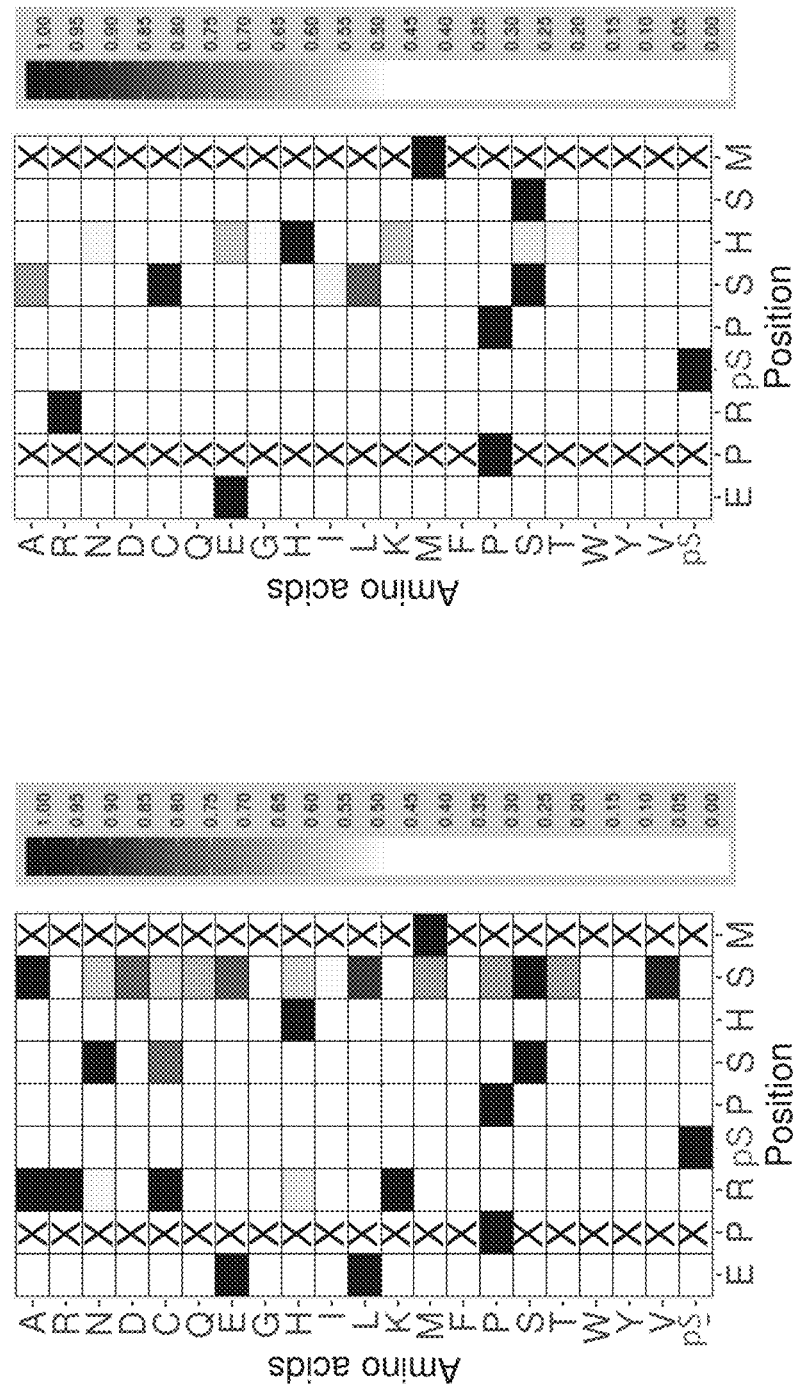

FIGS. 7A and 7B are heat maps comparing specificities of the indicated TCRs (FIG. 7A: TCR0077; FIG. 7B: TCR0081) to a panel of variants of the peptide EPR[pS]PSHSM (SEQ ID NO: 45), where each amino acid position in each peptide, except for the anchor positions P2 (P) and P9 (M), of SEQ ID NO: 45 was individually substituted with each of the 19 other possible naturally occurring amino acids, and position P4 ([pS]) was additionally substituted with non-phosphorylated serine. Each peptide of the panel was separately loaded onto T2 target cells, prior to co-culturing with TCR-expressing AK-D10R3 effector cells. Upon binding of the TCR to a resulting mutant peptide, the AK-D10R3 cells were activated to express an EGFP reporter, which was detected by FACS. The results are shown as heat maps in which each block represents the amino acid residue substitution of the native residue in the MLL-pM peptide EPR[pS]PSHSM (SEQ ID NO: 45). The native residues are shown on the horizontal axis and the substituted residues indicated on the vertical axis. Each block is shaded in scale to the normalized mean activation (with normalized values cropped to a minimum of 0.0 and to a maximum of 1.0). "X" denotes untested mutants. Background activation (no peptide loaded) was subtracted from all peptide-loaded samples (altered and native sequences).

Figure 8A:
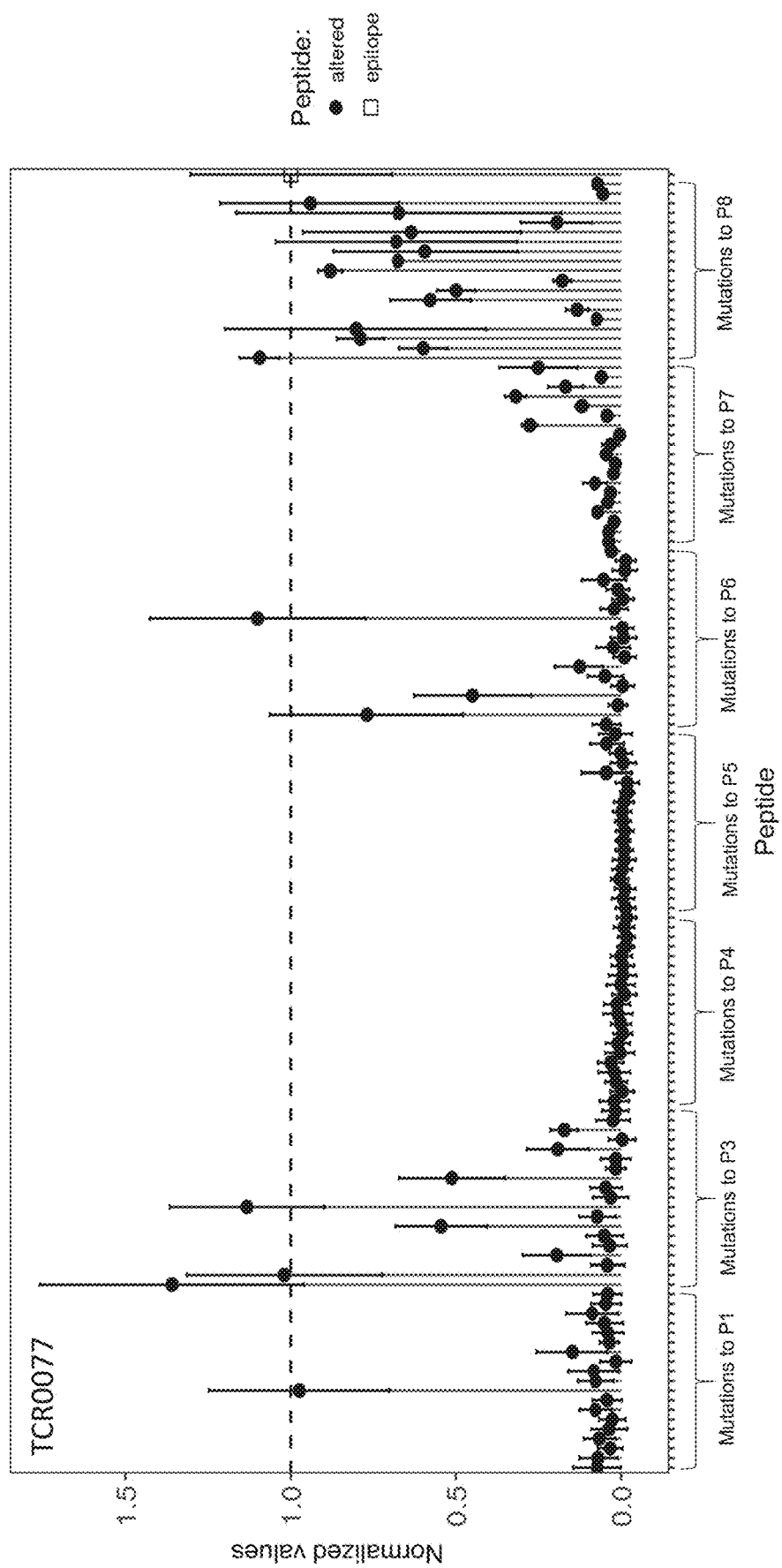
Figure 8B:
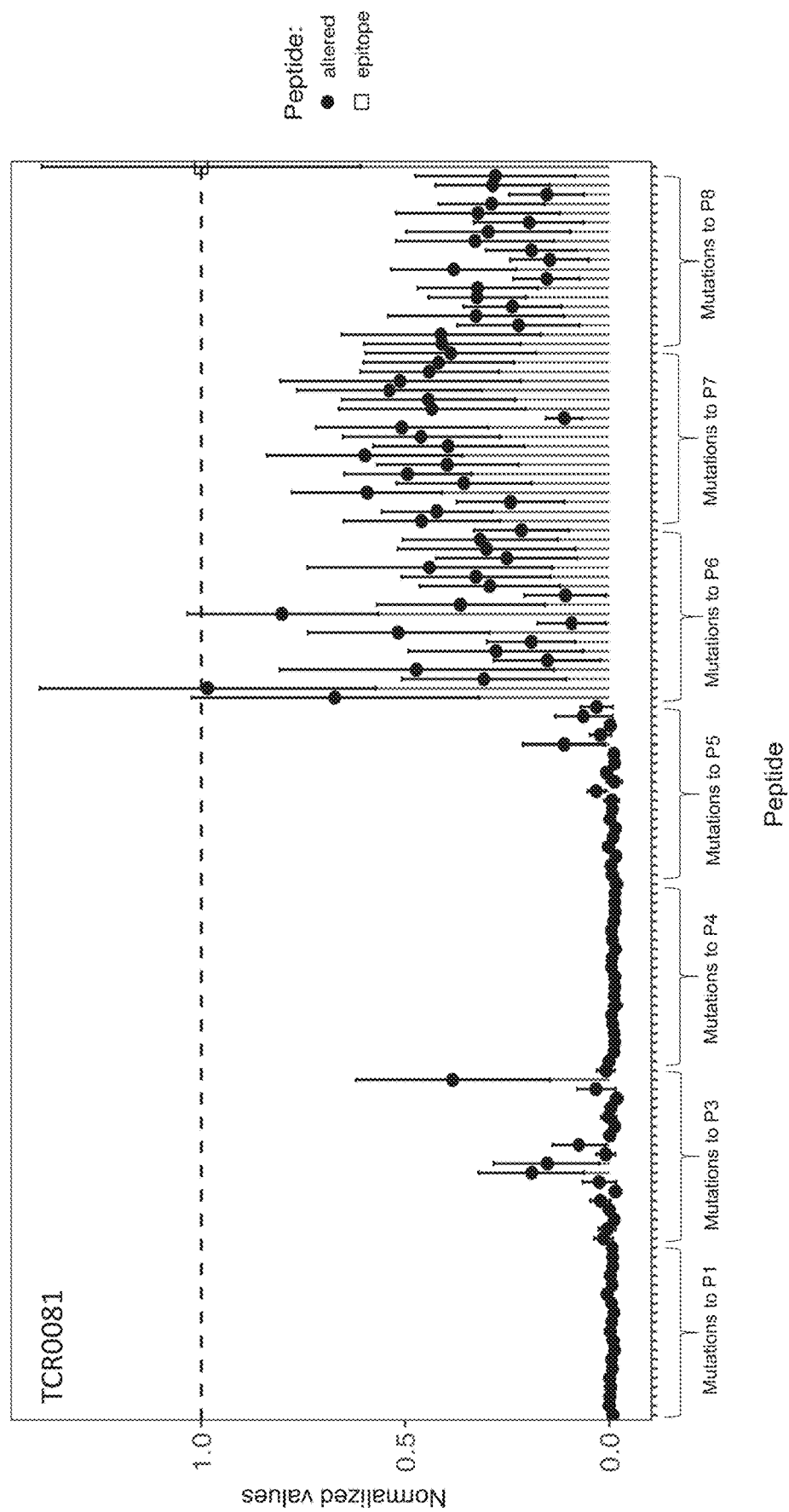

FIGS. 8A and 8B are bar graphs comparing the specificity profiles of the indicated TCRs (FIG. 8A: TCR0077; FIG. 8B: TCR0081), and show normalized mean activation values for each variant MLL-pM peptide (black dot, "altered") described in Table 8, as well as the values for the peptide EPR[pS]PSHSM (SEQ ID NO: 45) (open square. "epitope"). Normalized mean activation values corresponding to the variant MLL-pM peptides in Table 8 are displayed, left to right, according to the peptide sequence in Table 8, i.e., SEQ ID NOs: 49, 110-127, 51, 128-145, 52, 146-159, 46, 160-163, 53, 164-181, 54, 182-199, 55, 200-217, 56, and 218-235. Brackets were used to designate groups of variant MLL-pM peptides according to the position of their variant residue in the MLL-pM peptide sequence. Error bars represent the standard error of the mean (SEM).

Figures 9C, 9D:
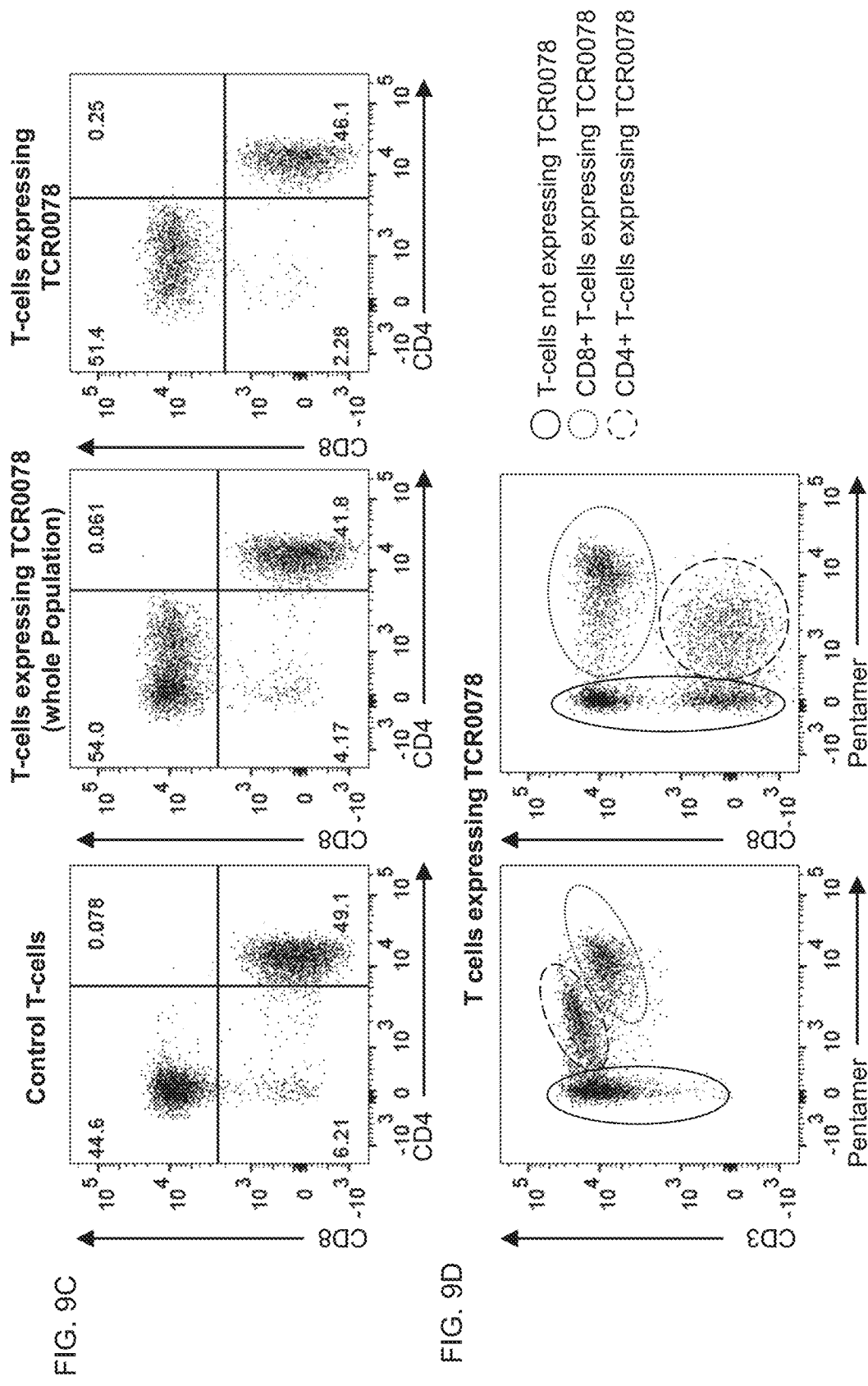

FIGS. 9A-9D are flow cytometry plots showing the phenotype of control T cells and TCR0078-transduced T cells. Specifically, stimulated primary T cells, with or without TCR transduction, were stained with a Zombie NIR™ Live/Dead reagent, anti-CD3-FITC, anti-CD4-PerCp/Cy5.5 and anti-CD8-PE/Cy7 antibodies, and the PE-conjugated HLA-B*0702 pentamer loaded with the MLL-pM peptide EPR[pS]PSHSM (SEQ ID NO:45). FIG. 9A shows the sequence of flow cytometry gates used to identify intact, live, singlet cells. Specifically, the left panel shows the gate used for the selection of intact cells from the whole sample, the middle panel shows the gate used for the selection of live cells from intact cells; and the right panel shows the gate for used for the selection of singlet cells from live cells. The data in FIG. 9A are for control T cells. Similar data was obtained for TCR0078-transduced T cells using the same flow cytometry gate parameters. Numbers in each panel show the percentage of cells passing through each gate, with intact, live, singlet cells used for the remainder of the experiment. In FIG. 9B, anti-CD3-FITC antibody staining was used to identify T cells and pentamer staining was used to identify cells expressing TCR0078 in both control (left) and TCR0078-transduced (right) T cells. FIG. 9C shows the expression of CD4 and CD8 in each of three conditions: the left panel shows data from the whole population of control T cells (from left panel. FIG. 9B); the middle panel shows data from the whole population of TCR0078 transduced cells (from right panel. FIG. 9B); and, the right panel shows data from the 58.1% of cells identified as expressing TCR0078 by pentamer staining (from gated cells in right panel of FIG. 9B). CD4 and CD8 were identified by staining with anti-CD4-PerCp/Cy5.5 and anti-CD8-PE/Cy7 antibodies respectively. Two cell populations were identified (CD4+/CD8− and CD4−/CD8+). The two cell populations were also apparent with other staining, such as anti-CD3 or anti-CD8 antibodies with pentamer staining (FIG. 9D).

Figure 10:
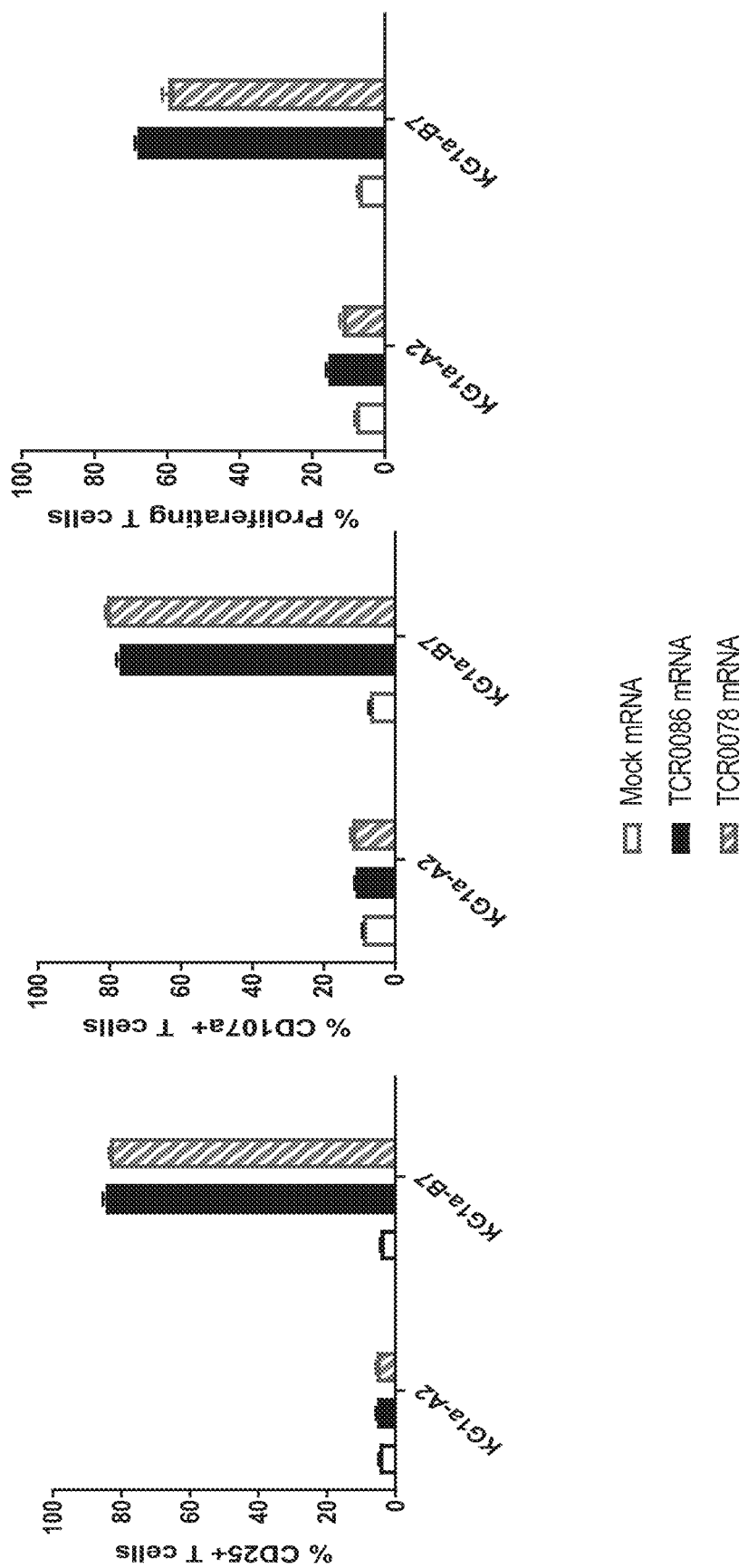

FIG. 10 is a set of bar graphs showing results from an assay testing the activation of T cells that were electroporated with mock mRNA, TCR0086 mRNA, or TCR0078 mRNA and co-cultured with KG1a-A2 cells expressing MLL or KG1a-B7 cells expressing MLL, at an effector: target ratio of 2:1. The left panel shows the percentage of CD25+ T cells. The middle panel shows the percentage of CD107a+ T cells. The right panel shows the percentage of proliferating T cells.

Figure 11:
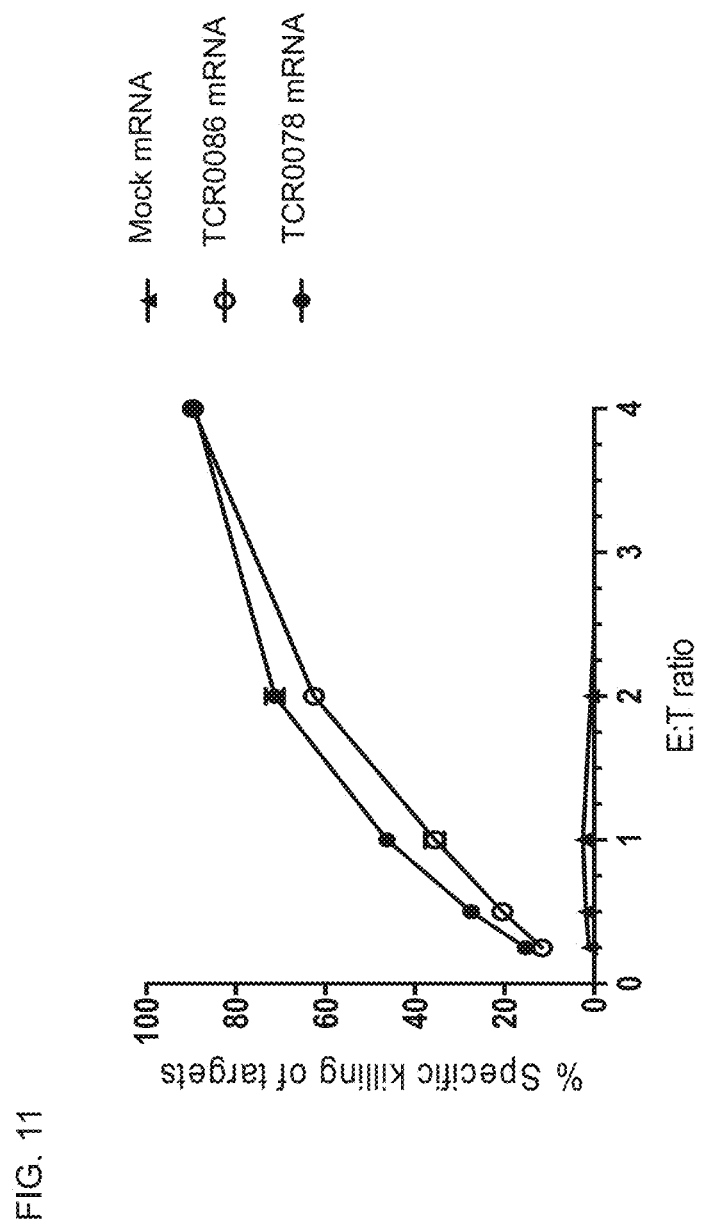

FIG. 11 is a graph showing the percentage of specific killing of KG1a-B7 target cells by T cells electroporated with mock mRNA, TCR0086 mRNA, or TCR0078 mRNA. The x axis shows the effector:target (E:T) ratios used in this study.

FIGS. 12A-12C are a set of bar graphs showing activation of a Jurkat IL-2-NFAT-luciferase reporter cell line expressing TCR0078, upon co-culturing with various tumor cell lines expressing HLA-B*0702. In FIG. 12A, the Jurkat cells (Effector) were co-cultured with KG1a cells overexpressing HLA-B*0702 ("KG1a B7"), K562 cells overexpressing HLA-B*0702 ("K562 B7"), Namalwa cells, or Loucy cells (Target) for 24 hours at various effector:target ratios (as the x-axis). Activation of the Jurkat cells was assessed by measuring luciferase activity (represented on the y-axis by arbitrary units (a.u.)) resulting from the activation of the IL-2-NFAT-luciferase reporter. FIG. 12B represents a negative control in which Jurkat reporter cells not transduced with TCR0078 were co-cultured with the same tumor cells. As a positive control, the luminescence was measured after Jurkat cells, either expressing TCR0078 or not, were stimulated with phorbol 12-myristate 13-acetate (PMA) and Ionomycin (representing maximum NFAT-luciferase expression) (FIG. 12C). For "Jurkat control," the non-transduced Jurkat report cells described for FIG. 12B were used. For "Jurkat expressing TCR," TCR0078-transduced Jurkat reporter cells originating from one cell clone ("c75") with optimal TCR expression were used.

FIGS. 13A-13C are a set of bar graphs showing activation of a Jurkat NFAT-luciferase reporter cell line expressing TCR0078, after co-culturing with various tumor cell lines. TCR0078-transduced Jurkat reporter cells expressing HLA-B*0702 (Effector) were co-cultured for 24 hours at various ratios with tumor cell lines such as Loucy. H929, and KG1a overexpressing HLA-B*0702 ("KG1a B7") (FIG. 13A): Raji, YT-Indy, J.RT3-T3.5, KG1a B7, and Raji overexpressing HLA-B*0702 (FIG. 13B); and THP-1, LCL 721.221, THP-1 overexpressing HLA-B*0702, U266B1, KG1a B7, and LCL 721.221 overexpressing HLA-B*0702 ("721.221 B7") (FIG. 13C). Activation of the Jurkat cells was assessed by measuring luciferase bioluminescence activity (represented on the y-axis by arbitrary units (a.u.)) resulting from the activation of the IL-2-NFAT-Luciferase reporter. KG1a-HLA-B*0702 cell line was used as a reference for other tumor cell lines in each Figure.

Figure 14:
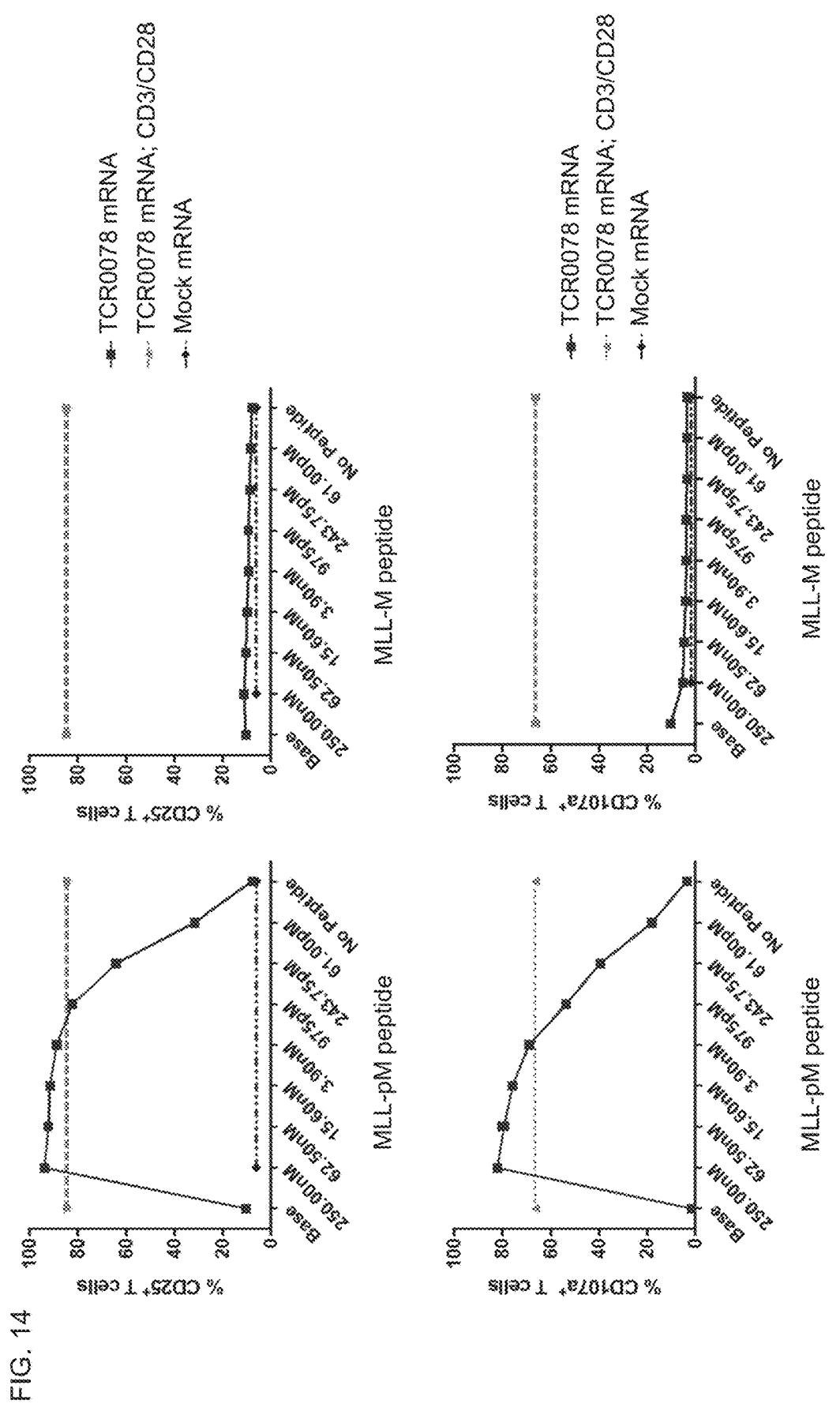

FIG. 14 is a panel of graphs showing results from an assay testing the activation of T cells that were electroporated with mock mRNA or TCR0078-encoding mRNA and co-cultured with T2-B7 target cells pulsed with either the MLL-pM phosphopeptide or the non-phosphorylated MLL-M control peptide. T cells incubated with anti-CD3 and anti-CD28 antibodies were used as positive controls ("TCR0078 mRNA; CD3/CD28"). The upper two panels show the percentage of CD25+ T cells. The lower two panels show the percentage of CD107a+ T cells. In all four panels, the x axis shows the concentrations of the peptides used to pulse the T2-B7 cells.

Figure 15:
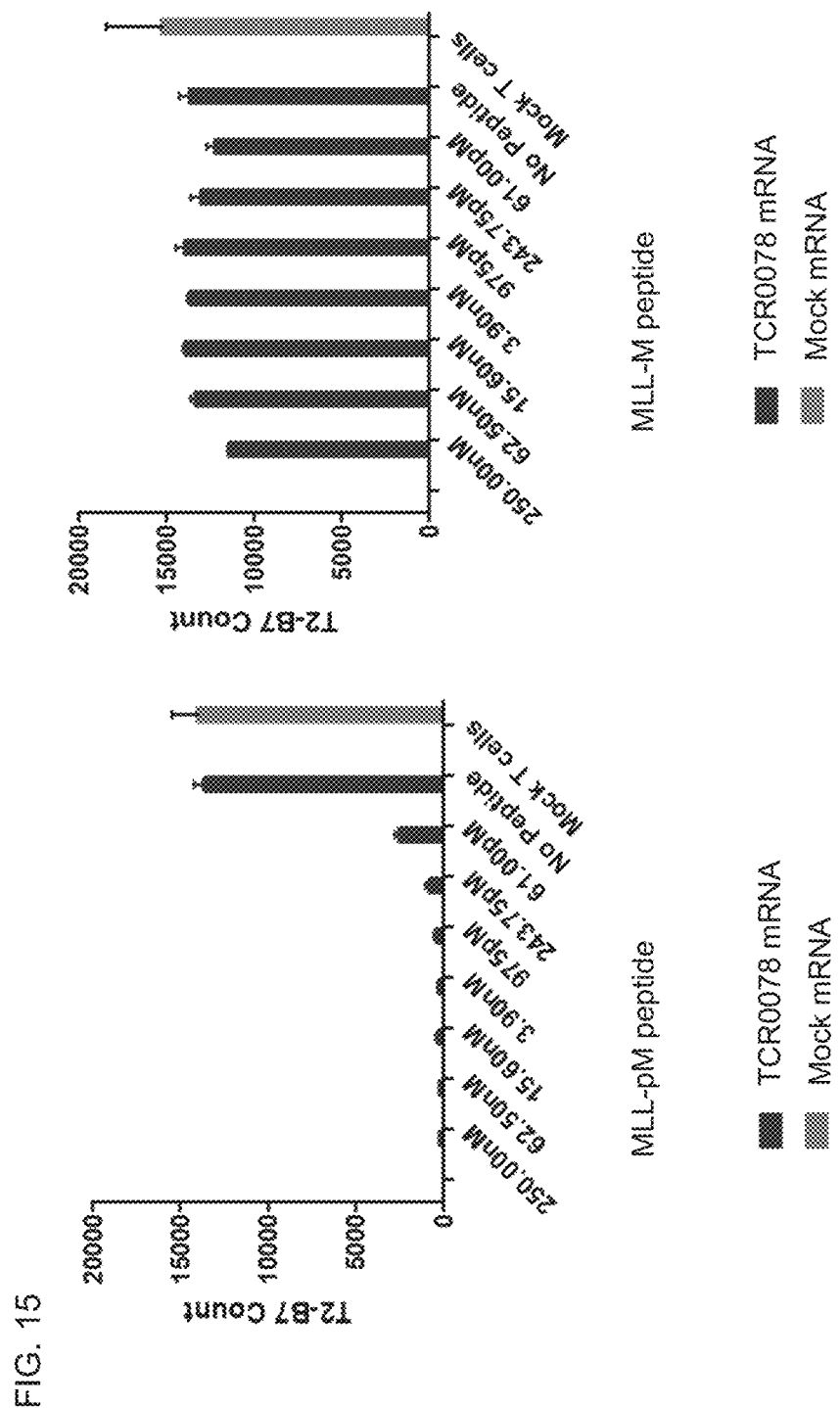

FIG. 15 is a pair of graphs showing the counts of peptide-pulsed T2-B7 cells after being co-cultured with T cells electroporated with mock mRNA or TCR0078 mRNA. The T2-B7 cell had been pulsed with the MLL-pM phosphopeptide or the non-phosphorylated MLL-M control peptide before co-culturing. The x axis shows the concentrations of the peptides used to pulse the T2-B7 cells.

FIGS. 16A-16C are a set of graphs showing an assay testing the activation and cytotoxic activity of TCR0078-transduced T cells co-cultured with T2-HLA-B*0702 ("T2-B7 cells") pulsed with the MLL phosphopeptide EPR[pS]SHSM (SEQ ID NO: 45) or the non-phosphorylated control peptide EPRSPSHSM (SEQ ID NO: 46). T2 cells expressing HLA-B*0702 were labeled with CFSE and then pulsed for 2.5 hours with a dose titration of either peptide, prior to co-culturing with primary T cells stably expressing TCR0078 for 20 hours. FIG. 16A shows the percentage of killing of T2-HLA-B*0702 cells (calculated by subtracting the alive T2-B7 cell number from the total T2-B7 number without co-culturing with the effector primary T cell, then divided by the total T2-B7 number without co-culturing) by TCR0078-transduced T cells after co-culturing. FIGS. 16B and 16C show the percentage of CD25 and IFN-γ positive primary T cells, respectively, in all primary T cells, detected by anti-CD25-PE/Cy7 and anti-IFNγ-FITC antibodies and measured by fluorescence emitted from the corresponding fluorescent-dye. The x-axis shows the concentration of the peptides used to pulse the T2-B7 cells. A two-way ANOVA with Bonferroni test was used. "**" signifies p=0.001.

Figure 17B:
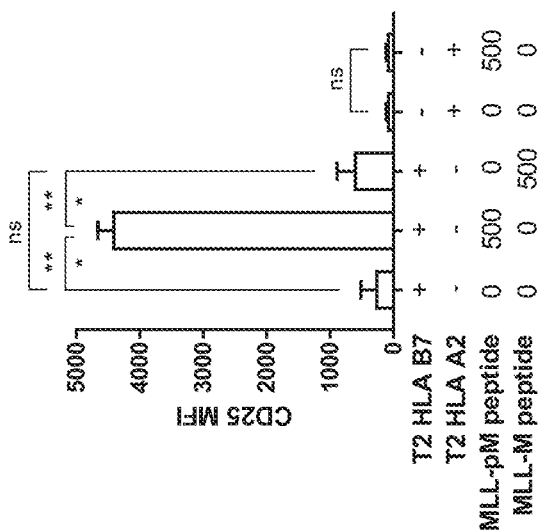
Figure 17A:
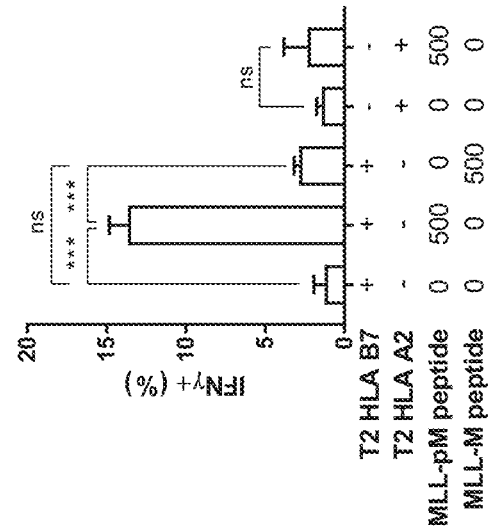

FIGS. 17A and 17B are a pair of bar graphs showing an assay testing the activation of TCR0078-transduced primary T cells co-cultured with T2 cells expressing HLA*A02.01 or T2-HLA-B*0702 and pulsed with either the phosphopeptide EPR[pS]PSHSM (SEQ ID NO: 45) or non-phosphorylated peptide EPRSPSHSM (SEQ ID NO: 46). CD25 and IFNγ expression by the effector primary T cells were measured as in FIG. 16. FIG. 17A compares the surface expression of CD25 on the T cells (MFI=Mean Fluorescent Expression) after co-culturing with T2 target cells pulsed with different peptides. FIG. 17B compares the percentage of IFN-γ positive T cells of the total effector primary T cells after the co-culturing. A two-way ANOVA with Bonferroni test was used. "*" signifies p=0.05. "" signifies p=0.01. "*" signifies p=0.001. "ns" signifies non-significant.

FIGS. 18A-18C are a set of bar graphs showing an assay testing the cytotoxic activity and activation of control or TCR0078-transduced primary T cells, co-cultured with either KG1a-HLA*A02.01 or KG1a-HLA-B*0702. The co-culturing, cell staining, and number counting methods were the same as those in FIG. 16. FIG. 18A shows the percentage of killing of KG1a tumor cells by primary T cells after co-culturing, representing the cytotoxic activity of T cells toward KG1a tumor cells. FIG. 18B and FIG. 18C show the percentage of CD25 and IFN-γ positive primary T cells, respectively, after co-culturing. A two-way ANOVA with Bonferroni test was used. "***" signifies p=0.001.

FIGS. 19A-19E are a set of bar graphs showing assays testing the cytotoxic activity of control and TCR0078-transduced primary T cells co-cultured with KG1a-HLA-B*0702, K562-HLA-B*0702, SK-MEL-5, U266B1, or Namalwa tumor cell lines. The co-culturing, cell staining, and number counting methods were the same as those used in the experiments set forth in FIGS. 18A-18C. The x-axis indicates the ratio of T cell/Tumor cells used. A two-way ANOVA with Bonferroni test was used. "*" signifies p=0.05. "" signifies p=0.01. "*" signifies p=0.001.

Figure 20B:
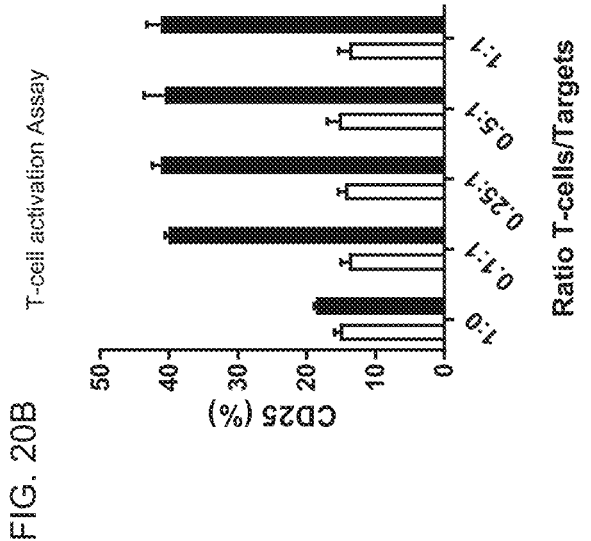
Figure 20A:
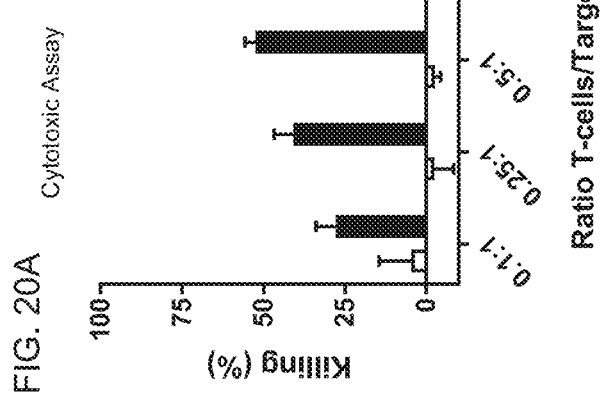

FIGS. 20A and 20B are a set of bar graphs showing an in vitro assay of cytotoxic activity and activation of TCR0078-transduced T cells co-cultured with KG1a-HLA-B*0702 before adoptive transfer to NOG mice bearing KG1a-HLA-B*0702 tumor. FIG. 20A and FIG. 20B compare the cytotoxic activity and T cell activation (represented by CD25 expression), respectively, between control and TCR0078-transduced T cells. The x-axis indicates the various T cell/tumor cell ratios.

FIGS. 21A-21C are a set of graphs and flow cytometry plots showing the anti-tumor activity of TCR0078-transduced human primary T cells after adoptive transfer to NOG mice bearing a KG1a-HLA-B*0702 tumor. Twenty mice were each injected with one million tumor cells (KG1a-HLA-B*0702) subcutaneously. One day post-injection ten of the twenty mice were injected intravenously with 5 million TCR0078-transduced primary T cells ("T cells expressing TCR0078") and the other ten mice remained un-injected ("no T cells"). FIG. 21A compares tumor volumes (average+/−SEM) in the two groups (n=10 each) of mice measured every 3-5 days from Day 7 to Day 42. A two-way ANOVA with Bonferroni test was used. "***" signifies p=0.001. FIG. 21B compares tumor volumes of the 10 individual mice injected with the T cells expressing TCR0078. After the first measurement at Day 7, two of the ten mice were sacrificed to confirm T cells injection and homing; hence, no data points after Day 7 were available for these two mice. Each line in FIG. 21B represents the tumor volumes of one of the eight remaining mice throughout the 42-day period. Except for two mice with significant tumor growth (white circles), six of the eight mice had minimal tumor growth (black circles). FIG. 21C shows a pair of flow cytometry plots identifying human T-cells and metastatic tumor cells in the spleen of mice injected with TCR0078 transduced T cells. All mice were sacrificed at day 41 post tumor implantation and their spleens were collected, processed and stained with anti-CD3 and anti-CD45 antibodies for subsequent detection by Fluorescence-activated cell sorting (FACS). The left panel of FIG. 21C shows the percentage of T cells (CD3+/CD45+, 0.027% of all cells in the sample) and tumor cells (CD3−/CD45+, 0.25% of all cells in the sample) in an injected mouse with significant tumor growth in FIG. 21B. The right panel of FIG. 21C shows the percentage of T cells (72.5%) and tumor cells (0.037%) in the spleen of an injected mouse with minimal tumor growth in FIG. 21B. The percentage of cells within each gate is indicated.

5. DETAILED DESCRIPTION

Provided are TCRs (e.g., TCRs that bind to MLL phosphopeptides), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells displaying MLL phosphopeptides on the cell surface, and hence for treating a MLL-expressing cancer in a subject.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "MLL" refers to mixed lineage leukemia (also known as Histone-lysine N-methyltransferase 2A), that in human is encoded by the KMT2A gene.

As used herein, the terms "T cell receptor" and "TCR" are used interchangeably and refer to molecules comprising CDRs or variable regions from αβ or γδ T cell receptors. Examples of TCRs include, but are not limited to, full-length TCRs, antigen-binding fragments of TCRs, soluble TCRs lacking transmembrane and cytoplasmic regions, single-chain TCRs containing variable regions of TCRs attached by a flexible linker, TCR chains linked by an engineered disulfide bond, single TCR variable domains, single peptide-MHC-specific TCRs, multi-specific TCRs (including bispecific TCRs), TCR fusions, TCRs comprising co-stimulatory regions, human TCRs, humanized TCRs, chimeric TCRs, recombinantly produced TCRs, and synthetic TCRs. In certain embodiments, the TCR is a full-length TCR comprising a full-length α chain and a full-length β chain. In certain embodiments, the TCR is a soluble TCR lacking transmembrane and/or cytoplasmic region(s). In certain embodiments, the TCR is a single-chain TCR (scTCR) comprising Vα and Vβ linked by a peptide linker, such as a scTCR having a structure as described in PCT Publication No.: WO 2003/020763, WO 2004/033685, or WO 2011/044186, each of which is incorporated by reference herein in its entirety. In certain embodiments, the TCR comprises a transmembrane region. In certain embodiment, the TCR comprises a co-stimulatory signaling region.

As used herein, the term "full-length TCR" refers to a TCR comprising a dimer of a first and a second polypeptide chain, each of which comprises a TCR variable region and a TCR constant region comprising a TCR transmembrane region and a TCR cytoplasmic region. In certain embodiments, the full-length TCR comprises one or two unmodified TCR chains, e.g., unmodified α, β, γ, or δ TCR chains. In certain embodiments, the full-length TCR comprises one or two altered TCR chains, such as chimeric TCR chains and/or TCR chains comprising one or more amino acid substitutions, insertions, or deletions relative to an unmodified TCR chain. In certain embodiments, the full-length TCR comprises a mature, full-length TCR α chain and a mature, full-length TCR β chain. In certain embodiments, the full-length TCR comprises a mature, full-length TCR γ chain and a mature, full-length TCR δ chain.

As used herein, the term "TCR variable region" refers to the portion of a mature TCR polypeptide chain (e.g., a TCR α chain or β chain) which is not encoded by the TRAC gene for TCR α chains, either the TRBC1 or TRBC2 genes for TCR β chains, the TRDC gene for TCR S chains, or either the TRGC1 or TRGC2 gene for TCR γ chains. In some embodiments, the TCR variable region of a TCR α chain encompasses all amino acids of a mature TCR α chain polypeptide which are encoded by a TRAV and/or TRAJ gene, and the TCR variable region of a TCR β chain encompasses all amino acids of a mature TCR β chain polypeptide which are encoded by a TRBV, TRBD, and/or TRBJ gene (see, e.g., T cell receptor Factsbook, (2001) LeFranc and LeFranc, Academic Press, ISBN 0-12-441352-8, which is incorporated by reference herein in its entirety). TCR variable regions generally comprise framework regions (FR) 1, 2, 3 and 4 and complementarity determining regions (CDR) 1, 2 and 3.

As used herein, the terms "α chain variable region" and "Vα" are used interchangeably and refer to the variable region of a TCR α chain.

As used herein, the terms "13 chain variable region" and "Vβ" are used interchangeably and refer to the variable region of a TCR β chain.

As used herein in the context of a TCR, the term "CDR" or "complementarity determining region" means the non-contiguous antigen combining sites found within the variable regions of a TCR chain (e.g., an α chain or a β chain). These regions have been described in Lefranc, (1999) The Immunologist 7: 132-136, Lefranc et al., (1999) Nucleic Acids Res 27: 209-212, LeFranc (2001) *T cell receptor Factsbook*, Academic Press, ISBN 0-12-441352-8, Lefranc et al., (2003) Dev Comp Immunol. 27(1):55-77, and in Kabat et al., (1991) *Sequences of protein of immunological interest*, each of which is herein incorporated by reference in its entirety. In certain embodiments, CDRs are determined according to the IMGT numbering system described in Lefranc (1999) supra. In certain embodiments, CDRs are defined according to the Kabat numbering system described in Kabat supra. In certain embodiments, CDRs are defined empirically, e.g., based upon a structural analysis of the interaction of a TCR with a cognate antigen (e.g., a peptide or a peptide-MHC complex). In certain embodiments, the α chain and β chain CDRs of a TCR are defined according to different conventions (e.g., according to the Kabat or IMGT numbering systems, or empirically based upon structural analysis).

As used herein, the term "framework amino acid residues" refers to those amino acids in the framework region of a TCR chain (e.g., an α chain or a β chain). The term "framework region" or "FR" as used herein includes the amino acid residues that are part of the TCR variable region, but are not part of the CDRs.

As used herein, the term "constant region" with respect to a TCR refers to the portion of a TCR that is encoded by the TRAC gene (for TCR α chains), either the TRBC1 or TRBC2 gene (for TCR β chains), the TRDC gene (for TCR S chains), or either the TRGC1 or TRGC2 gene (for TCR γ chains), optionally lacking all or a portion of a transmembrane region and/or all or a portion of a cytoplasmic region. In certain embodiments, a TCR constant region lacks a transmembrane region and a cytoplasmic region. A TCR constant region does not include amino acids encoded by a TRAV, TRAJ, TRBV, TRBD, TRBJ, TRDV, TRDD, TRDJ, TRGV, or TRGJ gene (see, e.g., *T cell receptor Factsbook*, (2001) LeFranc and LeFranc. Academic Press, ISBN 0-12-441352-8, which is incorporated by reference herein in its entirety).

As used herein, the terms "major histocompatibility complex" and "MHC" are used interchangeably and refer to an MHC class I molecule and/or an MHC class II molecule.

As used herein, the term "MHC class I" refers to a dimer of an MHC class I α chain and a β2 microglobulin chain and the term "MHC class II" refers to a dimer of an MHC class II α chain and an MHC class II β chain.

As used herein, the term "peptide-MHC complex" refers to an MHC molecule (MHC class I or MHC class II) with a peptide bound in the art-recognized peptide binding pocket of the MHC. In some embodiments, the MHC molecule is a membrane-bound protein expressed on cell surface. In some embodiments, the MHC molecule is a soluble protein lacking transmembrane or cytoplasmic regions.

As used herein, the terms "[pS]" and "(pS)" are used interchangeably and refer to phosphoserine.

As used herein, the term "extracellular" with respect to TCR refers to the portion or portions of a recombinant transmembrane protein that are located outside of a cell.

As used herein, the term "transmembrane" with respect to a TCR chain refers to the portion or portions of a TCR chain that are embedded in the plasma membrane of a cell.

As used herein, the term "cytoplasmic" with respect to a TCR chain refers to the portion or portions of a TCR chain that are located in the cytoplasm of a cell.

As used herein, the term "co-stimulatory signaling region" refers to the intracellular portion of a co-stimulatory molecule that is responsible for mediating intracellular signaling events.

"Binding affinity" generally refers to the strength of the sum total of non-covalent interactions between a single binding site of a molecule (e.g., a TCR) and its binding partner (e.g., a peptide-MHC complex). Unless indicated otherwise, as used herein, "binding affinity" refers to intrinsic binding affinity which reflects a 1:1 interaction between members of a binding pair (e.g., a TCR and a peptide-MHC complex). The affinity of a molecule X for its partner Y can generally be represented by the dissociation constant ($K_D$). Affinity can be measured and/or expressed in a number of ways known in the art, including, but not limited to, equilibrium dissociation constant ($K_D$) and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., a TCR to a peptide-MHC complex, and $k_{off}$ refers to the dissociation rate constant of, e.g., a TCR to a peptide-MHC complex. The $k_{on}$ and $k_{off}$ can be determined by techniques known to one of ordinary skill in the art, such as use of BIAcore® or KinExA. As used herein, a "lower affinity" refers to a larger $K_D$.

As used herein, the term "specifically binds to" refers to the ability of a TCR to preferentially bind to a particular antigen (e.g., a specific peptide or a specific peptide-MHC complex combination) as such binding is understood by one skilled in the art. For example, a TCR that specifically binds to an antigen can bind to other antigens, generally with lower affinity as determined by, e.g., BIAcore®, or other immunoassays known in the art (see, e.g., Savage et al., Immunity. 1999, 10(4):485-92, which is incorporated by reference herein in its entirety). In a specific embodiment, a TCR that specifically binds to an antigen binds to the antigen with an association constant ($K_a$) that is at least 2-fold, 5-fold, 10-fold, 50-fold, 100-fold, 500-fold, 1,000-fold, 5,000-fold, or 10,000-fold greater than the $K_a$ when the TCR binds to another antigen. In certain embodiments, the TCRs disclosed herein specifically bind to a peptide consisting of the amino acid sequence set forth in SEQ ID NO: 45. In certain embodiments, the TCRs disclosed herein specifically bind to a peptide consisting of the amino acid sequence set forth in SEQ ID NO: 47.

In some embodiments, a TCR does not substantially bind to an antigen when the TCR binds to the antigen with an association constant ($K_a$) that is at least 2-fold, 5-fold, 10-fold, 50-fold, 100-fold, 500-fold, 1,000-fold, 5,000-fold, or 10,000-fold smaller than the $K_a$ when the TCR binds to another antigen. In some embodiments, a TCR does not substantially bind to an antigen when the binding between the TCR and the antigen is at least 2-fold, 5-fold, 10-fold, 50-fold, 100-fold, 500-fold, 1,000-fold, 5,000-fold, or 10,000-fold weaker than the binding between the TCR and another antigen.

As used herein, the binding between a test TCR and a first antigen is "substantially weakened" relative to the binding between the test TCR and a second antigen if the binding between the test TCR and the first antigen is reduced by at least 30%, 40%, 50%, 60%, 70%, or 80%, relative to the binding between the test TCR and the second antigen, e.g., in a given experiment, or using mean values from multiple experiments.

In some embodiments, when a TCR is expressed on the surface of a T cell, the T cell is not substantially activated when the T cell is co-cultured with a second cell displaying a peptide if the activation of the T cell is at least 2-fold, 5-fold, 10-fold, 50-fold, 100-fold, 500-fold, 1.000-fold, 5,000-fold, or 10,000-fold weaker than the activation of the T cell when the T cell is co-cultured with a third cell displaying another peptide.

As used herein, when a test TCR is expressed on the surface of a T cell, the activation of the T cell when the T cell is co-cultured with a second cell displaying a first peptide is "substantially weakened" relative to the activation of the T cell when the T cell is co-cultured with a third cell displaying a second peptide if the activation of the T cell when co-cultured with the second cell displaying the first peptide is reduced by at least 30%, 40%, 50%, 60%, 70%, or 80%, relative to the activation of the T cell when co-cultured with the third cell displaying the second peptide, e.g., in a given experiment, or using mean values from multiple experiments, as assessed by, e.g., an assay comprising the following steps: (a) expressing the test TCR in a T cell comprising an IL-2-(NFAT)$_3$-EGFP reporter construct; (b) pulsing a HLA-B*0702 positive T2 cell ("T2-B7 cell") with the first peptide or the second peptide: (c) co-culturing the TCR-expressing T cell with the peptide-pulsed T2-B7 target cell at a ratio of 1:2 for 16 hours at 37° C. and 10% $CO_2$; (d) analyzing the expression of TCR and EGFP using flow cytometry; (e) determining the percentage of TCR+ EGFP+ cells; and (f) determining the reduction of T cell activation when co-cultured with a T2-B7 target cell displaying the first peptide relative to when co-cultured with a T2-B7 target cell displaying the second peptide based on the respective percentages of TCR+EGFP+ cells.

As used herein, an "epitope" is a term in the art and refers to a localized region of an antigen (e.g., a peptide or a peptide-MHC complex) to which a TCR can bind. In certain embodiments, the epitope to which a TCR binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), flow cytometry analysis, mutagenesis mapping (e.g., site-directed mutagenesis mapping), and/or structural modeling. For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). TCR:antigen crystals may be studied using well-known X-ray diffraction techniques and may be refined using computer software such as X-PLOR (Yale University, 1992, distributed by Molecular Simulations, Inc.: see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. In a specific embodiment, the epitope of an antigen is determined using alanine scanning mutagenesis studies. In a specific embodiment, the epitope of an antigen is determined using hydrogen/deuterium exchange coupled with mass spectrometry. In certain embodiments, the antigen is a peptide-MHC complex. In certain embodiments, the antigen is a peptide presented by an MHC molecule.

As used herein, the terms "treat," "treating," and "treatment" refer to therapeutic or preventative measures described herein. In some embodiments, the methods of "treatment" employ administration of a TCR or a cell expressing a TCR to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "effector moiety" refers to a component or functional group of a molecule that increases or decreases a natural activity of the molecule, or confers a novel activity upon the molecule. In certain embodiments, the effector moiety is a binding moiety. In an embodiment, the binding moiety binds to a cell surface protein. In certain embodiments, the binding moiety is an antibody.

As used herein, the terms "antibody" and "antibodies" include full-length antibodies, antigen-binding fragments of full-length antibodies, and molecules comprising antibody CDRs, VH regions or VL regions. Examples of antibodies include monoclonal antibodies, recombinantly produced antibodies, monospecific antibodies, multi-specific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies. Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

5.2 T Cell Receptors

In one aspect, the instant disclosure provides TCRs that bind to a peptide consisting of the amino acid sequence of EPR[pS]PSHSM (SEQ ID NO: 45). In certain embodiments, the TCR specifically binds to a peptide consisting of the amino acid sequence of EPR[pS]PSHSM (SEQ ID NO: 45). In certain embodiments, the TCR binds to a peptide-MHC complex comprising a peptide consisting of the amino acid sequence of EPR[pS]PSHSM (SEQ ID NO: 45). In certain embodiments, the TCR specifically binds to the peptide-MHC complex comprising a peptide consisting of the amino acid sequence set forth in SEQ ID NO: 45. In one aspect, the instant disclosure provides TCRs that bind to EPR[pS]PSHSM (SEQ ID NO: 45) presented by a major histocompatibility complex (MHC) molecule. In one aspect, the instant disclosure provides TCRs that bind to a EPR[pS]PSHSM (SEQ ID NO: 45)-HLA-B*0702 complex. The amino acid sequences of exemplary TCRs are set forth in Table 1, herein.

In one aspect, the instant disclosure provides TCRs that bind to a peptide consisting of the amino acid sequence of RVR[pS]PTRSP (SEQ ID NO: 47). In certain embodiments, the TCR specifically binds to a peptide consisting of the amino acid sequence of RVR[pS]PTRSP (SEQ ID NO: 47). In certain embodiments, the TCR binds to a peptide-MEC complex comprising a peptide consisting of the amino acid sequence of RVR[pS]PTRSP (SEQ ID NO: 47). In certain embodiments, the TCR specifically binds to the peptide-MHC complex comprising a peptide consisting of the amino acid sequence set forth in SEQ ID NO: 47. In one aspect, the instant disclosure provides TCRs that bind to RVR[pS]PTRSP (SEQ ID NO: 47) presented by a major histocompatibility complex (MHC) molecule. In one aspect, the instant disclosure provides TCRs that bind to a RVR[pS]PTRSP (SEQ ID NO: 47)-HLA-B*0702 complex. The amino acid sequences of exemplary TCRs are set forth in Table 1, herein.

TABLE 1

Amino acid sequences of exemplary TCRs.

| SEQ ID NO: | Description | Amino acid sequence |
| --- | --- | --- |
| 1 | TCR0077 Vα | TQLLEQSPQFLSIQEGENLTVYCNSSSVFSSLQWYRQEPGEGPVLLVTVVTGGEVKKLKRLTFQFGDARKDSSLHITAAQPGDTGLYLCAGYGGGSNYKLTFGAGTRLTVKP |
| 2 | TCR0077 Vβ | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASRLTGRVHGYTFGPGTRLTVL |
| 3 | TCR0079 Vα | KNQVEQSPQSLIILEGKNCTLQCNYTVSPFSNLRWYKQDTGRGPVSLTIMTFSENTKSNGRYTATLDADTKQSSLHITASQLSDSASYICVVRGGAAGNKLTFGAGTRLTVKP |
| 4 | TCR0079 Vβ | DAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSSGGANTEAFFGPGTRLTVL |
| 5 | TCR0081 Vα | AQSVTQLGSHVSVSEGALILLRCNYSSSVPPYLFWYVQYPNQGLQLLLKYTTGATLVKGINGFEAEFKKSETSFHLTKPSAHMSDAAEYFCAVSARYNFNKFYFGSGTKLSVIP |
| 6 | TCR0081 Vβ | DSGVTQTPKHLITATGQRVTLRCSPRSGDLSVYWYQQSLDQGLQFLIQYYNGEERAKGNILERFSAQQFPDLHSELNLSSLELGDSALYFCASSASGGRSYEQYFGPGTRLTVV |
| 7 | TCR0083 Vα; TCR0084 Vα | EDQVTQSPEALRLQEGESSSLNCSYTVSGLRGLFWYRQDPGKGPEFLFTLYSAGEEKEKERLKATLTKKESFLHITAPKPEDSATYLCAVRNTGFQKLVFGTGTRLLVSP |
| 8 | TCR0083 Vβ | DTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSWRTGREETQYFGPGTRLLVL |
| 9 | TCR0085 Vα, TCR0086 Vα | KQEVTQIPAALSVPEGENLVLNCSFTDSAIYNLQWFRQDPGKGLTSLLLIQSSQREQTSGRLNASLDKSSGRSTLYIAASQPGDSATYLCAVMLWNQGGKLIFGQGTELSVKP |
| 10 | TCR0085 Vβ, TCR0086 Vβ | KAGVTQTPRYLIKTRGQQVTLSCSPISGHRSVSWYQQTPGQGLQFLFEYFSETQRNKGNFPGRFSGRQFSNSRSEMNVSTLELGDSALYLCASSLGRGYEQYFGPGTRLTVT |
| 86 | TCR0078 Vα | TQLLEQSPQFLSIQEGENLTVYCNSSSVFSSLQWYRQEPGEGPVLLVTVVTGGEVKKLKRLTFQFGDARKDSSLHITAAQPGDTGLYLCAGYGGGSNYKLTFGKGTLLTVNP |
| 87 | TCR0078 Vβ | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASRLTGRVHGYTFGSGTRLTVV |
| 88 | TCR0080 Vα | KNQVEQSPQSLIILEGKNCTLQCNYTVSPFSNLRWYKQDTGRGPVSLTIMTFSENTKSNGRYTATLDADTKQSSLHITASQLSDSASYICVVRGGAAGNKLTFGGGTRVLVKP |
| 89 | TCR0080 Vβ | DAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSSGGANTEAFFGQGTRLTVV |

TABLE 1-continued

Amino acid sequences of exemplary TCRs.

| SEQ ID NO: | Description | Amino acid sequence |
|---|---|---|
| 106 | TCR0082 Vα | AQSVTQLGSHVSVSEGALVLLRCNYSSSVPPYLFWYV QYPNQGLQLLLKYTSAATLVKGINGFEAEFKKSETSF HLTKPSAHMSDAAEYFCAVSARYNFNKFYFGSGTKLN VKP |
| 107 | TCR0082 Vβ | DSGVTQTPKHLITATGQRVTLRCSPRSGDLSVYWYQQ SLDQGLQFLIHYYNGEERAKGNILERFSAQQFPDLHS ELNLSSLELGDSALYFCASSASGGRSYEQYFGPGTRL TVT |
| 108 | TCR0084 Vβ | DTGVSQNPRHKITKRGQNVTFRCDPISEHNRLYWYRQ TLGQGPEFLTYFQNEAQLEKSRLLSDRFSAERPKGSF STLEIQRTEQGDSAMYLCASSWRTGREETQYFGPGTR LLVL |
| 11 | TCR0078 CDR1α | SVFSS |
| 12 | TCR0080 CDR1α | VSPFSN |
| 13 | TCR0082 CDR1α | SSVPPY |
| 14 | TCR0084 CDR1α | VSGLRG |
| 15 | TCR0086 CDR1α | DSAIYN |
| 16 | TCR0078 CDR2α | VVTGGEV |
| 17 | TCR0080 CDR2α | MTFSENT |
| 18 | TCR0081 CDR2α | YTTGATLV |
| 109 | TCR0082 CDR2α | YTSAATLV |
| 19 | TCR0084 CDR2α | LYSAGEE |
| 20 | TCR0086 CDR2α | IQSSQRE |
| 21 | TCR0078 CDR3α | AGYGGGSNYKLT |
| 22 | TCR0080 CDR3α | VVRGGAAGNKLT |
| 23 | TCR0082 CDR3α | AVSARYNFNKFY |
| 24 | TCR0084 CDR3α | AVRNTGFQKLV |
| 25 | TCR0086 CDR3α | AVMLWNQGGKLI |
| 26 | TCR0078 CDR1β | MNHEY |
| 27 | TCR0080 CDR1β | SGHNS |
| 28 | TCR0082 CDR1β | SGDLS |
| 29 | TCR0084 CDR1β | SEHNR |
| 30 | TCR0086 CDR1β | SGHRS |
| 31 | TCR0078 CDR2β | SMNVEV |
| 32 | TCR0080 CDR2β | FNNNVP |
| 33 | TCR0082 CDR2β | YYNGEE |
| 34 | TCR0084 CDR2β | FQNEAQ |
| 35 | TCR0086 CDR2β | YFSETQ |
| 36 | TCR0078 CDR3β | ASRLTGRVHGYT |
| 37 | TCR0080 CDR3β | ASSSGGANTEAF |
| 38 | TCR0082 CDR3β | ASSASGGRSYEQY |
| 39 | TCR0084 CDR3β | ASSWRTGREETQY |
| 40 | TCR0086 CDR3β | ASSLGRGYEQY |

TABLE 1-continued

Amino acid sequences of exemplary TCRs.

| SEQ ID NO: | Description | Amino acid sequence |
|---|---|---|
| 41 | TCR α chain human constant region consensus sequence (TRAC*01) | XIQNPDPAVYQLRDSKSSDKSVCLFTDFDSQTNVSQS KDSDVYITDKTVLDMRSMDFKSNSAVAWSNKSDFACA NAFNNSIIPEDTFFPSPESSCDVKLVEKSFETDTNLN FQNLSVIGFRILLLKVAGFNLLMTLRLWSS, wherein X is N, Y, H, or D |
| 42 | TCR α chain human constant region | YIQNPDPAVYQLRDSKSSDKSVCLFTDFDSQTNVSQS KDSDVYITDKTVLDMRSMDFKSNSAVAWSNKSDFACA NAFNNSIIPEDTFFPSPESSCDVKLVEKSFETDTNLN FQNLSVIGFRILLLKVAGFNLLMTLRLWSS |
| 247 | TCR α chain mouse constant region | YIQNPEPAVYQLKDPRSQDSTLCLFTDFDSQINVPKT MESGTFITDKTVLDMKAMDSKSNGAIAWSNQTSFTCQ DIFKETNATYPSSDVPCDATLTEKSFETDMNLNFQNL SVMGLRILLLKVAGFNLLMTLRLWSS |
| 43 | TCR β chain human constant region variant 1 (TRBC1*01) | EDLNKVFPPEVAVFEPSEAEISHTQKATLVCLATGFF PDHVELSWWVNGKEVHSGVSTDPQPLKEQPALNDSRY CLSSRLRVSATFWQNPRNHFRCQVQFYGLSENDEWTQ DRAKPVTQIVSAEAWGRADCGFTSVSYQQGVLSATIL YEILLGKATLYAVLVSALVLMAMVKRKDF |
| 44 | TCR β chain human constant region variant 2 (TRBC2*01) | EDLKNVFPPEVAVFEPSEAEISHTQKATLVCLATGFY PDHVELSWWVNGKEVHSGVSTDPQPLKEQPALNDSRY CLSSRLRVSATFWQNPRNHFRCQVQFYGLSENDEWTQ DRAKPVTQIVSAEAWGRADCGFTSESYQQGVLSATIL YEILLGKATLYAVLVSALVLMAMVKRKDSRG |
| 248 | TCR β chain mouse constant region | EDLRNVTPPKVSLFEPSKAEIANKQKATLVCLARGFF PDHVELSWWVNGKEVHSGVSTDPQAYKESNYSYCLSS RLRVSATFWHNPRNHFRCQVQFHGLSEEDKWPEGSPK PVTQNISAEAWGRADCGITSASYHQGVLSATILYEIL LGKATLYAVLVSGLVLMAMVKKKNS |
| 249 | TCR0077 full-length α chain | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGAGTRLTVK PYIQNPEPAVYQLKDPRSQDSTLCLFTDFDSQINVPK TMESGTFITDKTVLDMKAMDSKSNGAIAWSNQTSFTC QDIFKETNATYPSSDVPCDATLTEKSFETDMNLNFQN LSVMGLRILLLKVAGFNLLMTLRLWSS |
| 250 | TCR0077 full-length β chain | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGPGTRLT VLEDLRNVTPPKVSLFEPSKAEIANKQKATLVCLARG FFPDHVELSWWVNGKEVHSGVSTDPQAYKESNYSYCL SSRLRVSATFWHNPRNHFRCQVQFHGLSEEDKWPEGS PKPVTQNISAEAWGRADCGITSASYHQGVLSATILYE ILLGKATLYAVLVSGLVLMAMVKKKNS |
| 251 | TCR0079 full-length α chain | KNQVEQSPQSLIILEGKNCTLQCNYTVSPFSNLRWYK QDTGRGPVSLTIMTFSENTKSNGRYTATLDADTKQSS LHITASQLSDSASYICVVRGGAAGNKLTFGAGTRLTV KPYIQNPEPAVYQLKDPRSQDSTLCLFTDFDSQINVP KTMESGTFITDKTVLDMKAMDSKSNGAIAWSNQTSFT CQDIFKETNATYPSSDVPCDATLTEKSFETDMNLNFQ NLSVMGLRILLLKVAGFNLLMTLRLWSS |
| 252 | TCR0079 full-length β chain | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGPGTRL TVLEDLRNVTPPKVSLFEPSKAEIANKQKATLVCLAR GFFPDHVELSWWVNGKEVHSGVSTDPQAYKESNYSYC LSSRLRVSATFWHNPRNHFRCQVQFHGLSEEDKWPEG SPKPVTQNISAEAWGRADCGITSASYHQGVLSATILY EILLGKATLYAVLVSGLVLMAMVKKKNS |
| 253 | TCR0081 full-length α chain | AQSVTQLGSHVSVSEGALILLRCNYSSSVPPYLFWYV QYPNQGLQLLLKYTTGATLVKGINGFEAEFKKSETSF HLTKPSAHMSDAAEYFCAVSARYNFNKFYFGSGTKLS VIPYIQNPEPAVYQLKDPRSQDSTLCLFTDFDSQINV PKTMESGTFITDKTVLDMKAMDSKSNGAIAWSNQTSF |

TABLE 1-continued

Amino acid sequences of exemplary TCRs.

| SEQ ID NO: | Description | Amino acid sequence |
|---|---|---|
| | | TCQDIFKETNATYPSSDVPCDATLTEKSFETDMNLNF
QNLSVMGLRILLLKVAGFNLLMTLRLWSS |
| 254 | TCR0081 full-length β chain | DSGVTQTPKHLITATGQRVTLRCSPRSGDLSVYWYQQ
SLDQGLQFLIQYYNGEERAKGNILERFSAQQFPDLHS
ELNLSSLELGDSALYFCASSASGGRSYEQYFGPGTRL
TVVEDLRNVTPPKVSLFEPSKAEIANKQKATLVCLAR
GFFPDHVELSWWVNGKEVHSGVSTDPQAYKESNYSYC
LSSRLRVSATFWHNPRNHFRCQVQFHGLSEEDKWPEG
SPKPVTQNISAEAWGRADCGITSASYHQGVLSATILY
EILLGKATLYAVLVSGLVLMAMVKKKNS |
| 255 | TCR0083 full-length α chain | EDQVTQSPEALRLQEGESSSLNCSYTVSGLRGLFWYR
QDPGKGPEFLFTLYSAGEEKEKERLKATLTKKESFLH
ITAPKPEDSATYLCAVRNTGFQKLVFGTGTRLLVSPY
IQNPEPAVYQLKDPRSQDSTLCLFTDFDSQINVPKTM
ESGTFITDKTVLDMKAMDSKSNGAIAWSNQTSFTCQD
IFKETNATYPSSDVPCDATLTEKSFETDMNLNFQNLS
VMGLRILLLKVAGFNLLMTLRLWSS |
| 256 | TCR0083 full-length β chain | DTGVSQDPRHKITKRGQNVTFRCDPISEHNRLYWYRQ
TLGQGPEFLTYFQNEAQLEKSRLLSDRFSAERPKGSF
STLEIQRTEQGDSAMYLCASSWRTGREETQYFGPGTR
LLVLEDLRNVTPPKVSLFEPSKAEIANKQKATLVCLA
RGFFPDHVELSWWVNGKEVHSGVSTDPQAYKESNYSY
CLSSRLRVSATFWHNPRNHFRCQVQFHGLSEEDKWPE
GSPKPVTQNISAEAWGRADCGITSASYHQGVLSATIL
YEILLGKATLYAVLVSGLVLMAMVKKKNS |
| 257 | TCR0085 full-length α chain | KQEVTQIPAALSVPEGENLVLNCSFTDSAIYNLQWFR
QDPGKGLTSLLLIQSSQREQTSGRLNASLDKSSGRST
LYIAASQPGDSATYLCAVMLWNQGGKLIFGQGTELSV
KPYIQNPEPAVYQLKDPRSQDSTLCLFTDFDSQINVP
KTMESGTFITDKTVLDMKAMDSKSNGAIAWSNQTSFT
CQDIFKETNATYPSSDVPCDATLTEKSFETDMNLNFQ
NLSVMGLRILLLKVAGFNLLMTLRLWSS |
| 258 | TCR0085 full-length β chain | KAGVTQTPRYLIKTRGQQVTLSCSPISGHRSVSWYQQ
TPGQGLQFLFEYFSETQRNKGNFPGRFSGRQFSNSRS
EMNVSTLELGDSALYLCASSLGRGYEQYFGPGTRLTV
TEDLRNVTPPKVSLFEPSKAEIANKQKATLVCLARGF
FPDHVELSWWVNGKEVHSGVSTDPQAYKESNYSYCLS
SRLRVSATFWHNPRNHFRCQVQFHGLSEEDKWPEGSP
KPVTQNISAEAWGRADCGITSASYHQGVLSATILYEI
LLGKATLYAVLVSGLVLMAMVKKKNS |
| 58 | TCR0078 full-length α chain | TQLLEQSPQFLSIQEGENLTVYCNSSSVFSSLQWYRQ
EPGEGPVLLVTVVTGGEVKKLKRLTFQFGDARKDSSL
HITAAQPGDTGLYLCAGYGGGSNYKLTFGKGTLLTVN
PYIQNPDPAVYQLRDSKSSDKSVCLFTDFDSQTNVSQ
SKDSDVYITDKTVLDMRSMDFKSNSAVAWSNKSDFAC
ANAFNNSIIPEDTFFPSPESSCDVKLVEKSFETDTNL
NFQNLSVIGFRILLLKVAGFNLLMTLRLWSS |
| 236 | TCR0078 full-length α chain, with a GS extension | TQLLEQSPQFLSIQEGENLTVYCNSSSVFSSLQWYRQ
EPGEGPVLLVTVVTGGEVKKLKRLTFQFGDARKDSSL
HITAAQPGDTGLYLCAGYGGGSNYKLTFGKGTLLTVN
PYIQNPDPAVYQLRDSKSSDKSVCLFTDFDSQTNVSQ
SKDSDVYITDKTVLDMRSMDFKSNSAVAWSNKSDFAC
ANAFNNSIIPEDTFFPSPESSCDVKLVEKSFETDTNL
NFQNLSVIGFRILLLKVAGFNLLMTLRLWSSGS |
| 259 | TCR0078 full-length α chain, with Furin residues (cleaved), variant 1 | TQLLEQSPQFLSIQEGENLTVYCNSSSVFSSLQWYRQ
EPGEGPVLLVTVVTGGEVKKLKRLTFQFGDARKDSSL
HITAAQPGDTGLYLCAGYGGGSNYKLTFGKGTLLTVN
PYIQNPDPAVYQLRDSKSSDKSVCLFTDFDSQTNVSQ
SKDSDVYITDKTVLDMRSMDFKSNSAVAWSNKSDFAC
ANAFNNSIIPEDTFFPSPESSCDVKLVEKSFETDTNL
NFQNLSVIGFRILLLKVAGFNLLMTLRLWSSRAKR |

TABLE 1-continued

Amino acid sequences of exemplary TCRs.

| SEQ ID NO: | Description | Amino acid sequence |
|---|---|---|
| 260 | TCR0078 full-length α chain, with Furin residues (cleaved), variant 2 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSRA |
| 272 | TCR0078 full-length α chain, with Furin residues (cleaved), variant 3 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSRAK |
| 261 | TCR0078 full-length α chain, with P2A residues (cleaved) | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSGSGATN FSLLKQAGDVEENPG |
| 59 | TCR0078 full-length β chain variant 1 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDF |
| 237 | TCR0078 full-length β chain variant 1, with P2A residues (cleaved) | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFGSGATN FSLLKQAGDVEENPG |
| 262 | TCR0078 full-length β chain variant 1, with a GS extension | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFGS |
| 263 | TCR0078 full-length β chain variant 1, with Furin residues (cleaved), variant 1 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRAKR |
| 264 | TCR0078 full-length β chain variant 1, with Furin residues (cleaved), variant 2 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRA |

TABLE 1-continued

Amino acid sequences of exemplary TCRs.

| SEQ ID NO: | Description | Amino acid sequence |
| --- | --- | --- |
| 273 | TCR0078 full-length β chain variant 1, with Furin residues (cleaved), variant 3 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRAK |
| 60 | TCR0078 full-length β chain variant 2 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLKNVFPPEVAVFEPSEAEISHTQKATLVCLATG FYPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSESYQQGVLSAT ILYEILLGKATLYAVLVSALVLMAMVKRKDSRG |
| 61 | TCR0080 full-length α chain | KNQVEQSPQSLIILEGKNCTLQCNYTVSPFSNLRWYK QDTGRGPVSLTIMTFSENTKSNGRYTATLDADTKQSS LHITASQLSDSASYICVVRGGAAGNKLTFGGGTRVLV KPYIQNPDPAVYQLRDSKSSDKSVCLFTDFDSQTNVS QSKDSDVYITDKTVLDMRSMDFKSNSAVAWSNKSDFA CANAFNNSIIPEDTFFPSPESSCDVKLVEKSFETDTN LNFQNLSVIGFRILLLKVAGFNLLMTLRLWSS |
| 62 | TCR0080 full-length β chain variant 1 | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGQGTRL TVVEDLNKVFPPEVAVFEPSEAEISHTQKATLVCLAT GFFPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSVSYQQGVLSA TILYEILLGKATLYAVLVSALVLMAMVKRKDF |
| 63 | TCR0080 full-length β chain variant 2 | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGQGTRL TVVEDLKNVFPPEVAVFEPSEAEISHTQKATLVCLAT GFYPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSESYQQGVLSA TILYEILLGKATLYAVLVSALVLMAMVKRKDSRG |
| 64 | TCR0082 full-length α chain | AQSVTQLGSHVSVSEGALVLLRCNYSSSVPPYLFWYV QYPNQGLQLLLKYTSAATLVKGINGFEAEFKKSETSF HLTKPSAHMSDAAEYFCAVSARYNFNKFYFGSGTKLN VKPYIQNPDPAVYQLRDSKSSDKSVCLFTDFDSQTNV SQSKDSDVYITDKTVLDMRSMDFKSNSAVAWSNKSDF ACANAFNNSIIPEDTFFPSPESSCDVKLVEKSFETDT NLNFQNLSVIGFRILLLKVAGFNLLMTLRLWSS |
| 65 | TCR0082 full-length β chain variant 1 | DSGVTQTPKHLITATGQRVTLRCSPRSGDLSVYWYQQ SLDQGLQFLIHYYNGEERAKGNILERFSAQQFPDLHS ELNLSSLELGDSALYFCASSASGGRSYEQYFGPGTRL TVTEDLNKVFPPEVAVFEPSEAEISHTQKATLVCLAT GFFPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSVSYQQGVLSA TILYEILLGKATLYAVLVSALVLMAMVKRKDF |
| 66 | TCR0082 full-length β chain variant 2 | DSGVTQTPKHLITATGQRVTLRCSPRSGDLSVYWYQQ SLDQGLQFLIHYYNGEERAKGNILERFSAQQFPDLHS ELNLSSLELGDSALYFCASSASGGRSYEQYFGPGTRL TVTEDLKNVFPPEVAVFEPSEAEISHTQKATLVCLAT GFYPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSESYQQGVLSA TILYEILLGKATLYAVLVSALVLMAMVKRKDSRG |
| 67 | TCR0084 full-length α chain | EDQVTQSPEALRLQEGESSSLNCSYTVSGLRGLFWYR QDPGKGPEFLFTLYSAGEEKEKERLKATLTKKESFLH ITAPKPEDSATYLCAVRNTGFQKLVFGTGTRLLVSPY IQNPDPAVYQLRDSKSSDKSVCLFTDFDSQTNVSQSK DSDVYITDKTVLDMRSMDFKSNSAVAWSNKSDFACAN |

TABLE 1-continued

Amino acid sequences of exemplary TCRs.

| SEQ ID NO: | Description | Amino acid sequence |
|---|---|---|
| | | AFNNSIIPEDTFFPSPESSCDVKLVEKSFETDTNLNF<br>QNLSVIGFRILLLKVAGFNLLMTLRLWSS |
| 68 | TCR0084 full-length β chain variant 1 | DTGVSQNPRHKITKRGQNVTFRCDPISEHNRLYWYRQ<br>TLGQGPEFLTYFQNEAQLEKSRLLSDRFSAERPKGSF<br>STLEIQRTEQGDSAMYLCASSWRTGREETQYFGPGTR<br>LLVLEDLNKVFPPEVAVFEPSEAEISHTQKATLVCLA<br>TGFFPDHVELSWWVNGKEVHSGVSTDPQPLKEQPALN<br>DSRYCLSSRLRVSATFWQNPRNHFRCQVQFYGLSEND<br>EWTQDRAKPVTQIVSAEAWGRADCGFTSVSYQQGVLS<br>ATILYEILLGKATLYAVLVSALVLMAMVKRKDF |
| 69 | TCR0084 full-length β chain variant 2 | DTGVSQNPRHKITKRGQNVTFRCDPISEHNRLYWYRQ<br>TLGQGPEFLTYFQNEAQLEKSRLLSDRFSAERPKGSF<br>STLEIQRTEQGDSAMYLCASSWRTGREETQYFGPGTR<br>LLVLEDLKNVFPPEVAVFEPSEAEISHTQKATLVCLA<br>TGFYPDHVELSWWVNGKEVHSGVSTDPQPLKEQPALN<br>DSRYCLSSRLRVSATFWQNPRNHFRCQVQFYGLSEND<br>EWTQDRAKPVTQIVSAEAWGRADCGFTSESYQQGVLS<br>ATILYEILLGKATLYAVLVSALVLMAMVKRKDSRG |
| 70 | TCR0086 full-length α chain | KQEVTQIPAALSVPEGENLVLNCSFTDSAIYNLQWFR<br>QDPGKGLTSLLLIQSSQREQTSGRLNASLDKSSGRST<br>LYIAASQPGDSATYLCAVMLWNQGGKLIFGQGTELSV<br>KPYIQNPDPAVYQLRDSKSSDKSVCLFTDFDSQTNVS<br>QSKDSDVYITDKTVLDMRSMDFKSNSAVAWSNKSDFA<br>CANAFNNSIIPEDTFFPSPESSCDVKLVEKSFETDTN<br>LNFQNLSVIGFRILLLKVAGFNLLMTLRLWSS |
| 71 | TCR0086 full-length β chain variant 1 | KAGVTQTPRYLIKTRGQQVTLSCSPISGHRSVSWYQQ<br>TPGQGLQFLFEYFSETQRNKGNFPGRFSGRQFSNSRS<br>EMNVSTLELGDSALYLCASSLGRGYEQYFGPGTRLTV<br>TEDLNKVFPPEVAVFEPSEAEISHTQKATLVCLATGF<br>FPDHVELSWWVNGKEVHSGVSIDPQPLKEQPALNDSR<br>YCLSSRLRVSATFWQNPRNHFRCQVQFYGLSENDEWT<br>QDRAKPVTQIVSAEAWGRADCGFTSVSYQQGVLSATI<br>LYEILLGKATLYAVLVSALVLMAMVKRKDF |
| 72 | TCR0086 full-length β chain variant 2 | KAGVTQTPRYLIKTRGQQVTLSCSPISGHRSVSWYQQ<br>TPGQGLQFLFEYFSETQRNKGNFPGRFSGRQFSNSRS<br>EMNVSTLELGDSALYLCASSLGRGYEQYFGPGTRLTV<br>TEDLKNVFPPEVAVFEPSEAEISHTQKATLVCLATGF<br>YPDHVELSWWVNGKEVHSGVSTDPQPLKEQPALNDSR<br>YCLSSRLRVSATFWQNPRNHFRCQVQFYGLSENDEWT<br>QDRAKPVTQIVSAEAWGRADCGFTSESYQQGVLSATI<br>LYEILLGKATLYAVLVSALVLMAMVKRKDSRG |
| 73 | α chain germline sequence TRAV27 | TQLLEQSPQFLSIQEGENLTVYCNSSSVFSSLQWYRQ<br>EPGEGPVLLVTVVTGGEVKKLKRLTFQFGDARKDSSL<br>HITAAQPGDTGLYLCAG |
| 74 | β chain germline sequence TRBV27 | EAQVTQNPRYLITVTGKKLTVTCSQNMNHEYMSWYRQ<br>DPGLGLRQIYYSMNVEVTDKGDVPEGYKVSRKEKRNF<br>PLILESPSPNQTSLYFCAS |
| 75 | α chain germline sequence TRAV10 | KNQVEQSPQSLIILEGKNCTLQCNYTVSPFSNLRWYK<br>QDTGRGPVSLTIMTFSENTKSNGRYTATLDADTKQSS<br>LHITASQLSDSASYICVV |
| 76 | β chain germline sequence TRBV12-3 | DAGVIQSPRHEVTEMGQEVTLRCKPISGHNSLFWYRQ<br>TMMRGLELLIYFNNNVPIDDSGMPEDRFSAKMPNASF<br>STLKIQPSEPRDSAVYFCASS |
| 77 | α chain germline sequence TRAV8-4 | AQSVTQLGSHVSVSEGALVLLRCNYSSSVPPYLFWYV<br>QYPNQGLQLLLKYTSAATLVKGINGFEAEFKKSETSF<br>HLTKPSAHMSDAAEYFCAVS |
| 78 | β chain germline sequence TRBV9 | DSGVTQTPKHLITATGQRVTLRCSPRSGDLSVYWYQQ<br>SLDQGLQFLIHYYNGEERAKGNILERFSAQQFPDLHS<br>ELNLSSLELGDSALYFCASS |
| 79 | α chain germline sequence TRAV20 | EDQVTQSPEALRLQEGESSSLNCSYTVSGLRGLFWYR<br>QDPGKGPEFLFTLYSAGEEKEKERLKATLTKKESFLH<br>ITAPKPEDSATYLCAV |

TABLE 1-continued

Amino acid sequences of exemplary TCRs.

| SEQ ID NO: | Description | Amino acid sequence |
|---|---|---|
| 80 | β chain germline sequence TRBV7-9 | DTGVSQNPRHKITKRGQNVTFRCDPISEHNRLYWYRQ TLGQGPEFLTYFQNEAQLEKSRLLSDRFSAERPKGSF STLEIQRTEQGDSAMYLCASS |
| 81 | α chain germline sequence TRAV21 | KQEVTQIPAALSVPEGENLVLNCSFTDSAIYNLQWFR QDPGKGLTSLLLIQSSQREQTSGRLNASLDKSSGRST LYIAASQPGDSATYLCAV |
| 82 | β chain germline sequence TRBV5-1 | KAGVTQTPRYLIKTRGQQVTLSCSPISGHRSVSWYQQ TPGQGLQFLFEYFSETQRNKGNFPGRFSGRQFSNSRS EMNVSTLELGDSALYLCASSL |
| 83 | Immature TCR0078 β chain-P2A cleavage site-TCR0078 α chain sequence | MGPQLLGYVVLCLLGAGPLEAQVTQNPRYLITVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFGSGATNFSLLKQAGDVEENPGPMV LKFSVSILWIQLAWVSTQLLEQSPQFLSIQEGENLTV YCNSSSVFSSLQWYRQEPGEGPVLLVTVVTGGEVKKL KRLTFQFGDARKDSSLHITAAQPGDTGLYLCAGYGGG SNYKLTFGKGTLLTVNPYIQNPDPAVYQLRDSKSSDK SVCLFTDFDSQTNVSQSKDSDVYITDKTVLDMRSMDF KSNSAVAWSNKSDFACANAFNNSIIPEDTFFPSPESS CDVKLVEKSFETDTNLNFQNLSVIGFRILLLKVAGFN LLMTLRLWSSGS |
| 266 | Immature TCR0078 β chain-Furin-P2A-TCR0078 α chain sequence | MGPQLLGYVVLCLLGAGPLEAQVTQNPRYLTTVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFRAKRSGSGATNFSLLKQAGDVEEN PGPMVLKFSVSILWIQLAWVSTQLLEQSPQFLSIQEG ENLTVYCNSSSVFSSLQWYRQEPGEGPVLLVTVVTGG EVKKLKRLTFQFGDARKDSSLHITAAQPGDTGLYLCA GYGGGSNYKLIFGKGTLLTVNPYIQNPDPAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSS |
| 267 | Immature TCR0078 β chain-Furin-P2A-TCR0078 α chain sequence, with a GS extension | MGPQLLGYVVLCLLGAGPLEAQVTQNPRYLITVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFRAKRSGSGATNFSLLKQAGDVEEN PGPMVLKFSVSILWIQLAWVSTQLLEQSPQFLSIQEG ENLTVYCNSSSVFSSLQWYRQEPGEGPVLLVTVVTGG EVKKLKRLTFQFGDARKDSSLHITAAQPGDTGLYLCA GYGGGSNYKLIFGKGILLTVNPYIQNPDPAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSSGS |
| 268 | Immature TCR0078 α chain-Furin-P2A-TCR0078 β chain sequence | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSRAKRSGSGATNFSLLKQAGDVEENP GPMGPQLLGYVVLCLLGAGPLEAQVTQNPRYLITVTG |

TABLE 1-continued

Amino acid sequences of exemplary TCRs.

| SEQ ID NO: | Description | Amino acid sequence |
|---|---|---|
| | | KKLTVTCSQNMNHEYMSWYRQDPGLGLRQIYYSMNVE VTDKGDVPEGYKVSRKEKRNFPLILESPSPNQTSLYF CASRLTGRVHGYTFGSGTRLTVVEDLNKVFPPEVAVF EPSEAEISHTQKATLVCLATGFFPDHVELSWWVNGKE VHSGVSTDPQPLKEQPALNDSRYCLSSRLRVSATFWQ NPRNHFRCQVQFYGLSENDEWTQDRAKPVTQIVSAEA WGRADCGFTSVSYQQGVLSATILYEILLGKATLYAVL VSALVLMAMVKRKDF |
| 269 | Immature TCR0078 α chain-Furin-P2A-TCR0078 β chain sequence, with a GS extension | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GGSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSRAKRSGSGATNFSLLKQAGDVEENP GPMGPQLLGYVVLCLLGAGPLEAQVTQNPRYLITVTG KKLTVTCSQNMNHEYMSWYRQDPGLGLRQIYYSMNVE VTDKGDVPEGYKVSRKEKRNFPLILESPSPNQTSLYF CASRLTGRVHGYTFGSGTRLTVVEDLNKVFPPEVAVF EPSEAEISHTQKATLVCLATGFFPDHVELSWWVNGKE VHSGVSTDPQPLKEQPALNDSRYCLSSRLRVSATFWQ NPRNHFRCQVQFYGLSENDEWTQDRAKPVTQIVSAEA WGRADCGFTSVSYQQGVLSATILYEILLGKATLYAVL VSALVLMAMVKRKDFGS |
| 270 | Immature TCR0078 α chain-P2A cleavage site-TCR0078 β chain sequence | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GGSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSGSGATNFSLLKQAGDVEENPGPMGP QLLGYVVLCLLGAGPLEAQVTQNPRYLITVTGKKLTV TCSQNMNHEYMSWYRQDPGLGLRQIYYSMNVEVTDKG DVPEGYKVSRKEKRNFPLILESPSPNQTSLYFCASRL TGRVHGYTFGSGTRLTVVEDLNKVFPPEVAVFEPSEA EISHTQKATLVCLATGFFPDHVELSWWVNGKEVHSGV STDPQPLKEQPALNDSRYCLSSRLRVSATFWQNPRNH FRCQVQFYGLSENDEWTQDRAKPVTQIVSAEAWGRAD CGFTSVSYQQGVLSATILYEILLGKATLYAVLVSALV LMAMVKRKDF |
| 271 | Immature TCR0078 α chain-P2A cleavage site-TCR0078 β chain sequence, with GS extension | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GGSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSGSGATNFSLLKQAGDVEENPGPMGP QLLGYVVLCLLGAGPLEAQVTQNPRYLITVTGKKLTV TCSQNMNHEYMSWYRQDPGLGLRQIYYSMNVEVTDKG DVPEGYKVSRKEKRNFPLILESPSPNQTSLYFCASRL TGRVHGYTFGSGTRLTVVEDLNKVFPPEVAVFEPSEA EISHTQKATLVCLATGFFPDHVELSWWVNGKEVHSGV STDPQPLKEQPALNDSRYCLSSRLRVSATFWQNPRNH FRCQVQFYGLSENDEWTQDRAKPVTQIVSAEAWGRAD CGFTSVSYQQGVLSATILYEILLGKATLYAVLVSALV LMAMVKRKDFGS |
| 90 | Kozak-TCR0078 β chain-P2A cleavage site-TCR0078 α chain nucleic acid sequence variant 1 | gccaccatgggacctcagctgctgggatacgttgtgc tgtgtctgcttggagccggacctctggaagcccaagt gacacagaaccccagatacctgatcaccgtgaccggc aagaaactgaccgtgacctgcagccagaacatgaacc acgagtacatgagctggtacagacaggaccctggcct gggcctgagacagatctactacagcatgaacgtggaa gtgaccgacaagggcgacgtgcccgagggctacaagg tgtccagaaaagagaagcggaacttcccactgatcct ggaaagcccatctcctaaccagaccagcctgtacttc tgcgccagcagactgacaggcagagtgcacggctaca catttggcagcggcaccagactgactgtggtggaaga tctgaacaaggtgttccctccagaggtggccgtgttc gagccttctgaggccgagatcagccacacacagaaag |

TABLE 1-continued

Amino acid sequences of exemplary TCRs.

| SEQ ID NO: | Description | Amino acid sequence |
|---|---|---|
| | | ccacactcgtgtgcctggccaccggcttttttcccga<br>tcacgtggaactgtcttggtgggtcaacggcaaagag<br>gtgcacagcggcgtcagcacagatccccagcctctga<br>aagaacagcccgctctgaacgacagccggtactgcct<br>gtcctccagactgagagtgtccgccaccttctggcag<br>aaccctcggaaccacttcagatgccaggtgcagttct<br>acggcctgagcgagaacgatgagtggacccaggatag<br>agccaagcctgtgactcagatcgtgtctgccgaagcc<br>tggggcagagccgattgtggctttaccagcgtgtcct<br>atcagcagggcgtgctgtctgccaccatcctgtatga<br>gatcctgctgggcaaagccactctgtacgccgtgctg<br>gtttctgccctggtgctgatggccatggtcaagagaa<br>aggactttggctccggcgccaccaacttcagcctgct<br>gaaacaggctggcgacgtggaagagaaccccggacct<br>atggtgctgaagttctccgtgtccatcctgtggattc<br>agctggcttgggtgtccacacagctgctcgaacagag<br>ccctcagttcctgagcatccaagagggcgagaacctg<br>acagtgtactgcaacagcagcagcgtgttcagcagcc<br>tgcagtggtacaggcaagagcctggcgaaggacctgt<br>gctgctggtcacagttgtgacaggcggcgaagtgaag<br>aagctgaagcggctgaccttccagttcggcgacgcca<br>gaaaggatagctccctgcacattaccgctgctcagcc<br>aggcgataccggcctgtatctgtgtgctggatatggc<br>ggcggaagcaactacaagctgacctttggcaagggca<br>ccctgctgacagtgaaccccctacattcagaaccccga<br>tccagccgtgtatcagctgagagacagcaagagcagc<br>gacaagagcgtgtgtctgttcaccgacttcgacagcc<br>agaccaacgtgtcccagagcaaggacagcgacgtgta<br>catcaccgacaagaccgtgctggacatgcggagcatg<br>gacttcaagagcaacagcgccgtggcctggtccaaca<br>agagcgatttcgcctgcgccaacgccttcaacaacag<br>cattatccccgaggacacattcttcccaagtcctgag<br>agcagctgcgacgtgaagctggtggaaaagagcttcg<br>agacagacaccaacctgaacttccagaacctgagcgt<br>gatcggcttcagaatcctgctgctgaaggtggccggc<br>ttcaatctgctgatgaccctgagactgtggtccagcg<br>atcctga |
| 238 | Kozak-TCR0078 β chain-<br>P2A cleavage site-<br>TCR0078 α chain nucleic<br>acid sequence variant 2 | gccaccatgggacctcagctgctgggatacgttgtgc<br>tgtgtctgcttggagccggacctctggaagcccaagt<br>gacacagaaccccagatacctgatcaccgtgaccggc<br>aagaaactgaccgtgacctgcagccagaacatgaacc<br>acgagtacatgagctggtacagacaggaccctggcct<br>gggcctgagacagatctactacagcatgaacgtggaa<br>gtgaccgacaagggcgacgtgcccgagggctacaagg<br>tgtccagaaaagagaagcggaacttcccactgatcct<br>ggaaagcccatctcctaaccagaccagcctgtacttc<br>tgcgccagcagactgacaggcagagtgcacggctaca<br>catttggcagcggcaccagactgactgtggtggaaga<br>tctgaacaaggtgttcccgccggaagtggccgtgttc<br>gagccttctgaggccgagatcagccacacacagaaag<br>ccacactcgtgtgcctggccaccggcttttttcccga<br>tcacgtggaactgtcttggtgggtcaacggcaaagag<br>gtgcacagcggcgtcagcacagatccccagcctctga<br>aagaacagcccgctctgaacgacagccggtactgcct<br>gtcctcccgactgagagtgtccgccaccttctggcag<br>aaccctcggaaccacttcagatgccaggtgcagttct<br>acggcctgagcgagaacgatgagtggacccaggatag<br>agccaagcctgtgactcagatcgtgtctgccgaagcc<br>tggggcagagccgattgtggctttaccagcgtgtcct<br>atcagcagggcgtgctgtctgccaccatcctgtatga<br>gatcctgctgggcaaagccactctgtacgccgtgctg<br>gtttctgccctggtgctgatggccatggtcaagagaa<br>aggactttggctccggcgccaccaacttcagcctgct<br>gaaacaggctggcgacgtggaagagaaccccggacct<br>atggtgctgaagttctccgtgtccatcctgtggattc<br>agctggcttgggtgtccacacagctgctcgaacagag<br>ccctcagttcctgagcatccaagagggcgagaacctg<br>acagtgtactgcaacagcagcagcgtgttcagcagcc<br>tgcagtggtacaggcaagagcctggcgaaggacctgt<br>gctgctggtcacagttgtgacaggcggcgaagtgaag<br>aagctgaagcggctgaccttccagttcggcgacgcca<br>gaaaggatagctccctgcacattaccgctgctcagcc<br>aggcgataccggcctgtatctgtgtgctggatatggc<br>ggcggaagcaactacaagctgacctttggcaagggca<br>ccctgctgacagtgaaccccctacattcagaaccccga |

TABLE 1-continued

Amino acid sequences of exemplary TCRs.

| SEQ ID NO: | Description | Amino acid sequence |
|---|---|---|
| | | tccagccgtgtatcagctgagagacagcaagagcagc gacaagagcgtgtgtctgttcaccgacttcgacagcc agaccaacgtgtcccagagcaaggacagcgacgtgta catcaccgacaagaccgtgctggacatgcggagcatg gacttcaagagcaacagcgccgtggcctggtccaaca agagcgatttcgcctgcgccaacgccttcaacaacag cattatccccgaggacacattcttcccaagtcctgag agcagctgcgacgtgaagctggtggaaaagagcttcg agacagacaccaacctgaacttccagaacctgagcgt gatcggcttcagaatcctgctgctgaaggtggccggc ttcaatctgctgatgaccctgagactgtggtccagcg gatcctga |
| 91 | Immature TCR0080 β chain-P2A cleavage site-TCR0080 α chain sequence | MDSWTFCCVSLCILVAKHTDAGVIQSPRHEVTEMGQE VTLRCKPISGHNSLFWYRQTMMRGLELLIYFNNNVPI DDSGMPEDRFSAKMPNASFSTLKIQPSEPRDSAVYFC ASSSGGANTEAFFGQGTRLTVVEDLNKVFPPEVAVFE PSEAEISHTQKATLVCLATGFFPDHVELSWWVNGKEV HSGVSTDPQPLKEQPALNDSRYCLSSRLRVSATFWQN PRNHFRCQVQFYGLSENDEWTQDRAKPVTQIVSAEAW GRADCGFTSVSYQQGVLSATILYEILLGKATLYAVLV SALVLMAMVKRKDFGSGATNFSLLKQAGDVEENPGPM KKHLTTFLVILWLYFYRGNGKNQVEQSPQSLIILEGK NCTLQCNYTVSPFSNLRWYKQDTGRGPVSLTIMTFSE NTKSNGRYTATLDADTKQSSLHITASQLSDSASYICV VRGGAAGNKLTFGGGTRVLVKPYIQNPDAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSSGS |
| 265 | Immature TCR0080 β chain-Furin-P2A-TCR0080 α chain sequence | MDSWTFCCVSLCILVAKHTDAGVIQSPRHEVTEMGQE VTLRCKPISGHNSLFWYRQTMMRGLELLIYFNNNVPI DDSGMPEDRFSAKMPNASFSTLKIQPSEPRDSAVYFC ASSSGGANTEAFFGQGTRLTVVEDLNKVFPPEVAVFE PSEAEISHTQKATLVCLATGFFPDHVELSWWVNGKEV HSGVSTDPQPLKEQPALNDSRYCLSSRLRVSATFWQN PRNHFRCQVQFYGLSENDEWTQDRAKPVTQIVSAEAW GRADCGFTSVSYQQGVLSATILYEILLGKATLYAVLV SALVLMAMVKRKDFRAKRSGSGATNFSLLKQAGDVEE NPGPMKKHLTTFLVILWLYFYRGNGKNQVEQSPQSLI ILEGKNCTLQCNYTVSPFSNLRWYKQDTGRGPVSLTI MTFSENTKSNGRYTATLDADTKQSSLHITASQLSDSA SYICVVRGGAAGNKLTFGGGTRVLVKPNIQNPDPAVY QLRDSKSSDKSVCLFTDFDSQTNVSQSKDSDVYITDK TVLDMRSMDFKSNSAVAWSNKSDFACANAFNNSIIPE DTFFPSPESSCDVKLVEKSFETDTNLNFQNLSVIGFR ILLLKVAGFNLLMTLRLWSS |
| 92 | Immature TCR0086 β chain-P2A cleavage site-TCR0086 α chain sequence | MGSRLLCWVLLCLLGAGPVKAGVTQTPRYLIKTRGQQ VTLSCSPISGHRSVSWYQQTPGQGLQFLFEYFSETQR NKGNFPGRFSGRQFSNSRSEMNVSTLELGDSALYLCA SSLGRGYEQYFGPGTRLTVTEDLNKVFPPEVAVFEPS EAEISHTQKATLVCLATGFFPDHVELSWWVNGKEVHS GVSTDPQPLKEQPALNDSRYCLSSRLRVSATFWQNPR NHFRCQVQFYGLSENDEWTQDRAKPVTQIVSAEAWGR ADCGFTSVSYQQGVLSATILYEILLGKATLYAVLVSA LVLMAMVKRKDFGSGATNFSLLKQAGDVEENPGPMET LLGLLILWLQLQWVSSKQEVTQIPAALSVPEGENLVL NCSFTDSAIYNLQWFRQDPGKGLTSLLLIQSSQREQT SGRLNASLDKSSGRSTLYIAASQPGDSATYLCAVMLW NQGGKLIFGQGTELSVKPYIQNPDPAVYQLRDSKSSD KSVCLFTDFDSQTNVSQSKDSDVYITDKTVLDMRSMD FKSNSAVAWSNKSDFACANAFNNSIIPEDTFFPSPES SCDVKLVEKSFETDTNLNFQNLSVIGFRILLLKVAGF NLLMTLRLWSSGS |

TABLE 2

Alpha chain CDR amino acid sequences of exemplary MLL TCRs. *

| Vα (SEQ ID NO:) | CDR1α (SEQ ID NO:) | CDR2α (SEQ ID NO:) | CDR3α (SEQ ID NO:) |
|---|---|---|---|
| TCR0077 Vα (1)/ TCR0078 Vα (86) | SVFSS (11) | VVTGGEV (16) | AGYGGGSNYKLT (21) |
| TCR0079 Vα (3)/ TCR0080 Vα (88) | VSPFSN (12) | MTFSENT (17) | VVRGGAAGNKLT (22) |
| TCR0081 Vα (5) | SSVPPY (13) | YTTGATLV (18) | AVSARYNFNKFY (23) |
| TCR0082 Vα (106) | SSVPPY (13) | YTSAATLV (109) | AVSARYNFNKFY (23) |
| TCR0083 Vα (7)/ TCR0084 Vα (7) | VSGLRG (14) | LYSAGEE (19) | AVRNTGFQKLV (24) |
| TCR0085 Vα (9)/ TCR0086 Vα (9) | DSAIYN (15) | IQSSQRE (20) | AVMLWNQGGKLI (25) |

*CDRs are defined according to Lefranc et al., Dev Comp Immunol. 2003; 27(1): 55-77.

TABLE 3

Beta chain CDR amino acid sequences of exemplary MLL TCRs.*

| Vβ (SEQ ID NO:) | CDR1β (SEQ ID NO:) | CDR2β (SEQ ID NO:) | CDR3β (SEQ ID NO:) |
|---|---|---|---|
| TCR0077 Vβ (2)/ TCR0078 Vβ (87) | MNHEY (26) | SMNVEV (31) | ASRLTGRVHGYT (36) |
| TCR0079 Vβ (4)/ TCR0080 Vβ (89) | SGHNS (27) | FNNNVP (32) | ASSSGGANTEAF (37) |
| TCR0081 Vβ (6)/ TCR0082 Vβ (107) | SGDLS (28) | YYNGEE (33) | ASSASGGRSYEQY (38) |
| TCR0083 Vβ (8)/ TCR0084 Vβ (108) | SEHNR (29) | FQNEAQ (34) | ASSWRTGREETQY (39) |
| TCR0085 Vβ (10)/ TCR0086 Vβ (10) | SGHRS (30) | YFSETQ (35) | ASSLGRGYEQY (40) |

*CDRs are defined according to Lefranc et al, Dev Comp Immunol. 2003; 27(1): 55-77.

TABLE 4

Variable region amino acid sequences of exemplary MLL TCRs.

| Chimeric TCR name | SEQ ID NO of Vα | SEQ ID NO of Vβ | Human TCR name | SEQ ID NO of Vα | SEQ ID NO of Vβ |
|---|---|---|---|---|---|
| TCR0077 | 1 | 2 | TCR0078 | 86 | 87 |
| TCR0079 | 3 | 4 | TCR0080 | 88 | 89 |
| TCR0081 | 5 | 6 | TCR0082 | 106 | 107 |
| TCR0083 | 7 | 8 | TCR0084 | 7 | 108 |
| TCR0085 | 9 | 10 | TCR0086 | 9 | 10 |

TABLE 5

Exemplary peptide sequences.

| SEQ ID NO: | Description | Amino acid Sequence |
|---|---|---|
| 45 | MLL-pM | EPR[pS]PSHSM |
| 46 | MLL-M | EPRSPSHSM |
| 47 | MLL-pP | RVR[pS]PTRSP |
| 48 | MLL-P | RVRSPTRSP |
| 49 | MLL-pM-A1 | APR[pS]PSHSM |
| 50 | MLL-pM-A2 | EAR[pS]PSHSM |
| 51 | MLL-pM-A3 | EPA[pS]PSHSM |
| 52 | MLL-pM-A4 | EPRAPSHSM |
| 53 | MLL-pM-A5 | EPR[pS]ASHSM |
| 54 | MLL-pM-A6 | EPR[pS]PAHSM |
| 55 | MLL-pM-A7 | EPR[pS]PSASM |
| 56 | MLL-pM-A8 | EPR[pS]PSHAM |
| 57 | MLL-pM-A9 | EPR[pS]PSHSA |

TABLE 5-continued

Exemplary peptide sequences.

| SEQ ID NO: | Description | Amino acid Sequence |
|---|---|---|
| 84 | Flu peptide | QPEWFRNVL |
| 85 | CMV peptide | TPRVTGGGAM |

The CDRs of a TCR disclosed herein can be defined using any art recognized numbering convention. Additionally or alternatively, the CDRs can be defined empirically, e.g., based upon structural analysis of the interaction of the TCR with a cognate antigen (e.g., a peptide or a peptide-MHC complex).

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are defined according to the IMGT numbering system, for example, as described in Lefranc M-P (1999) supra and Lefranc M-P et al., (1999) supra.

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are defined according to the Kabat numbering system described in Kabat supra.

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are determined empirically. e.g., based upon structural analysis of the interaction of the TCR with a cognate antigen (e.g., a peptide-MHC complex).

In certain embodiments, the instant disclosure provides a TCR that binds to SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein each CDR is defined in accordance with the IMGT or the Kabat numbering system, or is determined empirically, e.g., based upon structural analysis of the interaction of the TCR with a cognate antigen (e.g., a peptide or a peptide-MHC complex).

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 1, respectively, and the CDR1β, CDR2β, and CDR3β comprise the CDR1β, CDR2β, and CDR3β amino acid sequences of SEQ ID NO: 2, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 86, respectively, and the CDR1β, CDR2β, and CDR3β comprise the CDR1β, CDR2β, and CDR3β amino acid sequences of SEQ ID NO: 87, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1βp, CDR2β, and CDR3β, wherein the CDR1α, CDR2α, and CDR3α comprise the CDR1α. CDR2α, and CDR3α amino acid sequences of SEQ ID NO: 3, respectively, and the CDR1β, CDR2β, and CDR3β comprise the CDR p0, CDR2β, and CDR3β amino acid sequences of SEQ ID NO: 4, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 88, respectively, and the CDR1β, CDR2β, and CDR3β comprise the CDR1β, CDR2β, and CDR3β amino acid sequences of SEQ ID NO: 89, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α. CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 5, respectively, and the CDR1β, CDR2β, and CDR3β comprise the CDR1β, CDR2β, and CDR3β amino acid sequences of SEQ ID NO: 6, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO. 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α. CDR2α, and CDR3α amino acid sequences of SEQ ID NO: 106, respectively, and the CDR1β, CDR2β, and CDR3β comprise the CDR1β, CDR2β, and CDR3β amino acid sequences of SEQ ID NO: 107, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 7, respectively, and the CDR1β, CDR2β, and CDR3β comprise the CDR1β, CDR2β, and CDR3β amino acid sequences of SEQ ID NO: 8, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 7, respectively, and the CDR1β, CDR2β, and CDR3β comprise the CDR1β, CDR2β, and CDR3β amino acid sequences of SEQ ID NO: 108, respectively. In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 9, respectively, and the CDR1β, CDR2β, and CDR3β comprise the CDR1β, CDR2β, and CDR3β amino acid sequences of SEQ ID NO: 10, respectively. In one embodiment, each CDR is defined in accordance with the IMGT numbering system. In one embodiment, each CDR is defined in accordance with the Kabat numbering system. In one embodiment, each CDR is defined empirically. e.g., based upon structural analysis of the interaction of the TCR with a cognate antigen (e.g., a peptide or a peptide-MHC complex). In one embodiment, each CDR is independently defined in accordance with the IMGT or Kabat numbering system, or is determined empirically, e.g., based upon structural analysis of the interaction of the TCR with a cognate antigen (e.g., a peptide-MHC complex).

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising:
 (a) a CDR1α comprising the amino acid sequence of SEQ ID NO: 11, and/or
 (b) a CDR2α comprising the amino acid sequence of SEQ ID NO: 16, and/or
 (c) a CDR3α comprising the amino acid sequence of SEQ ID NO: 21, and/or
 (d) a CDR1β comprising the amino acid sequence of SEQ ID NO: 26, and/or
 (e) a CDR2β comprising the amino acid sequence of SEQ ID NO: 31, and/or
 (f) a CDR3β comprising the amino acid sequence of SEQ ID NO: 36.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising:
 (a) a CDR1α comprising the amino acid sequence of SEQ ID NO: 12, and/or
 (b) a CDR2α comprising the amino acid sequence of SEQ ID NO: 17, and/or
 (c) a CDR3α comprising the amino acid sequence of SEQ ID NO: 22, and/or
 (d) a CDR1β comprising the amino acid sequence of SEQ ID NO: 27, and/or
 (e) a CDR2β comprising the amino acid sequence of SEQ ID NO: 32, and/or
 (f) a CDR3β comprising the amino acid sequence of SEQ ID NO: 37.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising
 (a) a CDR1α comprising the amino acid sequence of SEQ ID NO: 13, and/or
 (b) a CDR2α comprising the amino acid sequence of SEQ ID NO: 18, and/or
 (c) a CDR3α comprising the amino acid sequence of SEQ ID NO: 23, and/or
 (d) a CDR1β comprising the amino acid sequence of SEQ ID NO: 28, and/or
 (e) a CDR2β comprising the amino acid sequence of SEQ ID NO: 33, and/or
 (f) a CDR3β comprising the amino acid sequence of SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising
 (a) a CDR1α comprising the amino acid sequence of SEQ ID NO: 13, and/or
 (b) a CDR2α comprising the amino acid sequence of SEQ ID NO: 109, and/or
 (c) a CDR3α comprising the amino acid sequence of SEQ ID NO: 23, and/or
 (d) a CDR1β comprising the amino acid sequence of SEQ ID NO: 28, and/or
 (e) a CDR2β comprising the amino acid sequence of SEQ ID NO: 33, and/or
 (f) a CDR3β comprising the amino acid sequence of SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising
 (a) a CDR1α comprising the amino acid sequence of SEQ ID NO: 14, and/or
 (b) a CDR2α comprising the amino acid sequence of SEQ ID NO: 19, and/or
 (c) a CDR3α comprising the amino acid sequence of SEQ ID NO: 24, and/or
 (d) a CDR1β comprising the amino acid sequence of SEQ ID NO: 29, and/or
 (e) a CDR2β comprising the amino acid sequence of SEQ ID NO: 34, and/or
 (f) a CDR3β comprising the amino acid sequence of SEQ ID NO: 39.

In certain embodiments, the instant disclosure provides a TCR (e.g., an isolated TCR) that binds to a peptide consisting of the amino acid sequence set forth in SEQ ID NO: 47

(e.g., a TCR that binds to a RVR[pS]PTRSP (SEQ ID NO: 47)-HLA-B*0702 complex), the TCR comprising
(a) a CDR1α comprising the amino acid sequence of SEQ ID NO: 15, and/or
(b) a CDR2α comprising the amino acid sequence of SEQ ID NO: 20, and/or
(c) a CDR3α comprising the amino acid sequence of SEQ ID NO: 25, and/or
(d) a CDR1β comprising the amino acid sequence of SEQ ID NO: 30, and/or
(e) a CDR2β comprising the amino acid sequence of SEQ ID NO: 35, and/or
(f) a CDR3β comprising the amino acid sequence of SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 21 and/or a CDR3β comprising the amino acid sequence of SEQ ID NO: 36. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 22 and/or a CDR3β comprising the amino acid sequence of SEQ ID NO: 37. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 23 and/or a CDR3β comprising the amino acid sequence of SEQ ID NO: 38. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 24 and/or a CDR3β comprising the amino acid sequence of SEQ ID NO: 39. In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a CDR3α comprising the amino acid sequence of SEQ ID NO: 25 and/or a CDR3β comprising the amino acid sequence of SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having the CDR1α, CDR2α, and CDR3α amino acid sequences set forth in SEQ ID NOs: 11, 16, and 21; 12, 17, and 22; 13, 18, and 23; 13, 109, and 23; or 14, 19, and 24, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having the CDR1α, CDR2α, and CDR3α amino acid sequences set forth in SEQ ID NOs: 11, 16, and 21, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vβ having the CDR1β, CDR2β, and CDR3β amino acid sequences set forth in SEQ ID NOs: 26, 31, and 36; 27, 32, and 37; 28, 33, and 38; or 29, 34, and 39, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vβ having the CDR1β, CDR2β, and CDR3β amino acid sequences set forth in SEQ ID NOs: 26, 31, and 36, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vα having the CDR1α, CDR2α, and CDR3α amino acid sequences set forth in SEQ ID NOs: 15, 20, and 25, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vβ having the CDR1β, CDR2β, and CDR3β amino acid sequences set forth in SEQ ID NOs: 30, 35, and 40, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1β, CDR2β, and CDR3β comprise the amino acid sequences set forth in SEQ ID NOs: 11, 16, 21, 26, 31, and 36; 12, 17, 22, 27, 32, and 37; 13, 18, 23, 28, 33, and 38; 13, 109, 23, 28, 33, and 38; or 14, 19, 24, 29, 34, and 39, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having CDR1α. CDR2α, and CDR3α, and a Vβ having CDR1β, CDR2β, and CDR3β, and wherein the CDR1α, CDR2α. CDR3α, CDR1β, CDR2β, and CDR3β comprise the amino acid sequences set forth in SEQ ID NOs: 11, 16, 21, 26, 31, and 36, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1$i, CDR2β, and CDR3β comprise the amino acid sequences set forth in SEQ ID NOs: 15, 20, 25, 30, 35, and 40, respectively.

In certain embodiments, the instant disclosure provides a TCR (e.g., an isolated TCR) that binds to a peptide consisting of the amino acid sequence set forth in SEQ ID NO: 45

(e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 3, 5, 7, 86, 88, or 106. In certain embodiments, the TCR comprises a Vα having the amino acid sequence set forth in SEQ ID NO: 1, 3, 5, 7, 86, 88, or 106. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 86. In certain embodiments, the TCR comprises a Vα having the amino acid sequence set forth in SEQ ID NO: 86.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 2, 4, 6, 8, 87, 89, 107, or 108. In certain embodiments, the TCR comprises a Vβ having the amino acid sequence set forth in SEQ ID NO: 2, 4, 6, 8, 87, 89, 107, or 108. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, %, 97, 98 or 99%) identical to the amino acid sequence set forth in SEQ ID NO: 87. In certain embodiments, the TCR comprises a Vβ having the amino acid sequence set forth in SEQ ID NO: 87.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, %, 97, 98 or 99%) identical to the amino acid sequence set forth in SEQ ID NO: 9. In certain embodiments, the TCR comprises a Vα having the amino acid sequence set forth in SEQ ID NO: 9.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, %, 97, 98 or 99%) identical to the amino acid sequence set forth in SEQ ID NO: 10. In certain embodiments, the TCR comprises a Vβ having the amino acid sequence set forth in SEQ ID NO: 10.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, %, 97, 98 or 99%) identical to the amino acid sequence set forth in SEQ ID NO: 1, 3, 5, 7, 86, 88, 106, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 2, 4, 6, 8, 87, 89, 107, or 108. In certain embodiments, the TCR comprises a Vα and a Vβ comprising the amino acid sequences set forth in SEQ ID NOs: 1 and 2, 3 and 4, 5 and 6, 7 and 8, 86 and 87, 88 and 89, 106 and 107, 7 and 108, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, %, 97, 98 or 99%) identical to the amino acid sequence set forth in SEQ ID NO: 86, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 87. In certain embodiments, the TCR comprises a Vα and a Vβ comprising the amino acid sequences set forth in SEQ ID NOs: 86 and 87, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 9, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 10. In certain embodiments, the TCR comprises a Vα and a Vβ comprising the amino acid sequences set forth in SEQ ID NOs: 9 and 10, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV27 germline sequence (e.g., comprising the amino acid sequence of SEQ ID NO: 73). One or more regions selected from framework 1, framework 2, framework 3, CDR1α, and CDR2α (e.g., two, three, four, or five of these regions) can be derived from a human TRAV27 germline sequence (e.g., comprising the amino acid sequence of SEQ ID NO: 73). In certain embodiments, framework 1, framework 2, framework 3, CDR1α, and CDR2α are all derived from a human TRAV27 germline sequence (e.g., comprising the amino acid sequence of SEQ ID NO: 73). In certain embodiments, the TCR comprises a Vα having an amino acid sequence derived a human TRAV27 germline sequence (e.g., comprising the amino acid sequence of SEQ ID NO: 73) and a CDR3α having the amino acid sequence set forth in SEQ ID NO: 21.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV27 germline sequence (e.g., comprising the amino acid sequence of SEQ ID NO: 74). One or more regions selected from framework 1, framework 2, framework 3, CDR1β, and CDR2β (e.g., two, three, four or five of these regions) can be derived from a human TRBV27 germline sequence (e.g., comprising the amino acid sequence of SEQ ID NO: 74). In certain embodiments, framework 1, framework 2, framework 3, CDR1β, and CDR2β are all derived from a human TRBV27 germline sequence (e.g., comprising the amino acid sequence of SEQ ID NO: 74). In certain embodiments, the TCR comprises a Vβ having an amino acid sequence derived from a human TRBV27 germline sequence (e.g., comprising the amino acid sequence of SEQ ID NO: 74) and a CDR3β having the amino acid sequence set forth in SEQ ID NO: 36.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV10 germline sequence (e.g., comprising the amino acid sequence of SEQ ID NO: 75). One or more regions selected from framework 1, framework 2, framework 3, CDR1α, and CDR2α (e.g., two, three, four, or five of these regions) can be derived from a human TRAV10 germline sequence (e.g., comprising the amino acid sequence of SEQ ID NO: 75). In certain embodiments, framework 1, framework 2, framework 3, CDR1α, and CDR2α are all derived from a human TRAV10 germline sequence (e.g., comprising the amino acid sequence of SEQ ID NO: 75). In certain embodiments, the TCR comprises a Vα having an amino acid sequence derived a human TRAV10 germline sequence (e.g., comprising the amino acid sequence of SEQ ID NO: 75) and a CDR3α having the amino acid sequence set forth in SEQ ID NO: 22.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV12-3 germline sequence (e.g., comprising the amino acid sequence of SEQ ID NO: 76). One or more regions selected from framework 1, framework 2, framework 3, CDR1β, and CDR2β (e.g., two, three, four or five of these regions) can be derived from a human TRBV12-3 germline sequence (e.g., comprising the amino acid sequence of SEQ ID NO: 76). In certain embodiments, framework 1, framework 2, framework 3, CDR1β, and CDR2β are all derived from a human TRBV12-3 germline sequence (e.g., comprising the amino acid sequence of SEQ ID NO: 76). In certain embodiments, the TCR comprises a Vβ having an amino acid sequence derived from a human TRBV12-3 germline sequence (e.g., comprising the amino acid sequence of SEQ ID NO: 76) and a CDR3β having the amino acid sequence set forth in SEQ ID NO: 37.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV8-4 germline sequence (e.g., comprising the amino acid sequence of SEQ ID NO: 77). One or more regions selected from framework 1, framework 2, framework 3, CDR1α, and CDR2α (e.g., two, three, four, or five of these regions) can be derived from a human TRAV8-4 germline sequence (e.g., comprising the amino acid sequence of SEQ ID NO: 77). In certain embodiments, framework 1, framework 2, framework 3, CDR1α, and CDR2α are all derived from a human TRAV8-4 germline sequence (e.g., comprising the amino acid sequence of SEQ ID NO: 77). In certain embodiments, the TCR comprises a Vα having an amino acid sequence derived a human TRAV8-4 germline sequence (e.g., comprising the amino acid sequence of SEQ ID NO: 77) and a CDR3α having the amino acid sequence set forth in SEQ ID NO: 23.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV9 germline sequence (e.g., comprising the amino acid sequence of SEQ ID NO: 78). One or more regions selected from framework 1, framework 2, framework 3. CDR1β, and CDR2β (e.g., two, three, four or five of these regions) can be derived from a human TRBV9 germline sequence (e.g., comprising the amino acid sequence of SEQ ID NO: 78). In certain embodiments, framework 1, framework 2, framework 3, CDR1β, and CDR2β are all derived from a human TRBV9 germline sequence (e.g., comprising the amino acid sequence of SEQ ID NO: 78). In certain embodiments, the TCR comprises a Vβ having an amino acid sequence derived from a human TRBV9 germline sequence (e.g., comprising the amino acid sequence of SEQ ID NO: 78) and a CDR3β having the amino acid sequence set forth in SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV20 germline sequence (e.g., comprising the amino acid sequence of SEQ ID NO: 79). One or more regions selected from framework 1, framework 2, framework 3, CDR1α, and CDR2α (e.g., two, three, four, or five of these regions) can be derived from a human TRAV20 germline sequence (e.g., comprising the amino acid sequence of SEQ ID NO: 79). In certain embodiments, framework 1, framework 2, framework 3, CDR1α, and CDR2α are all derived from a human TRAV20 germline sequence (e.g., comprising the amino acid sequence of SEQ ID NO: 79). In certain embodiments, the TCR comprises a Vα having an amino acid sequence derived a human TRAV20 germline sequence (e.g., comprising the amino acid sequence of SEQ ID NO: 79) and a CDR3α having the amino acid sequence set forth in SEQ ID NO: 24.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV7-9 germline sequence (e.g., comprising the amino acid sequence of SEQ ID NO: 80). One or more regions selected from framework 1, framework 2, framework 3, CDR1β, and CDR2β (e.g., two, three, four or five of these regions) can be derived from a human TRBV7-9 germline sequence (e.g., comprising the amino acid sequence of SEQ ID NO: 80). In certain embodiments, framework 1, framework 2, framework 3, CDR1β, and CDR2β are all derived from a human TRBV7-9 germline sequence (e.g., comprising the amino acid sequence of SEQ ID NO: 80). In certain embodiments, the TCR comprises a Vβ having an amino acid sequence derived from a human TRBV7-9 germline sequence (e.g., comprising the amino acid sequence of SEQ ID NO: 80) and a CDR3β having the amino acid sequence set forth in SEQ ID NO: 39.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence derived from a human TRAV21 germline sequence (e.g., comprising the amino acid sequence of SEQ ID NO: 81). One or more regions selected from framework 1, framework 2, framework 3, CDR1α, and CDR2α (e.g., two, three, four, or five of these regions) can be derived from a human TRAV21 germline sequence (e.g., comprising the amino acid sequence of SEQ ID NO: 81). In certain embodiments, framework 1, framework 2, framework 3, CDR1α, and CDR2α are all derived from a human TRAV21 germline sequence (e.g., comprising the amino acid sequence of SEQ ID NO: 81). In certain embodiments, the TCR comprises a Vα having an amino acid sequence derived a human TRAV21 germline sequence (e.g., comprising the amino acid sequence of SEQ ID NO: 81) and a CDR3α having the amino acid sequence set forth in SEQ ID NO: 25.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vβ having an amino acid sequence derived from a human TRBV5-1 germline sequence (e.g., comprising the amino acid sequence of SEQ ID NO: 82). One or more regions selected from framework 1, framework 2, framework 3, CDR1D, and CDR2β (e.g., two, three, four or five of these regions) can be derived from a human TRBV5-1 germline sequence (e.g., comprising the amino acid sequence of SEQ ID NO: 82). In certain embodiments, framework 1, framework 2, framework 3. CDR1β3, and CDR2β are all derived from a human TRBV5-1 germline sequence (e.g., comprising the amino acid sequence of SEQ ID NO: 82). In certain embodiments, the TCR comprises a Vβ having an amino acid sequence derived from a human TRBV5-1 germline sequence (e.g., comprising the amino acid sequence of SEQ ID NO: 82) and a CDR3β having the amino acid sequence set forth in SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 249 and 250, 251 and 252, 253 and 254, 255 and 256, or 257 and 258, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 249 and 250, 251 and 252, 253 and 254, 255 and 256, or 257 and 258, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 58 and 59, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 58 and 60, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus. In certain embodiments, the α chain and the β chain comprise the amino acid sequences set forth in SEQ ID NOs: 236 and 237, respectively. In certain embodiments, the α chain comprises an amino acid sequences selected from the group consisting of SEQ ID NOs: 58, 236, 259, 260, 272, and 261, and the β chain further comprises an amino acid sequences selected from the group consisting of SEQ ID NOs: 59, 237, 262, 263, 264, 273, and 60, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 61 and 62, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 61 and 63, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 64 and 65, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 64 and 66, respectively. In certain embodiments, the α chain further comprises the amino acid sequence of GSGATNFSLLKQAGDVEENPG (SEQ ID NO: 93) at the C-terminus, or the D chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a D chain comprising the amino acid sequences set forth in SEQ ID NOs: 67 and 68, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a D chain comprising the amino acid sequences set forth in SEQ ID NOs: 67 and 69, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising an α chain and a β chain comprising the amino acid sequences set forth in SEQ ID NOs: 70 and 71, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 70 and 72, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein are TCRs which bind to the same epitope (e.g., the same amino acid residues) of a peptide comprising the amino acid sequence set forth in SEQ ID NO: 45 or 47 as the TCRs described supra. In certain embodiments, the peptide is in complex with an MHC as described supra (e.g., HLA-B*0702). In certain embodiments, the TCR comprises sequences that do not naturally exist within the TCR germline repertoire of an animal or mammal (e.g., human) in vivo.

In one aspect, provided herein is a TCR that binds to one, two, three, or all four of: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, and iv) a peptide consisting of an amino acid sequence selected from the group consisting of SEQ ID NOs: 117, 128, 135, 192, and 233. In one embodiment, the TCR does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof, e.g., as measured in a flow cytometry analysis or a Biacore analysis. In one embodiment, the TCR does not bind to, or does not substantially bind to, any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47, e.g., as measured in a flow cytometry analysis or a Biacore analysis. In one embodiment, the binding between the TCR and a peptide consisting of the amino acid sequence set forth in SEQ ID NO: 46, 49, 50, 52, 53, 54, 55, 57, or 47 is substantially weakened (e.g., is weakened by at least 30%, 40%, 50%, 60%, 70%, 80%, or 90%) relative to the binding between the TCR and a peptide consisting of the amino acid sequence set forth in SEQ ID NO; 45, 51, 56, 117, 128, 135, 192, or 233, e.g., as measured in a flow cytometry analysis or a Biacore analysis.

In one aspect, provided herein is a TCR, wherein when the TCR is expressed on the surface of a T cell, the T cell is activated: i) when co-cultured with a second cell displaying a peptide consisting of the amino acid sequence set forth in SEQ ID NO: 45, ii) when co-cultured with a second cell displaying a peptide consisting of the amino acid sequence set forth in SEQ ID NO: 51; iii) when co-cultured with a second cell displaying a peptide consisting of the amino acid sequence set forth in SEQ ID NO: 56, or when co-cultured with a second cell displaying a peptide consisting of the amino acid sequence set forth in SEQ ID NOs: 117, 128, 135, 192, and 233, or v) any combination thereof, e.g., as measured by an assay described herein, e.g., as measured using an IL-2-(NFAT)$_3$-EGFP reporter construct. In one embodiment, when the TCR is expressed on the surface of a T cell, the T cell is not activated, or is not substantially activated: i) when co-cultured with a second cell displaying a peptide consisting of the amino acid sequence set forth in SEQ ID NO: 46, ii) when co-cultured with a second cell displaying a peptide consisting of the amino acid sequence set forth in SEQ ID NO: 49, 50, 52, 53, 54, 55, or 57, or iii) when co-cultured with a second cell displaying a peptide consisting of the amino acid sequence set forth in SEQ ID NO: 47, or iv) any combination thereof, e.g., as measured by an assay described herein, e.g., as measured using an IL-2-(NFAT)$_3$-EGFP reporter construct. In one embodiment, when the TCR is expressed on the surface of a T cell, the T cell is not activated, or is not substantially activated, when co-cultured with a second cell displaying any of the following peptides: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47, e.g., as measured by an assay described herein, e.g., as measured using an IL-2-(NFAT)$_3$-EGFP reporter construct. In one embodiment, when the TCR is expressed on the surface of a T cell, the activation of the T cell is substantially weakened (e.g., is weakened by at least 30%, 40%, 50%, 60%, 70%, 80%, or 90%) when the T cell is co-cultured with a second cell displaying a peptide consisting of the amino acid sequence set forth in SEQ ID NO: 46, 49, 50, 52, 53, 54, 55, 57, or 47 relative to the activation of the T cell when the T cell is co-cultured with a third cell displaying a peptide consisting of the amino acid sequence set forth in SEQ ID NO: 45, 51, 56, 117, 128, 135, 192, or 233, e.g., as measured by an assay described herein, e.g., using an assay comprising the following steps: (a) expressing the test TCR in a T cell comprising an IL-2-(NFAT)$_3$-EGFP reporter construct; (b) pulsing a HLA-B*0702 positive T2 cell ("T2-B7 cell") with the first peptide or the second peptide; (c) co-culturing the TCR-expressing T cell with the peptide-pulsed T2-B7 target cell at a ratio of 1:2 for 16 hours at 37° C. and 10% CO$_2$; (d) analyzing the expression of TCR and EGFP using flow cytometry; (e) determining the percentage of TCR+ EGFP+ cells; and (f) determining the reduction of T cell activation when co-cultured with a T2-B7 target cell displaying the first peptide relative to when co-cultured with a T2-B7 target cell displaying the second peptide based on the respective percentages of TCR+EGFP+ cells.

Any TCR constant region from any species can be used in the TCRs disclosed herein. In certain embodiments, the TCR comprises a human α, β, γ, or δ TCR constant region. In certain embodiments, the TCR comprises a wild-type constant region. In certain embodiments, the TCR comprises an altered constant region, such as a chimeric constant region or constant region comprising one or more amino acid substitutions, insertions, or deletions relative to a wild-type constant region. In some embodiments, the TCR comprises an α chain comprising an α chain constant region of SEQ ID NO: 41. In some embodiments, the TCR comprises an α chain comprising an α chain constant region of SEQ ID NO: 42. In some embodiments, the TCR comprises a β chain comprising a β chain constant region of SEQ ID NO: 43 or 44. In certain embodiments, the TCR comprises a mouse TCR constant region. In certain embodiments, the TCR comprises a wild-type mouse constant region. In certain embodiments, the TCR comprises an altered mouse constant region, such as a chimeric constant region or constant region comprising one or more amino acid substitutions, insertions, or deletions relative to a wild-type mouse constant region. In some embodiments, the TCR comprises an α chain comprising an α chain constant region of SEQ ID NO: 247. In some embodiments, the TCR comprises a β chain comprising a β chain constant region of SEQ ID NO: 248.

The TCRs disclosed herein can be used in any TCR structural format. For example, in certain embodiments, the TCR is a full-length TCR comprising a full-length α chain and a full-length β chain. The transmembrane regions (and optionally also the cytoplasmic regions) can be removed from a full-length TCR to produce a soluble TCR. Accordingly, in certain embodiments, the TCR is a soluble TCR lacking transmembrane and/or cytoplasmic region(s). The methods of producing soluble TCRs are well-known in the art. In some embodiments, the soluble TCR comprises an engineered disulfide bond that facilitates dimerization, see, e.g., U.S. Pat. No. 7,329,731, which is incorporated by reference herein in its entirety. In some embodiments, the soluble TCR is generated by fusing the extracellular domain of a TCR described herein to other protein domains, e.g., maltose binding protein, thioredoxin, human constant kappa domain, or leucine zippers, see, e.g., Loset et al., Front Oncol. 2014, 4: 378, which is incorporated by reference herein in its entirety. A single-chain TCR (scTCR) comprising Vα and Vβ linked by a peptide linker can also be generated. Such scTCRs can comprise Vα and Vβ, each linked to a TCR constant region. Alternatively, the scTCRs can comprise Vα and V0, where either the Vα, the V0, or both the Vα and Vβ are not linked to a TCR constant region. Exemplary scTCRs are described in PCT Publication Nos. WO 2003/020763, WO 2004/033685, and WO 2011/044186, each of which is incorporated by reference herein in its entirety. Furthermore, the TCRs disclosed herein can comprise two polypeptide chains (e.g., an α chain and a β chain) in which the chains have been engineered to each have a cysteine residue that can form an interchain disulfide bond. Accordingly, in certain embodiments, the TCRs disclosed herein comprise two polypeptide chains linked by an engineered disulfide bond. Exemplary TCRs having an engineered disulfide bond are described in U.S. Pat. Nos. 8,361,794 and 8,906,383, each of which is incorporated by reference herein in its entirety.

In certain embodiments, the TCRs disclosed herein comprise one or more chains (e.g., an α chain and/or a D chain) having a transmembrane region. In certain embodiments, the TCRs disclosed herein comprise two chains (e.g., an α chain and a β chain) having a transmembrane region. The transmembrane region can be the endogenous transmembrane region of that TCR chain, a variant of the endogenous transmembrane region, or a heterologous transmembrane region. In certain embodiments, the TCRs disclosed herein comprise an α chain and a β chain having endogenous transmembrane regions.

In certain embodiments, the TCRs disclosed herein comprise one or more chains (e.g., an α chain and/or a β chain) having a cytoplasmic region. In certain embodiments, the TCRs disclosed herein comprise two chains (e.g., an α chain and a β chain) each having a cytoplasmic region. The cytoplasmic region can be the endogenous cytoplasmic region of that TCR chain, variant of the endogenous cytoplasmic region, or a heterologous cytoplasmic region. In certain embodiments, the TCRs disclosed herein comprise two chains (e.g., an α chain and a β chain) where both chains have transmembrane regions but one chain is lacking a cytoplasmic region. In certain embodiments, the TCRs disclosed herein comprise two chains (e.g., an α chain and a D chain) where both chains have endogenous transmembrane regions but lack an endogenous cytoplasmic region. In certain embodiments, the TCRs disclosed herein comprise an α chain and a β chain where both chains have endogenous transmembrane regions but lack an endogenous cytoplasmic region. In certain embodiments, the TCRs disclosed herein comprise a co-stimulatory signaling region from a co-stimulatory molecule; see, e.g., PCT Publication Nos.: WO 1996/018105, WO 1999/057268, and WO 2000/031239, and U.S. Pat. No. 7,052,906, all of which incorporated herein by reference in their entireties.

In certain embodiments, the TCRs described herein bind to a peptide-MHC complex comprising a peptide having the amino acid sequence set forth in SEQ ID NO: 45 or 47, wherein the MHC may be any MHC. In certain embodiments, the MHC is a human MHC. In certain embodiments, the MHC is an MHC class I molecule comprising an MHC class I heavy chain (e.g., an HLA-A, an HLA-B, or an HLA-C, including any subtypes in any polymorphic forms) and a 02-microglobulin light chain. In certain embodiments, the MHC is HLA-B*0702. In certain embodiments, the peptide-MHC complex is EPR[pS]PSHSM (SEQ ID NO: 45)-HLA-B*0702. In certain embodiments, the peptide-MHC complex is RVR[pS]PTRSP (SEQ ID NO: 47)-HLA-B*0702. In certain embodiments, the MHC is an MHC class II molecule comprising an MHC class II α chain (e.g., an α chain of an HLA-DR, an HLA-DQ, or an HLA-DP, including any subtypes in any polymorphic forms) and an MHC class II β chain (e.g., a β chain of an HLA-DR, an HLA-DQ, or an HLA-DP, including any subtypes in any polymorphic forms). In certain embodiments, the MHC class II α chain and the MHC class II chain are derived from the same type (e.g., HLA-DR, HLA-DQ, or HLA-DP).

In certain embodiments, the instant disclosure provides a polypeptide comprising an α chain variable region (Vα) and a β chain variable region (Vβ) of a TCR fused together. For example, such polypeptide may comprise, in order, the Vα and Vβ, or the Vβ and the Vα, optionally with a linker (e.g., a peptide linker) between the two regions. For example, a Furin and/or a 2A cleavage site (e.g., one of the sequences in Table 7), or combinations thereof, may be used in the linker for the Vα/Vβ fusion polypeptide.

In certain embodiments, the instant disclosure provides a polypeptide comprising an α chain and a β chain of a TCR fused together. For example, such polypeptide may comprise, in order, an α chain and a β chain, or a β chain and an α chain, optionally with a linker (e.g., a peptide linker) between the two chains. For example, a Furin and/or a 2A cleavage site (e.g., one of the sequences in Table 7), or combinations thereof, may be used in the linker for the a/P fusion polypeptide. For example, a fusion polypeptide may comprise, from the N-terminus to the C-terminus: the α chain of a TCR, a furin cleavage site, a 2A cleavage site, and the β chain of the TCR Exemplary α chain-Furin-P2A-β chain fusion TCR sequences for TCR0078 include SEQ ID NOs: 268 and 269. In certain embodiments, the polypeptide comprises, from the N-terminus to the C-terminus: the β chain of a TCR, a furin cleavage site, a 2A element, and the α chain of the TCR Exemplary β chain-Furin-P2A-α chain fusion TCR sequences include SEQ ID NOs: 265 (for TCR0080), 266 (for TCR0078), and 267 (for TCR0078). In certain embodiments, the polypeptide comprises, from the N-terminus to the C-terminus: the α chain of a TCR, a 2A cleavage site, and the β chain of the TCR. Exemplary α chain-P2A-β chain fusion TCR sequences for TCR0078 include SEQ ID NOs: 270 and 271. In certain embodiments, the polypeptide comprises from the N-terminus to the C-terminus: the β chain of a TCR, a 2A element, and the α chain of the TCR. In certain embodiments, the polypeptide comprises, from the N-terminus to the C-terminus: the α chain of a TCR, a Furin cleavage site, and the β chain of the TCR. In certain embodiments, the polypeptide comprises from the N-terminus to the C-terminus: the β chain of a TCR, a Furin element, and the α chain of the TCR. Exemplary β chain-P2A-α chain fusion TCR sequences include SEQ ID NOs: 83 (for TCR0078), 91 (for TCR0080), and 92 (for TCR0086).

5.3 Cells Presenting T Cell Receptors

In another aspect, the instant disclosure provides a mammalian cell (e.g., an engineered mammalian cell) or a population thereof presenting a TCR disclosed herein on the cell surface. Any mammalian cell can be used to present a TCR disclosed herein. In certain embodiments, the mammalian cell expresses CD3 (e.g., a CD3γ chain, a CD3δ chain, and two CD3ε chains). In certain embodiments, the mammalian cell is a human cell. Effector cells of the cellular immune system are particularly useful for presenting a TCR disclosed herein because the cell surface TCR can target these effector cells to tumor cells expressing a MLL polypeptide (e.g., a MLL phosphopeptide, e.g., a peptide consisting of the amino acid sequence of SEQ ID NO: 45 or 47), thereby facilitating killing of the tumor cells. Accordingly, in certain embodiments, the mammalian cell is a lymphocyte (e.g., a human lymphocyte), such as a T cell or a natural killer (NK) cell. In certain embodiments, the lymphocyte is a T cell. Any T cell at any developmental stage can be used to present a TCR disclosed herein. For example, in certain embodiments, the T cell is selected from the group consisting of a CD8$^+$ cytotoxic T cell, a CD4$^+$ cytotoxic T cell, a CD4$^+$ helper T cell (e.g., a Th1 or a Th2 cell), a CD4/CD8 double positive T cells, a tumor infiltrating T cell, a thymocyte, a memory T cell, a naïve T cell, and a natural killer T cell, e.g., an invariant natural killer T cell. Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian cell is a pluripotent stem cell (e.g., an embryonic stem cell, an induced pluripotent stem cell), a hematopoietic stem cell, or a lymphocyte progenitor cell. In certain embodiments, the hematopoietic stem cell or lymphocyte progenitor cell is isolated and/or enriched from, e.g., bone marrow, umbilical cord blood, or peripheral blood.

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase.

In certain embodiments, the mammalian cell is a population of cells presenting a TCR disclosed herein on the cell surface. The population of cells can be heterogeneous or homogenous. In certain embodiments, at least 50% (e.g., at least 60%, 70%, 80%, 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

Populations of cells can be enriched or purified, as needed. In certain embodiments, regulatory T cells (e.g., $CD25^+$ T cells) are depleted from the population, e.g., by using an anti-CD25 antibody conjugated to a surface such as a bead, particle, or cell. In certain embodiments, an anti-CD25 antibody is conjugated to a fluorescent dye (e.g., for use in fluorescence-activated cell sorting). In certain embodiments, cells expressing checkpoint receptors (e.g., CTLA-4, PD-1, TIM-3, LAG-3, TIGIT, VISTA, BTLA, TIGIT, CD137, or CEACAM1) are depleted from the population, e.g., by using an antibody that binds specifically to a checkpoint receptor conjugated to a surface such as a bead, particle, or cell. In certain embodiments, a T cell population can be selected so that it expresses one or more of IFNγ, TNFα, IL-17A, IL-2, IL-3, IL-4. GM-CSF, IL-13, granzyme (e.g., granzyme B), and perforin, or other appropriate molecules, e.g., other cytokines. Methods for determining such expression are described, for example, in PCT Publication No.: WO 2013/126712, which is incorporated by reference herein in its entirety.

Cells can be stimulated ex vivo to increase viability, proliferation, and/or activity. In some embodiments, the induction does not include any defined antigen, thus providing a cell population which is polyclonal with respect to antigen reactivity. In certain embodiments, the cell is contacted with a first agent, which induces or activates a TCR/CD3 complex-associated signal (e.g., an anti-CD3 antibody). In certain embodiments, the cell is contacted with a second agent, which stimulates an accessory molecule on the T cell surface (e.g., a ligand of CD28 or an anti-CD28 antibody). In certain embodiments, the cell is contacted with a molecule or complex that interacts with both CD3 and CD28, wherein the molecule or complex may be presented on a surface (e.g., a bead, particle, or cell). In certain embodiments, the cell is contacted with a surface (e.g., a bead, particle, or cell) presenting an anti-CD3 antibody and an anti-CD28 antibody. In certain embodiments, the cell is contacted with one or more agents that bind to cell surface receptors to increase T cell viability, proliferation, and/or activity (e.g., IL-2 or IL-7). In certain embodiments, the cell is contacted with phytohemagglutinin. In certain embodiments, the cell is contacted with an agent that stimulates one or more intracellular signals such as $Ca^{2+}$ release (e.g., phorbol 12-myristate 13-acetate and/or ionomycin). Alternatively, the induction may include an antigen comprising a peptide (e.g., a MLL polypeptide (e.g., a MLL phosphopeptide, e.g., a peptide consisting of the amino acid sequence of SEQ ID NO. 45 or 47)) which binds to the TCR presented on the cell surface, thus providing a cell population which is enriched (e.g., monoclonal) with respect to antigen reactivity. The antigen may further comprise an MHC molecule (e.g., an HLA molecule) in complex with the peptide. The antigen may be presented as a soluble form, bound to a membrane, or presented on a surface. The agents as described above can be used in any combination, and may be contacted with the effector cell or precursor thereof either simultaneously or sequentially. The contact can be terminated while the cell may remain in a state of increased viability, proliferation, and/or activity. Sustained proliferation of T cells over an extended period of time can yield a multi-fold increase in the number of cells relative to the original T cell population. In some embodiments, activation may be performed to promote metabolic fitness through provision of bioenergetic fuel sources, which enables conditioning of T cells for optimal biological activity and survival.

In certain embodiments, the mammalian cell (e.g., lymphocyte) expresses a TCR disclosed herein from a transgene introduced into the cell and presents the TCR on the cell surface. The TCR may be displayed constitutively on the cell surface. Alternatively, the cell may be capable of conditional expression and/or display of the TCR. For example, the expression or display of the TCR may be induced by an exogenous stimulus or by cellular differentiation. In certain embodiments, the transgene encodes a TCR α chain and/or β chain, or a fragment thereof (e.g., Vα, Vβ, CDR3α and/or CDR3β). In certain embodiments, the transgene is operably linked to an exogenous transcriptional and/or translational control sequence (e.g., a promoter, an enhancer, and/or a Kozak sequence). In certain embodiments, the transgene is operably linked to an endogenous transcriptional and/or translational control sequence (e.g., a promoter, an enhancer, and/or a Kozak sequence) not at its native genomic locus (e.g., introduced by a vector). In certain embodiments, the transgene is operably linked to an endogenous transcriptional and/or translational control sequence (e.g., a promoter, an enhancer, and/or a Kozak sequence) at its native genomic locus (e.g., by inserting the transgene into the native genomic locus).

In certain embodiments, the transgene is a DNA integrated into the host cell genome, wherein the integration occurs through site-specific integration (e.g., homologous recombination) or random insertion of the DNA. In certain embodiments, the transgene is a DNA not integrated into the host cell genome (e.g., maintained as a non-integrating viral genome or as an episomal DNA). In certain embodiments, the transgene is a polynucleotide (including but not limited to DNA, RNA, modified DNA, and modified RNA) that can be transcribed and/or translated to express the TCR disclosed herein. In certain embodiments, the transgene is an RNA having a cap on the 5' end and/or a poly(A) tail on the 3' end, wherein the cap and the poly(A) tail may modulate ribosome binding, initiation of translation and stability of the RNA in the cell.

In certain embodiments, the transgene comprises a first and a second sequence, the first sequence encoding a polypeptide comprising a TCR α chain or a fragment thereof (e.g., Vα or CDR3α), and the second sequence encoding a polypeptide comprising a TCR β chain or a fragment thereof (e.g., Vβ or CDR3β). In certain embodiments, the first and the second sequences are each operably linked to a transcriptional and/or translational control sequence (e.g., a promoter, an enhancer, and/or a Kozak sequence). In certain embodiments, the first and second sequences are in different polynucleotides (e.g., DNA, RNA, modified DNA, or modified RNA) molecules. In certain embodiments, the first and second sequences of the transgene are in the same polynucleotide (e.g., DNA, RNA, modified DNA, or modified RNA) molecule. In certain embodiments, the first and second sequences are operably linked by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease). In certain embodiments, the first and second sequences can be transcribed and/or translated independently. In certain embodiments, the first and second sequences are each integrated into the host cell genome. In certain embodiments, the first and second sequences are each integrated into different regions of the host cell genome.

Alternatively, in certain embodiments, the cell does not express the TCR, but instead the TCR is attached to the outside surface of the cell by chemical means or by binding of the TCR to a cell surface antigen. Accordingly, in certain embodiments, the TCR is linked to a binding moiety that binds to a cell surface antigen. Any type of binding moiety can be linked (covalently or non-covalently) to a TCR disclosed herein. In certain embodiments, the TCR is fused (chemically or genetically) to an antibody or antigen binding fragment thereof that specifically binds to a cell surface antigen of the cell (e.g., lymphocyte).

In certain embodiments, the cell further comprises a polynucleotide encoding a polypeptide capable of inducing cell death. In certain embodiments, the polypeptide is a chimeric polypeptide comprising a multimerization (e.g., dimerization or oligomerization) region and a cell death-inducing region, wherein the cell death-inducing region is activated by multimerization. In certain embodiments, the cell death-inducing region comprises a sequence of a caspase (e.g., caspase-9) that has protease activity. In certain embodiments, the cell death-inducing region comprises the full-length human caspase-9 polypeptide. In certain embodiments, the cell death-inducing region comprises a truncated human caspase-9 polypeptide (e.g., wherein the CARD domain of caspase-9 is deleted).

In certain embodiments, the cell further comprises a polynucleotide encoding a polypeptide capable of inducing T cell activation. In certain embodiments, the polypeptide is an inducible chimeric stimulating molecule, for example, as described in PCT Publication No. WO 2015/123527, incorporated herein by reference in its entirety. In certain embodiments, the polypeptide comprises a multimerization (e.g., dimerization or oligomerization) region, wherein the polypeptide induces T cell activation upon multimerization.

A multimerization region present, for example, in a polypeptide capable of inducing cell death or a polypeptide capable of inducing T cell activation, can comprise a ligand-binding domain that will multimerize upon binding to a ligand (e.g., a synthetic ligand). The ligand may have two or more binding sites, each binding site capable of binding to a ligand-binding domain of the chimeric polypeptide. In certain embodiments, the ligand has two binding sites and is capable of inducing dimerization of the chimeric polypeptide. A variety of synthetic ligands and corresponding ligand-binding domains can be employed. For example, a multimeric (e.g., dimeric) FK506 can be used to multimerize an FK506 binding protein (FKBP; e.g., FKBP12 or a variant thereof): a multimeric (e.g., dimeric) cyclosporin A can be used to multimerize a cyclophilin receptor; a multimeric (e.g., dimeric) estrogen can be used to multimerize an estrogen receptor; a multimeric (e.g., dimeric) glucocorticoid can be used to multimerize a glucocorticoid receptor; a multimeric (e.g., dimeric) tetracycline can be used to multimerize a tetracycline receptor; a multimeric (e.g., dimeric) vitamin D can be used to multimerize a vitamin D receptor. The ligand-binding domain can be internal or external to the cellular membrane, depending upon the nature of the construct and the choice of ligand. Non-limiting examples of ligands and corresponding ligand-binding domains are described in U.S. Pat. No. 9,089,520; Kopytek, S. J., et al., Chemistry & Biology 7:313-321 (2000): Gestwicki, J. E., et al., Combinatorial Chem. & High Throughput Screening 10:667-675 (2007); Clackson T Chem Biol Drug Des 67:440-2 (2006); and Schreiber, et al., *Chemical Biology From Small Molecules to Systems Biology and Drug Design* (Wiley, 2007), the contents of which are incorporated by reference herein in their entireties.

In certain embodiments, the polypeptide capable of inducing cell death is a chimeric polypeptide comprising an FKBP12 polypeptide and a full-length or truncated caspase-9 (e.g., human caspase-9) polypeptide. In certain embodiments, the FKBP12 polypeptide comprises a valine at position 36. In certain embodiments, the FKBP12 polypeptide comprises the amino acid sequence set forth in SEQ ID NO: 94. In certain embodiments, the ligand capable of inducing FKBP12 multimerization is AP1903 (CAS Registry Number: 195514-63-7; Molecular Formula: C78H98N4O20; Molecular Weight: 1411.65). In certain embodiments, the ligand is AP20187 or an AP20187 analog (e.g., AP1510). In certain embodiments, the caspase-9 polypeptide comprises the amino acid sequence set forth in SEQ ID NO: 95.

TABLE 6

FKBP12 and caspase-9 sequences.

| SEQ ID NO: | Description | Amino acid Sequence |
|---|---|---|
| 94 | FKBP12 | GVQVETISPGDGRTFPKRGQTCVVHYTGML EDGKKVDSSRDRNKPFKFMLGKQEVIRGWE EGVAQMSVGQRAKLTISPDYAYGATGHPGI IPPHATLVFDVELLKLE |
| 95 | caspase-9 | GFGDVGALESLRGNADLAYILSMEPCGHCL IINNVNFCRESGLRTRTGSNIDCEKLRRRF SSLHFMVEVKGDLTAKKMVLALLELAQQDH GALDCCVVVILSHGCQASHLQFPGAVYGTD GCPVSVEKIVNIFNGTSCPSLGGKPKLFFI QACGGEQKDHGFEVASTSPEDESPGSNPEP |

TABLE 6-continued

FKBP12 and caspase-9 sequences.

| SEQ ID NO: | Description | Amino acid Sequence |
|---|---|---|
| | | DATPFQEGLRTFDQLDAISSLPTPSDIFVS YSTFPGFVSWRDPKSGSWYVETLDDIFEQW AHSEDLQSLLLRVANAVSVKGIYKQMPGCF NFLRKKLFFKTS |

In certain embodiments, the polynucleotide encoding the polypeptide capable of inducing cell death is operably linked to a transcriptional and/or translational control sequence (e.g., a promoter, an enhancer, and/or a Kozak sequence). The polynucleotide may be integrated into the host cell genome. Alternatively, the polynucleotide may be maintained as a non-integrating viral genome or as an episomal DNA. In certain embodiments, the polynucleotide is operably linked to the first and/or second sequences encoding a TCR by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease). In certain embodiments, the polynucleotide is transcribed and/or translated independently from the first and/or second sequences.

In certain embodiments, the cell is provided in a solution. In certain embodiments, the cell is cryopreserved at about or lower than −80° C. (e.g., in a liquid nitrogen storage tank). Methods of cryopreservation are well-known in the art, e.g., as described in U.S. Pat. Nos. 5,580,714 and 6,740,484, which are incorporated by reference herein in their entireties. The cryopreserved cell may be recovered by thawing, and any of the isolation, purification, enrichment, stimulation, and display of the TCR as described above may be conducted prior to the cryopreservation or after the recovery.

5.4 Methods of Use

In another aspect, the instant disclosure provides a method of treating a subject using the TCRs, polynucleotides, vectors, engineered cells (e.g., a cell comprising a heterologous and/or recombinant nucleic acid), or pharmaceutical compositions disclosed herein. Any disease or disorder in a subject that would benefit from the targeting of a TCR to a MLL peptide (e.g., a MLL phosphopeptide, e.g., a peptide consisting of the amino acid sequence of SEQ ID NO: 45 or 47) can be treated using the TCRs disclosed herein. The TCRs, polynucleotides, vectors, engineered cells, and pharmaceutical compositions disclosed herein are particularly useful for inducing immunity to tumors displaying a MLL peptide (e.g., a peptide-MHC complex comprising a MLL peptide, e.g., a peptide-MHC complex comprising a MLL phosphopeptide, e.g., EPR[pS]PSHSM (SEQ ID NO: 45)-HLA-B*0702 or RVR[pS]PTRSP (SEQ ID NO: 47)-HLA-B*0702), and accordingly can be used as an immunotherapy for subjects with MLL-positive cancer (e.g., MLL phosphopeptide-positive cancer). For example, in certain embodiments, the instant disclosure provides a method of inducing cell-mediated immunity in response to a MLL peptide (e.g., a MLL phosphopeptide, e.g., a peptide consisting of the amino acid sequence of SEQ ID NO: 45 or 47) in a subject, the method comprising administering to the subject an effective amount of a TCR, polynucleotide, vector, engineered cell, or pharmaceutical composition as described herein. In certain embodiments, the instant disclosure provides a method of treating cancer in a subject, the method comprising administering to the subject an effective amount of the TCR, polynucleotide, vector, engineered cell, or pharmaceutical composition, as disclosed herein.

In certain embodiments, the method comprises administering to the subject an effective amount of a cell or population thereof as disclosed herein. In certain embodiments, the cell is engineered to constitutively display a TCR as disclosed herein on the cell surface. In certain embodiments, the cell is engineered to conditionally display a TCR as disclosed herein on the cell surface in response to an induction event. This induction event can be either a stimulus by an exogenous agent administered prior to, simultaneously with, or after the administration of the cell. Additionally or alternatively, the induction event can be a stimulus by a cell, tissue, or lesion in the subject.

In certain embodiments, the cell further comprises a polynucleotide encoding a chimeric polypeptide comprising a ligand-binding multimerization (e.g., dimerization or oligomerization) region and a cell death-inducing region, and the method further comprises a step of administering a ligand of the multimerization region. In certain embodiments, the chimeric polypeptide comprises an FKBP12 polypeptide and a caspase-9 (e.g., human caspase-9) polypeptide, and the method further comprises a step of administering an FKBP12 ligand (e.g., AP1903). In certain embodiments, the FKBP12 ligand is administered after observing an indication of an improvement of a disease (e.g., shrinkage of a cancer, reduction of a cancer marker, and/or improvement of a cancer symptom) or after identifying an intolerable side effect (e.g., a high level of an inflammatory cytokine, and/or a rejection of the administered cell by the host).

As disclosed supra, cells administered to the subject can be autologous or allogeneic. In certain embodiments, autologous cells are obtained from a patient directly following a cancer treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase. Further, in certain aspects, mobilization and conditioning regimens can be used to create a condition in a subject wherein repopulation, recirculation, regeneration, and/or expansion of particular cell types is favored, especially during a defined window of time following therapy. The mobilization agent can be selected from the group consisting of CXCL12-interacting heparinoids, GM-CSF, G-CSF (e.g., unmodified, glycosylated, or PEGylated), IL-2 (e.g., unmodified, glycosylated, or PEGylated), CXCR4 antagonists (e.g., plerixafor), integrin α4β1 antagonists (e.g., BIO5192), cyclophosphamide, 5-fluorouracil, cisplatin, etoposide, ifosfamide, cytarabine, and a combination thereof.

The number of cells that are employed will depend upon a number of circumstances including, the lifetime of the cells, the protocol to be used (e.g., the number of administrations), the ability of the cells to multiply, the stability of the recombinant construct, and the like. In certain embodiments, the cells are applied as a dispersion, generally being injected at or near the site of interest. The cells may be administered in any physiologically acceptable medium.

Cancers that can be treated with the TCRs, polynucleotide, vector, engineered cells, or pharmaceutical compositions disclosed herein can be any tumor expressing MLL (e.g., any tumor displaying a MLL phosphopeptide/MHC complex on the cell surface). Examples of tumors expressing MLL (e.g., tumor displaying a MLL phosphopeptide/MHC complex on the cell surface) have been disclosed in, e.g., Cobbold et al., Sci Transl Med. 2013 Sep. 18; 5(203): 203ra125; Rao et al., Nat Rev Cancer. 2015 June; 15(6): 334-46; Li et al., Exp Hematol. 2014 December; 42(12): 995-1012; and Krivtsov et al., Nat Rev Cancer. 2007 November; 7(11):823-33, each of which is incorporated by reference herein in its entirety.

In certain embodiments, the cancer is leukemia (e.g., mixed lineage leukemia, acute lymphocytic leukemia, acute myeloid leukemia, chronic lymphocytic leukemia, or chronic myeloid leukemia), alveolar rhabdomyosarcoma, bone cancer, brain cancer (e.g., glioblastoma), breast cancer, cancer of the anus, anal canal, or anorectum, cancer of the eye, cancer of the intrahepatic bile duct (e.g., intrahepatic cholangiocellular cancer), cancer of the joints, cancer of the neck, gallbladder, or pleura, cancer of the nose, nasal cavity, or middle ear, cancer of the oral cavity, cancer of the vulva, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer (e.g., hepatocellular carcinoma), lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma (e.g., myxoid/round cell liposarcoma).

In certain embodiments, these methods further comprise administering an additional therapeutic agent to the subject. In certain embodiments, the additional therapeutic agent is a chemotherapeutic, radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist VISTA antibody, an antagonist CD96 antibody, an antagonist anti-CEACAM1 antibody, an antagonist anti-TIGIT antibody, an agonist anti-CD137 antibody, an agonist anti-GITR antibody, and an agonist anti-OX40 antibody.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MED10680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1: PCT Publication No. WO 2014/179664 A2; PCT Publication No. WO 2014/209804 A1: PCT Publication No. WO 2014/206107 A1; PCT Publication No. WO 2015/058573 A1; PCT Publication No. WO 2015/085847 A1; PCT Publication No. WO 2015/200119 A1: PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1: U.S. Publication No. US 2003/0232323 A1; U.S. Publication No. US 2013/0323249 A1; U.S. Publication No. US 2014/0341917 A1: U.S. Publication No. US 2014/0044738 A1: U.S. Publication No. US 2015/0203580 A1; U.S. Publication No. US 2015/0225483 A1: U.S. Publication No. US 2015/0346208 A1; U.S. Publication No. US 2015/0355184 A1; and PCT Publication No. WO 2014/100079 A1: PCT Publication No. WO 2014/022758 A1; PCT Publication No. WO 2014/055897 A2; PCT Publication No. WO 2015/061668 A1; PCT Publication No. WO 2015/109124 A1: PCT Publication No. WO 2015/195163 A1; PCT Publication No. WO 2016/000619 A1; and PCT Publication No. WO 2016/030350 A1.

In certain embodiments, a TCR, cell, or pharmaceutical composition disclosed herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., PCT Publication No. WO 2010/005958 which is incorporated by reference herein in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, the TCR, cell, or pharmaceutical composition disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the TCR, cell, or pharmaceutical composition as described herein and the IDO inhibitor as described herein can be administered separately, sequentially, or concurrently as separate dosage forms. In one embodiment, the cell, or pharmaceutical composition is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is incorporated herein by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, a TCR, cell, or pharmaceutical composition disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, a TCR, cell, or pharmaceutical composition disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress, or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes, and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dwomiczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser. Thr, Arg, Lys, or His amino acid that has been phosphorylated on a side chain hydroxyl or amine.

In a specific embodiment, a TCR, cell, or pharmaceutical composition disclosed herein is administered to a subject in combination with a heat shock protein peptide complex (HSPPC), e.g., heat shock protein peptide complex-% (HSPPC-96), to treat cancer. HSPPC-96 comprises a % kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659.

In certain embodiments, a TCR, cell, or pharmaceutical composition disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands. STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678, and 7,858,589, all of which are incorporated herein by reference in their entireties. In one embodiment, the adjuvant used herein is QS-21 STIMULON.

In certain embodiments, a TCR, polynucleotide, vector, engineered cell, or pharmaceutical composition disclosed herein is administered to a subject in combination with a tumor microenvironment (TME)-conditioning agent. In certain embodiments, the TME-conditioning agent is a cytokine (e.g., interleukin-2, interferon-α, interferon-β, interferon-γ, tumor necrosis factor superfamily member 14 (TNFSF14)). In certain embodiments, the cytokine is a chemokine (e.g., (C-C motif) ligand 21 (CCL21) and C-X-C motif chemokine 10 (CXCL10)). In certain embodiments, the TME-conditioning agent is an agonist of a pattern recognition receptor (PRR). In certain embodiments, the agonist is a synthetic agonist of TLR9 (e.g., CpG). In certain embodiments, the agonist is a synthetic agonist of STING (e.g., cGAMP).

The TCR, polynucleotide, vector, engineered cell, or pharmaceutical composition and the additional therapeutic agent (e.g., chemotherapeutic, radiotherapeutic, checkpoint targeting agent, IDO inhibitor, vaccine, adjuvant, and/or TME-conditioning agent) can be administered separately, sequentially or concurrently as separate dosage forms. In one embodiment, the TCR, polynucleotide, vector, engineered cell, or pharmaceutical composition is administered parenterally, and an IDO inhibitor is administered orally.

A TCR, polynucleotide, vector, engineered cell, or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intrathecal, and subcutaneous routes. Pulmonary administration can also be employed, e.g., by use of an inhaler or nebulizer, and formulation with an aerosolizing agent for use as a spray. In certain embodiments, the TCR, polynucleotide, vector, engineered cell, or pharmaceutical composition described herein is delivered intravenously. In certain embodiments, the TCR, polynucleotide, vector, engineered cell, or pharmaceutical composition described herein is delivered subcutaneously. In certain embodiments, the TCR, polynucleotide, vector, engineered cell, or pharmaceutical composition described herein is delivered intratumorally. In certain embodiments, the TCR, polynucleotide, vector, engineered cell, or pharmaceutical composition described herein is delivered into a tumor draining lymph node.

The amount of the TCR, polynucleotide, vector, engineered cell, or pharmaceutical composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is a human or an animal, other medications administered, or whether treatment is prophylactic or therapeutic. Usually, the patient is a human but non-human mammals including transgenic mammals can also be treated. Treatment dosages are optimally titrated to optimize safety and efficacy.

A TCR described herein can also be used to assay the levels of a peptide-MHC complex comprising a MLL peptide (e.g., a MLL phosphopeptide, e.g., a peptide consisting of the amino acid sequence of SEQ ID NO; 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in a biological sample using classical immunohistological methods known to those of skill in the art, including immunoassays, such as the enzyme linked immunosorbent assay (ELISA), immunoprecipitation, or Western blotting. Suitable TCR assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label a TCR described herein. Alternatively, a molecule that recognizes a TCR described herein can be labeled and used in combination with a TCR described herein to detect a peptide-MHC complex comprising a MLL peptide (e.g., a MLL phosphopeptide, e.g., a peptide consisting of the amino acid sequence of SEQ ID NO: 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in a biological sample.

Assaying for the levels of a peptide-MHC complex comprising a MLL peptide (e.g., a MLL phosphopeptide, e.g., a peptide consisting of the amino acid sequence of SEQ ID NO: 45 or 47) is intended to include qualitatively or quantitatively measuring or estimating the level of a peptide-MHC complex comprising a MLL peptide (e.g., a MLL phosphopeptide, e.g., a peptide consisting of the amino acid sequence of SEQ ID NO: 45 or 47) in a first biological sample either directly (e.g., by determining or estimating absolute protein level) or relatively (e.g., by comparing to the disease associated protein level in a second biological sample). The level of a peptide-MHC complex comprising a MLL peptide (e.g., a MLL phosphopeptide, e.g., a peptide consisting of the amino acid sequence of SEQ ID NO: 45 or 47) in the first biological sample can be measured or estimated and compared to a standard level, the standard being taken from a second biological sample obtained from an individual not having the disease or being determined by averaging levels from a population of individuals not having the disease. As will be appreciated in the art, once the "standard" level is known, it can be used repeatedly as a standard for comparison.

As used herein, the term "biological sample" refers to any biological sample obtained from a subject, cell line, tissue, or other source of cells potentially displaying a peptide-MHC complex comprising a MLL peptide (e.g., a MLL phosphopeptide, e.g., a peptide consisting of the amino acid sequence of SEQ ID NO: 45 or 47). Methods for obtaining tissue biopsies and body fluids from animals (e.g., humans) are well-known in the art. Biological samples include peripheral mononuclear blood cells.

A TCR described herein can be used for prognostic, diagnostic, monitoring and screening applications, including in vitro and in vivo applications well-known and standard to the skilled artisan and based on the present description. Prognostic, diagnostic, monitoring and screening assays and kits for in vitro assessment and evaluation of immune system status and/or immune response may be utilized to predict, diagnose, and monitor to evaluate patient samples including those known to have or suspected of having a disorder associated with cells displaying a peptide-MHC complex comprising a MLL peptide (e.g., a MLL phosphopeptide. e.g., a peptide consisting of the amino acid sequence of SEQ ID NO: 45 or 47). In vivo applications include directed cell therapy and immune system modulation and radio imaging of a cell, tissue, or organ displaying a peptide-MHC complex comprising a MLL peptide (e.g., a MLL phosphopeptide, e.g., a peptide consisting of the amino acid sequence of SEQ ID NO: 45 or 47).

In one embodiment, a TCR described herein can be used for detecting a peptide-MHC complex comprising a MLL peptide (e.g., a MLL phosphopeptide, e.g., a peptide consisting of the amino acid sequence of SEQ ID NO: 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in immunohistochemistry of biopsy samples. A TCRs described herein may carry a detectable or functional label. When fluorescence labels are used, currently available microscopy and fluorescence-activated cell sorter analysis (FACS) or a combination of both methods known in the art may be utilized to identify and to quantitate the specific binding members. A TCR described herein may carry a fluorescence label. Exemplary fluorescence labels include, for example, reactive and conjugated probes, e.g., aminocoumarin, fluorescein and Texas red, Alexa Fluor dyes, Cy dyes, and DyLight dyes. A TCR described herein may carry a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{1117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of the TCR to a peptide-MHC complex comprising a MLL polypeptide (e.g., a MLL phosphopeptide, e.g., a peptide consisting of the amino acid sequence of SEQ ID NO: 45 or 47). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with a TCR described herein under conditions that allow for the formation of a complex between the TCR and the peptide-MHC complex comprising a MLL peptide (e.g., a MLL phosphopeptide, e.g., a peptide consisting of the amino acid sequence of SEQ ID NO: 45 or 47). Any complexes formed between the TCR and the peptide-MHC complex are detected and compared in the sample and the control. In light of the specific binding of the TCRs described herein for a peptide-MHC complex comprising a MLL peptide (e.g., a MLL phosphopeptide, e.g., a peptide consisting of the amino acid sequence of SEQ ID NO: 45 or 47), the TCRs can be used to detect cells displaying a peptide-MHC complex comprising a MLL polypeptide (e.g., a MLL phosphopeptide, e.g., a peptide consisting of the amino acid sequence of SEQ ID NO: 45 or 47). The TCR described herein can also be used to purify such a complex or cell via immunoaffinity purification. Also included herein is an assay system which may be prepared in the form of a test kit for semi-quantitative or quantitative analysis of the extent of the presence of, for instance, a peptide-MHC complex comprising a MLL peptide (e.g., a MLL phosphopeptide, e.g., a peptide consisting of the amino acid sequence of SEQ ID NO: 45 or 47), or a complex comprising the peptide-MHC complex. The system or test kit may comprise a labeled component, e.g., a labeled TCR, and one or more additional immunochemical reagents.

5.5 Polynucleotides, Vectors and Methods of Producing TCRs

In another aspect, provided herein are polynucleotides comprising a nucleotide sequence encoding a TCR described herein (e.g., α chain. β chain, Vα domain, and/or Vβ domain) that binds to a MLL peptide (e.g., a MLL phosphopeptide, e.g., a peptide consisting of the amino acid sequence of SEQ ID NO: 45 or 47), and vectors, e.g., vectors comprising such polynucleotides for recombinant expression in host cells (e.g., E. coli and mammalian cells). Provided herein are polynucleotides comprising nucleotide sequences encoding an α chain and/or β chain of any of the TCRs provided herein, as well as vectors comprising such polynucleotide sequences, e.g., expression vectors for their efficient expression in host cells, e.g., mammalian cells.

In certain embodiments, a polynucleotide or nucleic acid molecule described herein is isolated or purified. In general, an isolated polynucleotide or nucleic acid molecule is one which is separated from other nucleic acid molecules which are present in the natural source (e.g., in a mouse or a human) of the nucleic acid molecule. Additionally or alternatively, an isolated polynucleotide or nucleic acid molecule (e.g., a cDNA molecule) is substantially free of other cellular material, or culture medium when produced by recombinant techniques, or substantially free of chemical precursors or other chemicals when chemically synthesized. For example, the language "substantially free" includes preparations of polynucleotides or nucleic acid molecules having less than about 15%, 10%, 5%, 2%, 1%, 0.5%, or 0.1% (in particular less than about 10%) of other material, e.g., cellular material, culture medium, other nucleic acid molecules, chemical precursors, and/or other chemicals.

In a particular aspect, provided herein are polynucleotides comprising nucleotide sequences encoding TCRs which bind to the same epitope of a peptide comprising the amino acid sequence set forth in SEQ ID NO: 45 or 47 as the TCRs described supra. In certain embodiments, the peptide is in complex with an MHC as described supra (e.g., HLA-B*0702). In certain embodiments, the TCR comprises sequences that do not naturally exist within the TCR germline repertoire of an animal or mammal (e.g., human) in vivo. In certain embodiments, the polynucleotide comprises sequences that do not naturally exist within the TCR-encoding DNA germline repertoire of an animal or mammal (e.g., human) in vivo.

In certain aspects, provided herein are polynucleotides comprising a nucleotide sequence encoding the α chain and/or β chain of a TCR described herein. The polynucleotides can comprise nucleotide sequences encoding an α chain comprising the α chain FRs and CDRs of TCRs described herein (see, e.g., Table 1) or nucleotide sequences encoding a β chain comprising the β chain FRs and CDRs of TCRs described herein (see, e.g., Table 1).

In certain embodiments, the polynucleotide encodes the α chain and β chain of a TCR described herein. In certain embodiments, the polynucleotide encodes a polypeptide comprising from the N-terminus to the C-terminus: the α chain of the TCR, a 2A cleavage site, and the β chain of the TCR. In certain embodiments, the polynucleotide encodes a polypeptide comprising from the N-terminus to the C-terminus: the β chain of the TCR, a 2A cleavage site, and the α chain of the TCR. In certain embodiments, the polynucleotide encodes a polypeptide comprising from the N-terminus to the C-terminus: the α chain of the TCR, a furin cleavage site, a 2A cleavage site, and the β chain of the TCR. In certain embodiments, the polynucleotide encodes a polypeptide comprising from the N-terminus to the C-terminus: the β chain of the TCR, a furin cleavage site, a 2A cleavage site, and the α chain of the TCR. The furin cleavage site generally has a consensus sequence of $RX_1X_2R$, wherein $X_1$ can be any amino acid, and $X_2$ is K or R (SEQ ID NO: 96). In certain embodiments, $X_1$ is K or R. In certain embodiments, the furin cleavage site has a sequence of RAKR (SEQ ID NO: 97). In certain embodiments, the furin cleavage site is cleaved after the second arginine residue. The 2A cleavage site generally comprises a consensus sequence of $X_1X_2EX_3NPGP$, wherein $X_1$ is D or G, $X_2$ is V or I, and $X_3$ is any amino acid (SEQ ID NO: 99). In certain embodiments, the 2A cleavage site is cleaved between the C-terminal proline residue and the preceding glycine residue. In certain embodiments, the 2A cleavage site comprises an amino acid sequence selected from SEQ ID NOs: 100-105 and 239-246 (Table 7). In certain embodiments, the 2A cleavage site is a porcine teschovirus-1 2A (P2A) cleavage site having the amino acid sequence set forth in SEQ ID NO: 10. In certain embodiments the 2A cleavage site is a porcine teschovirus-1 2A (P2A) cleavage site having the amino acid sequence set forth in SEQ ID NO; 239. In certain embodiments, the polynucleotide comprises a nucleic acid sequence encoding SEQ ID NO: 90. In certain embodiments, the polynucleotide comprises a nucleic acid sequence encoding SEQ ID NO: 238.

TABLE 7

Exemplary 2A cleavage sites

| SEQ ID NO: | Description | Amino acid Sequence |
|---|---|---|
| 100 | porcine teschovirus-1 2A (P2A) variant 1 | ATNFSLLKQAGDVEENPGP |
| 239 | porcine teschovirus-1 2A (P2A) variant 2 | GSGATNFSLLKQAGDVEENPGP |
| 101 | thosea-asigna virus 2A peptide (T2A) variant 1 | EGRGSLLTCGDVEENPGP |
| 240 | thosea-asigna virus 2A peptide (T2A) variant 2 | GSGEGRGSLLTCGDVEENPGP |
| 102 | equine rhinitis A virus 2A peptide (E2A) variant 1 | QCTNYALLKLAGDVESNPGP |
| 241 | equine rhinitis A virus 2A peptide (E2A) variant 2 | GSGQCTNYALLKLAGDVESNPGP |
| 103 | foot-and-mouth disease virus 2A peptide (F2A) variant 1 | VKQTLNFDLLKLAGDVESNPGP |
| 242 | foot-and-mouth disease virus 2A peptide (F2A) variant 2 | GSGVKQTLNFDLLKLAGDVESNPGP |
| 104 | cytoplasmic polyhedrosis virus 2A peptide (BmCPV 2A) variant 1 | DVFRSNYDLLKLCGDIESNGPG |
| 243 | cytoplasmic polyhedrosis virus 2A peptide (BmCPV 2A) variant 2 | GSGDVFRSNYDLLKLCGDIESNPGP |
| 105 | flacherie virus of B. mori 2A peptide (BmIFV 2A) variant 1 | TLTRAKIEDELIRAGIESNPGP |

TABLE 7-continued

Exemplary 2A cleavage sites

| SEQ ID NO: | Description | Amino acid Sequence |
|---|---|---|
| 244 | flacherie virus of *B. mori* 2A peptide (BmIFV 2A) variant 2 | GSGTLTRAKIEDELIRAGIESNPGP |
| 245 | Dual P2A-T2A peptide variant 1 | ATNFSLLKQAGDVEENPGPEGRGSLLTCGDVEENPGP |
| 246 | Dual P2A-T2A peptide variant 2 | GSGATNFSLLKQAGDVEENPGPEGRGSLLTCGDVEENPGP |

Also provided herein are polynucleotides encoding a TCR described herein that are optimized, e.g., by codon/RNA optimization, replacement with heterologous signal sequences, and elimination of mRNA instability elements. Methods to generate optimized nucleic acids encoding a TCR (e.g., α chain, β chain, Vα domain, and/or Vβ domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/f or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of a TCR by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of a TCR encoded by polynucleotides that have not been optimized.

In certain embodiments, an optimized polynucleotide sequence encoding a TCR described herein (e.g., α chain, β chain, Vα domain and/or Vβ domain) can hybridize to an antisense (e.g., complementary) polynucleotide of an unoptimized polynucleotide sequence encoding a TCR described herein (e.g., α chain, β chain, Vα domain, and/or Vβ domain). In specific embodiments, an optimized nucleotide sequence encoding a TCR described herein under high stringency conditions to antisense polynucleotide of an unoptimized polynucleotide sequence encoding a TCR described herein. In a specific embodiment, an optimized nucleotide sequence encoding a TCR described herein hybridizes under high stringency, intermediate or lower stringency hybridization conditions to an antisense polynucleotide of an unoptimized nucleotide sequence encoding a TCR described herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding TCRs described herein, e.g., TCRs described in Tables 1-4, and modified versions of these TCRs can be determined using methods well-known in the art, i.e., nucleotide codons known to encode particular amino acids are assembled in such a way to generate a nucleic acid that encodes the TCR. Such a polynucleotide encoding the TCR can be assembled from chemically synthesized oligonucleotides (e.g., as described in Kutmeier G et al., (1994). BioTechniques 17: 242-6), which, briefly, involves the synthesis of overlapping oligonucleotides containing portions of the sequence encoding the TCR, annealing and ligating of those oligonucleotides, and then amplification of the ligated oligonucleotides by PCR.

Alternatively, a polynucleotide encoding a TCR described herein can be generated from nucleic acid from a suitable source (e.g., a T lymphocyte) using methods well-known in the art (e.g., PCR and other molecular cloning methods). For example, PCR amplification using synthetic primers hybridizable to the 3' and 5' ends of a known sequence can be performed using genomic DNA obtained from T cells expressing the TCR of interest. Such PCR amplification methods can be used to obtain nucleic acids comprising the sequence encoding the α chain and/or β chain of a TCR. Such PCR amplification methods can be used to obtain nucleic acids comprising the sequence encoding the Vα domain and/or Vβ domain of a TCR. The amplified nucleic acids can be cloned into vectors for expression in host cells and for further cloning, for example, to generate chimeric and humanized TCRs.

If a clone containing a nucleic acid encoding a particular TCR is not available, but the sequence of the TCR molecule is known, a nucleic acid encoding the TCR can be chemically synthesized or obtained from a suitable source (e.g., a TCR cDNA library or a cDNA library generated from, or nucleic acid, e.g., poly A⁺ RNA, isolated from, any tissue or cells expressing the TCR, such as T lymphocytes selected to express a TCR described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes TCRs. Amplified nucleic acids generated by PCR can then be cloned into replicable cloning vectors using any method well-known in the art.

DNA encoding TCRs described herein can be readily isolated and sequenced using conventional procedures, e.g., by using oligonucleotide probes that are capable of binding specifically to genes encoding the α chain and/or β chain of the TCR. T lymphocytes can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce TCR protein, to obtain the synthesis of TCRs in the recombinant host cells.

To generate whole TCRs, PCR primers including Vα or Vβ nucleotide sequences, a restriction site, and a flanking sequence to protect the restriction site can be used to amplify the Vα or Vβ sequences into clones, e.g., clones of individual Vα or Vβ nucleotide sequences, or clones of single-chain TCRs containing variable regions of TCRs attached by a flexible linker. Utilizing cloning techniques known to those of skill in the art, the PCR amplified Vα domains can be cloned into vectors expressing an α chain constant region, and the PCR amplified Vβ domains can be cloned into vectors expressing a β chain constant region. In certain embodiments, the vectors for expressing the Vα or Vβ domains comprise an EF-1α promoter, a secretion signal, a cloning site for the variable region, constant domains, and a selection marker such as neomycin. The α chain and β chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

The DNA also can be modified, for example, by substituting the coding sequence for human α chain and β chain constant domains in place of the murine sequences, or by covalently joining to the TCR coding sequence all or part of the coding sequence for a non-TCR polypeptide.

Also provided are polynucleotides that hybridize under high, intermediate, or low stringency hybridization conditions to polynucleotides that encode a TCR described herein. In specific embodiments, polynucleotides described herein hybridize under high, intermediate, or low stringency hybridization conditions to polynucleotides encoding a Vα domain and/or Vβ domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) *Current Protocols in Molecular Biology*, Vol. 1, Green Publishing Associates. Inc, and John Wiley & Sons, Inc., New York at pages 6.3.1-6.3.6 and 2.10.3.

In certain aspects, provided herein are cells (e.g., host cells) expressing (e.g., recombinantly) TCRs described herein which bind to a MLL polypeptide (e.g., a MLL phosphopeptide, e.g., a peptide consisting of the amino acid sequence of SEQ ID NO: 45 or 47), and related polynucleotides and expression vectors. Provided herein are vectors (e.g., expression vectors) comprising polynucleotides comprising nucleotide sequences encoding such TCRs for recombinant expression in host cells, e.g., in mammalian cells. Also provided herein are host cells comprising such vectors for recombinantly expressing TCRs described herein (e.g., human or humanized TCR). In a particular aspect, provided herein are methods for producing a TCR described herein, comprising expressing such TCR from a host cell.

In another aspect, provided herein are methods for producing an engineered cell (e.g., a cell comprising a heterologous and/or recombinant nucleic acid) as described herein. In certain embodiments, the method comprises contacting a cell with a vector as described herein under conditions that allow introduction of the vector into the cell. In certain embodiments, the condition allows transfection of the cell with the vector (e.g., by liposome or electroporation). In one embodiment, the condition allows transfection of the cell with an mRNA vector by electroporation. In certain embodiments, the vector is a viral vector, and the conditions allow transduction of the cell with the viral vector. In certain embodiments, the vector is introduced to the cell in vitro or ex vivo. In certain embodiments, the vector is introduced to the cell in vivo.

Recombinant expression of a TCR described herein (e.g., a full-length TCR, α chain and/or β chain of a TCR, or a single-chain TCR described herein) that binds to a MLL polypeptide (e.g., a MLL phosphopeptide, e.g., a peptide consisting of the amino acid sequence of SEQ ID NO. 45 or 47) involves construction of an expression vector containing a polynucleotide that encodes the TCR. Once a polynucleotide encoding a TCR described herein has been obtained, the vector for the production of the TCR molecule can be produced by recombinant DNA technology using techniques well-known in the art. Thus, methods for preparing a protein by expressing a polynucleotide containing a TCR encoding nucleotide sequence are described herein. Methods which are well-known to those skilled in the art can be used to construct expression vectors containing TCR encoding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a TCR molecule described herein (e.g., a full-length TCR, α chain or β chain of a TCR, Vα or Vβ of a TCR, or an α or β chain CDR), operably linked to a promoter.

The vector can comprise any type of nucleotides (including but not limited to DNA and RNA) which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. In one embodiment, the non-naturally occurring or altered nucleotides or inter-nucleotide linkages do not hinder the transcription or replication of the vector. The expression vector can be a viral vector (e.g., a retroviral vector, an adenoviral vector, an adeno-associated viral vector, or a baculoviral vector). In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

An expression vector can be transferred to a cell (e.g., a host cell) by conventional techniques and the resulting cell can then be cultured by conventional techniques to produce a TCR described herein. Thus, provided herein are host cells containing a polynucleotide encoding a TCR molecule described herein (e.g., a full-length TCR, α chain or β chain of a TCR, Vα or Vβ of a TCR, or an α or β chain CDR) operably linked to a promoter for expression of such sequences in the host cell. In certain embodiments, for the expression of double-chained TCRs, vectors encoding both the α and β chains, individually, can be co-expressed in the host cell for expression of the entire TCR molecule, as detailed below. In certain embodiments, a host cell contains a vector comprising a polynucleotide encoding both the α chain and β chain of a TCR described herein. In specific embodiments, a host cell contains two different vectors, a first vector comprising a polynucleotide encoding an α chain or an α chain variable region of a TCR described herein, and a second vector comprising a polynucleotide encoding a β chain or a β chain variable region of a TCR described herein. In other embodiments, a first host cell comprises a first vector comprising a polynucleotide encoding an α chain or an α chain variable region of a TCR described herein, and a second host cell comprises a second vector comprising a polynucleotide encoding a β chain or a β chain variable region of a TCR described herein. In specific embodiments, an α chain or α chain variable region expressed by a first cell associated with a β chain or β chain variable region expressed by a second cell to form a TCR described herein. In certain embodiments, provided herein is a population of host cells comprising such first host cell and such second host cell.

In a particular embodiment, provided herein is a population of vectors comprising a first vector comprising a polynucleotide encoding an α chain or α chain variable region of a TCR described herein, and a second vector comprising a polynucleotide encoding a β chain or D chain variable region of a TCR described herein.

A variety of host-expression vector systems can be utilized to express TCR molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a TCR molecule described herein in situ. These include but are not limited to microorganisms such as bacteria (e.g., *E. coli* and *B. subtilis*) transformed with recombinant bacteriophage DNA, plasmid DNA, or cosmid DNA expression vectors containing TCR coding sequences; yeast (e.g., *Saccharomyces Pichia*) transformed with recombinant yeast expression vectors containing TCR coding sequences; insect cell systems infected with recombinant virus expression vectors (e.g., baculovirus) containing TCR coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing TCR coding sequences; or mammalian cell systems (e.g., COS (e.g., COS1 or COS), CHO, BHK, MDCK, HEK 293. NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing TCRs described herein are CHO cells, for example CHO cells from the CHO GS System™ (Lonza). In a particular embodiment, cells for expressing TCRs described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant TCR molecule, are used for the expression of a recombinant TCR molecule. For example, mammalian cells such as Chinese hamster ovary (CHO) cells, in conjunction with a vector such as the major intermediate early gene promoter element from human cytomegalovirus, are an effective expression system for TCRs (Foecking M K & Hofstetter H (1986) Gene 45: 101-5; and Cockett M I et al., (1990) Biotechnology 8(7): 662-7). In certain embodiments, TCRs described herein are produced by CHO cells or NS0 cells. In a specific embodiment, the expression of nucleotide sequences encoding TCRs described herein is regulated by a constitutive promoter, inducible promoter, or tissue specific promoter.

In certain embodiments, the mammalian host cell is a lymphocyte (e.g., a human lymphocyte), such as a T cell or a natural killer (NK) cell. In certain embodiments, the lymphocyte is a T cell. Any T cell at any developmental stage can be used to express a TCR disclosed herein. For example, in certain embodiments, the T cell is selected from the group consisting of a CD8$^+$ cytotoxic T cell, a CD4$^+$ cytotoxic T cell, a CD4$^+$ helper T cell (e.g., a Th1 or a Th2 cell), a CD4/CD8 double positive T cells, a tumor infiltrating T cell, a thymocyte, a memory T cell, a naïve T cell, and a natural killer T cell (e.g., an invariant natural killer T cell). Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian host cell is a pluripotent stem cell (e.g., an embryonic stem cell, an induced pluripotent stem cell), lymphocyte progenitor cell, or a hematopoietic stem cell (e.g., isolated and/or enriched from bone marrow, umbilical cord blood, or peripheral blood).

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase.

In certain embodiments, the mammalian host cell is a population of cells presenting a TCR disclosed herein on the cell surface. The population of cells can be heterogeneous or homogenous. In certain embodiments, at least 50% (e.g., at least 60%, 70%, 80%., 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

In bacterial systems, a number of expression vectors can be advantageously selected depending upon the use intended for the TCR molecule being expressed. For example, when a large quantity of such a TCR is to be produced, for the generation of pharmaceutical compositions of a TCR molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the TCR coding sequence can be ligated individually into the vector in frame with the lac Z coding region so that a fusion protein is produced: pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system. *Autographa californica* nuclear polyhedrosis virus (AcNPV), for example, can be used as a vector to express foreign genes. The virus grows in *Spodoptera frugiperda* cells. The TCR coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the TCR encoding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g. region E1 or E3) will result in a recombinant virus that is viable and capable of expressing the TCR molecule in infected hosts (e.g., see Logan J & Shenk T (1984) PNAS 81(12): 3655-9). Specific initiation signals can also be required for efficient translation of inserted TCR coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M. BSC1, BSC40, YB/20. BMT10 and HsS78Bst cells. In certain embodiments, TCR molecules described herein are produced in mammalian cells, such as CHO cells.

For long-term expression of the recombinant TCRs, stable expression cells can be generated. For example, cell lines which stably express a TCR described herein can be engineered. In specific embodiments, a cell provided herein stably expresses an α chain or α chain variable region and a β chain or β chain variable region which associate to form a TCR described herein.

In certain aspects, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a TCR described herein. Such engineered cell lines can be particularly useful in screening and evaluation of compositions that interact directly or indirectly with the TCR molecule.

A number of selection systems can be used, including but not limited to, the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034), and adenine phosphoribosyltransferase (Lowy I et al., (1980) Cell 22(3): 817-23) genes in tk-, hgprt- or aprt-cells, respectively, each of which is incorporated by reference herein in its entirety. Also, antimetabolite resistance can be used as the basis of selection for the following genes: dhfr, which confers resistance to methotrexate (Wigler M et al., (1980) PNAS 77(6): 3567-70: O'Hare K et al., (1981) PNAS 78: 1527-31): gpt, which confers resistance to mycophenolic acid (Mulligan R C & Berg P (1981) PNAS 78(4): 2072-6): neo, which confers resistance to the aminoglycoside G-418 (Wu G Y & Wu C H (1991) Biotherapy 3: 87-95; Tolstoshev P (1993) Ann Rev Pharmacol Toxicol 32: 573-596: Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), each of which is incorporated by reference herein in its entirety. Methods commonly known in the art of recombinant DNA technology can be routinely applied to select the desired recombinant clone and such methods are described, for example, in Ausubel F M et al., (eds.), *Current Protocols in Molecular Biology*, John Wiley & Sons, NY (1993): Kriegler M, *Gene Transfer and Expression*, A Laboratory Manual, Stockton Press, NY (1990); and in Chapters 12 and 13, Dracopoli N C et al., (eds.), *Current Protocols in Human Genetics*, John Wiley & Sons, NY (1994); Colbère-Garapin F et al., (1981) J Mol Biol 150: 1-14, which are incorporated by reference herein in their entireties.

The expression levels of a TCR molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is incorporated by reference herein in its entirety). When a marker in the vector system expressing TCR is amplifiable, increase in the level of inhibitor present in culture of host cells will result in selection of host cells with increased numbers of copies of the marker gene. Since the amplified region is associated with the TCR gene, production of the TCR will also increase (Crouse G F et al., (1983) Mol Cell Biol 3: 257-66, which is incorporated by reference herein in its entirety).

In other aspects, the host cell can be transduced with a viral vector (e.g., a retroviral vector, an adenoviral vector, an adeno-associated viral vector, or a baculoviral vector) comprising a sequence encoding a TCR as described herein. In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

In certain embodiments, the vector further comprises a transcriptional and/or translational control sequence (e.g., a promoter, an enhancer, and/or a Kozak sequence) operably linked to the sequence encoding a TCR as described herein. Alternatively, the sequence encoding the TCR may not be operably linked to a transcriptional and/or translational control sequence (e.g., a promoter, an enhancer, and/or a Kozak sequence), but is flanked by sequences homologous to the sequences flanking a locus of the host cell genome, wherein the integration of the TCR-coding sequence allows expression of the encoded TCR from the transcriptional and/or translational control sequence at or near the genomic locus.

The host cell can be co-transferred (e.g., co-transfected or co-transduced) with two or more expression vectors described herein, the first vector encoding an α chain derived polypeptide and the second vector encoding a β chain derived polypeptide. The two vectors can contain identical selectable markers which enable equal expression of α chain and β chain polypeptides. The host cells can be co-transferred with different amounts of the two or more expression vectors. For example, host cells can be co-transferred with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50. In some embodiments, the coding sequences for the a and 1 chains are DNA. In some embodiments, the coding sequences for the a and β chains are RNA.

Alternatively, a single vector can be used which encodes, and is capable of expressing, both a and 1 chain polypeptides. The coding sequences for the a and β chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., 1 chain of a TCR described herein), and a second gene (e.g., α chain of a TCR described herein). In such an expression vector, the transcription of both genes can be driven by the promoter, whereas the translation of the mRNA from the first gene can be initiated by a cap-dependent scanning mechanism and the translation of the mRNA from the second gene can be by a cap-independent mechanism. e.g., by an IRES. Alternatively, the two genes can be operably linked by a self-cleavage peptide (e.g., a 2A peptide) or a peptide sequence recognized by an intracellular or an extracellular protease.

Once a TCR molecule described herein has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the TCR described herein can be fused to heterologous polypeptide sequences described herein or otherwise known in the art to facilitate purification.

In specific embodiments, a TCR described herein is isolated or purified. Generally, an isolated TCR is one that is substantially free of other TCRs with different antigenic specificities than the isolated TCRs. For example, in a particular embodiment, a preparation of a TCR described herein is substantially free of cellular material and/or chemical precursors. The language "substantially free of cellular material" includes preparations of a TCR in which the TCR is separated from cellular components of the cells from which it is isolated or recombinantly produced. Thus, a TCR that is substantially free of cellular material includes preparations of the TCR having less than about 30%, 20%, 10%, 5%, 2%, 1%, 0.5%, or 0.1% (by dry weight) of heterologous protein (also referred to herein as a "contaminating protein") and/or variants of the TCR, for example, different post-translational modified forms of the TCR or other different versions of the TCR (e.g., fragments thereof). When the TCR is recombinantly produced, it is also generally substantially free of culture medium, i.e., culture medium represents less than about 20%, 10%, 2%, 1%, 0.5%, or 0.1% of the volume of the protein preparation. When the TCR is produced by chemical synthesis, it is generally substantially free of chemical precursors or other chemicals, i.e., it is separated from chemical precursors or other chemicals which are involved in the synthesis of the TCR Accordingly, such preparations of the TCR have less than about 30%, 20%, 10%, or 5% (by dry weight) of chemical precursors or compounds other than the TCR of interest. In a specific embodiment, TCRs described herein are isolated or purified.

TCRs that bind to a MLL polypeptide (e.g., a MLL phosphopeptide, e.g., a peptide consisting of the amino acid sequence of SEQ ID NO. 45 or 47) can be produced by any method known in the art for the synthesis of TCRs, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) *Molecular Cloning: A Laboratory Manual*, Cold Spring Harbor Laboratory Press; Sambrook J et al., (1989), *Molecular Cloning: A Laboratory Manual*, Second Edition, Cold Spring Harbor Laboratory Press: Sambrook J et al., (2001) *Molecular Cloning: A Laboratory Manual*, Cold Spring Harbor Laboratory Press, Cold Spring Harbor, NY: Ausubel F M et al., *Current Protocols in Molecular Biology*, John Wiley & Sons (1987 and annual updates): *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren B et al., (eds.) (1999) *Genome Analysis: A Laboratory Manual*, Cold Spring Harbor Laboratory Press, each of which is incorporated by reference herein in its entirety.

In a specific embodiment, a TCR described herein is a TCR (e.g., recombinant TCR) prepared, expressed, created, or isolated by any means that involves creation, e.g., via synthesis, genetic engineering of DNA sequences. In certain embodiments, such TCR comprises sequences (e.g., DNA sequences, RNA sequences, or amino acid sequences) that do not naturally exist within the TCR germline repertoire of an animal or mammal (e.g., human) in vivo.

In one aspect, provided herein is a method of making a TCR that binds to a MLL polypeptide (e.g., a MLL phosphopeptide, e.g., a peptide consisting of the amino acid sequence of SEQ ID NO: 45 or 47), the method comprising culturing a cell or host cell described herein. In a certain aspect, provided herein is a method of making a TCR which binds to a MLL polypeptide (e.g., a MLL phosphopeptide, e.g., a peptide consisting of the amino acid sequence of SEQ ID NO: 45 or 47), the method comprising expressing (e.g., recombinantly expressing) the TCR using a cell or host cell described herein (e.g., a cell or a host cell comprising polynucleotides encoding a TCR described herein). In a particular embodiment, the cell is an isolated cell. In a particular embodiment, the exogenous polynucleotides have been introduced into the cell. In a particular embodiment, the method further comprises the step of purifying the TCR obtained from the cell or host cell.

The TCRs described herein can be generated using various phage display methods known in the art. In phage display methods, functional TCR domains are displayed on the surface of phage particles which carry the polynucleotide sequences encoding them. In particular, DNA sequences encoding Vα and Vβ domains are amplified from animal cDNA libraries (e.g., human or murine cDNA libraries of affected tissues). The DNA encoding the Vα and Vβ domains are connected with a peptide linker by PCR and cloned into a phagemid vector. The vector is electroporated in E coil and the E col is infected with helper phage. Phage used in these methods are typically filamentous phage including fd and M13, and the Vα and Vβ domains are usually recombinantly fused to either the phage gene III or gene VIII. Phage expressing an antigen binding domain that binds to a particular antigen can be selected or identified with a peptide or a peptide-MHC complex, e.g., using such a complex displayed on the surface of a cell or captured to a solid surface or bead. Examples of phage display methods that can be used to make the TCRs described herein include those disclosed in Zhao Y et al., (2007) J Immunol 179: 5845-54, which is incorporated by reference herein in its entirety.

As described in the above references, after phage selection, the TCR coding regions from the phage can be isolated and used to generate whole TCRs, including human TCRs, and expressed in any desired host, including mammalian cells, insect cells, plant cells, yeast, and bacteria, e.g., as described below.

In certain embodiments, to generate whole TCRs, PCR primers including Vα or Vβ nucleotide sequences, a restriction site, and a flanking sequence to protect the restriction site can be used to amplify the Vα or Vβ sequences from a template, e.g., clones of single-chain TCRs containing variable regions of TCRs connected by a peptide linker. Utilizing cloning techniques known to those of skill in the art, the PCR amplified Vα domains can be cloned into vectors expressing a Vα constant region, and the PCR amplified Vβ domains can be cloned into vectors expressing a Vβ constant region. The α chain and D chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

In certain embodiments, to generate whole TCRs from a polynucleotide encoding the α chain and D chain of a TCR as described herein, or from a vector comprising thereof, a polypeptide comprising the α chain and β chain of the TCR is expressed from the polynucleotide or vector. The polypeptide is optionally isolated and/or purified. The polypeptide is contacted with a Furin enzyme. In certain embodiments, where the Furin cleavage site has the amino acid sequence of $RX_1X_2R$, wherein $X_1$ is K or R and $X_2$ is K or R (SEQ ID NO: 98), the polypeptide is further contacted with a carboxypeptidases either simultaneously or subsequently, wherein the carboxypeptidase removes the basic amino acids, K or R, from the C-terminus of a polypeptide.

A chimeric TCR is a molecule in which different portions of the TCR are derived from different TCR molecules, e.g., TCRs from different species.

In particular embodiments, a TCR described herein, which binds to the same epitope of a peptide comprising the amino acid sequence set forth in SEQ ID NO: 45 or 47 as a TCR described herein, is a human TCR. Human TCRs can be produced using any method known in the art. For example, transgenic mice which are incapable of expressing functional endogenous TCRs, but which can express human TCR genes, can be used. In particular, the human a and β chain TCR genes can be introduced randomly or by homologous recombination into mouse embryonic stem cells. The mouse a and D chain TCR genes can be rendered non-functional separately or simultaneously with the introduction of human TCR loci by homologous recombination. In particular, homozygous deletion of the JH region prevents endogenous TCR production. The modified embryonic stem cells are expanded and microinjected into blastocysts to produce chimeric mice. The chimeric mice are then bred to produce homozygous offspring which express human TCRs. The transgenic mice are immunized in the normal fashion with a selected antigen, e.g., all or a portion of an antigen (e.g., a MLL peptide, e.g., a MLL phosphopeptide). T lymphocytes comprising TCRs directed against the antigen can be obtained from the immunized, transgenic mice. The human TCR transgenes harbored by the transgenic mice rearrange during T cell differentiation. Thus, using such a technique, it is possible to produce therapeutically useful TCRs arising from in vivo immunization.

Human TCRs which bind to a MLL peptide (e.g., a MLL phosphopeptide, e.g., a peptide consisting of the amino acid sequence of SEQ ID NO: 45 or 47) can be made by a variety of methods known in the art including phage display methods or mammalian display using TCR libraries derived from human TCR sequences.

5.6 Kits

Also provided are kits comprising one or more TCRs described herein, pharmaceutical compositions or conjugates thereof, polynucleotides (e.g., expression vectors) encoding one or more TCRs described herein, or cells expressing one or more TCRs described herein. In a specific embodiment, provided herein is a pharmaceutical pack or kit comprising one or more containers filled with one or more of the ingredients of the pharmaceutical compositions described herein, such as one or more TCRs, polynucleotides, or cells provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol 12-myristate 13-acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises a TCR described herein, e.g., a purified TCR, in one or more containers. In a specific embodiment, kits described herein contain a substantially isolated peptide-MHC complex comprising a MLL peptide (e.g., a MLL phosphopeptide, e.g., a peptide consisting of the amino acid sequence of SEQ ID NO: 45 or 47) as a control antigen. In another specific embodiment, the kits described herein further comprise a control TCR which does not react with a peptide-MHC complex comprising a MLL peptide (e.g., a MLL phosphopeptide, e.g., a peptide consisting of the amino acid sequence of SEQ ID NO: 45 or 47). In another specific embodiment, kits described herein contain one or more elements for detecting the binding of a TCR to a peptide-MHC complex comprising a MLL peptide (e.g., a MLL phosphopeptide, e.g., a peptide consisting of the amino acid sequence of SEQ ID NO: 45 or 47) (e.g., the TCR can be conjugated to a detectable substrate such as a fluorescent compound, an enzymatic substrate, a radioactive compound or a luminescent compound, or a binding molecule which recognizes the TCR can be conjugated to a detectable substrate). In specific embodiments, a kit provided herein can include a recombinantly produced or chemically synthesized peptide-MHC complex comprising a MLL peptide (e.g., a MLL phosphopeptide, e.g., a peptide consisting of the amino acid sequence of SEQ ID NO: 45 or 47). The peptide-MHC complex comprising a MLL peptide (e.g., a MLL phosphopeptide, e.g., a peptide consisting of the amino acid sequence of SEQ ID NO: 45 or 47) provided in the kit can be attached to a solid support (e.g., a solid surface or a bead) or be integrated into a lipid membrane (e.g., a liposome, or a fixed cell). In a more specific embodiment, the detecting means of the above described kit includes a solid support to which a peptide-MHC complex comprising a MLL peptide (e.g., a MLL phosphopeptide, e.g., a peptide consisting of the amino acid sequence of SEQ ID NO: 45 or 47) is attached. Such a kit can also include a non-attached reporter-labeled binding molecule which recognizes the TCR. In this embodiment, binding of the TCR to the peptide-MHC complex can be detected by binding of the said reporter-labeled binding molecule.

6. EXAMPLES

The examples in this Section (i.e., Section 6) are offered by way of illustration, and not by way of limitation.

6.1 Example 1: Discovery of Novel MLL TCRs

Novel TCRs that bind to MLL phosphopeptides were identified using two proprietary platforms. The first platform is a primary T cell expansion platform in which phosphopeptide-specific cognate TCRαβ pairs were identified by functional screening and NGS-based sequencing. The second platform is a TCR display platform in which a and P chain libraries were generated from donor PBMCs, optionally without previous target-specific stimulation, followed by rounds of TCR enrichment for target-specific phosphopeptide binding.

6.1.1 Preparation of Cells

Human dendritic cells (DCs) and CD8+ T cells were isolated from healthy donor HLA-B*0702+ PBMCs (Cellular Technologies Ltd., Shaker Heights, OH).

Briefly, CD14+ monocytes were isolated from the PBMCs by positive selection via magnetic separation using anti-CD14 microbeads according to the manufacturer's instructions (Miltenyi Biotech, Bergisch Gladbach, Germany, Cat. No.: 130-050-201) and cultivated in growth medium composed of CellGro® DC-medium (Cell Genix, Cat. No.: 20801-05500) supplemented with 5% human serum (Sigma, Cat. No.: H3667-100 mL), 1% Penicillin/Streptomycin (Amimed Direct, London. UK, Cat. No.: 4-01F00-H), 800 U/mL of GM-CSF (Miltenyi Biotech, Cat. No.: 130-095-372), and 10 ng/mL of IL-4 (Miltenyi Biotech, Cat. No.: 130-093-917) for three days to induce differentiation to DCs. Following full differentiation after an additional 16-hour incubation in growth medium supplemented with 10 ng/mL of *Escherichia coli* LPS (Sigma-Aldrich, St. Louis, MO, #L4391-1MG), 100 U/mL of IFNγ (Peprotech, Rocky Hill, NJ, Cat. No.: 300-02), and 20 µg/mL of the MLL-pM peptide (EPR[pS]PSHSM; SEQ ID NO: 45) or FLU and CMV control peptides, DCs were incubated in the presence of 50 µg/mL of Mitomycin (Sigma, Cat. No.: M05053-2MG) for 60 min to inhibit dendritic cell proliferation. DCs incubated in the absence of antigen peptide were prepared as control samples.

CD8+ T cells were isolated from CD14+ monocyte depleted PBMCs via negative selection using a magnetic bead human CD8+ T cell isolation kit according to the manufacturer's instructions (Miltenyi Biotech, Cat. No.: 130-096-495). CD8+ T cells were separated into CD45RO+/CD57− memory T cell and CD45RA+/CCR7+/CD62L+ naïve T cell populations after surface staining with a cocktail of anti-CD8-PerCP (eBioscience, Thermo Fisher, Waltham, MA, Cat. No.: 9043-0087-120), anti-CD45RA-PE-Cy7 (eBiosciences, Cat. No.: 25-0458-42), anti-CD45RO-FITC (eBioscience. Cat. No.: 11-0457-42), anti-CD57-PE (Biolegend, San Diego, CA, Cat. No.: 322312), anti-CCR7-BV421 (BD horizon, Cat. No.: 562555), and anti-CD62L-APC (eBioscience, Cat. No.: 17-0629-42) reagents using a FACSAriaIII (Becton Dickinson, Franklin Lakes, NJ) cell sorter.

6.1.2 Phosphopeptide-Specific Stimulation and Staining of Human CD8+ T Cells Memory and naïve CD8+ T cell subsets ($1.0 \times 10^6$ cells/mL) treated with 5 µg/mL of IL-7 (Miltenyi Biotech. Cat. No.: 130-093-937) for 16 hours were co-incubated with peptide-pulsed or non-pulsed DCs ($2.5 \times 10^1$ cells/mL) at a T cell:DC ratio of 4:1 in growth medium supplemented with 30 ng/mL of IL-21 (Peprotech, Cat. No.: 200-21) for 10 days. After days 3, 6, 8, and 10, fresh growth medium supplemented with 5 ng/mL (10 ng/mL at day 10) of IL-15 (BioLegend, Cat. No.: 570302) and IL-7 was added to the co-cultures.

1.0×10⁶ cells from the co-cultures were treated with 1 pM of Dasatinib (Cell Signaling Technology. Cat. No.: 90525) before 10 µL of HLA-B*0702 pentamers loaded with the MLL-pM peptide EPR[pS]PSHSM (SEQ ID NO; 45), the Flu control peptide QPEWFRNVL (SEQ ID NO: 84), or the CMV control peptide TPRVTGGGAM (SEQ ID NO: 85) were added. Following addition of an anti-CD8-Per-CP reagent, pentamer-binding of CD8+ T cells was assessed by flow cytometry using a FACSCantoII cytometer. Subsequently, up to 1.0×10⁶ cells of the co-cultures containing memory or naïve CD8+ T cells that bind to the MLL-pM peptide were treated with Monensin (1:1000) (eBioscience, Cat. No.: 00-4505-51) and Brefeldin A (1:1000) (eBioscience, Cat. No.: 004506-61) and stained with pMHC pentamers as described above. Cocktails comprising anti-CD8-FITC, anti-KLGR1-PerCP-eFluor710 (eBioscience, Cat. No.; 46-9488-49), anti-4-1BB-BV421, anti-CD69-PE-Cy7 (eBioscience, Cat. No.: 25-069942), anti-IFNγ-APC (eBioscience, Cat. No.: 17-7319-82) or anti-IFNγ-PE (eBioscience, Cat. No.: 12-7319-82), and anti-TNFα-BV510 (BioLegend. Cat. No.; 502950) were used to detect surface and intracellular expression of T cell activation markers. Cells were permeabilized using Cytofix/Cytoperm (BD, Cat. No.: 51-2090KZ) and PermWash Buffer (BD, Cat. No.: 51-2091KZ) according to the manufacturer's instructions. Peptide pentamer-binding was re-assessed using a FACSCantoII cytometer and memory and naïve CD8+ T cell subsets that bind to the MLL-pM peptide and/or respond to the MLL-pM stimulation were then acquired using a FACSAriaII cytometer.

6.1.3 Exemplary Data from the Screening Process

Figure 1:
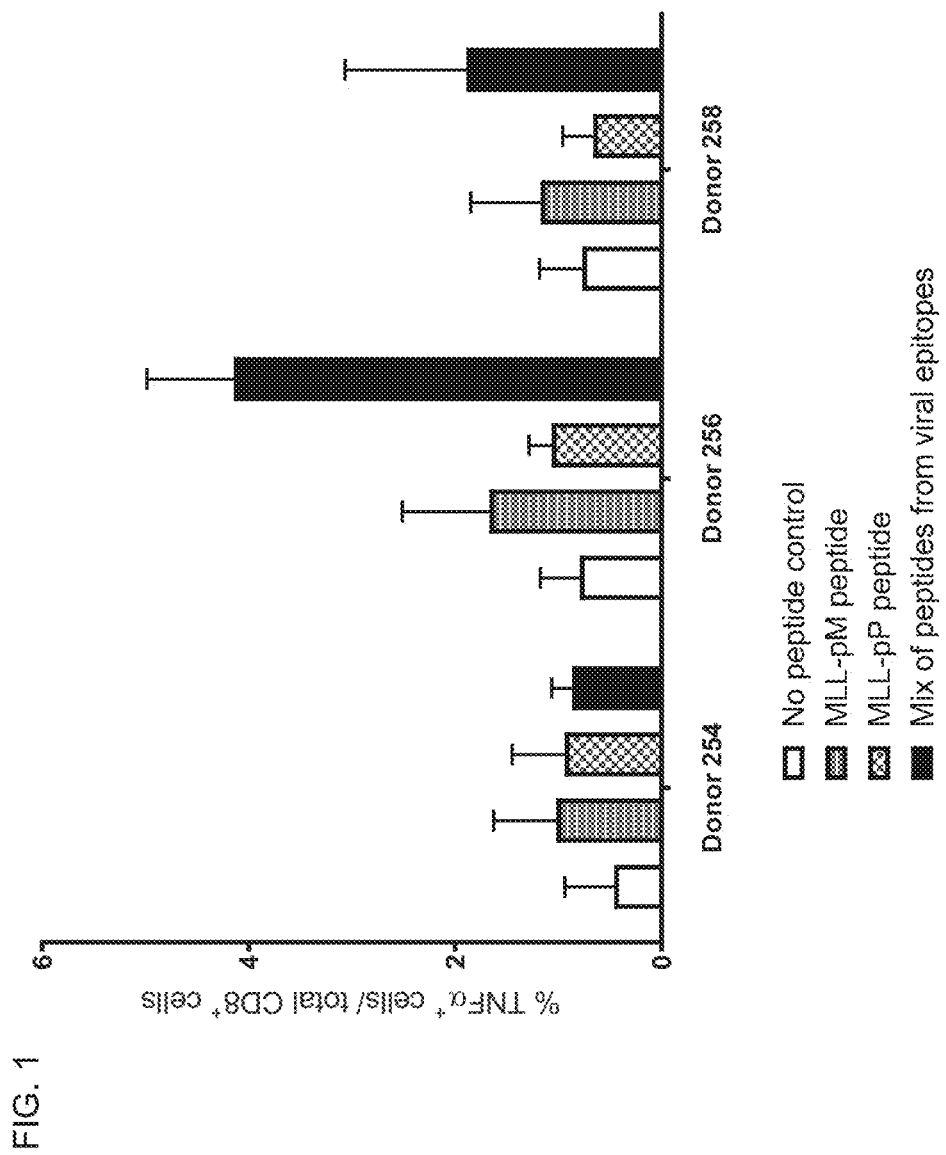
FIG. 1 is a bar graph showing the percentage of TNFα+ cells among the total CD8+ cells from three HLA-B*0702 healthy donors after their PBMCs were stimulated with the MLL-pM peptide (EPR[pS]PSHSM, SEQ ID NO: 45), the MLL-pP peptide (RVR[pS]PTRSP; SEQ ID NO: 47), or a mix of peptides selected from viral T cell epitopes.

In a first study, PBMCs from 17 HLA-B*0702 healthy donors were stimulated for 7 days with the MLL-pM peptide (EPR[pS]PSHSM; SEQ ID NO: 45) or the MLL-pP peptide (RVR[pS]PTRSP; SEQ ID NO: 47), followed by intracellular cytokine staining (ICS) for IFNγ and TNFα. A pool of 32 peptides selected from viral T cell epitopes was used as a positive control. Shown in FIG. 1 are representative data from three donors with increased TNFα production over the no peptide negative control.

Figure 2:
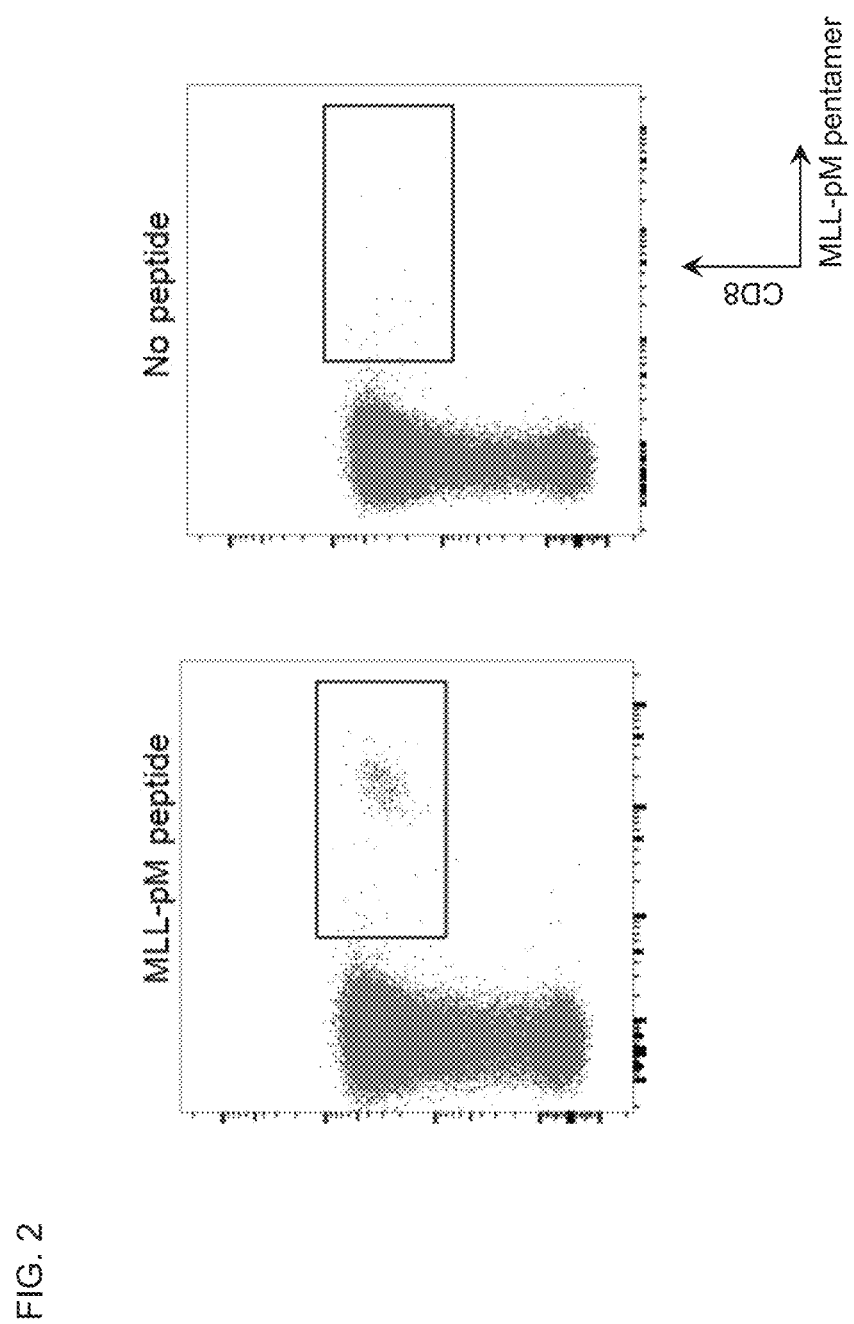
FIG. 2 is a pair of flow cytometry plots showing analysis of memory CD8+ T cells that were co-cultured with non-pulsed DCs ("No peptide") or DCs pulsed with the peptide EPR[pS]PSHSM (SEQ ID NO: 45) ("MLL-pM peptide"). After co-culturing, the cells were stained with the MLL-pM/HLA-B*0702 pentamers and an anti-CD8 antibody.

In a second study, memory CD8+ T cell subsets were co-cultured with peptide-pulsed or non-pulsed DCs for 10 days. Cells from the co-cultures were stained with HLA-B*0702 pentamers loaded with the MLL-pM peptide EPR[pS]PSHSM (SEQ ID NO: 45) and an anti-CD8 antibody, followed by binding assessment by flow cytometry. As shown in FIG. 2, a CD8+ pentamer+ population of cells was detected after co-culturing with DCs pulsed with the MLL-pM peptide.

6.1.4 TCR Sublibrary Generation and Retroviral Transduction

Separate libraries were generated for TCR a and β chains. RNA was isolated from healthy donor HLA-B*0702+ PBMC-derived CD8+ T cells or CD8+ T cells enriched by stimulation with MLL-pM-pulsed DCs using the RNeasy® Midi kit (Qiagen, Cat. No.: 75142) or the AllPrep™ DNA/RNA Micro kit (Qiagen, Cat. No.: 80204). The isolated RNA was analyzed in a RNA6000 Pico assay (Agilent, Cat. No.: 5067-1513) using a 2100 Bioanalyzer (Agilent, Cat. No.: DE13701147) according to the manufacturer's instructions. RNA was transcribed into cDNA using the SMARTer® RACE 5'/3' kit (Clontech Laboratories, Cat. No.: 634860) and variable TCR a (TRAV and TRAJ genes) and β chains (TRBV and TRBJ genes) were separately amplified by multiplex PCR The resulting variable chain TCRα and TCRβ gene libraries were separately cloned into retroviral expression vectors (derived from MIGR1, Addgene, Cat. No.; 27490) containing murine non-variable α or β regions including transmembrane and intracellular domains to enable interactions with murine CD3 and signal transduction in murine T cells. The a and β chain expression vectors also comprise the expression markers CD6 and CD7, respectively. Diversity of the resulting plasmid library was assessed by next generation sequencing (NGS). To obtain a stable cellular TCRαβ library, TCRα and TCRβ library plasmids were consecutively introduced to a murine cell line AK-D10R3. AK-D10R3 is a murine thymoma-derived mouse TCR-negative, mouse CD8-negative cell line that expresses chimeric CD8 (human CD8 α and β extracellular regions fused to the corresponding mouse CD8 α and β transmembrane and intracellular regions) and a T cell activation reporter construct comprising a minimal IL-2 promoter, which includes three NFAT binding sites, operably linked to EGFP (the "IL-2-(NFAT)₃-EGFP" reporter construct). Expression of α and β chains was confirmed by flow cytometry after staining with anti-human CD6-bio (Antibodies Online, Cat. No.: ABIN609887) (1:1000) and anti-mouse-TCRβ-PE (BD Bioscience, Cat. No.: 553172) (1:1000) reagents and the final chain distribution and diversity determined via NGS.

6.2 Example 2: Characterization of Novel MLL TCRs in Murine Cells

Five novel TCRs that bind to MLL phosphopeptides were developed using a proprietary mammalian cell TCR display platform. Four of these TCRs, TCR0077, TCR0079, TCR0081, and TCR0083, bind to EPR[pS]PSHSM (SEQ ID NO: 45)-HLA-B*0702. One of these TCRs, TCR0085, binds to RVR[pS]PTRSP (SEQ ID NO: 47)-HLA-B*0702. The two phosphopeptides EPR[pS]PSHSM (SEQ ID NO: 45) and RVR[pS]PTRSP (SEQ ID NO: 47) were referred to as MLL-pM and MLL-pP peptides, respectively. The α chain variable region (Vα) and β chain variable region (Vβ) sequences of these five TCRs are provided in Table 4. These TCRs were expressed as chimeric proteins, with human variable regions fused to murine constant regions, on the surface of the murine cell line AK-D10R3 described above. The murine constant regions ensure proper anchoring and interaction with murine CD3 and proper triggering of murine signaling pathways.

6.2.1 Binding of TCR-Expressing AK-D10R3 Cells to Peptide-MHC Pentamers

AK-D10R3 cells were transduced to express the chimeric TCRs TCR0077, TCR0079, TCR0081, TCR0083, or TCR0085 and were expanded for three days at 37° C. and 10% CO₂ using SF-IMDM media (BioConcept, Cat. No.: 1-28S07-1). TCR-negative AK-D10R3 cells were included as a negative control. 1.0×10⁵ AK-D10R3 cells were plated per well of a 96-well assay plate, centrifuged at 300×g and 4° C. for 5 min, washed twice using 200 µL assay buffer (1×PBS supplemented with 2% FCS), and resuspended in assay buffer at a concentration of 1.0×10⁵ cells/100 µL. For staining, 20 µL of stock solutions of anti-mouse TCR p-chain-APC antibody (BD, Cat. No.: 553174, clone H57-597) (1:500) and PE-labeled HLA-B*0702 pentamers (Proimmune) loaded with the MLL-pM peptide EPR[pS]P-

SHSM (SEQ ID NO: 45) (5 µL/well or 0.5 µL/well), the MLL-pP peptide RVR[pS]PTRSP (SEQ ID NO: 47) (5 µL/well), or the non-phosphorylated control peptide MLL-M EPRSPSHSM (SEQ ID NO: 46) (5 µL/well) were added per well. Following 30 min incubation at room temperature, cells were washed twice and analyzed by flow cytometry using a BD FACSCanto II cytometer. Cells were analyzed for TCR expression (APC+) versus pMHC-binding (PE+). Using the FlowJo software, dot plots were generated and the percentage (%) of TCR+ pMHC+ cells was determined.

As shown in FIG. 3, the chimeric TCRs TCR0077, TCR0079, TCR0081, and TCR0083 all bind to the MLL-pM/HLA-B*0702 pentamers whereas the chimeric TCR TCR0085 binds to the MLL-pP/HLA-B*0702 pentamers. None of the five TCRs binds to HLA-B*0702 pentamers loaded with the non-phosphorylated control peptide MLL-M.

6.2.2 Activation of TCR-Expressing AK-D10R3 Cells by Peptide-Pulsed HLA-B*0702 T2 Cells AK-D10R3 cells expressing an IL-2-(NFAT)$_3$-EGFP reporter construct and the chimeric TCRs TCR0077, TCR0079, TCR0081, TCR0083, or TCR0085 were cultivated in SF-IMDM media as described above. In parallel, HLA-B*0702 positive T2 target cells ("T2-B7 cells") were pulsed with MLL peptides. Briefly. T2-B7 cells were centrifuged at 300×g and 4° C. for 5 min, washed using 1×PBS and resuspended in 1×PBS supplemented with 50 µg/mL or 5 µg/mL of the MLL-pM peptide EPR[pS]PSHSM (SEQ ID NO: 45), 50 µg/mL of the MLL-pP peptide RVR[pS]PTRSP (SEQ ID NO: 47), or 50 µg/mL of the non-phosphorylated control peptide MLL-M EPRSPSHSM (SEQ ID NO: 46) at a final concentration of $1.0 \times 10^6$ cells/250 µL. Cells were incubated for 3 hours at 37° C., washed twice using 1×PBS, and resuspended at a final concentration of $5.0 \times 10^6$ cells/20 mL using SF-IMDM media. 200 µL ($5.0 \times 10^4$ cells) of the TCR-expressing AK-D10R3 cells were added per well of a 96-well assay plate and centrifuged at 300×g for 5 min, and the supernatant was discarded. Next, 100 µL ($2.5 \times 10^4$ cells) of the T2-B7 target cell suspension was added to each well and co-incubated for 16 hours at 37° C. and 10% $CO_2$.

For staining, cell suspensions were centrifuged at 300×g for 10 min, washed twice using assay buffer, resuspended using 20 µL/well of staining solution (1×PBS supplemented with 1:500 APC-labeled anti-mouse TCR β-chain antibody) and incubated for 30 min at room temperature. Subsequently, cells were washed twice using assay buffer, resuspended in 80 µL assay buffer and analyzed by flow cytometry using a BD FACSCanto II cytometer. Cells were gated for TCR expression (APC+) versus T cell activation (EGFP+). Using FlowJo software, dot plots were generated and the percentage (%) of APC+ EGFP+ cells was determined. AK-D10R3 cultivated in the absence of T2-B7 target cells or co-cultures of TCR-expressing AK-D10R3 cells with non-pulsed T2-B7 cells served as negative controls.

AK-D10R3 cells expressing the chimeric TCRs TCR0077, TCR0079, TCR0081, or TCR0083 showed activation of the IL-2-NFAT reporter construct after being co-cultured with T2-B7 cells pulsed with the phosphopeptide MLL-pM, but not the non-phosphorylated control peptide MLL-M (FIG. 4A). The chimeric TCR TCR0085 mediated the activation of the IL-2-NFAT reporter construct after being co-cultured with T2-B7 cells pulsed with the phosphopeptide MLL-pP (FIG. 4A). The activation of AK-D10R3 cells was dependent on the interaction between the MLL TCRs and their cognate peptide-MHC complexes, since such activation was not observed when AK-D10R3 cells were tested on their own, or when TCR-expressing AK-D10R3 cells were incubated with T2-B7 cells that were not pulsed with any peptide (FIG. 4B).

6.2.3 Cytotoxicity Assays

Next, in a similar co-culture study, TCR-expressing AK-D10R3 cells were assessed for their potential to induce apoptosis in peptide-pulsed T2-B7 target cells. Briefly, T2-B7 target cells were pulsed with 5 µg/mL or 50 µg/mL of the MLL-pM peptide EPR[pS]PSHSM (SEQ ID NO: 45), 50 µg/mL of the MLL-pP peptide RVR[pS]PTRSP (SEQ ID NO: 47), or 50 µg/mL of the non-phosphorylated control peptide MLL-M EPRSPSHSM (SEQ ID NO: 46). AK-D10R3 cells expressing the chimeric TCRs TCR0077, TCR0079, TCR0081. TCR0083, or TCR0085 were co-cultured with peptide-pulsed T2-B7 target cells for 16 hours at 37° C. and 10% $CO_2$ in SF-IMDM medium (Amimed #1-28507-I) supplemented with 500 ng/mL anti-FAS reagent (Biolegend #305702, clone EOS9.1) and 10 µM Campothecin (Sigma #C9911) as described above. The cells were then stained with anti-mouse TCRβ-APC and anti-caspase3-PE (BD Biosciences #550821) and assessed by flow cytometry using a FACSCantoII cytometer. Co-cultures containing non-pulsed T2-B7 cells or T2-B7 cells in the absence of AK-D10R3 cells served as controls.

As shown in FIG. 5, AK-D10R3 cells expressing the chimeric TCRs TCR0077, TCR0079, TCR0081, or TCR0083 increased caspase 3 expression levels in T2-B7 target cells pulsed with the MLL-pM phosphopeptide, but not T2-B7 cells pulsed with the non-phosphorylated control peptide MLL-M. AK-D10R3 cells expressing the chimeric TCR TCR0085 increased caspase 3 expression levels in T2-B7 cells pulsed with the MLL-pP phosphopeptide (FIG. 5). Caspase 3 expression was minimal in co-cultures containing non-pulsed T2-B7 cells or T2-B7 cells in the absence of TCR-expressing AK-D10R3 cells (FIG. 5).

6.2.4 Characterization of TCR Specificity Using Alanine Scanning

To assess antigen recognition of the MLL-pM peptide EPR[pS]PSHSM (SEQ ID NO: 45), AK-D10R3 cells expressing an IL-2-(NFAT)$_3$-EGFP reporter construct and the chimeric TCR TCR0077 or TCR0085, or TCR negative AK-D10R3 cells were co-cultured with T2-B7 target cells pulsed with the MLL-pM peptide or its alanine modified variants: MLL-pM-A1 APR[pS]PSHSM (SEQ ID NO: 49), MLL-pM-A2 EAR[pS]PSHSM (SEQ ID NO: 50), MLL-pM-A3 EPA[pS]PSHSM (SEQ ID NO: 51), MLL-pM-A4 EPRAPSHSM (SEQ ID NO: 52), MLL-pM-A5 EPR[pS]ASHSM (SEQ ID NO: 53), MLL-pM-A6 EPR[pS]PAHSM (SEQ ID NO: 54), MLL-pM-A7 EPR[pS]PSASM (SEQ ID NO: 55), MLL-pM-A8 EPR[pS]PSHAM (SEQ ID NO: 56), or MLL-pM-A9 EPR[pS]PSHSA (SEQ ID NO: 57) at a target:effector ratio of 2:1 for 16 hours at 37° C. and 10% $CO_2$. After staining with anti-mouse TCRβ-APC antibody, expression of the IL-2-(NFAT)$_3$-EGFP reporter was assessed by flow cytometry. Cells were gated for TCR expression versus T cell activation (EGFP+). Using the FlowJo software, dot plots were generated and the percentage (%) of APC+ EGFP+ cells was determined. Data were copied into Microsoft Excel for background correction by subtraction of activation values determined for co-cultures containing T2-B7 cells not pulsed with peptides for graph generation.

As shown in FIG. 6A, AK-D10R3 cells expressing the chimeric TCR TCR0077 showed activation of the IL-2-NFAT reporter construct after being co-cultured with T2-B7 cells pulsed with the MLL-pM peptide, the MLL-pM-A3 peptide, or the MLL-pM-A8 peptide. Minimal activation was detected when TCR0077-expressing AK-D10R3 cells were incubated with T2-B7 cells pulsed with the other alanine modified variants of MLL-pM, the MLL-M control peptide, or the MLL-pP control peptide (FIG. 6A). As a control, AK-D10R3 cells expressing the chimeric TCR TCR0085 were tested under the same conditions and these cells showed increased EGFP expression only in the presence of MLL-pP-pulsed T2-B7 cells, but not T2-B7 cells pulsed with the MLL-M peptide, the MLL-pM peptide, or any alanine modified variants of the MLL-pM peptide (FIG. 6B).

6.2.5 Characterization of TCR Specificity Using X-Scan

Target specificity of TCR0077 and TCR0081 was assessed by "x-scan" assays using a library of variants of the peptide EPR[pS]PSHSM (SEQ ID NO: 45), as described below.

A set of variants of the peptide EPR[pS]PSHSM (SEQ ID NO: 45) was prepared, in which each amino acid position in each peptide, except for the anchor positions P2 (P) and P9 (M), of SEQ ID NO: 45 was individually substituted with each of the 19 other possible naturally occurring amino acids, with position P4 ([pS]) being additionally substituted with non-phosphorylated serine. The resulting 134 variant peptides are listed in Table 8. The specificity profiles of TCR0077 and TCR0081 were evaluated by measuring activation of TCR-expressing AK-D10R3 effector cells after co-culturing with T2-B7 target cells loaded with one of the 134 variant peptides or the parental peptide EPR[pS]PSHSM (SEQ ID NO: 45).

AK-D10R3 cells were stably transduced with chimeric TCRs TCR0077 or TCR0081, a chimeric mouse/human CD8, and an EGFP-reporter construct linked to a minimal IL-2 promoter comprising three NFAT-binding sites (3×NFAT). Cells were cultured in SF-IMDM (Amimed Direct, London, UK) supplemented with 3% Fetal Calf Serum (FCS: Amimed Direct), 1% Penicillin, Streptomycin (SIGMA-ALDRICH, St. Louis, MO), and 50 pM 0-mercaptoethanol (Gibco, Fisher Scientific, UK) at 37° C. and 10% $CO_2$. Antigen presenting Tap-deficient 12 (174×CEM.T2) cells from ATCC (CRL-1992™) were maintained in RPMI 1640 (SIGMA-ALDRICH) supplemented with 10% FCS and 1% penicillin/streptomycin at 37° C. and 5% $CO_2$.

Peptides (purchased from Peptides and Elephants, Germany. or produced in-house) were suspended in DMSO and the concentration was adjusted to 4 mg/ml.

T2-B7 cells were washed in PBS (Gibco) and incubated with 20 µg each of the 134 altered peptides per 1×10⁶ cells for 3 hours at 37° C. and 5% $CO_2$. After incubation, T2-B7 cells were washed in PBS/2% FCS and then resuspended in SF-IMDM media. Effector cells expressing the TCR of interest were co-cultured with peptide-pulsed T2-B7 cells in a 1:2 ratio (total 150,000 cells per well of a 96-well plate) for 16 hours in SF-IMDM media at 37° C. and 10% $CO_2$. Cells were washed twice in 2% FCS/PBS and stained with an anti-mouse TCR-β chain antibody (clone H57-597; BD Pharmingen, San Jose, CA) at a 1:500 dilution for 30 min at room temperature. Cells were washed twice, followed by FACS-analysis using a BD FACSCanto™ II flow cytometer (Becton Dickinson).

Data analysis was performed using FlowJo V10 Software. TCR activation was calculated as the proportion of EGFP-expressing cells in the AK-D10R3 population (AK-D10R3 cells were identified based on TCR expression). Background activation (where T2-B7 cells in the assay were not loaded with peptide) was subtracted from all peptide-loaded samples (altered and native sequences). The mean and standard error of the mean (SEM) of background-subtracted values were calculated from all replicates (at least 3 replicates for each TCR) and values were normalized to those of the peptide EPR[pS]PSHSM (SEQ ID NO: 45), with normalized values cropped to a minimum of 0.0 (heat maps only) and to a maximum of 1.0 (heat maps only) for display purposes. Normalized values are shown in heat map format in FIGS. 7A (TCR0077) and 7B (TCR0081) and in bar chart format in FIGS. 8A (TCR0077) and 8B (TCR0081).

The heat maps and bar charts reveal the distinct specificity profiles of each TCR tested. In general, a larger percentage of white (low normalized values) indicates lower tolerance for mutations in the MLL-pM cognate peptide and a higher degree of specificity for the MLL-pM cognate peptide in the context of the above-described assay. As shown in FIGS. 7A and 71B, TCR0077 and TCR0081 both exhibited variable degrees of specificity for each residue position of the MLL-pM cognate peptide.

TABLE 8

Altered peptides used to generate specificity profiles of chimeric TCRs.

| SEQ ID NO | Target Peptide Sequence |
|---|---|
| 49 | APR[pS]PSHSM |
| 110 | CPR[pS]PSHSM |
| 111 | DPR[pS]PSHSM |
| 112 | FPR[pS]PSHSM |
| 113 | GPR[pS]PSHSM |
| 114 | HPR[pS]PSHSM |
| 115 | IPR[pS1PSHSM |
| 116 | KPR[pS]PSHSM |
| 117 | LPR[pS]PSHSM |
| 118 | MPR[pS]PSHSM |
| 119 | NPR[pS]PSHSM |
| 120 | PPR[pS]PSHSM |
| 121 | QPR[pS]PSHSM |
| 122 | RPR[pS]PSHSM |
| 123 | SPR[pS]PSHSM |
| 124 | TPR[pS]PSHSM |
| 125 | VPR[pS]PSHSM |
| 126 | WPR[pS]PSHSM |
| 127 | YPR[pS]PSHSM |
| 128 | EPC[pS]PSHSM |
| 129 | EPD[pS]PSHSM |

TABLE 8-continued

Altered peptides used to generate specificity profiles of chimeric TCRs.

| SEQ ID NO | Target Peptide Sequence |
|---|---|
| 130 | EPE[pS]PSHSM |
| 131 | EPF[pS]PSHSM |
| 132 | EPG[pS]PSHSM |
| 133 | EPH[pS]PSHSM |
| 134 | EPI[pS]PSHSM |
| 135 | EPK[pS]PSHSM |
| 136 | EPL[pS]PSHSM |
| 137 | EPM[pS]PSHSM |
| 138 | EPN[pS]PSHSM |
| 139 | EPP[pS]PSHSM |
| 140 | EPQ[pS]PSHSM |
| 141 | EPS[pS]PSHSM |
| 142 | EPT[pS]PSHSM |
| 143 | EPV[pS]PSHSM |
| 144 | EPW[pS]PSHSM |
| 145 | EPY[pS]PSHSM |
| 52 | EPRAPSHSM |
| 146 | EPRCPSHSM |
| 147 | EPRDPSHSM |
| 148 | EPREPSHSM |
| 149 | EPRFPSHSM |
| 150 | EPRGPSHSM |
| 151 | EPRHPSHSM |
| 152 | EPRIPSHSM |
| 153 | EPRKPSHSM |
| 154 | EPRLPSHSM |
| 155 | EPRMPSHSM |
| 156 | EPRNPSHSM |
| 157 | EPRPPSHSM |
| 158 | EPRQPSHSM |
| 159 | EPRRPSHSM |
| 46 | EPRSPSHSM |
| 160 | EPRTPSHSM |
| 161 | EPRVPSHSM |
| 162 | EPRWPSHSM |
| 163 | EPRYPSHSM |
| 53 | EPR[pS]ASHSM |

TABLE 8-continued

Altered peptides used to generate specificity profiles of chimeric TCRs.

| SEQ ID NO | Target Peptide Sequence |
|---|---|
| 164 | EPR[pS]CSHSM |
| 165 | EPR[pS]DSHSM |
| 166 | EPR[pS]ESHSM |
| 167 | EPR[pS]FSHSM |
| 168 | EPR[pS]GSHSM |
| 169 | EPR[pS]HSHSM |
| 170 | EPR[pS]ISHSM |
| 171 | EPR[pS]KSHSM |
| 172 | EPR[pS]LSHSM |
| 173 | EPR[pS]MSHSM |
| 174 | EPR[pS]NSHSM |
| 175 | EPR[pS]QSHSM |
| 176 | EPR[pS]RSHSM |
| 177 | EPR[pS]SSHSM |
| 178 | EPR[pS]TSHSM |
| 179 | EPR[pS]VSHSM |
| 180 | EPR[pS]WSHSM |
| 181 | EPR[pS]YSHSM |
| 54 | EPR[pS]PAHSM |
| 182 | EPR[pS]PCHSM |
| 183 | EPR[pS]PDHSM |
| 184 | EPR[pS]PEHSM |
| 185 | EPR[pS]PFHSM |
| 186 | EPR[pS]PGHSM |
| 187 | EPR[pS]PHHSM |
| 188 | EPR[pS]PIHSM |
| 189 | EPR[pS]PKHSM |
| 190 | EPR[pS]PLHSM |
| 191 | EPR[pS]PMHSM |
| 192 | EPR[pS]PNHSM |
| 193 | EPR[pS]PPHSM |
| 194 | EPR[pS]PQHSM |
| 195 | EPR[pS]PRHSM |
| 196 | EPR[pS]PTHSM |
| 197 | EPR[pS]PVHSM |
| 198 | EPR[pS]PWHSM |
| 199 | EPR[pS]PYHSM |

TABLE 8-continued

Altered peptides used to generate specificity profiles of chimeric TCRs.

| SEQ ID NO | Target Peptide Sequence |
|---|---|
| 55 | EPR[pS]PSASM |
| 200 | EPR[pS]PSCSM |
| 201 | EPR[pS]PSDSM |
| 202 | EPR[pS]PSESM |
| 203 | EPR[pS]PSFSM |
| 204 | EPR[pS]PSGSM |
| 205 | EPR[pS]PSISM |
| 206 | EPR[pS]PSKSM |
| 207 | EPR[pS]PSLSM |
| 208 | EPR[pS]PSMSM |
| 209 | EPR[pS]PSNSM |
| 210 | EPR[pS]PSPSM |
| 211 | EPR[pS]PSQSM |
| 212 | EPR[pS]PSRSM |
| 213 | EPR[pS]PSSSM |
| 214 | EPR[pS]PSTSM |
| 215 | EPR[pS]PSVSM |
| 216 | EPR[pS]PSWSM |
| 217 | EPR[pS]PSYSM |
| 56 | EPR[pS]PSHAM |
| 218 | EPR[pS]PSHCM |
| 219 | EPR[pS]PSHDM |
| 220 | EPR[pS]PSHEM |
| 221 | EPR[pS]PSHFM |
| 222 | EPR[pS]PSHGM |
| 223 | EPR[pS]PSHHM |
| 224 | EPR[pS]PSHIM |
| 225 | EPR[pS]PSHKM |
| 226 | EPR[pS]PSHLM |
| 227 | EPR[pS]PSHMM |
| 228 | EPR[pS]PSHNM |
| 229 | EPR[pS]PSHPM |
| 230 | EPR[pS]PSHQM |
| 231 | EPR[pS]PSHRM |
| 232 | EPR[pS]PSHTM |
| 233 | EPR[pS]PSHVM |
| 234 | EPR[pS]PSHWM |
| 235 | EPR[pS]PSHYM |
| 45 | EPR[pS]PSHSM (MLL-pM peptide) |

6.3 Example 3: Characterization of Novel MLL TCRs in Primary Human T Cells

In this example, the chimeric TCRs TCR0077 and TCR0085 described above were expressed as fully human TCRs, designated TCR0078 and TCR0086, respectively. TCR0078 shares variable region sequences with TCR0077 except for a small number of mutations in framework 4 of the variable regions and contains human constant regions. Specifically, TCR0078 comprises an α chain and a β chain comprising the amino acid sequences set forth in SEQ ID NOs: 58 and 59, respectively. TCR0086 shares variable region sequences with TCR0085 and contains human constant regions. TCR0086 comprises an α chain and a β chain comprising the amino acid sequences set forth in SEQ ID NOs: 70 and 71, respectively. An exemplary expression construct for TCR0078 or TCR0086, as described in this Example, encodes a fusion protein encoding, in order, the TCR β chain, a P2A self-cleavage site, and the TCR α chain. As listed in Table 1, an exemplary immature TCR0078 or TCR0086 fusion protein (containing signal peptides for both a and 1 chains) has the amino acid sequence set forth in SEQ ID NO: 83 or 92, respectively. After expression, the fusion protein is cleaved at the P2A site to produce mature a and D chains of TCR0078 (SEQ ID NOs: 236 and 237, respectively) or TCR0086. As shown in SEQ ID NO: 236, the exemplary mature α chain of TCR0078 comprises a GS amino acid residue extension to the C-terminus of its core sequence (SEQ ID NO: 58), resulting from a cloning scar on the fusion protein. As shown in SEQ ID NO: 237, the exemplary mature β chain of TCR0078 comprises a short peptide extension (GSGATNFSLLKQAGDVEENPG, SEQ ID NO: 93) to the C-terminus of its core sequence (SEQ ID NO: 59), resulting from the P2A cleavage of the fusion protein. Additional exemplary immature TCR0078 fusion proteins (containing signal peptides for both a and β chains) have the amino acid sequences set forth in SEQ ID NOs: 266-271, as shown in Table 1.

6.3.1 Expression of TCR0078 on the Surface of Transduced T Cells

Primary T cells were stimulated by co-incubation with CD3/CD28 Dynabeads® (Thermo Fisher, Waltham. MA) at a concentration of $1\times10^6$ cells/ml and a T cells:beads ratio of 1:1 at 37° C. for 48 hours. The T cells were then transduced with a lentivirus encoding, in order, the β chain, a P2A cleavage site, and the α chain of TCR0078 (SEQ ID NO: 83), manufactured by Lentigen (Gaithersburg, MD). For transduction, the T cells/beads were resuspended at $1\times10^1$ cells/ml in fresh T cell medium containing 8 μg/ml polybrene (EMD, Millipore). The cell suspension was mixed with the lentivirus (MOI 10:1) and then centrifuged for 90 minutes at 1200 g, 32° C. to facilitate transduction. The cell/bead suspension was incubated at 37° C. for 4 hours, after which time 1 volume of T cell medium was added and the cells/beads were further incubated at 37° C. overnight. The following day, cells were washed and resuspended at $1 \times 10^6$ cells/ml in T cell medium, followed by further incubation at 37° C. At Day 3 post-transduction, beads were removed from the cell culture using DynaMag magnet (Thermo Fisher). At Day 5 post-transduction, TCR0078 expression was evaluated by flow cytometry. Specifically, cells were first stained with Zombie NIR™ (Biolegend) to discriminate live from dead cells, according to the manufacturer's instructions. Cells were then washed and stained with PE-conjugated HLA-B*0702 pentamer loaded with the MLL-pM peptide EPR[pS]PSHSM (SEQ ID NO:45: ProImmune, Inc, Oxford, UK), and an antibody cocktail comprising anti-CD3-FITC, anti-CD4-PerCp/Cy5.5 and anti-CD8-PE/Cy7 antibodies (Biolegend) for 30 minutes at room temperature protected from light. Untransduced T cells were used as a negative control. The stained T cells were washed and analyzed by flow cytometry using a BD FACSCanto™ II cytometer.

TCR0078 was efficiently expressed in intact, live, singlet T cells. As shown in FIG. 9A, for control cells, 62.8% of the detected cells were intact (left panel). Of these intact cells, 99.2% were living cells (middle panel). Of these living cells, 81.3% were singlets (right panel). The same flow cytometry gates were used for cells transduced with TCR0078 and obtained similar data (data not shown). Intact, live, singlet cells were selected for use in the remainder of the experiment. For control T cells, only 1.11% were positive for both CD3 and pentamer staining (FIG. 9B, left panel). In cells transduced with TCR0078, 58.1% were both CD3 and pentamer positive (FIG. 9B, right panel). The high level of pentamer staining in the TCR0078-transduced cells was indicative of positive expression of TCR0078 in stimulated T cells.

Both control and TCR0078 expressing stimulated T cells were predominantly in one of two populations: a CD8+/CD4− cell population and a CD8−/CD4+ cell population. Control T cells were 44.6% CD8+/CD4− and 49.1% CD8−/CD4+ (FIG. 9C, left panel). Similar results were obtained for the whole population of TCR0078-transduced cells (FIG. 9C, middle panel) and TCR0078 expressing cells determined by pentamer staining (FIG. 9C, right panel). CD8+ or CD4+ populations were also identifiable in the flow cytometry data presented to show the level of pentamer staining (FIG. 9D, both panels).

6.3.2 Characterization of Human T Cells Expressing MLL TCRs Co-Cultured with KG1a Target Cells Primary human T cells were mixed with mRNA encoding TCR0078 or TCR0086 and electroporated on Day 0. The two TCRs were expressed from vectors encoding, in order, the TCR § chain, a P2A cleavage site, and the TCR α chain. On Day 1, target TCR expression was evaluated by flow cytometry following staining with HLA-B*0702 pentamers loaded with the MLL-pM peptide EPR[pS]PSHSM (SEQ ID NO: 45) or the MLL-pP peptide RVR[pS]PTRSP (SEQ ID NO: 47). T cells were then labeled using the Celltrace Violet cell proliferation kit (Life Technologies, Cat. No.: C34557). In parallel, KG1a cells (a myelogenous leukemia cell line endogenously expressing MLL and overexpressing HLA-B*0702 ("KG1a-B7 cells") or HLA-A*0201 ("KG1a-A2 cells") were labeled with carboxyfluorescein succinimidyl ester (CFSE) (Biolegend, Cat. No.: 423801). The Celltrace Violet-labeled T cells were co-cultured with the CFSE-labeled KG1a-B2 cells or KG1a-A2 cells at an effector:target ratio ranging from 4:1 to 0.25:1. T cells that were incubated with anti-CD3 and anti-CD28 antibodies were used as positive controls. On Day 2, the cells were evaluated for CD25 expression, CD107a expression, T cell proliferation, and specific killing of target cells using flow cytometry. Primary human T cells electroporated with mock mRNA (mRNA encoding a control TCR) were used as a negative control.

A representative experiment with an effector:target ratio of 2:1 is shown in FIG. 10. T cells expressing the MLL TCR TCR0078 or TCR0086 were only activated by KG1a cells expressing HLA-B*0702, but not KG1a cells expressing HLA-A*0201, as measured by CD25 expression, CD107a expression, and T cell proliferation. The activation of T cells was dependent on the expression of the MLL TCRs since T cells electroporated with mock mRNA were not activated under the same conditions (FIG. 10).

T cells expressing the MLL TCR TCR0078 or TCR0086 were able to specifically kill KG1-B7 target cells even at low effector:target ratios, while T cells electroporated with mock mRNA did not kill the target cells (FIG. 11).

6.3.3 Characterization of TCR0078 Using an IL-2-NFAT Luciferase Reporter-Expressing T Cell Line This study assesses the specificity of activation of T cells expressing TCR0078 upon co-culturing with various tumor cell lines, using an IL-2-NFAT luciferase reporter T cell line. Specifically, Jurkat cell line J.RT3-T3.5 (ATCC® Cat. No.: TIB-153™), stably expressing a luciferase reporter under the control of an IL-2-NFAT response element and a short CMV minimal promoter, was transduced with the same lentivirus as described in Section 6.3.1. Briefly, control (not transduced) or TCR0078-transduced Jurkat cells were co-cultured with KG1a cells stably expressing HLA-B*0702, K562 cells (a myelogenous leukemia cell line endogenously expressing MLL) stably expressing HLA-B*0702, Loucy cells (alymphoblastic leukemia cell line endogenously expressing MLL and HLA-B*0702), or Namalwa cells (a Burkitt's Lymphoma cell line endogenously expressing MLL and HLA-B*0702) at various Jurkat:tumor (effector:target) cell ratios (ranging from 0.1:1 to 2:1) for 24 hours at 37° C. Cells were then washed, lysed, and mixed with Nano-Glo® Luciferase Assay reagent (Promega, Madison, WI), according to the manufacturer's instructions. The luminescence from the expressed IL-2-NFAT-luciferase reporter, representing the degree of Jurkat cell activation, was recorded. As a positive control for activation of the IL-2-NFAT reporter, phorbol 12-myristate 13-acetate (PMA) and Ionomycin (Biolegend) were used to induce maximum NFAT-luciferase expression in the control and TCR0078-transduced Jurkat effector cells, according to the manufacturer's instructions.

As shown in FIG. 12A, Jurkat cells expressing TCR0078 were significantly activated when co-cultured, at various ratios, with KG1a cells or K562 cells stably expressing HLA-B*0702. Namalwa cells activated TCR0078-expressing Jurkat cells at all effector:target ratios tested. Loucy cells activated TCR0078-expressing Jurkat cells at higher effector:target ratios, compared to the control Jurkat cell activation levels shown in FIG. 12B. As expected, PMA/Ionomycin induced maximal reporter activation in the Jurkat cells (FIG. 12C).

The foregoing reporter activation assays were also performed with other tumor target cells. H929 cells and U266B1 cells (which both endogenously express HLA-B*0702), as well as THP-1 cells (HLA-B*0702 negative) overexpressing HLA-B*0702, all activated the Jurkat effector cells (FIGS. 13A and 13C). Raji cells (ATCC® CCL-86™, an HLA-B*0702 negative cell line) and LCL 721.221 cells (an MHC-I-negative human cell line), when both were overexpressing HLA-B*0702, significantly activated the Jurkat effector cells, more potently than KG1a-HLA-B*0702 cells (FIGS. 13B and 13C). By contrast, YT-Indy cells (HLA-B*0702 negative), J.RT3-T3.5 cells (HLA-B*0702 negative), Raji cells, THP-1 cells, and LCL 721.221 cells did not activate Jurkat effector cells (FIGS. 13A-13C).

6.3.4 Impact of Peptide Dose Titration on T Cell Activation and Target Cell Killing Next, a study was conducted to assess sensitivity of MLL-specific TCRs. Briefly, on Day 0, primary human T cells were electroporated with mock mRNA (mRNA encoding a control TCR) or TCR0078 mRNA as described above. On Day 1, T2 cells expressing HLA-B*0702 ("T2-B7 cells") were labeled using the Celltrace Violet cell proliferation kit (Life Technologies, Cat. No.: C34557) and pulsed with a dose titration of the MLL-pM peptide EPR[pS]PSHSM (SEQ ID NO: 45) or the non-phosphorylated MLL-M control peptide EPRSPSHSM (SEQ ID NO: 46). The T2-B7 target cells were then co-cultured with electroporated T cells that had been labeled with CFSE (Biolegend, Cat. No.: 423801) at an effector:target ratio of 1:1. T cells that were incubated with anti-CD3 and anti-CD28 antibodies were used as positive controls. On Day 2, the cells were evaluated for CD25 expression, CD107a expression, and specific killing of target cells using flow cytometry.

As shown in FIG. 14, T cells expressing the MLL TCR TCR0078 were activated by T2-B7 target cells pulsed with the phosphopeptide MLL-pM, even at low doses of the peptide. The activation of T cells was dependent on the presence of the phosphoseryl moiety as the non-phosphorylated MLL-M control peptide did not activate the T cells (FIG. 14, upper right and lower right panels). T cells electroporated with mock mRNA were not activated by target cells (FIG. 14).

Consistent with the observations of T cell activation, T cells expressing the MLL TCR TCR0078 killed the T2-B7 target cells pulsed with the MLL-pM peptide effectively, but not the T2-B7 target cells pulsed with the non-phosphorylated MLL-M control peptide (FIG. 15). T cells electroporated with mock mRNA did not kill the target cells (FIG. 15).

A similar study assessing TCR sensitivity to the MLL phosphopeptide EPR[pS]PSHSM (SEQ ID NO: 45) was conducted using primary T cells stably expressing TCR0078. Briefly, primary T cells were transduced with lentivirus encoding TCR0078 (SEQ ID NO: 83), as described in Section 6.3.1. After 13 days, the transduced T cells were tested for their activation and cytotoxic activity toward target cells in presence of the MLL phosphopeptide. T2 cells expressing HLA-B*0702 ("T2-B7 cells") were labeled with carboxyfluorescein succinimidyl ester (CFSE) (Biolegend, Cat. No.: 423801) and then pulsed for 2.5 hours with a dose titration of either EPR[pS]PSHSM (SEQ ID NO: 45) phosphopeptide or EPRSPSHSM (SEQ ID NO: 46) peptide. The pulsed T2-B7 cells (Target) were then co-cultured with the primary T cells expressing TCR0078 (Effector), previously labeled using the Cell Trace™ Violet cell proliferation kit (Life Technologies, Carlsbad, CA, Cat. No.: C34557), at an effector:target ratio of 1:1 for 20 hours at 37° C. Cytotoxic activity (measured by killing of T2-B7 cells) and CD25 and IFN-γ expression of the effector primary T cells were assessed the following day by flow cytometry. The numbers of living T2-B7 cells, detected by Cell Trace™ Violet staining, were counted. The percentage of dead T2-B7 cells (calculated by subtracting the living T2-B7 cell number after co-culturing from the total T2-B7 cell number without co-culturing with the effector primary T cells, then divided by the total T2-B7 cell number without co-culturing) represents the cytotoxic activity of the effector primary T cells. For detection of CD25, cells were first stained with Zombie NIR™ (Biolegend) to discriminate living cells and then stained with an anti-CD25-PE/Cy7 antibody (Biolegend), according to the manufacturer's instructions. For detection of IFN-γ expression, cells were incubated with Brefeldin A and Monensin (Biolegend) for 5 hours before staining. Following cell viability staining and surface staining for CD25-PE/Cy7, CD4-PerCP/Cy5.5, and CD8/PE, as previously described, cells were fixed and permeabilized (Biolegend), according to the manufacturer's instructions, and then stained with an anti-IFN-γ-FITC antibody (Biolegend). The measured fluorescence indicated CD25 and IFN-γ expression levels.

As shown in FIGS. 16A-16C, an increase of cytotoxic activity, CD25 expression and IFN-γ expression was observed in the effector primary T cells in a dose dependent manner with increasing phosphopeptide EPR[pS]PSHSM (SEQ ID NO. 45) concentrations. In contrast, the unmodified MLL-M peptide did not increase the cytotoxic activity, CD25 expression, or IFN-γ expression of the T cells (FIGS. 16A-16C). These results indicate that TCR0078 is specific for the phosphopeptide EPR[pS]PSHSM (SEQ ID NO: 45).

To further characterize TCR0078 specificity for HLA-B*0702 and phosphopeptide EPR[pS]PSHSM (SEQ ID NO: 45), primary T cells transduced with TCR0078 were co-cultured with peptide-pulsed T2 cells expressing either HLA-B*0702 or HLA-A*02.01. Cells were then stained, and CD25 and IFN-γ T cell expression was analyzed by flow cytometry, using the same methods described above.

As shown in FIGS. 17A and 17B, primary T cells were activated when co-cultured with T2-HLA-B*0702 pulsed with the phosphopeptide EPR[pS]PSHSM (SEQ ID NO: 45). By contrast, primary T cells were not activated when co-cultured with T2-HLA-A*02.02 pulsed with either the phosphopeptide or unmodified peptide.

6.4 Example 4: Characterization of TCR0078 as a Cancer Therapy

6.4.1 Characterization of TCR0078 Using Tumor Cells as Target Cells

To assess the efficacy of TCR0078 against tumor cell lines, primary T cells, not transduced or transduced with TCR0078, were co-cultured for 20 hours with KG1a cells (endogenously expressing MLL and overexpressing HLA-B*0702 or HLA-A*02.02), at various effector:target ratios, as described in Example 3. Cells were stained (e.g., with Zombie NIR™, anti-CD25 antibody, and anti-IFN-γ antibody) and cytotoxic activity and activation of the effector primary T cells were analyzed by flow cytometry, as described in Example 3.

Activation of TCR0078-expressing primary T cells by KG1a cells stably expressing-HLA-B*0702, but not KG1a cells expressing HLA-A*02.01, at various effector:target ratios, was confirmed by increased killing of the target KG1a cells (FIG. 18A) and increased CD25 (FIG. 18B) and IFN-γ (FIG. 18C) expression in the effector primary T cells. In contrast, untransduced primary T cells (negative control) were not activated by either of the foregoing KG1a cell lines.

Similar assays were performed using primary T cells (with or without TCR0078 transduction) co-cultured with various tumor cells (KG1a cell, K562 cells, SK-MEL-5 cells, U266B1 cells, and Namalwa cells) expressing endogenous or recombinant HLA-B*0702, at various effector:target ratios. The activation of the primary T cells was measured by killing of the target tumor cells, using the same protocol and flow cytometry methods as described in Example 3. As shown in FIG. 19, TCR0078-expressing primary T cells, but not control T cells not expressing TCR0078, significantly promoted killing, at various effector:target ratios, of target KG1a (FIG. 19A) and K562 (FIG. 19B) cells, stably expressing recombinant HLA-B*0702, as well as SK-MEL-5 cells (FIG. 19C) and U266B1 cells (FIG. 19D). The cytotoxic activity of the effector primary T cells was less potent but still statistically significant toward target Namalwa cells (FIG. 19E).

6.4.2 In Vivo Anti-Cancer Activities of TCR0078

To assess efficacy of TCR0078-expressing primary T cells in vivo, a T cell adoptive transfer experiment in immunosuppressed NOG mice (Jackson Laboratory, Bar Harbor, ME) bearing a KG1a-HLA-B*0702 tumor was conducted.

Prior to the adoptive transfer, TCR0078-transduced primary T cells were tested in vitro to confirm their activation and cytotoxic activity toward KG1a-HLA-B*0702 tumor cells. As previously described, control and TCR0078-transduced T cells were co-cultured with tumor cells at various effector:target ratios. Killing efficiency and T cells activation were analyzed by flow cytometry, as described in Example 3.

As shown in FIG. 20A, the T cells expressing TCR0078, but not control T cells, significantly promoted killing, at various effector:target ratios, of target KG1a cells expressing HLA-B*0702. CD25 expression in the primary T cells expressing TCR0078 was also significantly increased, compared to the CD25 levels in control T cells (FIG. 20B). Thus, the TCR0078-expressing primary T cells were activated by and had cytotoxic activity toward KG1a-HLA-B*0702 cells in vitro.

For the adoptive transfer, at Day 0, one million of KG1a-HLA-B*0702 tumors cells were injected subcutaneously to each of twenty mice. At Day 1, $5 \times 10^6$ primary T cells, transduced with TCR0078 fifteen days prior, were injected intravenously into ten of the mice. The other ten mice remained un-injected as control. Two of the ten injected mice were sacrificed at Day 7, after measuring the length and width of their tumors and calculating the volume of tumors (by multiplying the measured length and width and then 0.52), to confirm T cells injection and homing. The volume of tumors on other injected and control mice was calculated by the same method at Day 7 and then every 3-5 days, until Day 42. All mice were then sacrificed at Day 42 post tumor implantation and their spleens were collected, processed and stained with Zombie NIR™ reagent, anti-CD3 antibody, and anti-CD45 antibody (Biolegend) to detect T cells and tumor cells.

As shown in FIG. 21A, mice injected with TCR0078-expressing T cells showed significantly slower tumor growth on average, compared to un-injected mice. Among all eight injected mice alive for the 42-day period, only two showed significant tumor growth (white circles in FIG. 21B, comparable to tumor volumes in un-injected mice in FIG. 21A), while the other six had minimal tumor growth (black circles in FIG. 21B), indicating significant tumor inhibition. As detected by flow cytometry, one mouse with significant tumor growth in FIG. 21B had 0.027% of spleen cells as injected human T cells (CD45+/CD3+) and 0.25% of spleen cells as metastatic tumoral cells (CD45+/CD3−) (FIG. 21C, left panel). In contrast, one mouse with minimal tumor growth in FIG. 21B had a larger percentage of spleen cells as CD45+/CD3+ T cells (72.5%) and a smaller percentage of spleen cells as metastatic CD45+/CD3− tumor cells (0.037%) (FIG. 21C, right panel), indicating that the injection of TCR0078-expressing T cells inhibited metastasis as well as tumor volume.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of treating cancer in a subject, the method comprising administering to the subject an engineered cell comprising a T cell receptor (TCR) that comprises:

(a) a CDR1α comprising the amino acid sequence of SEQ ID NO: 11, a CDR2α comprising the amino acid sequence of SEQ ID NO: 16, a CDR3α comprising the amino acid sequence of SEQ ID NO: 21, a CDR1β comprising the amino acid sequence of SEQ ID NO: 26, a CDR2β comprising the amino acid sequence of SEQ ID NO: 31, and a CDR3β comprising the amino acid sequence of SEQ ID NO: 36;

(b) a CDR1α comprising the amino acid sequence of SEQ ID NO: 12, a CDR2α comprising the amino acid sequence of SEQ ID NO: 17, a CDR3α comprising the amino acid sequence of SEQ ID NO: 22, a CDR1β comprising the amino acid sequence of SEQ ID NO: 27, a CDR2β comprising the amino acid sequence of SEQ ID NO: 32, and a CDR3β comprising the amino acid sequence of SEQ ID NO: 37;

(c) a CDR1α comprising the amino acid sequence of SEQ ID NO: 13, a CDR2α comprising the amino acid sequence of SEQ ID NO: 18, a CDR3α comprising the amino acid sequence of SEQ ID NO: 23, a CDR1β comprising the amino acid sequence of SEQ ID NO: 28, a CDR2β comprising the amino acid sequence of SEQ ID NO: 33, and a CDR3β comprising the amino acid sequence of SEQ ID NO: 38;

(d) a CDR1α comprising the amino acid sequence of SEQ ID NO: 13, a CDR2α comprising the amino acid sequence of SEQ ID NO: 109, a CDR3α comprising the amino acid sequence of SEQ ID NO: 23, a CDR1β comprising the amino acid sequence of SEQ ID NO: 28, a CDR2β comprising the amino acid sequence of SEQ ID NO: 33, and a CDR3β comprising the amino acid sequence of SEQ ID NO: 38;

(e) a CDR1α comprising the amino acid sequence of SEQ ID NO: 14, a CDR2α comprising the amino acid sequence of SEQ ID NO: 19, a CDR3α comprising the amino acid sequence of SEQ ID NO: 24, a CDR1β comprising the amino acid sequence of SEQ ID NO: 29, a CDR2β comprising the amino acid sequence of SEQ ID NO: 34, and a CDR3β comprising the amino acid sequence of SEQ ID NO: 39; or (f) a CDR1α comprising the amino acid sequence of SEQ ID NO: 15, a CDR2α comprising the amino acid sequence of SEQ ID NO: 20, a CDR3α comprising the amino acid sequence of SEQ ID NO: 25, a CDR1β comprising the amino acid sequence of SEQ ID NO: 30, a CDR2β comprising the amino acid sequence of SEQ ID NO: 35, and a CDR3β comprising the amino acid sequence of SEQ ID NO: 40.

2. The method of claim 1, wherein the TCR comprises a CDR1α comprising the amino acid sequence of SEQ ID NO: 11, a CDR2α comprising the amino acid sequence of SEQ ID NO: 16, a CDR3α comprising the amino acid sequence of SEQ ID NO: 21, a CDR1β comprising the amino acid sequence of SEQ ID NO: 26, a CDR2β comprising the amino acid sequence of SEQ ID NO: 31, and a CDR3β comprising the amino acid sequence of SEQ ID NO: 36.

3. The method of claim 1, wherein the TCR is a human TCR.

4. The method of claim 1, wherein the TCR comprises:

(a) an α chain variable region (Vα) comprising the amino acid sequence of SEQ ID NO: 1, and a β chain variable region (Vβ) comprising the amino acid sequence of SEQ ID NO: 2;

(b) an α chain variable region (Vα) comprising the amino acid sequence of SEQ ID NO: 86, and a β chain variable region (Vβ) comprising the amino acid sequence of SEQ ID NO: 87;

(c) an α chain variable region (Vα) comprising the amino acid sequence of SEQ ID NO: 3, and a β chain variable region (Vβ) comprising the amino acid sequence of SEQ ID NO: 4;

(d) an α chain variable region (Vα) comprising the amino acid sequence of SEQ ID NO: 88, and a β chain variable region (Vβ) comprising the amino acid sequence of SEQ ID NO: 89;

(e) an α chain variable region (Vα) comprising the amino acid sequence of SEQ ID NO: 5, and a β chain variable region (Vβ) comprising the amino acid sequence of SEQ ID NO: 6;

(f) an α chain variable region (Vα) comprising the amino 5 acid sequence of SEQ ID NO: 106, and a β chain variable region (Vβ) comprising the amino acid sequence of SEQ ID NO: 107;

(g) an α chain variable region (Vα) comprising the amino acid sequence of SEQ ID NO: 7, and a β chain variable 10 region (Vβ) comprising the amino acid sequence of SEQ ID NO: 8;

(h) an α chain variable region (Vα) comprising the amino acid sequence of SEQ ID NO: 7, and a β chain variable region (Vβ) comprising the amino acid sequence of 15 SEQ ID NO: 108; or (i) an α chain variable region (Vα) comprising the amino acid sequence of SEQ ID NO: 9, and a β chain variable region (Vβ) comprising the amino acid sequence of SEQ ID NO: 10.

5. The method of claim 1, wherein the TCR comprises an α chain variable region (Vα) comprising the amino acid sequence of SEQ ID NO: 86, and a β chain variable region (Vβ) comprising the amino acid sequence of SEQ ID NO: 87.

6. The method of claim 1, wherein the TCR comprises:

(a) an α chain comprising the amino acid sequence of SEQ ID NO: 249, and a β chain comprising the amino acid sequence of SEQ ID NO: 250;

(b) an α chain comprising the amino acid sequence of any one of SEQ ID NOs: 58, 236, 259, 260, 272, 261, or 249, and a β chain comprising the amino acid sequence of any one of SEQ ID NOs: 59, 237, 262, 263, 264, 273, 60, and 250;

(c) an α chain comprising the amino acid sequence of SEQ ID NO: 251, and a β chain comprising the amino acid sequence of SEQ ID NO: 252;

(d) an α chain comprising the amino acid sequence of SEQ ID NO: 61, and a β chain comprising the amino acid sequence of SEQ ID NOs: 62 or 63;

(e) an α chain comprising the amino acid sequence of SEQ ID NO: 64, and a β chain comprising the amino acid sequence of SEQ ID NOs: 65 or 66;

(f) an α chain comprising the amino acid sequence of SEQ ID NO: 255, and a β chain comprising the amino acid sequence of SEQ ID NO: 256;

(g) an α chain comprising the amino acid sequence of SEQ ID NO: 67, and a β chain comprising the amino acid sequence of SEQ ID NOs: 68 or 69;

(h) an α chain comprising the amino acid sequence of SEQ ID NO: 257, and a β chain comprising the amino acid sequence of SEQ ID NO: 258; or (i) an α chain comprising the amino acid sequence of SEQ ID NO: 70, and a β chain comprising the amino acid sequence of SEQ ID NOs: 71 or 72.

7. The method of claim 1, wherein the TCR comprises an α chain comprising the amino acid sequence of SEQ ID NO: 58, and a β chain comprising the amino acid sequence of SEQ ID NO: 59.

8. The method of claim 1, wherein the engineered cell is administered intravenously.

9. The method of claim 1, further comprising administering an additional therapeutic agent to the subject.

10. The method of claim 9, wherein the additional therapeutic agent is a chemotherapeutic, a radiotherapeutic, or a checkpoint targeting agent.

11. The method of claim 10, wherein the checkpoint targeting agent is an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist VISTA antibody, an antagonist CD96 antibody, an antagonist anti-CEACAM1 antibody, an antagonist anti-TIGIT antibody, an agonist anti-CD137 antibody, an agonist anti-GITR antibody, or an agonist anti-OX40 antibody.

12. The method of claim 9, wherein the additional therapeutic agent is a vaccine.

13. The method of claim 12, wherein the vaccine comprises a heat shock protein peptide complex (HSPPC) comprising a heat shock protein complexed with an antigenic peptide.

14. The method of claim 13, wherein the heat shock protein is hsc70 or gp96, and is complexed with a tumor-associated antigenic peptide.

15. The method of claim 1, wherein the cancer is a MLL positive cancer.

16. The method of claim 15, wherein the cancer is leukemia, myeloma, or sarcoma.

17. The method of claim 16, wherein the leukemia is mixed lineage leukemia, acute lymphocytic leukemia, acute myeloid leukemia, chronic lymphocytic leukemia, or chronic myeloid leukemia.

18. The method of claim 16, wherein the myeloma is chronic myeloid cancer.

19. The method of claim 16, wherein the sarcoma is synovial sarcoma or liposarcoma.

20. The method of claim 1, wherein the engineered cell is a T cell, a natural killer T (NKT) cell, an invariant natural killer T (iNKT) cell, a mucosal-associated invariant T (MaiT) cell, or a natural killer (NK) cell.

* * * * *